US012533409B2

(12) United States Patent
Bear et al.

(10) Patent No.: US 12,533,409 B2
(45) Date of Patent: Jan. 27, 2026

(54) COMPOSITIONS AND METHODS FOR TARGETING MUTANT RAS

(71) Applicant: The Trustees of the University of Pennsylvania, Philadelphia, PA (US)

(72) Inventors: Adham Bear, Philadelphia, PA (US); Robert Vonderheide, Merion Station, PA (US); Gerald Linette, Gladwyne, PA (US); Beatriz Carreno, Gladwyne, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1216 days.

(21) Appl. No.: 17/425,498

(22) PCT Filed: Jan. 24, 2020

(86) PCT No.: PCT/US2020/014988
§ 371 (c)(1),
(2) Date: Jul. 23, 2021

(87) PCT Pub. No.: WO2020/154617
PCT Pub. Date: Jul. 30, 2020

(65) Prior Publication Data

US 2022/0088190 A1 Mar. 24, 2022

Related U.S. Application Data

(60) Provisional application No. 62/796,733, filed on Jan. 25, 2019.

(51) Int. Cl.
*A61K 39/39* (2006.01)
*A61K 39/385* (2006.01)
(Continued)

(52) U.S. Cl.
CPC ............ *A61K 39/39* (2013.01); *A61K 39/385* (2013.01); *A61K 40/11* (2025.01); *A61K 40/19* (2025.01);
(Continued)

(58) Field of Classification Search
CPC ...... A61K 39/39; A61K 39/385; A61K 40/11; A61K 40/19; A61K 40/24; A61K 40/32;
(Continued)

(56) References Cited

U.S. PATENT DOCUMENTS

| | | | | |
|---|---|---|---|---|
| 2010/0074945 A1* | 3/2010 | Schlom | A61K 40/11 424/85.4 |
| 2017/0158749 A1 | 6/2017 | Cooper | |
| 2018/0369280 A1 | 12/2018 | Schmitt | |

FOREIGN PATENT DOCUMENTS

| | | |
|---|---|---|
| CN | 107223134 A | 9/2017 |
| CN | 117957015 A | 4/2024 |

(Continued)

OTHER PUBLICATIONS

Hobbs, G et al. "RAS isoforms and mutations in cancer at a glance." Journal of cell science 129.7 (2016): 1287-1292.) (Year: 2016).*
(Continued)

*Primary Examiner* — Tracy Vivlemore
*Assistant Examiner* — Thomas R. Amick
(74) *Attorney, Agent, or Firm* — Riverside Law LLP

(57) ABSTRACT

This invention relates to compositions and methods of treating cancer associated with mutant RAS. In certain aspects, the invention relates to antigenic RAS peptide
(Continued)

fragments and T-cell receptors that bind to specific mutant RAS peptide fragments in the context of specific HLA types.

8 Claims, 44 Drawing Sheets

Specification includes a Sequence Listing.

(51) Int. Cl.
*A61K 40/11* (2025.01)
*A61K 40/19* (2025.01)
*A61K 40/24* (2025.01)
*A61K 40/32* (2025.01)
*A61K 40/34* (2025.01)
*A61K 40/42* (2025.01)
*A61P 35/00* (2006.01)
*C07K 14/725* (2006.01)

(52) U.S. Cl.
CPC .............. *A61K 40/24* (2025.01); *A61K 40/32* (2025.01); *A61K 40/34* (2025.01); *A61K 40/4201* (2025.01); *A61K 40/4253* (2025.01); *A61P 35/00* (2018.01); *C07K 14/7051* (2013.01)

(58) Field of Classification Search
CPC ................ A61K 40/34; A61K 40/4201; A61K 40/4253; A61K 31/7088; A61P 35/00; C07K 14/7051; C07K 2317/32; C07K 2317/33; C07K 2317/34; C07K 2317/73; C07K 14/82; C07K 16/2833; C07K 16/32; C07K 16/40
See application file for complete search history.

(56) References Cited

FOREIGN PATENT DOCUMENTS

| | | | |
|---|---|---|---|
| WO | 9740156 | A1 | 10/1997 |
| WO | 2015123532 | | 8/2015 |
| WO | 2016085904 | A1 | 6/2016 |
| WO | 2017046201 | A1 | 3/2017 |
| WO | 2018026691 | A1 | 2/2018 |
| WO | 2019060349 | A1 | 3/2019 |
| WO | 2019112932 | A1 | 6/2019 |
| WO | 2019112941 | A1 | 6/2019 |
| WO | 2020037239 | A1 | 2/2020 |
| WO | 2020172332 | A1 | 8/2020 |
| WO | 2021068938 | A1 | 4/2021 |
| WO | 2021097365 | A2 | 5/2021 |

OTHER PUBLICATIONS

Garcia, K. Christopher, and Erin J. Adams. "How the T cell receptor sees antigen—a structural view." Cell 122.3 (2005): 333-336 (Year: 2005).*

Webpage, Immunology Guidebook, 2004, screenshot attached (Year: 2004).*

Aggen, David H, et al., "Single-chain VαVβ T-cell receptors function without mispairing with endogenous TCR chains." Gene therapy, 2012, 19(4 ): 365-374.

Carreno BM, et al., "A dendritic cell vaccine increases the breadth and diversity of melanoma neoantigen-specific T cells", Science, 2015, 348:803-8.

Chinese Office Action (including English translation) issued in App. No. CN202080024782, dated Jun. 21, 2024, 18 pages.

Chinese Office Action (including English translation) issued in App. No. CN20208024782, dated Jun. 21, 2024, 15 pages.

International Search Report and Written Opinion issued in App. No. PCT/US2020/014988, mailing date Apr. 20, 2020, 19 pages.

Keenan BP, et al., "A listeria vaccine and depletion of T-regulatory cells activate immunity against early stage pancreatic intraepithelial neoplasms and prolong survival of mice", Gastroenterology, 2014, 146:1784-94.

Linette GP, et al., "Neoantigen vaccines pass the immunogenicity test", Trends Mol Med, 2017, 23:869-71.

Morrison AH, et al., "Immunotherapy and prevention of pancreatic cancer", Trends Cancer, 2018, 4:418-28.

Pan, Y, "Progress in treatment of colorectal cancer with K-Ras gene mutation", Tumor, 2017, 412-418.

Rech AJ, et al., "T-Cell transfer therapy targeting mutant KRAS", N Engl J Med, 2017, 376:e11. 3 pages.

Rech AJ, et al., "Tumor immunity and survival as a function of alternative neopeptides in human cancer", Cancer Immunol Res, 2018, 6:276-87.

Tran E, et al., "T-Cell transfer therapy targeting mutant KRAS in cancer", N Engl J Med, 2016, 375:2255-62.

Trojan et al., "Generation of Cytotoxic T Lymphocytes against Native and Altered Peptides of Human Leukocyte Antigen-A*0201 Restricted Epitopes from the Human Epithelial Cell Adhesion Molecule", Cancer Research, 2001, 61:4761-4765.

Wang et al., "Identification of T-cell Receptors Targeting KRAS-mutated Human Tumors", Cancer Immunol Res, 2015, 4(3):204-214.

Yarchoan M, et al., "Targeting neoantigens to augment antitumour immunity", Nat Rev Cancer, 2017, 17:209-222.

* cited by examiner

RAS --- MTEYKLVVVGAGGVGKSALTIQLI (SEQ ID NO:177)
**RAS$^{G12*}$** --- MTEYKLVVVGA*GVGKSALTIQLI (SEQ ID NO:178)

| Nine(ten)mer | SEQ ID NO: |
|---|---|
| *GVGKSALT(I) | 179 |
| A*GVGKSAL(T) | 180 |
| GA*GVGKSA(L) | 181 |
| VGA*GVGKS(A) | 182 |
| VVGA*GVGK(S) | 183 |
| VVVGA*GVG(K) | 184 |
| LVVVGA*GV(G) | 185 |
| KLVVVGA*G(V) | 186 |
| YKLVVVGA*(G) | 187 |
| EYKLVVVGA(*) | 188 |

| ID | G12 | n-mer | aa | A*02:01 | Predicted Affinity (nM) A*03:01 | A*11:01 | B*07:02 | SEQ ID NO: |
|---|---|---|---|---|---|---|---|---|
| KLV_G | wt | 10 | KLVVVGAGGV | 1524 | ---- | ---- | ---- | SEQ ID NO: 189 |
| KLV_C | C | 10 | KLVVVGACGV | 274 | ---- | ---- | ---- | SEQ ID NO:1 |
| KLV_D | D | 10 | KLVVVGADGV | 762 | ---- | ---- | ---- | SEQ ID NO:2 |
| KLV_R | R | 10 | KLVVVGARGV | 1573 | ---- | ---- | ---- | SEQ ID NO:3 |
| KLV_V | V | 10 | KLVVVGAVGV | 323 | ---- | ---- | ---- | SEQ ID NO:4 |
| VV_G | wt | 9 | VVGAGGVGK | ---- | 537 | 111 | --- | SEQ ID NO: 190 |
| VVV_G | wt | 10 | VVVGAGGVGK | ---- | 152 | 76 | --- | SEQ ID NO: 191 |
| VV_C | C | 9 | VVGACGVGK | ---- | 248 | 85 | --- | SEQ ID NO:5 |
| VVV_C | C | 10 | VVVGACGVGK | ---- | 166 | 99 | --- | SEQ ID NO:6 |
| VV_D | D | 9 | VVGADGVGK | ---- | 1234 | 169 | --- | SEQ ID NO:7 |
| VVV_D | D | 10 | VVVGADGVGK | ---- | 409 | 156 | --- | SEQ ID NO:8 |
| VV_R | R | 9 | VVGARGVGK | ---- | 223 | 87 | --- | SEQ ID NO:9 |
| VVV_R | R | 10 | VVVGARGVGK | ---- | 98 | 118 | --- | SEQ ID NO:10 |
| VV_V | V | 9 | VVGAVGVGK | ---- | 107 | 54 | --- | SEQ ID NO:11 |
| VVV_V | V | 10 | VVVGAVGVGK | ---- | 120 | 63 | --- | SEQ ID NO:12 |
| GA_G | wt | 10 | GAGGVGKSAL | ---- | --- | --- | 2769 | SEQ ID NO: 192 |
| GA_C | C | 10 | GACGVGKSAL | ---- | --- | --- | 4240 | SEQ ID NO:13 |
| GA_D | D | 10 | GADGVGKSAL | ---- | --- | --- | 5244 | SEQ ID NO:14 |
| GA_R | R | 10 | GARGVGKSAL | ---- | --- | --- | 70 | SEQ ID NO:15 |
| GA_V | V | 10 | GAVGVGKSAL | ---- | --- | --- | 2695 | SEQ ID NO:16 |

FIG. 4B

Fluorescence Polarization Assay (competitive binding)

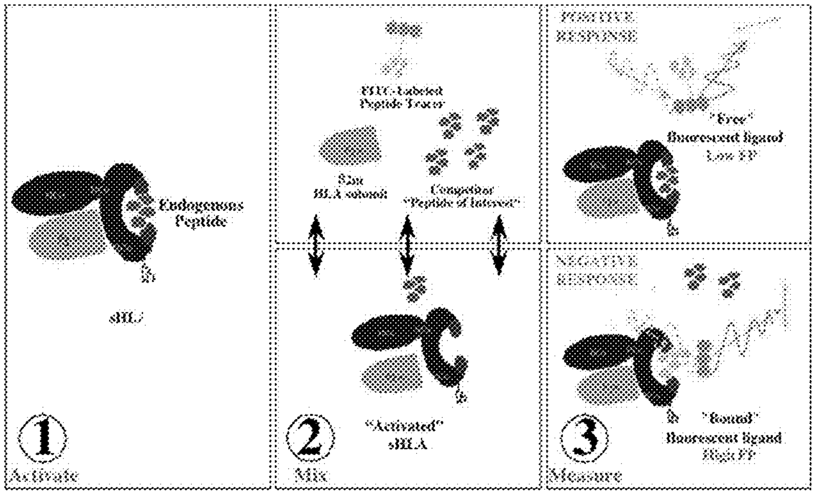

| MHC Peptide Sequence | SEQ ID NO: | MHC Allele | log[IC50] | Affinity |
|---|---|---|---|---|
| KLVVVGACGV | 1 | A*02:01 | 4.458 | Medium |
| KLVVVGADGV | 2 | A*02:01 | 4.291 | Medium |
| KLVVVGARGV | 3 | A*02:01 | 4.316 | Medium |
| KLVVVGAVGV | 4 | A*02:01 | 3.47 | High |
| VVVGACGVGK | 6 | A*03:01 | 3.898 | Medium |
| VVVGADGVGK | 8 | A*03:01 | 4.678 | Medium |
| VVVGARGVGK | 10 | A*03:01 | 3.51 | High |
| VVVGAVGVGK | 12 | A*03:01 | 3.62 | High |
| VVVGACGVGK | 6 | A*11:01 | 2.729 | High |
| VVVGADGVGK | 8 | A*11:01 | 2.839 | High |
| VVVGARGVGK | 10 | A*11:01 | 2.753 | High |
| VVVGAVGVGK | 12 | A*11:01 | 2.382 | High |
| GARGVGKSAL | 15 | B*07:02 | 1.648 | High |

| Log[IC50] | Affinity |
|---|---|
| <3.7 | High |
| 3.7-4.7 | Medium |
| 4.7-5.5 | Low |
| 5.5-6 | Very Low |
| >6 | None |

FIG. 5

| RAS | | |
|---|---|---|
| ID | aa | SEQ ID NO: |
| wt | MTEYKLVVVGAGGVGKSALTIQLIQ | SEQ ID NO: 193 |
| G12A | MTEYKLVVVGAAGVGKSALTIQLIQ | SEQ ID NO: 194 |
| G12C | MTEYKLVVVGACGVGKSALTIQLIQ | SEQ ID NO: 195 |
| G12D | MTEYKLVVVGADGVGKSALTIQLIQ | SEQ ID NO: 196 |
| G12R | MTEYKLVVVGARGVGKSALTIQLIQ | SEQ ID NO: 197 |
| G12S | MTEYKLVVVGASGVGKSALTIQLIQ | SEQ ID NO: 198 |
| G12V | MTEYKLVVVGAVGVGKSALTIQLIQ | SEQ ID NO: 199 |
| **Viral Controls** | | |
| ID | aa | |
| CMV pp65 - NLV (A*02:01) | GILARNLVPMVATVQGQNLK | SEQ ID NO:200 |
| Influenza A NP - ILR (A*03:01) | ARSALILRGSVAHKSCLPAC | SEQ ID NO:201 |
| EBV EBNA4 - IVT (A*11:01) | KKCRAIVTDFSVIKAIEEEH | SEQ ID NO:202 |
| CMV pp65 - TPR (B*07:02) | TTERKTPRVTGGGAMAGAST | SEQ ID NO:203 |

FIG. 7E

In Silico Prediction

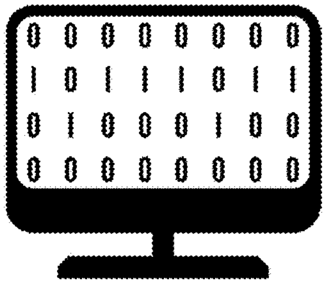

antigen.garnish mRAS Short Peptide Library (HLA- & Mutation-Specific)

**A*02:01**

G12C KLVVVGACGV (SEQ ID NO:1)
G12D KLVVVGADGV (SEQ ID NO:2)
G12R KLVVVGARGV (SEQ ID NO:3)
G12V KLVVVGAVGV (SEQ ID NO:4)

**A*03:01**

G12C VVVGACGVGK (SEQ ID NO:6)
G12D VVVGADGVGK (SEQ ID NO:8)
G12R VVVGARGVGK (SEQ ID NO:10)
VVGARGVGK (SEQ ID NO:9)
G12V VVVGAVGVGK (SEQ ID NO:12)
VVGAVGVGK (SEQ ID NO:11)

**A*11:01**

G12C VVVGACGVGK (SEQ ID NO:6)
VVGACGVGK (SEQ ID NO:5)
G12D VVVGADGVGK (SEQ ID NO:8)
VVGADGVGK (SEQ ID NO:7)
G12R VVVGARGVGK (SEQ ID NO:10)
VVGARGVGK (SEQ ID NO:9)
G12V VVVGAVGVGK (SEQ ID NO:12)
VVGAVGVGK (SEQ ID NO:11)

**B*07:02**

G12D GADGVGKSAL (SEQ ID NO:14)
G12R GARGVGKSAL (SEQ ID NO:15)

FIG. 10 p/MHC Binding

FIG. 10 (cont.)
POSITIVE
RESPONSE
"Free"
fluorescent ligand
Low FP

Fluorescence Polarization

| MHC Peptide Sequence | SEQ ID NO: | MHC Allele | log[IC50] | Affinity |
|---|---|---|---|---|
| KLVVVGACGV | 1 | A*02:01 | 4.458 | Medium |
| KLVVVGADGV | 2 | A*02:01 | 4.291 | Medium |
| KLVVVGARGV | 3 | A*02:01 | 4.316 | Medium |
| KLVVVGAVGV | 5 | A*02:01 | 3.47 | High |
| VVVGACGVGK | 6 | A*03:01 | 3.898 | Medium |
| VVVGADGVGK | 8 | A*03:01 | 4.678 | Medium |
| VVVGARGVGK | 10 | A*03:01 | 3.51 | High |
| VVVGAVGVGK | 12 | A*03:01 | 3.62 | High |
| VVVGACGVGK | 6 | A*11:01 | 2.729 | High |
| VVVGADGVGK | 8 | A*11:01 | 2.839 | High |
| VVVGARGVGK | 10 | A*11:01 | 2.753 | High |
| VVVGAVGVGK | 12 | A*11:01 | 2.382 | High |
| GARGVGKSAL | 15 | B*07:02 | 1.648 | High |

* IFN-γ ELISPOT

| Cell Line | Tumour Type | KRAS MUT | A Allele 1 | A Allele 2 | B Allele 1 | B Allele 2 | C Allele 1 | C Allele 2 |
|---|---|---|---|---|---|---|---|---|
| PSN1 | pancreatic adenocarcinoma | G12R | 24:02 | 24:02 | 52:01 | 52:01 | 12:02 | 12:02 |

| ID | Specificity | Restriction | Vα / Vβ | | |
|---|---|---|---|---|---|
| TCR896 | G12V | A*03:01 | TRAV19, TRAJ40 | CALSEAGTYKYIF | (SEQ ID NO:59) |
| | | | TRBV9, TRBD1, TRBJ2-5 | CASSVAGGGQETQYF | (SEQ ID NO:64) |
| TCR831 | G12V | A*11:01 | TRAV39, TRAJ13 | CAVDKDGGYQKVTF | (SEQ ID NO:19) |
| | | | TRBV20-1, TRBD1, TRBJ1-6 | CSASPRAGQLSSYNSPLHF | (SEQ ID NO:25) |
| TCR833 | G12V | A*11:01 | TRAV12-1, TRAJ8 | CAVNPPDTGFQKLVF | (SEQ ID NO:33) |
| | | | TRBV28, TRBD2, TRBJ2-7 | CASSLSFRQGLREQYF | (SEQ ID NO:39) |
| TCR897 | G12V | A*11:01 | TRAV17, TRAJ9 | CATDPGGFKTIF | (SEQ ID NO:47) |
| | | | TRBV11-2, TRBJ2-7 | CASSLYGGSISYEQYF | (SEQ ID NO:52) |
| TCR847 | G12R | B*07:02 | TRAV17, TRAJ48 | CATFPNFGNEKLTF | (SEQ ID NO:71) |
| | | | TRBV10-3, TRBD2, TRBJ2-7 | CAISESERYYEQYF | (SEQ ID NO:76) |
| TCR864 | G12R | B*07:02 | TRAV4, TRAJ41 | CLVGDFNSNSGYALNF | (SEQ ID NO:83) |
| | | | TRBV7-2, TRBJ1-2 | CASKVYGYTF | (SEQ ID NO:88) |

FIG. 20

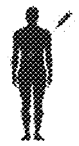

Vaccinated PDA Patient

Objectives

1. Evaluate safety / tolerability of mDC3/8-KRAS vaccine
2. Examine KRAS–specific immunologic response to mDC3/8-KRAS vaccination
3. Identify HLA-specific anti–Kras TCR sequences
4. Assess disease-free survival

Inclusion Criteria

1. Stage I-III PDA with NED s/p surgery +/- neoadjuvant or adjuvant chemotherapy and/or radiotherapy
2. Pathologically confirmed $KRAS^{G12C}$, $KRAS^{G12D}$, $KRAS^{G12R}$ or $KRAS^{G12V}$ mutation
3. HLA-A*02:01, HLA-A*03:01, HLA-A*11:01, HLA-B*07:02 and / or HLA-C*08:02

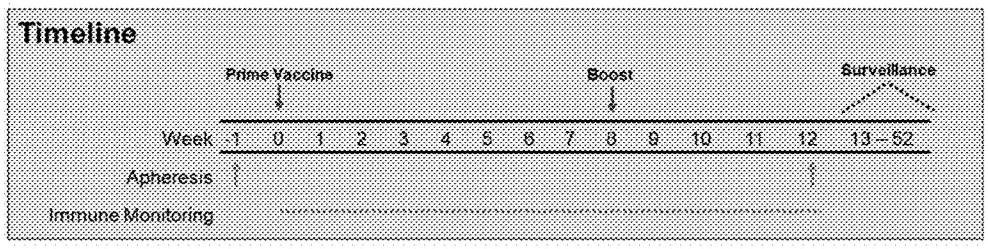

mRAS Short Peptide Library (HLA- & Mutation-Specific)

**A*02:01**

| | |
|---|---|
| **G12C** | KLVVVGACGV (SEQ ID NO:1) |
| **G12D** | KLVVVGADGV (SEQ ID NO:2) |
| **G12R** | KLVVVGARGV (SEQ ID NO:3) |
| **G12V** | KLVVVGAVGV (SEQ ID NO:4) |

**A*03:01**

| | |
|---|---|
| **G12C** | VVVGACGVGK (SEQ ID NO:6) |
| **G12D** | VVVGADGVGK (SEQ ID NO:8) |
| **G12R** | VVVGARGVGK (SEQ ID NO:10) |
| | VVGARGVGK (SEQ ID NO:9) |
| **G12V** | VVVGAVGVGK (SEQ ID NO:12) |
| | VVGAVGVGK (SEQ ID NO:11) |

**A*11:01**

| | |
|---|---|
| **G12C** | VVVGACGVGK (SEQ ID NO:6) |
| | VVGACGVGK (SEQ ID NO:5) |
| **G12D** | VVVGADGVGK (SEQ ID NO:8) |
| | VVGADGVGK (SEQ ID NO:7) |
| **G12R** | VVVGARGVGK (SEQ ID NO:10) |
| | VVGARGVGK (SEQ ID NO:9) |
| **G12V** | VVVGAVGVGK (SEQ ID NO:12) |
| | VVGAVGVGK (SEQ ID NO:11) |

**B*07:02**

| | |
|---|---|
| **G12D** | GADGVGKSAL (SEQ ID NO:14) |
| **G12R** | GARGVGKSAL (SEQ ID NO:15) |

FIG. 31

SEQUENCE LISTING

```
<160> NUMBER OF SEQ ID NOS: 203

<210> SEQ ID NO 1
<211> LENGTH: 10
<212> TYPE: PRT
<213> ORGANISM: Artificial Sequence
<220> FEATURE:
<223> OTHER INFORMATION: KLV_C

<400> SEQUENCE: 1

Lys Leu Val Val Val Gly Ala Cys Gly Val
```

```
1               5                   10


<210> SEQ ID NO 2
<211> LENGTH: 10
<212> TYPE: PRT
<213> ORGANISM: Artificial Sequence
<220> FEATURE:
<223> OTHER INFORMATION: KLV_D

<400> SEQUENCE: 2

Lys Leu Val Val Val Gly Ala Asp Gly Val
1               5                   10


<210> SEQ ID NO 3
<211> LENGTH: 10
<212> TYPE: PRT
<213> ORGANISM: Artificial Sequence
<220> FEATURE:
<223> OTHER INFORMATION: KLV_R

<400> SEQUENCE: 3

Lys Leu Val Val Val Gly Ala Arg Gly Val
1               5                   10


<210> SEQ ID NO 4
<211> LENGTH: 10
<212> TYPE: PRT
<213> ORGANISM: Artificial Sequence
<220> FEATURE:
<223> OTHER INFORMATION: KLV_V

<400> SEQUENCE: 4

Lys Leu Val Val Val Gly Ala Val Gly Val
1               5                   10


<210> SEQ ID NO 5
<211> LENGTH: 9
<212> TYPE: PRT
<213> ORGANISM: Artificial Sequence
<220> FEATURE:
<223> OTHER INFORMATION: VV_C

<400> SEQUENCE: 5

Val Val Gly Ala Cys Gly Val Gly Lys
1               5


<210> SEQ ID NO 6
<211> LENGTH: 10
<212> TYPE: PRT
<213> ORGANISM: Artificial Sequence
<220> FEATURE:
<223> OTHER INFORMATION: VVV_C

<400> SEQUENCE: 6

Val Val Val Gly Ala Cys Gly Val Gly Lys
1               5                   10


<210> SEQ ID NO 7
<211> LENGTH: 9
<212> TYPE: PRT
<213> ORGANISM: Artificial Sequence
<220> FEATURE:
<223> OTHER INFORMATION: VV_D

<400> SEQUENCE: 7

Val Val Gly Ala Asp Gly Val Gly Lys
1               5
```

<210> SEQ ID NO 8
<211> LENGTH: 10
<212> TYPE: PRT
<213> ORGANISM: Artificial Sequence
<220> FEATURE:
<223> OTHER INFORMATION: VVV_D

<400> SEQUENCE: 8

Val Val Val Gly Ala Asp Gly Val Gly Lys
1 5 10

<210> SEQ ID NO 9
<211> LENGTH: 9
<212> TYPE: PRT
<213> ORGANISM: Artificial Sequence
<220> FEATURE:
<223> OTHER INFORMATION: VV_R

<400> SEQUENCE: 9

Val Val Gly Ala Arg Gly Val Gly Lys
1 5

<210> SEQ ID NO 10
<211> LENGTH: 10
<212> TYPE: PRT
<213> ORGANISM: Artificial Sequence
<220> FEATURE:
<223> OTHER INFORMATION: VVV_R

<400> SEQUENCE: 10

Val Val Val Gly Ala Arg Gly Val Gly Lys
1 5 10

<210> SEQ ID NO 11
<211> LENGTH: 9
<212> TYPE: PRT
<213> ORGANISM: Artificial Sequence
<220> FEATURE:
<223> OTHER INFORMATION: VV_V

<400> SEQUENCE: 11

Val Val Gly Ala Val Gly Val Gly Lys
1 5

<210> SEQ ID NO 12
<211> LENGTH: 10
<212> TYPE: PRT
<213> ORGANISM: Artificial Sequence
<220> FEATURE:
<223> OTHER INFORMATION: VVV_V

<400> SEQUENCE: 12

Val Val Val Gly Ala Val Gly Val Gly Lys
1 5 10

<210> SEQ ID NO 13
<211> LENGTH: 10
<212> TYPE: PRT
<213> ORGANISM: Artificial Sequence
<220> FEATURE:
<223> OTHER INFORMATION: GA_C

<400> SEQUENCE: 13

Gly Ala Cys Gly Val Gly Lys Ser Ala Leu
1 5 10

<210> SEQ ID NO 14
<211> LENGTH: 10
<212> TYPE: PRT
<213> ORGANISM: Artificial Sequence
<220> FEATURE:
<223> OTHER INFORMATION: GA_D

<400> SEQUENCE: 14

Gly Ala Asp Gly Val Gly Lys Ser Ala Leu
1 5 10

<210> SEQ ID NO 15
<211> LENGTH: 10
<212> TYPE: PRT
<213> ORGANISM: Artificial Sequence
<220> FEATURE:
<223> OTHER INFORMATION: GA_R

<400> SEQUENCE: 15

Gly Ala Arg Gly Val Gly Lys Ser Ala Leu
1 5 10

<210> SEQ ID NO 16
<211> LENGTH: 10
<212> TYPE: PRT
<213> ORGANISM: Artificial Sequence
<220> FEATURE:
<223> OTHER INFORMATION: GA_V

<400> SEQUENCE: 16

Gly Ala Val Gly Val Gly Lys Ser Ala Leu
1 5 10

<210> SEQ ID NO 17
<211> LENGTH: 7
<212> TYPE: PRT
<213> ORGANISM: Artificial Sequence
<220> FEATURE:
<223> OTHER INFORMATION: TRAV39 CDR1

<400> SEQUENCE: 17

Ser Thr Thr Ser Asp Arg Leu
1 5

<210> SEQ ID NO 18
<211> LENGTH: 9
<212> TYPE: PRT
<213> ORGANISM: Artificial Sequence
<220> FEATURE:
<223> OTHER INFORMATION: TRAV39 CDR2

<400> SEQUENCE: 18

Val Leu Leu Ser Asn Gly Ala Val Lys
1 5

<210> SEQ ID NO 19
<211> LENGTH: 14
<212> TYPE: PRT
<213> ORGANISM: Artificial Sequence
<220> FEATURE:
<223> OTHER INFORMATION: TRAV39 CDR3

<400> SEQUENCE: 19

Cys Ala Val Asp Lys Asp Gly Gly Tyr Gln Lys Val Thr Phe
1 5 10

<210> SEQ ID NO 20
<211> LENGTH: 112
<212> TYPE: PRT
<213> ORGANISM: Artificial Sequence
<220> FEATURE:
<223> OTHER INFORMATION: TRAV39 VARIABLE DOMAIN

<400> SEQUENCE: 20

```
Glu Leu Lys Val Glu Gln Asn Pro Leu Phe Leu Ser Met Gln Glu Gly
1               5                   10                  15

Lys Asn Tyr Thr Ile Tyr Cys Asn Tyr Ser Thr Thr Ser Asp Arg Leu
            20                  25                  30

Tyr Trp Tyr Arg Gln Asp Pro Gly Lys Ser Leu Glu Ser Leu Phe Val
        35                  40                  45

Leu Leu Ser Asn Gly Ala Val Lys Gln Glu Gly Arg Leu Met Ala Ser
    50                  55                  60

Leu Asp Thr Lys Ala Arg Leu Ser Thr Leu His Ile Thr Ala Ala Val
65                  70                  75                  80

His Asp Leu Ser Ala Thr Tyr Phe Cys Ala Val Asp Lys Asp Gly Gly
                85                  90                  95

Tyr Gln Lys Val Thr Phe Gly Thr Gly Thr Lys Leu Gln Val Ile Pro
            100                 105                 110
```

<210> SEQ ID NO 21
<211> LENGTH: 140
<212> TYPE: PRT
<213> ORGANISM: Artificial Sequence
<220> FEATURE:
<223> OTHER INFORMATION: TCR831 ALPHA CONSTANT DOMAIN

<400> SEQUENCE: 21

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140
```

<210> SEQ ID NO 22
<211> LENGTH: 271
<212> TYPE: PRT
<213> ORGANISM: Artificial Sequence
<220> FEATURE:
<223> OTHER INFORMATION: TCR831 ALPHA CHAIN

<400> SEQUENCE: 22

```
Met Lys Lys Leu Leu Ala Met Ile Leu Trp Leu Gln Leu Asp Arg Leu
1               5                   10                  15
```

```
Ser Gly Glu Leu Lys Val Glu Gln Asn Pro Leu Phe Leu Ser Met Gln
            20                  25                  30

Glu Gly Lys Asn Tyr Thr Ile Tyr Cys Asn Tyr Ser Thr Thr Ser Asp
        35                  40                  45

Arg Leu Tyr Trp Tyr Arg Gln Asp Pro Gly Lys Ser Leu Glu Ser Leu
    50                  55                  60

Phe Val Leu Leu Ser Asn Gly Ala Val Lys Gln Glu Gly Arg Leu Met
65                  70                  75                  80

Ala Ser Leu Asp Thr Lys Ala Arg Leu Ser Thr Leu His Ile Thr Ala
                85                  90                  95

Ala Val His Asp Leu Ser Ala Thr Tyr Phe Cys Ala Val Asp Lys Asp
            100                 105                 110

Gly Gly Tyr Gln Lys Val Thr Phe Gly Thr Gly Thr Lys Leu Gln Val
        115                 120                 125

Ile Pro Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270
```

<210> SEQ ID NO 23
<211> LENGTH: 8
<212> TYPE: PRT
<213> ORGANISM: Artificial Sequence
<220> FEATURE:
<223> OTHER INFORMATION: TRBV20-1 CDR1

<400> SEQUENCE: 23

```
Leu Asp Phe Gln Ala Thr Thr Met
1               5
```

<210> SEQ ID NO 24
<211> LENGTH: 9
<212> TYPE: PRT
<213> ORGANISM: Artificial Sequence
<220> FEATURE:
<223> OTHER INFORMATION: TRBV20-1 CDR2

<400> SEQUENCE: 24

```
Thr Ser Asn Glu Gly Ser Lys Ala Thr
1               5
```

<210> SEQ ID NO 25
<211> LENGTH: 19
<212> TYPE: PRT

<213> ORGANISM: Artificial Sequence
<220> FEATURE:
<223> OTHER INFORMATION: TRBV20-1CDR3

<400> SEQUENCE: 25

```
Cys Ser Ala Ser Pro Arg Ala Gly Gln Leu Ser Ser Tyr Asn Ser Pro
1               5                   10                  15

Leu His Phe
```

<210> SEQ ID NO 26
<211> LENGTH: 120
<212> TYPE: PRT
<213> ORGANISM: Artificial Sequence
<220> FEATURE:
<223> OTHER INFORMATION: TRBV20-1 VARIABLE

<400> SEQUENCE: 26

```
Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Ser Pro Arg Ala Gly Gln Leu Ser Ser Tyr Asn Ser Pro Leu His Phe
            100                 105                 110

Gly Asn Gly Thr Arg Leu Thr Val
        115                 120
```

<210> SEQ ID NO 27
<211> LENGTH: 177
<212> TYPE: PRT
<213> ORGANISM: Artificial Sequence
<220> FEATURE:
<223> OTHER INFORMATION: TCR831 BETA CONSTANT DOMAIN

<400> SEQUENCE: 27

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125
```

```
Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe


<210> SEQ ID NO 28
<211> LENGTH: 323
<212> TYPE: PRT
<213> ORGANISM: Artificial Sequence
<220> FEATURE:
<223> OTHER INFORMATION: TCR831 BETA CHAIN

<400> SEQUENCE: 28

Met Leu Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
        35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Ser Pro Arg Ala Gly Gln Leu
        115                 120                 125

Ser Ser Tyr Asn Ser Pro Leu His Phe Gly Asn Gly Thr Arg Leu Thr
    130                 135                 140

Val Thr Glu Asp Leu Asn Lys Val Phe Pro Pro Glu Val Ala Val Phe
145                 150                 155                 160

Glu Pro Ser Glu Ala Glu Ile Ser His Thr Gln Lys Ala Thr Leu Val
                165                 170                 175

Cys Leu Ala Thr Gly Phe Phe Pro Asp His Val Glu Leu Ser Trp Trp
            180                 185                 190

Val Asn Gly Lys Glu Val His Ser Gly Val Ser Thr Asp Pro Gln Pro
        195                 200                 205

Leu Lys Glu Gln Pro Ala Leu Asn Asp Ser Arg Tyr Cys Leu Ser Ser
    210                 215                 220

Arg Leu Arg Val Ser Ala Thr Phe Trp Gln Asn Pro Arg Asn His Phe
225                 230                 235                 240

Arg Cys Gln Val Gln Phe Tyr Gly Leu Ser Glu Asn Asp Glu Trp Thr
                245                 250                 255

Gln Asp Arg Ala Lys Pro Val Thr Gln Ile Val Ser Ala Glu Ala Trp
            260                 265                 270

Gly Arg Ala Asp Cys Gly Phe Thr Ser Val Ser Tyr Gln Gln Gly Val
        275                 280                 285

Leu Ser Ala Thr Ile Leu Tyr Glu Ile Leu Leu Gly Lys Ala Thr Leu
    290                 295                 300

Tyr Ala Val Leu Val Ser Ala Leu Val Leu Met Ala Met Val Lys Arg
```

305 310 315 320

Lys Asp Phe

<210> SEQ ID NO 29
<211> LENGTH: 21
<212> TYPE: PRT
<213> ORGANISM: Artificial Sequence
<220> FEATURE:
<223> OTHER INFORMATION: Linker

<400> SEQUENCE: 29

Gly Ser Gly Glu Gly Arg Gly Ser Leu Leu Thr Cys Gly Asp Val Glu
1 5 10 15

Glu Asn Pro Gly Pro
20

<210> SEQ ID NO 30
<211> LENGTH: 615
<212> TYPE: PRT
<213> ORGANISM: Artificial Sequence
<220> FEATURE:
<223> OTHER INFORMATION: TCR831 fusion

<400> SEQUENCE: 30

Met Lys Lys Leu Leu Ala Met Ile Leu Trp Leu Gln Leu Asp Arg Leu
1 5 10 15

Ser Gly Glu Leu Lys Val Glu Gln Asn Pro Leu Phe Leu Ser Met Gln
20 25 30

Glu Gly Lys Asn Tyr Thr Ile Tyr Cys Asn Tyr Ser Thr Thr Ser Asp
35 40 45

Arg Leu Tyr Trp Tyr Arg Gln Asp Pro Gly Lys Ser Leu Glu Ser Leu
50 55 60

Phe Val Leu Leu Ser Asn Gly Ala Val Lys Gln Glu Gly Arg Leu Met
65 70 75 80

Ala Ser Leu Asp Thr Lys Ala Arg Leu Ser Thr Leu His Ile Thr Ala
85 90 95

Ala Val His Asp Leu Ser Ala Thr Tyr Phe Cys Ala Val Asp Lys Asp
100 105 110

Gly Gly Tyr Gln Lys Val Thr Phe Gly Thr Gly Thr Lys Leu Gln Val
115 120 125

Ile Pro Asn Ile Gln Asn Pro Asp Pro Ala Val Tyr Gln Leu Arg Asp
130 135 140

Ser Lys Ser Ser Asp Lys Ser Val Cys Leu Phe Thr Asp Phe Asp Ser
145 150 155 160

Gln Thr Asn Val Ser Gln Ser Lys Asp Ser Asp Val Tyr Ile Thr Asp
165 170 175

Lys Thr Val Leu Asp Met Arg Ser Met Asp Phe Lys Ser Asn Ser Ala
180 185 190

Val Ala Trp Ser Asn Lys Ser Asp Phe Ala Cys Ala Asn Ala Phe Asn
195 200 205

Asn Ser Ile Ile Pro Glu Asp Thr Phe Phe Pro Ser Pro Glu Ser Ser
210 215 220

Cys Asp Val Lys Leu Val Glu Lys Ser Phe Glu Thr Asp Thr Asn Leu
225 230 235 240

Asn Phe Gln Asn Leu Ser Val Ile Gly Phe Arg Ile Leu Leu Leu Lys
245 250 255

Val Ala Gly Phe Asn Leu Leu Met Thr Leu Arg Leu Trp Ser Ser Gly

```
            260                 265                 270

Ser Gly Glu Gly Arg Gly Ser Leu Leu Thr Cys Gly Asp Val Glu Glu
        275                 280                 285

Asn Pro Gly Pro Met Leu Leu Leu Leu Leu Leu Leu Gly Pro Gly Ile
    290                 295                 300

Ser Leu Leu Leu Pro Gly Ser Leu Ala Gly Ser Gly Leu Gly Ala Val
305                 310                 315                 320

Val Ser Gln His Pro Ser Trp Val Ile Cys Lys Ser Gly Thr Ser Val
                325                 330                 335

Lys Ile Glu Cys Arg Ser Leu Asp Phe Gln Ala Thr Thr Met Phe Trp
            340                 345                 350

Tyr Arg Gln Phe Pro Lys Gln Ser Leu Met Leu Met Ala Thr Ser Asn
        355                 360                 365

Glu Gly Ser Lys Ala Thr Tyr Glu Gln Gly Val Glu Lys Asp Lys Phe
    370                 375                 380

Leu Ile Asn His Ala Ser Leu Thr Leu Ser Thr Leu Thr Val Thr Ser
385                 390                 395                 400

Ala His Pro Glu Asp Ser Ser Phe Tyr Ile Cys Ser Ala Ser Pro Arg
                405                 410                 415

Ala Gly Gln Leu Ser Ser Tyr Asn Ser Pro Leu His Phe Gly Asn Gly
            420                 425                 430

Thr Arg Leu Thr Val Thr Glu Asp Leu Asn Lys Val Phe Pro Pro Glu
        435                 440                 445

Val Ala Val Phe Glu Pro Ser Glu Ala Glu Ile Ser His Thr Gln Lys
    450                 455                 460

Ala Thr Leu Val Cys Leu Ala Thr Gly Phe Phe Pro Asp His Val Glu
465                 470                 475                 480

Leu Ser Trp Trp Val Asn Gly Lys Glu Val His Ser Gly Val Ser Thr
                485                 490                 495

Asp Pro Gln Pro Leu Lys Glu Gln Pro Ala Leu Asn Asp Ser Arg Tyr
            500                 505                 510

Cys Leu Ser Ser Arg Leu Arg Val Ser Ala Thr Phe Trp Gln Asn Pro
        515                 520                 525

Arg Asn His Phe Arg Cys Gln Val Gln Phe Tyr Gly Leu Ser Glu Asn
    530                 535                 540

Asp Glu Trp Thr Gln Asp Arg Ala Lys Pro Val Thr Gln Ile Val Ser
545                 550                 555                 560

Ala Glu Ala Trp Gly Arg Ala Asp Cys Gly Phe Thr Ser Val Ser Tyr
                565                 570                 575

Gln Gln Gly Val Leu Ser Ala Thr Ile Leu Tyr Glu Ile Leu Leu Gly
            580                 585                 590

Lys Ala Thr Leu Tyr Ala Val Leu Val Ser Ala Leu Val Leu Met Ala
        595                 600                 605

Met Val Lys Arg Lys Asp Phe
    610                 615


<210> SEQ ID NO 31
<211> LENGTH: 8
<212> TYPE: PRT
<213> ORGANISM: Artificial Sequence
<220> FEATURE:
<223> OTHER INFORMATION: TRAV12-1 CDR1

<400> SEQUENCE: 31

Ser Asn Ser Ala Ser Gln Ser Phe
```

1 5

<210> SEQ ID NO 32
<211> LENGTH: 8
<212> TYPE: PRT
<213> ORGANISM: Artificial Sequence
<220> FEATURE:
<223> OTHER INFORMATION: TRAV12-1 CDR2

<400> SEQUENCE: 32

Ser Val Tyr Ser Ser Gly Asn Glu
1 5

<210> SEQ ID NO 33
<211> LENGTH: 15
<212> TYPE: PRT
<213> ORGANISM: Artificial Sequence
<220> FEATURE:
<223> OTHER INFORMATION: TRAV12-1 CDR3

<400> SEQUENCE: 33

Cys Ala Val Asn Pro Pro Asp Thr Gly Phe Gln Lys Leu Val Phe
1 5 10 15

<210> SEQ ID NO 34
<211> LENGTH: 112
<212> TYPE: PRT
<213> ORGANISM: Artificial Sequence
<220> FEATURE:
<223> OTHER INFORMATION: TRAV12-1 VARIABLE DOMAIN

<400> SEQUENCE: 34

Arg Lys Glu Val Glu Gln Asp Pro Gly Pro Phe Asn Val Pro Glu Gly
1 5 10 15

Ala Thr Val Ala Phe Asn Cys Thr Tyr Ser Asn Ser Ala Ser Gln Ser
20 25 30

Phe Phe Trp Tyr Arg Gln Asp Cys Arg Lys Glu Pro Lys Leu Leu Met
35 40 45

Ser Val Tyr Ser Ser Gly Asn Glu Asp Gly Arg Phe Thr Ala Gln Leu
50 55 60

Asn Arg Ala Ser Gln Tyr Ile Ser Leu Leu Ile Arg Asp Ser Lys Leu
65 70 75 80

Ser Asp Ser Ala Thr Tyr Leu Cys Ala Val Asn Pro Pro Asp Thr Gly
85 90 95

Phe Gln Lys Leu Val Phe Gly Thr Gly Thr Arg Leu Leu Val Ser Pro
100 105 110

<210> SEQ ID NO 35
<211> LENGTH: 140
<212> TYPE: PRT
<213> ORGANISM: Artificial Sequence
<220> FEATURE:
<223> OTHER INFORMATION: TCR833 ALPHA CONSTANT DOMAIN

<400> SEQUENCE: 35

Ile Gln Asn Pro Asp Pro Ala Val Tyr Gln Leu Arg Asp Ser Lys Ser
1 5 10 15

Ser Asp Lys Ser Val Cys Leu Phe Thr Asp Phe Asp Ser Gln Thr Asn
20 25 30

Val Ser Gln Ser Lys Asp Ser Asp Val Tyr Ile Thr Asp Lys Thr Val
35 40 45

Leu Asp Met Arg Ser Met Asp Phe Lys Ser Asn Ser Ala Val Ala Trp

```
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140


<210> SEQ ID NO 36
<211> LENGTH: 274
<212> TYPE: PRT
<213> ORGANISM: Artificial Sequence
<220> FEATURE:
<223> OTHER INFORMATION: TCR833 ALPHA CHAIN

<400> SEQUENCE: 36

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
        35                  40                  45

Ser Ala Ser Gln Ser Phe Phe Trp Tyr Arg Gln Asp Cys Arg Lys Glu
    50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Ala Val Asn
            100                 105                 110

Pro Pro Asp Thr Gly Phe Gln Lys Leu Val Phe Gly Thr Gly Thr Arg
        115                 120                 125

Leu Leu Val Ser Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 37
<211> LENGTH: 7
<212> TYPE: PRT
<213> ORGANISM: Artificial Sequence
<220> FEATURE:
<223> OTHER INFORMATION: TRBV28 CDR1

<400> SEQUENCE: 37

Asp Met Asp His Glu Asn Met
1               5

<210> SEQ ID NO 38
<211> LENGTH: 8
<212> TYPE: PRT
<213> ORGANISM: Artificial Sequence
<220> FEATURE:
<223> OTHER INFORMATION: TRBV28 CDR2

<400> SEQUENCE: 38

Phe Ser Tyr Asp Val Lys Met Glu
1               5

<210> SEQ ID NO 39
<211> LENGTH: 16
<212> TYPE: PRT
<213> ORGANISM: Artificial Sequence
<220> FEATURE:
<223> OTHER INFORMATION: TRBV28 CDR3

<400> SEQUENCE: 39

Cys Ala Ser Ser Leu Ser Phe Arg Gln Gly Leu Arg Glu Gln Tyr Phe
1               5                   10                  15

<210> SEQ ID NO 40
<211> LENGTH: 134
<212> TYPE: PRT
<213> ORGANISM: Artificial Sequence
<220> FEATURE:
<223> OTHER INFORMATION: TRBV28 VARIABLE DOMAIN

<400> SEQUENCE: 40

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Ser Phe Arg Gln Gly Leu Arg Glu Gln Tyr Phe Gly Pro Gly
        115                 120                 125

Thr Arg Leu Thr Val Thr
    130

<210> SEQ ID NO 41

<211> LENGTH: 179
<212> TYPE: PRT
<213> ORGANISM: Artificial Sequence
<220> FEATURE:
<223> OTHER INFORMATION: TCR833 BETA CONSTANT DOMAIN

<400> SEQUENCE: 41

Glu Asp Leu Lys Asn Val Phe Pro Pro Glu Val Ala Val Phe Glu Pro
1 5 10 15

Ser Glu Ala Glu Ile Ser His Thr Gln Lys Ala Thr Leu Val Cys Leu
20 25 30

Ala Thr Gly Phe Tyr Pro Asp His Val Glu Leu Ser Trp Trp Val Asn
35 40 45

Gly Lys Glu Val His Ser Gly Val Ser Thr Asp Pro Gln Pro Leu Lys
50 55 60

Glu Gln Pro Ala Leu Asn Asp Ser Arg Tyr Cys Leu Ser Ser Arg Leu
65 70 75 80

Arg Val Ser Ala Thr Phe Trp Gln Asn Pro Arg Asn His Phe Arg Cys
85 90 95

Gln Val Gln Phe Tyr Gly Leu Ser Glu Asn Asp Glu Trp Thr Gln Asp
100 105 110

Arg Ala Lys Pro Val Thr Gln Ile Val Ser Ala Glu Ala Trp Gly Arg
115 120 125

Ala Asp Cys Gly Phe Thr Ser Glu Ser Tyr Gln Gln Gly Val Leu Ser
130 135 140

Ala Thr Ile Leu Tyr Glu Ile Leu Leu Gly Lys Ala Thr Leu Tyr Ala
145 150 155 160

Val Leu Val Ser Ala Leu Val Leu Met Ala Met Val Lys Arg Lys Asp
165 170 175

Ser Arg Gly

<210> SEQ ID NO 42
<211> LENGTH: 313
<212> TYPE: PRT
<213> ORGANISM: Artificial Sequence
<220> FEATURE:
<223> OTHER INFORMATION: TCR833 BETA CHAIN

<400> SEQUENCE: 42

Met Gly Ile Arg Leu Leu Cys Arg Val Ala Phe Cys Phe Leu Ala Val
1 5 10 15

Gly Leu Val Asp Val Lys Val Thr Gln Ser Ser Arg Tyr Leu Val Lys
20 25 30

Arg Thr Gly Glu Lys Val Phe Leu Glu Cys Val Gln Asp Met Asp His
35 40 45

Glu Asn Met Phe Trp Tyr Arg Gln Asp Pro Gly Leu Gly Leu Arg Leu
50 55 60

Ile Tyr Phe Ser Tyr Asp Val Lys Met Lys Glu Lys Gly Asp Ile Pro
65 70 75 80

Glu Gly Tyr Ser Val Ser Arg Glu Lys Lys Glu Arg Phe Ser Leu Ile
85 90 95

Leu Glu Ser Ala Ser Thr Asn Gln Thr Ser Met Tyr Leu Cys Ala Ser
100 105 110

Ser Leu Ser Phe Arg Gln Gly Leu Arg Glu Gln Tyr Phe Gly Pro Gly
115 120 125

Thr Arg Leu Thr Val Thr Glu Asp Leu Lys Asn Val Phe Pro Pro Glu
130 135 140

Val Ala Val Phe Glu Pro Ser Glu Ala Glu Ile Ser His Thr Gln Lys
145 150 155 160

Ala Thr Leu Val Cys Leu Ala Thr Gly Phe Tyr Pro Asp His Val Glu
165 170 175

Leu Ser Trp Trp Val Asn Gly Lys Glu Val His Ser Gly Val Ser Thr
180 185 190

Asp Pro Gln Pro Leu Lys Glu Gln Pro Ala Leu Asn Asp Ser Arg Tyr
195 200 205

Cys Leu Ser Ser Arg Leu Arg Val Ser Ala Thr Phe Trp Gln Asn Pro
210 215 220

Arg Asn His Phe Arg Cys Gln Val Gln Phe Tyr Gly Leu Ser Glu Asn
225 230 235 240

Asp Glu Trp Thr Gln Asp Arg Ala Lys Pro Val Thr Gln Ile Val Ser
245 250 255

Ala Glu Ala Trp Gly Arg Ala Asp Cys Gly Phe Thr Ser Glu Ser Tyr
260 265 270

Gln Gln Gly Val Leu Ser Ala Thr Ile Leu Tyr Glu Ile Leu Leu Gly
275 280 285

Lys Ala Thr Leu Tyr Ala Val Leu Val Ser Ala Leu Val Leu Met Ala
290 295 300

Met Val Lys Arg Lys Asp Ser Arg Gly
305 310

<210> SEQ ID NO 43
<211> LENGTH: 21
<212> TYPE: PRT
<213> ORGANISM: Artificial Sequence
<220> FEATURE:
<223> OTHER INFORMATION: Linker

<400> SEQUENCE: 43

Gly Ser Gly Glu Gly Arg Gly Ser Leu Leu Thr Cys Gly Asp Val Glu
1 5 10 15

Glu Asn Pro Gly Pro
20

<210> SEQ ID NO 44
<211> LENGTH: 608
<212> TYPE: PRT
<213> ORGANISM: Artificial Sequence
<220> FEATURE:
<223> OTHER INFORMATION: TCR833 FUSION

<400> SEQUENCE: 44

Met Ile Ser Leu Arg Val Leu Leu Val Ile Leu Trp Leu Gln Leu Ser
1 5 10 15

Trp Val Trp Ser Gln Arg Lys Glu Val Glu Gln Asp Pro Gly Pro Phe
20 25 30

Asn Val Pro Glu Gly Ala Thr Val Ala Phe Asn Cys Thr Tyr Ser Asn
35 40 45

Ser Ala Ser Gln Ser Phe Phe Trp Tyr Arg Gln Asp Cys Arg Lys Glu
50 55 60

Pro Lys Leu Leu Met Ser Val Tyr Ser Ser Gly Asn Glu Asp Gly Arg
65 70 75 80

Phe Thr Ala Gln Leu Asn Arg Ala Ser Gln Tyr Ile Ser Leu Leu Ile
85 90 95

Arg Asp Ser Lys Leu Ser Asp Ser Ala Thr Tyr Leu Cys Ala Val Asn

-continued

```
            100                 105                 110

Pro Pro Asp Thr Gly Phe Gln Lys Leu Val Phe Gly Thr Gly Thr Arg
        115                 120                 125

Leu Leu Val Ser Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser Gly Ser Gly Glu Gly Arg Gly Ser Leu Leu Thr Cys Gly Asp
        275                 280                 285

Val Glu Glu Asn Pro Gly Pro Met Gly Ile Arg Leu Leu Cys Arg Val
    290                 295                 300

Ala Phe Cys Phe Leu Ala Val Gly Leu Val Asp Val Lys Val Thr Gln
305                 310                 315                 320

Ser Ser Arg Tyr Leu Val Lys Arg Thr Gly Glu Lys Val Phe Leu Glu
                325                 330                 335

Cys Val Gln Asp Met Asp His Glu Asn Met Phe Trp Tyr Arg Gln Asp
            340                 345                 350

Pro Gly Leu Gly Leu Arg Leu Ile Tyr Phe Ser Tyr Asp Val Lys Met
        355                 360                 365

Lys Glu Lys Gly Asp Ile Pro Glu Gly Tyr Ser Val Ser Arg Glu Lys
    370                 375                 380

Lys Glu Arg Phe Ser Leu Ile Leu Glu Ser Ala Ser Thr Asn Gln Thr
385                 390                 395                 400

Ser Met Tyr Leu Cys Ala Ser Ser Leu Ser Phe Arg Gln Gly Leu Arg
                405                 410                 415

Glu Gln Tyr Phe Gly Pro Gly Thr Arg Leu Thr Val Thr Glu Asp Leu
            420                 425                 430

Lys Asn Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
    450                 455                 460

Phe Tyr Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525
```

Phe Tyr Gly Leu Ser Glu Asn Asp Glu Trp Thr Gln Asp Arg Ala Lys
530 535 540

Pro Val Thr Gln Ile Val Ser Ala Glu Ala Trp Gly Arg Ala Asp Cys
545 550 555 560

Gly Phe Thr Ser Glu Ser Tyr Gln Gln Gly Val Leu Ser Ala Thr Ile
565 570 575

Leu Tyr Glu Ile Leu Leu Gly Lys Ala Thr Leu Tyr Ala Val Leu Val
580 585 590

Ser Ala Leu Val Leu Met Ala Met Val Lys Arg Lys Asp Ser Arg Gly
595 600 605

<210> SEQ ID NO 45
<211> LENGTH: 7
<212> TYPE: PRT
<213> ORGANISM: Artificial Sequence
<220> FEATURE:
<223> OTHER INFORMATION: TRAV17 CDR1

<400> SEQUENCE: 45

Lys Thr Ser Ile Asn Asn Leu
1 5

<210> SEQ ID NO 46
<211> LENGTH: 9
<212> TYPE: PRT
<213> ORGANISM: Artificial Sequence
<220> FEATURE:
<223> OTHER INFORMATION: TRAV17 CDR2

<400> SEQUENCE: 46

Leu Ile Arg Ser Asn Glu Arg Glu Lys
1 5

<210> SEQ ID NO 47
<211> LENGTH: 12
<212> TYPE: PRT
<213> ORGANISM: Artificial Sequence
<220> FEATURE:
<223> OTHER INFORMATION: TRAV17 CDR3

<400> SEQUENCE: 47

Cys Ala Thr Asp Pro Gly Gly Phe Lys Thr Ile Phe
1 5 10

<210> SEQ ID NO 48
<211> LENGTH: 140
<212> TYPE: PRT
<213> ORGANISM: Artificial Sequence
<220> FEATURE:
<223> OTHER INFORMATION: TCR897 ALPHA CONSTANT DOMAIN

<400> SEQUENCE: 48

Ile Gln Asn Pro Asp Pro Ala Val Tyr Gln Leu Arg Asp Ser Lys Ser
1 5 10 15

Ser Asp Lys Ser Val Cys Leu Phe Thr Asp Phe Asp Ser Gln Thr Asn
20 25 30

Val Ser Gln Ser Lys Asp Ser Asp Val Tyr Ile Thr Asp Lys Thr Val
35 40 45

Leu Asp Met Arg Ser Met Asp Phe Lys Ser Asn Ser Ala Val Ala Trp
50 55 60

Ser Asn Lys Ser Asp Phe Ala Cys Ala Asn Ala Phe Asn Asn Ser Ile
65 70 75 80

```
Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140


<210> SEQ ID NO 49
<211> LENGTH: 271
<212> TYPE: PRT
<213> ORGANISM: Artificial Sequence
<220> FEATURE:
<223> OTHER INFORMATION: TCR897 ALPHA CHAIN

<400> SEQUENCE: 49

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
        35                  40                  45

Ile Asn Asn Leu Gln Trp Tyr Arg Gln Asn Ser Gly Arg Gly Leu Val
    50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Ser Leu Leu Ile
                85                  90                  95

Thr Ala Ser Arg Ala Ala Asp Thr Ala Ser Tyr Phe Cys Ala Thr Asp
            100                 105                 110

Pro Gly Gly Phe Lys Thr Ile Phe Gly Ala Gly Thr Arg Leu Phe Val
        115                 120                 125

Lys Ala Asn Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270


<210> SEQ ID NO 50
<211> LENGTH: 7
<212> TYPE: PRT
<213> ORGANISM: Artificial Sequence
```

<220> FEATURE:
<223> OTHER INFORMATION: TRBV11-2 CDR1

<400> SEQUENCE: 50

Ile Ser Gly His Ala Thr Leu
1               5

<210> SEQ ID NO 51
<211> LENGTH: 8
<212> TYPE: PRT
<213> ORGANISM: Artificial Sequence
<220> FEATURE:
<223> OTHER INFORMATION: TRBV11-2 CDR2

<400> SEQUENCE: 51

Gln Phe Gln Asn Asn Gly Val Val
1               5

<210> SEQ ID NO 52
<211> LENGTH: 16
<212> TYPE: PRT
<213> ORGANISM: Artificial Sequence
<220> FEATURE:
<223> OTHER INFORMATION: TRBV11-2 CDR3

<400> SEQUENCE: 52

Cys Ala Ser Ser Leu Tyr Gly Gly Ser Ile Ser Tyr Glu Gln Tyr Phe
1               5                   10                  15

<210> SEQ ID NO 53
<211> LENGTH: 179
<212> TYPE: PRT
<213> ORGANISM: Artificial Sequence
<220> FEATURE:
<223> OTHER INFORMATION: TCR897 BETA CONSTANT DOMAIN

<400> SEQUENCE: 53

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 54
<211> LENGTH: 314
<212> TYPE: PRT
<213> ORGANISM: Artificial Sequence
<220> FEATURE:
<223> OTHER INFORMATION: TCR897 BETA CHAIN

<400> SEQUENCE: 54

```
Met Gly Thr Arg Leu Leu Cys Trp Ala Ala Leu Cys Leu Leu Gly Ala
1               5                   10                  15

Glu Leu Thr Glu Ala Gly Val Ala Gln Ser Pro Arg Tyr Lys Ile Ile
            20                  25                  30

Glu Lys Arg Gln Ser Val Ala Phe Trp Cys Asn Pro Ile Ser Gly His
        35                  40                  45

Ala Thr Leu Tyr Trp Tyr Gln Gln Ile Leu Gly Gln Gly Pro Lys Leu
    50                  55                  60

Leu Ile Gln Phe Gln Asn Asn Gly Val Val Asp Asp Ser Gln Leu Pro
65                  70                  75                  80

Lys Asp Arg Phe Ser Ala Glu Arg Leu Lys Gly Val Asp Ser Thr Leu
                85                  90                  95

Lys Ile Gln Pro Ala Lys Leu Glu Asp Ser Ala Val Tyr Leu Cys Ala
            100                 105                 110

Ser Ser Leu Tyr Gly Gly Ser Ile Ser Tyr Glu Gln Tyr Phe Gly Pro
        115                 120                 125

Gly Thr Arg Leu Thr Val Thr Glu Asp Leu Lys Asn Val Phe Pro Pro
    130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Ser
            180                 185                 190

Thr Asp Pro Gln Pro Leu Lys Glu Gln Pro Ala Leu Asn Asp Ser Arg
        195                 200                 205

Tyr Cys Leu Ser Ser Arg Leu Arg Val Ser Ala Thr Phe Trp Gln Asn
    210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
            260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
    290                 295                 300

Ala Met Val Lys Arg Lys Asp Ser Arg Gly
305                 310
```

<210> SEQ ID NO 55
<211> LENGTH: 21
<212> TYPE: PRT
<213> ORGANISM: Artificial Sequence
<220> FEATURE:
<223> OTHER INFORMATION: LINKER

<400> SEQUENCE: 55

Gly Ser Gly Glu Gly Arg Gly Ser Leu Leu Thr Cys Gly Asp Val Glu
1 5 10 15

Glu Asn Pro Gly Pro
20

<210> SEQ ID NO 56
<211> LENGTH: 606
<212> TYPE: PRT
<213> ORGANISM: Artificial Sequence
<220> FEATURE:
<223> OTHER INFORMATION: TCR897 FUSION

<400> SEQUENCE: 56

Met Glu Thr Leu Leu Gly Val Ser Leu Val Ile Leu Trp Leu Gln Leu
1 5 10 15

Ala Arg Val Asn Ser Gln Gln Gly Glu Glu Asp Pro Gln Ala Leu Ser
20 25 30

Ile Gln Glu Gly Glu Asn Ala Thr Met Asn Cys Ser Tyr Lys Thr Ser
35 40 45

Ile Asn Asn Leu Gln Trp Tyr Arg Gln Asn Ser Gly Arg Gly Leu Val
50 55 60

His Leu Ile Leu Ile Arg Ser Asn Glu Arg Glu Lys His Ser Gly Arg
65 70 75 80

Leu Arg Val Thr Leu Asp Thr Ser Lys Lys Ser Ser Ser Leu Leu Ile
85 90 95

Thr Ala Ser Arg Ala Ala Asp Thr Ala Ser Tyr Phe Cys Ala Thr Asp
100 105 110

Pro Gly Gly Phe Lys Thr Ile Phe Gly Ala Gly Thr Arg Leu Phe Val
115 120 125

Lys Ala Asn Ile Gln Asn Pro Asp Pro Ala Val Tyr Gln Leu Arg Asp
130 135 140

Ser Lys Ser Ser Asp Lys Ser Val Cys Leu Phe Thr Asp Phe Asp Ser
145 150 155 160

Gln Thr Asn Val Ser Gln Ser Lys Asp Ser Asp Val Tyr Ile Thr Asp
165 170 175

Lys Thr Val Leu Asp Met Arg Ser Met Asp Phe Lys Ser Asn Ser Ala
180 185 190

Val Ala Trp Ser Asn Lys Ser Asp Phe Ala Cys Ala Asn Ala Phe Asn
195 200 205

Asn Ser Ile Ile Pro Glu Asp Thr Phe Phe Pro Ser Pro Glu Ser Ser
210 215 220

Cys Asp Val Lys Leu Val Glu Lys Ser Phe Glu Thr Asp Thr Asn Leu
225 230 235 240

Asn Phe Gln Asn Leu Ser Val Ile Gly Phe Arg Ile Leu Leu Leu Lys
245 250 255

Val Ala Gly Phe Asn Leu Leu Met Thr Leu Arg Leu Trp Ser Ser Gly
260 265 270

Ser Gly Glu Gly Arg Gly Ser Leu Leu Thr Cys Gly Asp Val Glu Glu
275 280 285

Asn Pro Gly Pro Met Gly Thr Arg Leu Leu Cys Trp Ala Ala Leu Cys
290 295 300

Leu Leu Gly Ala Glu Leu Thr Glu Ala Gly Val Ala Gln Ser Pro Arg
305 310 315 320

Tyr Lys Ile Ile Glu Lys Arg Gln Ser Val Ala Phe Trp Cys Asn Pro
325 330 335

Ile Ser Gly His Ala Thr Leu Tyr Trp Tyr Gln Gln Ile Leu Gly Gln
340 345 350

Gly Pro Lys Leu Leu Ile Gln Phe Gln Asn Asn Gly Val Val Asp Asp
355 360 365

Ser Gln Leu Pro Lys Asp Arg Phe Ser Ala Glu Arg Leu Lys Gly Val
370 375 380

Asp Ser Thr Leu Lys Ile Gln Pro Ala Lys Leu Glu Asp Ser Ala Val
385 390 395 400

Tyr Leu Cys Ala Ser Ser Leu Tyr Gly Gly Ser Ile Ser Tyr Glu Gln
405 410 415

Tyr Phe Gly Pro Gly Thr Arg Leu Thr Val Thr Glu Asp Leu Lys Asn
420 425 430

Val Phe Pro Pro Glu Val Ala Val Phe Glu Pro Ser Glu Ala Glu Ile
435 440 445

Ser His Thr Gln Lys Ala Thr Leu Val Cys Leu Ala Thr Gly Phe Tyr
450 455 460

Pro Asp His Val Glu Leu Ser Trp Trp Val Asn Gly Lys Glu Val His
465 470 475 480

Ser Gly Val Ser Thr Asp Pro Gln Pro Leu Lys Glu Gln Pro Ala Leu
485 490 495

Asn Asp Ser Arg Tyr Cys Leu Ser Ser Arg Leu Arg Val Ser Ala Thr
500 505 510

Phe Trp Gln Asn Pro Arg Asn His Phe Arg Cys Gln Val Gln Phe Tyr
515 520 525

Gly Leu Ser Glu Asn Asp Glu Trp Thr Gln Asp Arg Ala Lys Pro Val
530 535 540

Thr Gln Ile Val Ser Ala Glu Ala Trp Gly Arg Ala Asp Cys Gly Phe
545 550 555 560

Thr Ser Glu Ser Tyr Gln Gln Gly Val Leu Ser Ala Thr Ile Leu Tyr
565 570 575

Glu Ile Leu Leu Gly Lys Ala Thr Leu Tyr Ala Val Leu Val Ser Ala
580 585 590

Leu Val Leu Met Ala Met Val Lys Arg Lys Asp Ser Arg Gly
595 600 605

<210> SEQ ID NO 57
<211> LENGTH: 9
<212> TYPE: PRT
<213> ORGANISM: Artificial Sequence
<220> FEATURE:
<223> OTHER INFORMATION: TRAV19 CDR1

<400> SEQUENCE: 57

Glu Thr Arg Asp Thr Thr Tyr Tyr Leu
1 5

<210> SEQ ID NO 58
<211> LENGTH: 10
<212> TYPE: PRT
<213> ORGANISM: Artificial Sequence
<220> FEATURE:
<223> OTHER INFORMATION: TRAV19 CDR2

<400> SEQUENCE: 58

Arg Arg Asn Ser Phe Asp Glu Gln Asn Glu
1 5 10

<210> SEQ ID NO 59
<211> LENGTH: 13
<212> TYPE: PRT
<213> ORGANISM: Artificial Sequence
<220> FEATURE:
<223> OTHER INFORMATION: TRAV19 CDR3

<400> SEQUENCE: 59

```
Cys Ala Leu Ser Glu Ala Gly Thr Tyr Lys Tyr Ile Phe
1               5                   10
```

<210> SEQ ID NO 60
<211> LENGTH: 140
<212> TYPE: PRT
<213> ORGANISM: Artificial Sequence
<220> FEATURE:
<223> OTHER INFORMATION: TCR896 ALPHA CONSTANT DOMAIN

<400> SEQUENCE: 60

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140
```

<210> SEQ ID NO 61
<211> LENGTH: 275
<212> TYPE: PRT
<213> ORGANISM: Artificial Sequence
<220> FEATURE:
<223> OTHER INFORMATION: TCR896 ALPHA CHAIN

<400> SEQUENCE: 61

```
Met Leu Thr Ala Ser Leu Leu Arg Ala Val Ile Ala Ser Ile Cys Val
1               5                   10                  15

Val Ser Ser Met Ala Gln Lys Val Thr Gln Ala Gln Thr Glu Ile Ser
            20                  25                  30

Val Val Glu Lys Glu Asp Val Thr Leu Asp Cys Val Tyr Glu Thr Arg
        35                  40                  45

Asp Thr Thr Tyr Tyr Leu Phe Trp Tyr Lys Gln Pro Pro Ser Gly Glu
    50                  55                  60

Leu Val Phe Leu Ile Arg Arg Asn Ser Phe Asp Glu Gln Asn Glu Ile
65                  70                  75                  80

Ser Gly Arg Tyr Ser Trp Asn Phe Gln Lys Ser Thr Ser Ser Phe Asn
                85                  90                  95

Phe Thr Ile Thr Ala Ser Gln Val Val Asp Ser Ala Val Tyr Phe Cys
            100                 105                 110
```

Ala Leu Ser Glu Ala Gly Thr Tyr Lys Tyr Ile Phe Gly Thr Gly Thr
        115                 120                 125

Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser
        275

<210> SEQ ID NO 62
<211> LENGTH: 7
<212> TYPE: PRT
<213> ORGANISM: Artificial Sequence
<220> FEATURE:
<223> OTHER INFORMATION: TRBV9 CDR1

<400> SEQUENCE: 62

Arg Ser Gly Asp Leu Ser Val
1               5

<210> SEQ ID NO 63
<211> LENGTH: 8
<212> TYPE: PRT
<213> ORGANISM: Artificial Sequence
<220> FEATURE:
<223> OTHER INFORMATION: TRBV9 CDR2

<400> SEQUENCE: 63

Gln Tyr Tyr Asn Gly Glu Glu Arg
1               5

<210> SEQ ID NO 64
<211> LENGTH: 15
<212> TYPE: PRT
<213> ORGANISM: Artificial Sequence
<220> FEATURE:
<223> OTHER INFORMATION: TRBV9 CDR3

<400> SEQUENCE: 64

Cys Ala Ser Ser Val Ala Gly Gly Gly Gln Glu Thr Gln Tyr Phe
1               5                   10                  15

<210> SEQ ID NO 65
<211> LENGTH: 179
<212> TYPE: PRT
<213> ORGANISM: Artificial Sequence
<220> FEATURE:

<223> OTHER INFORMATION: TCR896 BETA CONSTANT DOMAIN

<400> SEQUENCE: 65

Glu Asp Leu Lys Asn Val Phe Pro Pro Glu Val Ala Val Phe Glu Pro
1 5 10 15

Ser Glu Ala Glu Ile Ser His Thr Gln Lys Ala Thr Leu Val Cys Leu
20 25 30

Ala Thr Gly Phe Tyr Pro Asp His Val Glu Leu Ser Trp Trp Val Asn
35 40 45

Gly Lys Glu Val His Ser Gly Val Ser Thr Asp Pro Gln Pro Leu Lys
50 55 60

Glu Gln Pro Ala Leu Asn Asp Ser Arg Tyr Cys Leu Ser Ser Arg Leu
65 70 75 80

Arg Val Ser Ala Thr Phe Trp Gln Asn Pro Arg Asn His Phe Arg Cys
85 90 95

Gln Val Gln Phe Tyr Gly Leu Ser Glu Asn Asp Glu Trp Thr Gln Asp
100 105 110

Arg Ala Lys Pro Val Thr Gln Ile Val Ser Ala Glu Ala Trp Gly Arg
115 120 125

Ala Asp Cys Gly Phe Thr Ser Glu Ser Tyr Gln Gln Gly Val Leu Ser
130 135 140

Ala Thr Ile Leu Tyr Glu Ile Leu Leu Gly Lys Ala Thr Leu Tyr Ala
145 150 155 160

Val Leu Val Ser Ala Leu Val Leu Met Ala Met Val Lys Arg Lys Asp
165 170 175

Ser Arg Gly

<210> SEQ ID NO 66
<211> LENGTH: 312
<212> TYPE: PRT
<213> ORGANISM: Artificial Sequence
<220> FEATURE:
<223> OTHER INFORMATION: TCR896 BETA CHAIN

<400> SEQUENCE: 66

Met Gly Phe Arg Leu Leu Cys Cys Val Ala Phe Cys Leu Leu Gly Ala
1 5 10 15

Gly Pro Val Asp Ser Gly Val Thr Gln Thr Pro Lys His Leu Ile Thr
20 25 30

Ala Thr Gly Gln Arg Val Thr Leu Arg Cys Ser Pro Arg Ser Gly Asp
35 40 45

Leu Ser Val Tyr Trp Tyr Gln Gln Ser Leu Asp Gln Gly Leu Gln Phe
50 55 60

Leu Ile Gln Tyr Tyr Asn Gly Glu Glu Arg Ala Lys Gly Asn Ile Leu
65 70 75 80

Glu Arg Phe Ser Ala Gln Gln Phe Pro Asp Leu His Ser Glu Leu Asn
85 90 95

Leu Ser Ser Leu Glu Leu Gly Asp Ser Ala Leu Tyr Phe Cys Ala Ser
100 105 110

Ser Val Ala Gly Gly Gly Gln Glu Thr Gln Tyr Phe Gly Pro Gly Thr
115 120 125

Arg Leu Leu Val Leu Glu Asp Leu Lys Asn Val Phe Pro Pro Glu Val
130 135 140

Ala Val Phe Glu Pro Ser Glu Ala Glu Ile Ser His Thr Gln Lys Ala
145 150 155 160

Thr Leu Val Cys Leu Ala Thr Gly Phe Tyr Pro Asp His Val Glu Leu
165 170 175

Ser Trp Trp Val Asn Gly Lys Glu Val His Ser Gly Val Ser Thr Asp
180 185 190

Pro Gln Pro Leu Lys Glu Gln Pro Ala Leu Asn Asp Ser Arg Tyr Cys
195 200 205

Leu Ser Ser Arg Leu Arg Val Ser Ala Thr Phe Trp Gln Asn Pro Arg
210 215 220

Asn His Phe Arg Cys Gln Val Gln Phe Tyr Gly Leu Ser Glu Asn Asp
225 230 235 240

Glu Trp Thr Gln Asp Arg Ala Lys Pro Val Thr Gln Ile Val Ser Ala
245 250 255

Glu Ala Trp Gly Arg Ala Asp Cys Gly Phe Thr Ser Glu Ser Tyr Gln
260 265 270

Gln Gly Val Leu Ser Ala Thr Ile Leu Tyr Glu Ile Leu Leu Gly Lys
275 280 285

Ala Thr Leu Tyr Ala Val Leu Val Ser Ala Leu Val Leu Met Ala Met
290 295 300

Val Lys Arg Lys Asp Ser Arg Gly
305 310

<210> SEQ ID NO 67
<211> LENGTH: 21
<212> TYPE: PRT
<213> ORGANISM: Artificial Sequence
<220> FEATURE:
<223> OTHER INFORMATION: LINKER

<400> SEQUENCE: 67

Gly Ser Gly Glu Gly Arg Gly Ser Leu Leu Thr Cys Gly Asp Val Glu
1 5 10 15

Glu Asn Pro Gly Pro
20

<210> SEQ ID NO 68
<211> LENGTH: 608
<212> TYPE: PRT
<213> ORGANISM: Artificial Sequence
<220> FEATURE:
<223> OTHER INFORMATION: TCR896 FUSION

<400> SEQUENCE: 68

Met Leu Thr Ala Ser Leu Leu Arg Ala Val Ile Ala Ser Ile Cys Val
1 5 10 15

Val Ser Ser Met Ala Gln Lys Val Thr Gln Ala Gln Thr Glu Ile Ser
20 25 30

Val Val Glu Lys Glu Asp Val Thr Leu Asp Cys Val Tyr Glu Thr Arg
35 40 45

Asp Thr Thr Tyr Tyr Leu Phe Trp Tyr Lys Gln Pro Pro Ser Gly Glu
50 55 60

Leu Val Phe Leu Ile Arg Arg Asn Ser Phe Asp Glu Gln Asn Glu Ile
65 70 75 80

Ser Gly Arg Tyr Ser Trp Asn Phe Gln Lys Ser Thr Ser Ser Phe Asn
85 90 95

Phe Thr Ile Thr Ala Ser Gln Val Val Asp Ser Ala Val Tyr Phe Cys
100 105 110

Ala Leu Ser Glu Ala Gly Thr Tyr Lys Tyr Ile Phe Gly Thr Gly Thr
115 120 125

```
Arg Leu Lys Val Leu Ala Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser Gly Ser Gly Glu Gly Arg Gly Ser Leu Leu Thr Cys Gly
        275                 280                 285

Asp Val Glu Glu Asn Pro Gly Pro Met Gly Phe Arg Leu Leu Cys Cys
    290                 295                 300

Val Ala Phe Cys Leu Leu Gly Ala Gly Pro Val Asp Ser Gly Val Thr
305                 310                 315                 320

Gln Thr Pro Lys His Leu Ile Thr Ala Thr Gly Gln Arg Val Thr Leu
                325                 330                 335

Arg Cys Ser Pro Arg Ser Gly Asp Leu Ser Val Tyr Trp Tyr Gln Gln
            340                 345                 350

Ser Leu Asp Gln Gly Leu Gln Phe Leu Ile Gln Tyr Tyr Asn Gly Glu
        355                 360                 365

Glu Arg Ala Lys Gly Asn Ile Leu Glu Arg Phe Ser Ala Gln Gln Phe
    370                 375                 380

Pro Asp Leu His Ser Glu Leu Asn Leu Ser Ser Leu Glu Leu Gly Asp
385                 390                 395                 400

Ser Ala Leu Tyr Phe Cys Ala Ser Ser Val Ala Gly Gly Gly Gln Glu
                405                 410                 415

Thr Gln Tyr Phe Gly Pro Gly Thr Arg Leu Leu Val Leu Glu Asp Leu
            420                 425                 430

Lys Asn Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
    450                 455                 460

Phe Tyr Pro Asp His Val Glu Leu Ser Trp Trp Val Asn Gly Lys Glu
465                 470                 475                 480

Val His Ser Gly Val Ser Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
    530                 535                 540
```

Pro Val Thr Gln Ile Val Ser Ala Glu Ala Trp Gly Arg Ala Asp Cys
545 550 555 560

Gly Phe Thr Ser Glu Ser Tyr Gln Gln Gly Val Leu Ser Ala Thr Ile
565 570 575

Leu Tyr Glu Ile Leu Leu Gly Lys Ala Thr Leu Tyr Ala Val Leu Val
580 585 590

Ser Ala Leu Val Leu Met Ala Met Val Lys Arg Lys Asp Ser Arg Gly
595 600 605

<210> SEQ ID NO 69
<211> LENGTH: 7
<212> TYPE: PRT
<213> ORGANISM: Artificial Sequence
<220> FEATURE:
<223> OTHER INFORMATION: TRAV17 CDR1

<400> SEQUENCE: 69

Lys Thr Ser Ile Asn Asn Leu
1 5

<210> SEQ ID NO 70
<211> LENGTH: 9
<212> TYPE: PRT
<213> ORGANISM: Artificial Sequence
<220> FEATURE:
<223> OTHER INFORMATION: TRAV17 CDR2

<400> SEQUENCE: 70

Leu Ile Arg Ser Asn Glu Arg Glu Lys
1 5

<210> SEQ ID NO 71
<211> LENGTH: 14
<212> TYPE: PRT
<213> ORGANISM: Artificial Sequence
<220> FEATURE:
<223> OTHER INFORMATION: TRAV17 CDR3

<400> SEQUENCE: 71

Cys Ala Thr Phe Pro Asn Phe Gly Asn Glu Lys Leu Thr Phe
1 5 10

<210> SEQ ID NO 72
<211> LENGTH: 140
<212> TYPE: PRT
<213> ORGANISM: Artificial Sequence
<220> FEATURE:
<223> OTHER INFORMATION: TCR847 ALPHA CONSTANT DOMAIN

<400> SEQUENCE: 72

Ile Gln Asn Pro Asp Pro Ala Val Tyr Gln Leu Arg Asp Ser Lys Ser
1 5 10 15

Ser Asp Lys Ser Val Cys Leu Phe Thr Asp Phe Asp Ser Gln Thr Asn
20 25 30

Val Ser Gln Ser Lys Asp Ser Asp Val Tyr Ile Thr Asp Lys Thr Val
35 40 45

Leu Asp Met Arg Ser Met Asp Phe Lys Ser Asn Ser Ala Val Ala Trp
50 55 60

Ser Asn Lys Ser Asp Phe Ala Cys Ala Asn Ala Phe Asn Asn Ser Ile
65 70 75 80

Ile Pro Glu Asp Thr Phe Phe Pro Ser Pro Glu Ser Ser Cys Asp Val
85 90 95

Lys Leu Val Glu Lys Ser Phe Glu Thr Asp Thr Asn Leu Asn Phe Gln
100 105 110

Asn Leu Ser Val Ile Gly Phe Arg Ile Leu Leu Leu Lys Val Ala Gly
115 120 125

Phe Asn Leu Leu Met Thr Leu Arg Leu Trp Ser Ser
130 135 140

<210> SEQ ID NO 73
<211> LENGTH: 273
<212> TYPE: PRT
<213> ORGANISM: Artificial Sequence
<220> FEATURE:
<223> OTHER INFORMATION: TCR847 ALPHA CHAIN

<400> SEQUENCE: 73

Met Glu Thr Leu Leu Gly Val Ser Leu Val Ile Leu Trp Leu Gln Leu
1 5 10 15

Ala Arg Val Asn Ser Gln Gln Gly Glu Glu Asp Pro Gln Ala Leu Ser
20 25 30

Ile Gln Glu Gly Glu Asn Ala Thr Met Asn Cys Ser Tyr Lys Thr Ser
35 40 45

Ile Asn Asn Leu Gln Trp Tyr Arg Gln Asn Ser Gly Arg Gly Leu Val
50 55 60

His Leu Ile Leu Ile Arg Ser Asn Glu Arg Glu Lys His Ser Gly Arg
65 70 75 80

Leu Arg Val Thr Leu Asp Thr Ser Lys Lys Ser Ser Ser Leu Leu Ile
85 90 95

Thr Ala Ser Arg Ala Ala Asp Thr Ala Ser Tyr Phe Cys Ala Thr Phe
100 105 110

Pro Asn Phe Gly Asn Glu Lys Leu Thr Phe Gly Thr Gly Thr Arg Leu
115 120 125

Thr Ile Ile Pro Asn Ile Gln Asn Pro Asp Pro Ala Val Tyr Gln Leu
130 135 140

Arg Asp Ser Lys Ser Ser Asp Lys Ser Val Cys Leu Phe Thr Asp Phe
145 150 155 160

Asp Ser Gln Thr Asn Val Ser Gln Ser Lys Asp Ser Asp Val Tyr Ile
165 170 175

Thr Asp Lys Thr Val Leu Asp Met Arg Ser Met Asp Phe Lys Ser Asn
180 185 190

Ser Ala Val Ala Trp Ser Asn Lys Ser Asp Phe Ala Cys Ala Asn Ala
195 200 205

Phe Asn Asn Ser Ile Ile Pro Glu Asp Thr Phe Phe Pro Ser Pro Glu
210 215 220

Ser Ser Cys Asp Val Lys Leu Val Glu Lys Ser Phe Glu Thr Asp Thr
225 230 235 240

Asn Leu Asn Phe Gln Asn Leu Ser Val Ile Gly Phe Arg Ile Leu Leu
245 250 255

Leu Lys Val Ala Gly Phe Asn Leu Leu Met Thr Leu Arg Leu Trp Ser
260 265 270

Ser

<210> SEQ ID NO 74
<211> LENGTH: 7
<212> TYPE: PRT
<213> ORGANISM: Artificial Sequence
<220> FEATURE:
<223> OTHER INFORMATION: TRBV10-3 CDR1

<400> SEQUENCE: 74

Thr Glu Asn His Arg Tyr Met
1 5

<210> SEQ ID NO 75
<211> LENGTH: 8
<212> TYPE: PRT
<213> ORGANISM: Artificial Sequence
<220> FEATURE:
<223> OTHER INFORMATION: TRBV10-3 CDR2

<400> SEQUENCE: 75

Tyr Ser Tyr Gly Val Lys Asp Thr
1 5

<210> SEQ ID NO 76
<211> LENGTH: 14
<212> TYPE: PRT
<213> ORGANISM: Artificial Sequence
<220> FEATURE:
<223> OTHER INFORMATION: TRBV10-3 CDR3

<400> SEQUENCE: 76

Cys Ala Ile Ser Glu Ser Glu Arg Tyr Tyr Glu Gln Tyr Phe
1 5 10

<210> SEQ ID NO 77
<211> LENGTH: 179
<212> TYPE: PRT
<213> ORGANISM: Artificial Sequence
<220> FEATURE:
<223> OTHER INFORMATION: TCR847 BETA CONSTANT DOMAIN

<400> SEQUENCE: 77

Glu Asp Leu Lys Asn Val Phe Pro Pro Glu Val Ala Val Phe Glu Pro
1 5 10 15

Ser Glu Ala Glu Ile Ser His Thr Gln Lys Ala Thr Leu Val Cys Leu
20 25 30

Ala Thr Gly Phe Tyr Pro Asp His Val Glu Leu Ser Trp Trp Val Asn
35 40 45

Gly Lys Glu Val His Ser Gly Val Ser Thr Asp Pro Gln Pro Leu Lys
50 55 60

Glu Gln Pro Ala Leu Asn Asp Ser Arg Tyr Cys Leu Ser Ser Arg Leu
65 70 75 80

Arg Val Ser Ala Thr Phe Trp Gln Asn Pro Arg Asn His Phe Arg Cys
85 90 95

Gln Val Gln Phe Tyr Gly Leu Ser Glu Asn Asp Glu Trp Thr Gln Asp
100 105 110

Arg Ala Lys Pro Val Thr Gln Ile Val Ser Ala Glu Ala Trp Gly Arg
115 120 125

Ala Asp Cys Gly Phe Thr Ser Glu Ser Tyr Gln Gln Gly Val Leu Ser
130 135 140

Ala Thr Ile Leu Tyr Glu Ile Leu Leu Gly Lys Ala Thr Leu Tyr Ala
145 150 155 160

Val Leu Val Ser Ala Leu Val Leu Met Ala Met Val Lys Arg Lys Asp
165 170 175

Ser Arg Gly

<210> SEQ ID NO 78

<211> LENGTH: 311
<212> TYPE: PRT
<213> ORGANISM: Artificial Sequence
<220> FEATURE:
<223> OTHER INFORMATION: TCR847 BETA CHAIN

<400> SEQUENCE: 78

Met Gly Thr Arg Leu Phe Phe Tyr Val Ala Leu Cys Leu Leu Trp Thr
1               5                   10                  15

Gly His Met Asp Ala Gly Ile Thr Gln Ser Pro Arg His Lys Val Thr
            20                  25                  30

Glu Thr Gly Thr Pro Val Thr Leu Arg Cys His Gln Thr Glu Asn His
        35                  40                  45

Arg Tyr Met Tyr Trp Tyr Arg Gln Asp Pro Gly His Gly Leu Arg Leu
    50                  55                  60

Ile His Tyr Ser Tyr Gly Val Lys Asp Thr Asp Lys Gly Glu Val Ser
65                  70                  75                  80

Asp Gly Tyr Ser Val Ser Arg Ser Lys Thr Glu Asp Phe Leu Leu Thr
                85                  90                  95

Leu Glu Ser Ala Thr Ser Ser Gln Thr Ser Val Tyr Phe Cys Ala Ile
            100                 105                 110

Ser Glu Ser Glu Arg Tyr Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 79
<211> LENGTH: 21
<212> TYPE: PRT
<213> ORGANISM: Artificial Sequence
<220> FEATURE:
<223> OTHER INFORMATION: LINKER

<400> SEQUENCE: 79

Gly Ser Gly Glu Gly Arg Gly Ser Leu Leu Thr Cys Gly Asp Val Glu 1 5 10 15

Glu Asn Pro Gly Pro
20

<210> SEQ ID NO 80
<211> LENGTH: 605
<212> TYPE: PRT
<213> ORGANISM: Artificial Sequence
<220> FEATURE:
<223> OTHER INFORMATION: TCR847 FUSION

<400> SEQUENCE: 80

Met Glu Thr Leu Leu Gly Val Ser Leu Val Ile Leu Trp Leu Gln Leu
1 5 10 15

Ala Arg Val Asn Ser Gln Gln Gly Glu Glu Asp Pro Gln Ala Leu Ser
20 25 30

Ile Gln Glu Gly Glu Asn Ala Thr Met Asn Cys Ser Tyr Lys Thr Ser
35 40 45

Ile Asn Asn Leu Gln Trp Tyr Arg Gln Asn Ser Gly Arg Gly Leu Val
50 55 60

His Leu Ile Leu Ile Arg Ser Asn Glu Arg Glu Lys His Ser Gly Arg
65 70 75 80

Leu Arg Val Thr Leu Asp Thr Ser Lys Lys Ser Ser Ser Leu Leu Ile
85 90 95

Thr Ala Ser Arg Ala Ala Asp Thr Ala Ser Tyr Phe Cys Ala Thr Phe
100 105 110

Pro Asn Phe Gly Asn Glu Lys Leu Thr Phe Gly Thr Gly Thr Arg Leu
115 120 125

Thr Ile Ile Pro Asn Ile Gln Asn Pro Asp Pro Ala Val Tyr Gln Leu
130 135 140

Arg Asp Ser Lys Ser Ser Asp Lys Ser Val Cys Leu Phe Thr Asp Phe
145 150 155 160

Asp Ser Gln Thr Asn Val Ser Gln Ser Lys Asp Ser Asp Val Tyr Ile
165 170 175

Thr Asp Lys Thr Val Leu Asp Met Arg Ser Met Asp Phe Lys Ser Asn
180 185 190

Ser Ala Val Ala Trp Ser Asn Lys Ser Asp Phe Ala Cys Ala Asn Ala
195 200 205

Phe Asn Asn Ser Ile Ile Pro Glu Asp Thr Phe Phe Pro Ser Pro Glu
210 215 220

Ser Ser Cys Asp Val Lys Leu Val Glu Lys Ser Phe Glu Thr Asp Thr
225 230 235 240

Asn Leu Asn Phe Gln Asn Leu Ser Val Ile Gly Phe Arg Ile Leu Leu
245 250 255

Leu Lys Val Ala Gly Phe Asn Leu Leu Met Thr Leu Arg Leu Trp Ser
260 265 270

Ser Gly Ser Gly Glu Gly Arg Gly Ser Leu Leu Thr Cys Gly Asp Val
275 280 285

Glu Glu Asn Pro Gly Pro Met Gly Thr Arg Leu Phe Phe Tyr Val Ala
290 295 300

Leu Cys Leu Leu Trp Thr Gly His Met Asp Ala Gly Ile Thr Gln Ser
305 310 315 320

Pro Arg His Lys Val Thr Glu Thr Gly Thr Pro Val Thr Leu Arg Cys
325 330 335

His Gln Thr Glu Asn His Arg Tyr Met Tyr Trp Tyr Arg Gln Asp Pro

```
            340                 345                 350

Gly His Gly Leu Arg Leu Ile His Tyr Ser Tyr Gly Val Lys Asp Thr
        355                 360                 365

Asp Lys Gly Glu Val Ser Asp Gly Tyr Ser Val Ser Arg Ser Lys Thr
    370                 375                 380

Glu Asp Phe Leu Leu Thr Leu Glu Ser Ala Thr Ser Ser Gln Thr Ser
385                 390                 395                 400

Val Tyr Phe Cys Ala Ile Ser Glu Ser Glu Arg Tyr Tyr Glu Gln Tyr
                405                 410                 415

Phe Gly Pro Gly Thr Arg Leu Thr Val Thr Glu Asp Leu Lys Asn Val
            420                 425                 430

Phe Pro Pro Glu Val Ala Val Phe Glu Pro Ser Glu Ala Glu Ile Ser
        435                 440                 445

His Thr Gln Lys Ala Thr Leu Val Cys Leu Ala Thr Gly Phe Tyr Pro
    450                 455                 460

Asp His Val Glu Leu Ser Trp Trp Val Asn Gly Lys Glu Val His Ser
465                 470                 475                 480

Gly Val Ser Thr Asp Pro Gln Pro Leu Lys Glu Gln Pro Ala Leu Asn
                485                 490                 495

Asp Ser Arg Tyr Cys Leu Ser Ser Arg Leu Arg Val Ser Ala Thr Phe
            500                 505                 510

Trp Gln Asn Pro Arg Asn His Phe Arg Cys Gln Val Gln Phe Tyr Gly
        515                 520                 525

Leu Ser Glu Asn Asp Glu Trp Thr Gln Asp Arg Ala Lys Pro Val Thr
    530                 535                 540

Gln Ile Val Ser Ala Glu Ala Trp Gly Arg Ala Asp Cys Gly Phe Thr
545                 550                 555                 560

Ser Glu Ser Tyr Gln Gln Gly Val Leu Ser Ala Thr Ile Leu Tyr Glu
                565                 570                 575

Ile Leu Leu Gly Lys Ala Thr Leu Tyr Ala Val Leu Val Ser Ala Leu
            580                 585                 590

Val Leu Met Ala Met Val Lys Arg Lys Asp Ser Arg Gly
        595                 600                 605


<210> SEQ ID NO 81
<211> LENGTH: 9
<212> TYPE: PRT
<213> ORGANISM: Artificial Sequence
<220> FEATURE:
<223> OTHER INFORMATION: TRAV4 CDR1

<400> SEQUENCE: 81

Asn Asn Ile Ala Thr Asn Asp Tyr Ile
1               5


<210> SEQ ID NO 82
<211> LENGTH: 7
<212> TYPE: PRT
<213> ORGANISM: Artificial Sequence
<220> FEATURE:
<223> OTHER INFORMATION: TRAV4 CDR2

<400> SEQUENCE: 82

Gln Gly Tyr Lys Thr Lys Val
1               5


<210> SEQ ID NO 83
<211> LENGTH: 16
```

<212> TYPE: PRT
<213> ORGANISM: Artificial Sequence
<220> FEATURE:
<223> OTHER INFORMATION: TRAV4 CDR3

<400> SEQUENCE: 83

Cys Leu Val Gly Asp Phe Asn Ser Asn Ser Gly Tyr Ala Leu Asn Phe
1 5 10 15

<210> SEQ ID NO 84
<211> LENGTH: 140
<212> TYPE: PRT
<213> ORGANISM: Artificial Sequence
<220> FEATURE:
<223> OTHER INFORMATION: TCR864 ALPHA CONSTANT DOMAIN

<400> SEQUENCE: 84

Ile Gln Asn Pro Asp Pro Ala Val Tyr Gln Leu Arg Asp Ser Lys Ser
1 5 10 15

Ser Asp Lys Ser Val Cys Leu Phe Thr Asp Phe Asp Ser Gln Thr Asn
20 25 30

Val Ser Gln Ser Lys Asp Ser Asp Val Tyr Ile Thr Asp Lys Thr Val
35 40 45

Leu Asp Met Arg Ser Met Asp Phe Lys Ser Asn Ser Ala Val Ala Trp
50 55 60

Ser Asn Lys Ser Asp Phe Ala Cys Ala Asn Ala Phe Asn Asn Ser Ile
65 70 75 80

Ile Pro Glu Asp Thr Phe Phe Pro Ser Pro Glu Ser Ser Cys Asp Val
85 90 95

Lys Leu Val Glu Lys Ser Phe Glu Thr Asp Thr Asn Leu Asn Phe Gln
100 105 110

Asn Leu Ser Val Ile Gly Phe Arg Ile Leu Leu Leu Lys Val Ala Gly
115 120 125

Phe Asn Leu Leu Met Thr Leu Arg Leu Trp Ser Ser
130 135 140

<210> SEQ ID NO 85
<211> LENGTH: 271
<212> TYPE: PRT
<213> ORGANISM: Artificial Sequence
<220> FEATURE:
<223> OTHER INFORMATION: TCR864 ALPHA CHAIN

<400> SEQUENCE: 85

Met Arg Gln Val Ala Arg Val Ile Val Phe Leu Thr Leu Ser Thr Leu
1 5 10 15

Ser Leu Ala Lys Thr Thr Gln Pro Ile Ser Met Asp Ser Tyr Glu Gly
20 25 30

Gln Glu Val Asn Ile Thr Cys Ser His Asn Asn Ile Ala Thr Asn Asp
35 40 45

Tyr Ile Thr Trp Tyr Gln Gln Phe Pro Ser Gln Gly Pro Arg Phe Ile
50 55 60

Ile Gln Gly Tyr Lys Thr Lys Val Thr Asn Glu Val Ala Ser Leu Phe
65 70 75 80

Ile Pro Ala Asp Arg Lys Ser Ser Thr Leu Ser Leu Pro Arg Val Ser
85 90 95

Leu Ser Asp Thr Ala Val Tyr Tyr Cys Leu Val Gly Asp Phe Asn Ser
100 105 110

Asn Ser Gly Tyr Ala Leu Asn Phe Gly Lys Gly Thr Ser Leu Leu Val

```
        115                 120                 125

Thr Pro His Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270


<210> SEQ ID NO 86
<211> LENGTH: 7
<212> TYPE: PRT
<213> ORGANISM: Artificial Sequence
<220> FEATURE:
<223> OTHER INFORMATION: TRBV7-2 CDR1

<400> SEQUENCE: 86

Ile Ser Gly His Thr Ala Leu
1               5


<210> SEQ ID NO 87
<211> LENGTH: 8
<212> TYPE: PRT
<213> ORGANISM: Artificial Sequence
<220> FEATURE:
<223> OTHER INFORMATION: TRBV7-2 CDR2

<400> SEQUENCE: 87

Tyr Phe Gln Gly Asn Ser Ala Pro
1               5


<210> SEQ ID NO 88
<211> LENGTH: 10
<212> TYPE: PRT
<213> ORGANISM: Artificial Sequence
<220> FEATURE:
<223> OTHER INFORMATION: TRBV7-2 CDR3

<400> SEQUENCE: 88

Cys Ala Ser Lys Val Tyr Gly Tyr Thr Phe
1               5                   10


<210> SEQ ID NO 89
<211> LENGTH: 177
<212> TYPE: PRT
<213> ORGANISM: Artificial Sequence
<220> FEATURE:
<223> OTHER INFORMATION: TCR864 BETA CONSTANT DOMAIN

<400> SEQUENCE: 89

Glu Asp Leu Asn Lys Val Phe Pro Pro Glu Val Ala Val Phe Glu Pro
```

-continued

```
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe


<210> SEQ ID NO 90
<211> LENGTH: 306
<212> TYPE: PRT
<213> ORGANISM: Artificial Sequence
<220> FEATURE:
<223> OTHER INFORMATION: TCR864 BETA CHAIN

<400> SEQUENCE: 90

Met Gly Thr Arg Leu Leu Phe Trp Val Ala Phe Cys Leu Leu Gly Ala
1               5                   10                  15

Tyr His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Arg Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Glu Ser Val Ser Thr Leu
                85                  90                  95

Thr Ile Gln Arg Thr Gln Gln Glu Asp Ser Ala Val Tyr Leu Cys Ala
            100                 105                 110

Ser Lys Val Tyr Gly Tyr Thr Phe Gly Ser Gly Thr Arg Leu Thr Val
        115                 120                 125

Val Glu Asp Leu Asn Lys Val Phe Pro Pro Glu Val Ala Val Phe Glu
    130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
                165                 170                 175

Asn Gly Lys Glu Val His Ser Gly Val Ser Thr Asp Pro Gln Pro Leu
            180                 185                 190
```

Lys Glu Gln Pro Ala Leu Asn Asp Ser Arg Tyr Cys Leu Ser Ser Arg
195 200 205

Leu Arg Val Ser Ala Thr Phe Trp Gln Asn Pro Arg Asn His Phe Arg
210 215 220

Cys Gln Val Gln Phe Tyr Gly Leu Ser Glu Asn Asp Glu Trp Thr Gln
225 230 235 240

Asp Arg Ala Lys Pro Val Thr Gln Ile Val Ser Ala Glu Ala Trp Gly
245 250 255

Arg Ala Asp Cys Gly Phe Thr Ser Val Ser Tyr Gln Gln Gly Val Leu
260 265 270

Ser Ala Thr Ile Leu Tyr Glu Ile Leu Leu Gly Lys Ala Thr Leu Tyr
275 280 285

Ala Val Leu Val Ser Ala Leu Val Leu Met Ala Met Val Lys Arg Lys
290 295 300

Asp Phe
305

<210> SEQ ID NO 91
<211> LENGTH: 21
<212> TYPE: PRT
<213> ORGANISM: Artificial Sequence
<220> FEATURE:
<223> OTHER INFORMATION: LINKER

<400> SEQUENCE: 91

Gly Ser Gly Glu Gly Arg Gly Ser Leu Leu Thr Cys Gly Asp Val Glu
1 5 10 15

Glu Asn Pro Gly Pro
20

<210> SEQ ID NO 92
<211> LENGTH: 598
<212> TYPE: PRT
<213> ORGANISM: Artificial Sequence
<220> FEATURE:
<223> OTHER INFORMATION: TCR864 FUSION

<400> SEQUENCE: 92

Met Arg Gln Val Ala Arg Val Ile Val Phe Leu Thr Leu Ser Thr Leu
1 5 10 15

Ser Leu Ala Lys Thr Thr Gln Pro Ile Ser Met Asp Ser Tyr Glu Gly
20 25 30

Gln Glu Val Asn Ile Thr Cys Ser His Asn Asn Ile Ala Thr Asn Asp
35 40 45

Tyr Ile Thr Trp Tyr Gln Gln Phe Pro Ser Gln Gly Pro Arg Phe Ile
50 55 60

Ile Gln Gly Tyr Lys Thr Lys Val Thr Asn Glu Val Ala Ser Leu Phe
65 70 75 80

Ile Pro Ala Asp Arg Lys Ser Ser Thr Leu Ser Leu Pro Arg Val Ser
85 90 95

Leu Ser Asp Thr Ala Val Tyr Tyr Cys Leu Val Gly Asp Phe Asn Ser
100 105 110

Asn Ser Gly Tyr Ala Leu Asn Phe Gly Lys Gly Thr Ser Leu Leu Val
115 120 125

Thr Pro His Ile Gln Asn Pro Asp Pro Ala Val Tyr Gln Leu Arg Asp
130 135 140

Ser Lys Ser Ser Asp Lys Ser Val Cys Leu Phe Thr Asp Phe Asp Ser

```
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser Gly
            260                 265                 270

Ser Gly Glu Gly Arg Gly Ser Leu Leu Thr Cys Gly Asp Val Glu Glu
        275                 280                 285

Asn Pro Gly Pro Met Gly Thr Arg Leu Leu Phe Trp Val Ala Phe Cys
    290                 295                 300

Leu Leu Gly Ala Tyr His Thr Gly Ala Gly Val Ser Gln Ser Pro Ser
305                 310                 315                 320

Asn Lys Val Thr Glu Lys Gly Lys Asp Val Glu Leu Arg Cys Asp Pro
                325                 330                 335

Ile Ser Gly His Thr Ala Leu Tyr Trp Tyr Arg Gln Arg Leu Gly Gln
            340                 345                 350

Gly Leu Glu Phe Leu Ile Tyr Phe Gln Gly Asn Ser Ala Pro Asp Lys
        355                 360                 365

Ser Gly Leu Pro Ser Asp Arg Phe Ser Ala Glu Arg Thr Gly Glu Ser
    370                 375                 380

Val Ser Thr Leu Thr Ile Gln Arg Thr Gln Gln Glu Asp Ser Ala Val
385                 390                 395                 400

Tyr Leu Cys Ala Ser Lys Val Tyr Gly Tyr Thr Phe Gly Ser Gly Thr
                405                 410                 415

Arg Leu Thr Val Val Glu Asp Leu Asn Lys Val Phe Pro Pro Glu Val
            420                 425                 430

Ala Val Phe Glu Pro Ser Glu Ala Glu Ile Ser His Thr Gln Lys Ala
        435                 440                 445

Thr Leu Val Cys Leu Ala Thr Gly Phe Phe Pro Asp His Val Glu Leu
    450                 455                 460

Ser Trp Trp Val Asn Gly Lys Glu Val His Ser Gly Val Ser Thr Asp
465                 470                 475                 480

Pro Gln Pro Leu Lys Glu Gln Pro Ala Leu Asn Asp Ser Arg Tyr Cys
                485                 490                 495

Leu Ser Ser Arg Leu Arg Val Ser Ala Thr Phe Trp Gln Asn Pro Arg
            500                 505                 510

Asn His Phe Arg Cys Gln Val Gln Phe Tyr Gly Leu Ser Glu Asn Asp
        515                 520                 525

Glu Trp Thr Gln Asp Arg Ala Lys Pro Val Thr Gln Ile Val Ser Ala
    530                 535                 540

Glu Ala Trp Gly Arg Ala Asp Cys Gly Phe Thr Ser Val Ser Tyr Gln
545                 550                 555                 560

Gln Gly Val Leu Ser Ala Thr Ile Leu Tyr Glu Ile Leu Leu Gly Lys
                565                 570                 575
```

Ala Thr Leu Tyr Ala Val Leu Val Ser Ala Leu Val Leu Met Ala Met
580 585 590

Val Lys Arg Lys Asp Phe
595

<210> SEQ ID NO 93
<211> LENGTH: 11
<212> TYPE: DNA
<213> ORGANISM: Artificial Sequence
<220> FEATURE:
<223> OTHER INFORMATION: TRAV39 CDR1

<400> SEQUENCE: 93
accacttcag a 11

<210> SEQ ID NO 94
<211> LENGTH: 21
<212> TYPE: DNA
<213> ORGANISM: Artificial Sequence
<220> FEATURE:
<223> OTHER INFORMATION: TRAV39 CDR2

<400> SEQUENCE: 94
ttgctatcaa atggagcagt g 21

<210> SEQ ID NO 95
<211> LENGTH: 25
<212> TYPE: DNA
<213> ORGANISM: Artificial Sequence
<220> FEATURE:
<223> OTHER INFORMATION: TRAV39 CDR3

<400> SEQUENCE: 95
gccgtggaca aggatggggg ttacc 25

<210> SEQ ID NO 96
<211> LENGTH: 391
<212> TYPE: DNA
<213> ORGANISM: Artificial Sequence
<220> FEATURE:
<223> OTHER INFORMATION: TRAV39 VARIABLE DOMAIN

<400> SEQUENCE: 96
atgaagaagc tactagcaat gattctgtgg cttcaactag accggttaag tggagagctg 60
aaagtggaac aaaaccctct gttcctgagc atgcaggagg gaaaaaacta taccatctac 120
tgcaattatt caaccacttc agacagactg tattggtaca ggcaggatcc tgggaaaagt 180
ctggaatctc tgtttgtgtt gctatcaaat ggagcagtga agcaggaggg acgattaatg 240
gcctcacttg ataccaaagc ccgtctcagc accctccaca tcacagctgc cgtgcatgac 300
ctctctgcca cctacttctg tgccgtggac aaggatgggg gttaccagaa agttaccttt 360
ggaactggaa caaagctcca agtcatccca a 391

<210> SEQ ID NO 97
<211> LENGTH: 422
<212> TYPE: DNA
<213> ORGANISM: Artificial Sequence
<220> FEATURE:
<223> OTHER INFORMATION: TCR831 ALPHA CONSTANT DOMAIN

<400> SEQUENCE: 97
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgttgg acatgcgcag catggacttc aagagcaaca 180
gtgctgtggc ctggagcaac aaatctgact ttgcatgtgc aaacgccttc aacaacagca 240
ttattccaga agacaccttc ttccccagcc cagaaagttc ctgtgatgtc aagctggtcg 300
agaaaagctt tgaaacagat acgaacctaa actttcaaaa cctgtcagtg attgggttcc 360
gaatcctcct cctgaaagtg gccgggttta atctgctcat gacgctgcgg ctgtggtcca 420
gc 422

<210> SEQ ID NO 98
<211> LENGTH: 813
<212> TYPE: DNA
<213> ORGANISM: Artificial Sequence
<220> FEATURE:
<223> OTHER INFORMATION: TCR831 ALPHA CHAIN

<400> SEQUENCE: 98
atgaagaagc tactagcaat gattctgtgg cttcaactag accggttaag tggagagctg 60
aaagtggaac aaaaccctct gttcctgagc atgcaggagg gaaaaaacta taccatctac 120
tgcaattatt caaccacttc agacagactg tattggtaca ggcaggatcc tgggaaaagt 180
ctggaatctc tgtttgtgtt gctatcaaat ggagcagtga agcaggaggg acgattaatg 240
gcctcacttg ataccaaagc ccgtctcagc accctccaca tcacagctgc cgtgcatgac 300
ctctctgcca cctacttctg tgccgtggac aaggatgggg gttaccagaa agttaccttt 360
ggaactggaa caaagctcca agtcatccca aatatccaga accctgaccc tgccgtgtac 420
cagctgagag actctaaatc cagtgacaag tctgtctgcc tattcaccga ttttgattct 480
caaacaaatg tgtcacaaag taaggattct gatgtgtata tcacagacaa aactgtgttg 540
gacatgcgca gcatggactt caagagcaac agtgctgtgg cctggagcaa caaatctgac 600
tttgcatgtg caaacgcctt caacaacagc attattccag aagacacctt cttccccagc 660
ccagaaagtt cctgtgatgt caagctggtc gagaaaagct ttgaaacaga tacgaaccta 720
aactttcaaa acctgtcagt gattgggttc cgaatcctcc tcctgaaagt ggccgggttt 780
aatctgctca tgacgctgcg gctgtggtcc agc 813

<210> SEQ ID NO 99
<211> LENGTH: 18
<212> TYPE: DNA
<213> ORGANISM: Artificial Sequence
<220> FEATURE:
<223> OTHER INFORMATION: TRBV20-1 CDR1

<400> SEQUENCE: 99
gactttcagg ccacaact 18

<210> SEQ ID NO 100
<211> LENGTH: 21
<212> TYPE: DNA
<213> ORGANISM: Artificial Sequence
<220> FEATURE:
<223> OTHER INFORMATION: TRBV20-1 CDR2

<400> SEQUENCE: 100
tccaatgagg gctccaaggc c 21

<210> SEQ ID NO 101
<211> LENGTH: 51

<212> TYPE: DNA
<213> ORGANISM: Artificial Sequence
<220> FEATURE:
<223> OTHER INFORMATION: TRBV20-1CDR3

<400> SEQUENCE: 101
agtgctagcc cacgggcggg acagttgagc tcctataatt caccccctcca c 51

<210> SEQ ID NO 102
<211> LENGTH: 437
<212> TYPE: DNA
<213> ORGANISM: Artificial Sequence
<220> FEATURE:
<223> OTHER INFORMATION: TRBV20-1 VARIABLE

<400> SEQUENCE: 102
atgctgctgc ttctgctgct tctggggcca ggtataagcc tccttctacc tgggagcttg 60
gcaggctccg ggcttggtgc tgtcgtctct caacatccga gctgggttat ctgtaagagt 120
ggaacctctg tgaagatcga gtgccgttcc ctggactttc aggccacaac tatgttttgg 180
tatcgtcagt tcccgaaaca gagtctcatg ctgatggcaa cttccaatga gggctccaag 240
gccacatacg agcaaggcgt cgagaaggac aagtttctca tcaaccatgc aagcctgacc 300
ttgtccactc tgacagtgac cagtgcccat cctgaagaca gcagcttcta catctgcagt 360
gctagcccac gggcgggaca gttgagctcc tataattcac ccctccactt tgggaatggg 420
accaggctca ctgtgac 437

<210> SEQ ID NO 103
<211> LENGTH: 531
<212> TYPE: DNA
<213> ORGANISM: Artificial Sequence
<220> FEATURE:
<223> OTHER INFORMATION: TCR831 BETA CONSTANT DOMAIN

<400> SEQUENCE: 103
gaggacctga acaaggtgtt cccacccgag gtcgctgtgt ttgagccatc agaagcagag 60
atctcccaca cccaaaaggc cacactggtg tgcctggcca caggcttctt ccccgaccac 120
gtggagctga gctggtgggt gaatgggaag gaggtgcaca gtggggtcag cacggacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga tgagtggaca caagataggg ccaaacccgt cacccagatc 360
gtcagcgccg aggcctgggg tagagcagac tgtggcttta cctcggtgtc ctaccagcaa 420
ggggtcctgt ctgccaccat cctctatgag atcctgctag ggaaggccac cctgtatgct 480
gtgctggtca gcgcccttgt gttgatggcc atggtcaaga gaaaggattt c 531

<210> SEQ ID NO 104
<211> LENGTH: 972
<212> TYPE: DNA
<213> ORGANISM: Artificial Sequence
<220> FEATURE:
<223> OTHER INFORMATION: TCR831 BETA CHAIN

<400> SEQUENCE: 104
atgctgctgc ttctgctgct tctggggcca ggtataagcc tccttctacc tgggagcttg 60
gcaggctccg ggcttggtgc tgtcgtctct caacatccga gctgggttat ctgtaagagt 120
ggaacctctg tgaagatcga gtgccgttcc ctggactttc aggccacaac tatgttttgg 180
tatcgtcagt tcccgaaaca gagtctcatg ctgatggcaa cttccaatga gggctccaag 240
gccacatacg agcaaggcgt cgagaaggac aagtttctca tcaaccatgc aagcctgacc 300
ttgtccactc tgacagtgac cagtgcccat cctgaagaca gcagcttcta catctgcagt 360
gctagcccac gggcgggaca gttgagctcc tataattcac ccctccactt tgggaatggg 420
accaggctca ctgtgacaga ggacctgaac aaggtgttcc cacccgaggt cgctgtgttt 480
gagccatcag aagcagagat ctcccacacc caaaaggcca cactggtgtg cctggccaca 540
ggcttcttcc ccgaccacgt ggagctgagc tggtgggtga atgggaagga ggtgcacagt 600
ggggtcagca cggacccgca gcccctcaag gagcagcccg ccctcaatga ctccagatac 660
tgcctgagca gccgcctgag ggtctcggcc accttctggc agaacccccg caaccacttc 720
cgctgtcaag tccagttcta cgggctctcg gagaatgatg agtggacaca agatagggcc 780
aaacccgtca cccagatcgt cagcgccgag gcctggggta gagcagactg tggctttacc 840
tcggtgtcct accagcaagg ggtcctgtct gccaccatcc tctatgagat cctgctaggg 900
aaggccaccc tgtatgctgt gctggtcagc gcccttgtgt tgatggccat ggtcaagaga 960
aaggatttct ga 972

<210> SEQ ID NO 105
<211> LENGTH: 63
<212> TYPE: DNA
<213> ORGANISM: Artificial Sequence
<220> FEATURE:
<223> OTHER INFORMATION: linker

<400> SEQUENCE: 105
ggcagcggag agggcagagg aagtcttcta acatgcggtg acgtggagga gaatcccggc 60
cct 63

<210> SEQ ID NO 106
<211> LENGTH: 1848
<212> TYPE: DNA
<213> ORGANISM: Artificial Sequence
<220> FEATURE:
<223> OTHER INFORMATION: TCR831 fusion

<400> SEQUENCE: 106
atgaagaagc tactagcaat gattctgtgg cttcaactag accggttaag tggagagctg 60
aaagtggaac aaaaccctct gttcctgagc atgcaggagg gaaaaaacta taccatctac 120
tgcaattatt caaccacttc agacagactg tattggtaca ggcaggatcc tgggaaaagt 180
ctggaatctc tgtttgtgtt gctatcaaat ggagcagtga agcaggaggg acgattaatg 240
gcctcacttg ataccaaagc ccgtctcagc accctccaca tcacagctgc cgtgcatgac 300
ctctctgcca cctacttctg tgccgtggac aaggatgggg gttaccagaa agttaccttt 360
ggaactggaa caaagctcca agtcatccca aatatccaga accctgaccc tgccgtgtac 420
cagctgagag actctaaatc cagtgacaag tctgtctgcc tattcaccga ttttgattct 480
caaacaaatg tgtcacaaag taaggattct gatgtgtata tcacagacaa aactgtgttg 540
gacatgcgca gcatggactt caagagcaac agtgctgtgg cctggagcaa caaatctgac 600
tttgcatgtg caaacgcctt caacaacagc attattccag aagacacctt cttccccagc 660
ccagaaagtt cctgtgatgt caagctggtc gagaaaagct ttgaaacaga tacgaaccta 720
aactttcaaa acctgtcagt gattgggttc cgaatcctcc tcctgaaagt ggccgggttt 780
aatctgctca tgacgctgcg gctgtggtcc agcggcagcg gagagggcag aggaagtctt 840
ctaacatgcg gtgacgtgga ggagaatccc ggccctatgc tgctgcttct gctgcttctg 900
gggccaggta taagcctcct tctacctggg agcttggcag gctccgggct tggtgctgtc 960
gtctctcaac atccgagctg ggttatctgt aagagtggaa cctctgtgaa gatcgagtgc 1020
cgttccctgg actttcaggc cacaactatg ttttggtatc gtcagttccc gaaacagagt 1080
ctcatgctga tggcaacttc caatgagggc tccaaggcca catacgagca aggcgtcgag 1140
aaggacaagt ttctcatcaa ccatgcaagc ctgaccttgt ccactctgac agtgaccagt 1200
gcccatcctg aagacagcag cttctacatc tgcagtgcta gcccacgggc gggacagttg 1260
agctcctata attcacccct ccactttggg aatgggacca ggctcactgt gacagaggac 1320
ctgaacaagg tgttcccacc cgaggtcgct gtgtttgagc catcagaagc agagatctcc 1380
cacacccaaa aggccacact ggtgtgcctg gccacaggct tcttccccga ccacgtggag 1440
ctgagctggt gggtgaatgg gaaggaggtg cacagtgggg tcagcacgga cccgcagccc 1500
ctcaaggagc agcccgccct caatgactcc agatactgcc tgagcagccg cctgagggtc 1560
tcggccacct tctggcagaa cccccgcaac cacttccgct gtcaagtcca gttctacggg 1620
ctctcggaga atgatgagtg gacacaagat agggccaaac ccgtcaccca gatcgtcagc 1680
gccgaggcct ggggtagagc agactgtggc tttacctcgg tgtcctacca gcaaggggtc 1740
ctgtctgcca ccatcctcta tgagatcctg ctagggaagg ccaccctgta tgctgtgctg 1800
gtcagcgccc ttgtgttgat ggccatggtc aagagaaagg atttctga 1848

<210> SEQ ID NO 107
<211> LENGTH: 18
<212> TYPE: DNA
<213> ORGANISM: Artificial Sequence
<220> FEATURE:
<223> OTHER INFORMATION: TRAV12-1 CDR1

<400> SEQUENCE: 107
aacagtgctt ctcagtct 18

<210> SEQ ID NO 108
<211> LENGTH: 18
<212> TYPE: DNA
<213> ORGANISM: Artificial Sequence
<220> FEATURE:
<223> OTHER INFORMATION: TRAV12-1 CDR2

<400> SEQUENCE: 108
gtatactcca gtggtaac 18

<210> SEQ ID NO 109
<211> LENGTH: 39
<212> TYPE: DNA
<213> ORGANISM: Artificial Sequence
<220> FEATURE:
<223> OTHER INFORMATION: TRAV12-1 CDR3

<400> SEQUENCE: 109
gcggtgaacc ccccggacac aggctttcag aaacttgta 39

<210> SEQ ID NO 110
<211> LENGTH: 400
<212> TYPE: DNA
<213> ORGANISM: Artificial Sequence
<220> FEATURE:
<223> OTHER INFORMATION: TRAV12-1 VARIABLE DOMAIN

<400> SEQUENCE: 110
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaacga agatggaagg 240
tttacagcac agctcaatag agccagccag tatatttccc tgctcatcag agactccaag 300
ctcagtgatt cagccaccta cctctgtgcg gtgaaccccc cggacacagg ctttcagaaa 360
cttgtatttg gaactggcac ccgacttctg gtcagtccaa 400

<210> SEQ ID NO 111
<211> LENGTH: 422
<212> TYPE: DNA
<213> ORGANISM: Artificial Sequence
<220> FEATURE:
<223> OTHER INFORMATION: TCR833 ALPHA CONSTANT DOMAIN

<400> SEQUENCE: 111
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgttgg acatgcgcag catggacttc aagagcaaca 180
gtgctgtggc ctggagcaac aaatctgact ttgcatgtgc aaacgccttc aacaacagca 240
ttattccaga agacaccttc ttccccagcc cagaaagttc ctgtgatgtc aagctggtcg 300
agaaaagctt tgaaacagat acgaacctaa actttcaaaa cctgtcagtg attgggttcc 360
gaatcctcct cctgaaagtg gccgggttta atctgctcat gacgctgcgg ctgtggtcca 420
gc 422

<210> SEQ ID NO 112
<211> LENGTH: 822
<212> TYPE: DNA
<213> ORGANISM: Artificial Sequence
<220> FEATURE:
<223> OTHER INFORMATION: TCR833 ALPHA CHAIN

<400> SEQUENCE: 112
atgatatcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct tctcagtctt tcttctggta cagacaggat 180
tgcaggaaag aacctaagtt gctgatgtcc gtatactcca gtggtaacga agatggaagg 240
tttacagcac agctcaatag agccagccag tatatttccc tgctcatcag agactccaag 300
ctcagtgatt cagccaccta cctctgtgcg gtgaaccccc cggacacagg ctttcagaaa 360
cttgtatttg gaactggcac ccgacttctg gtcagtccaa atatccagaa ccctgaccct 420
gccgtgtacc agctgagaga ctctaaatcc agtgacaagt ctgtctgcct attcaccgat 480
tttgattctc aaacaaatgt gtcacaaagt aaggattctg atgtgtatat cacagacaaa 540
actgtgttgg acatgcgcag catggacttc aagagcaaca gtgctgtggc ctggagcaac 600
aaatctgact ttgcatgtgc aaacgccttc aacaacagca ttattccaga agacaccttc 660
ttccccagcc cagaaagttc ctgtgatgtc aagctggtcg agaaaagctt tgaaacagat 720
acgaacctaa actttcaaaa cctgtcagtg attgggttcc gaatcctcct cctgaaagtg 780
gccgggttta atctgctcat gacgctgcgg ctgtggtcca gc 822

<210> SEQ ID NO 113
<211> LENGTH: 15
<212> TYPE: DNA
<213> ORGANISM: Artificial Sequence
<220> FEATURE:
<223> OTHER INFORMATION: TRBV28 CDR1

<400> SEQUENCE: 113
atggaccatg aaaat 15

<210> SEQ ID NO 114
<211> LENGTH: 18
<212> TYPE: DNA
<213> ORGANISM: Artificial Sequence
<220> FEATURE:
<223> OTHER INFORMATION: TRBV28 CDR2

<400> SEQUENCE: 114
tcatatgatg ttaaaatg 18

<210> SEQ ID NO 115
<211> LENGTH: 42
<212> TYPE: DNA
<213> ORGANISM: Artificial Sequence
<220> FEATURE:
<223> OTHER INFORMATION: TRBV28 CDR3

<400> SEQUENCE: 115
gccagcagtt tatccttccg gcagggcctt cgcgagcagt ac 42

<210> SEQ ID NO 116
<211> LENGTH: 402
<212> TYPE: DNA
<213> ORGANISM: Artificial Sequence
<220> FEATURE:
<223> OTHER INFORMATION: TRBV28 VARIABLE DOMAIN

<400> SEQUENCE: 116
atgggaatca ggctcctgtg tcgtgtggcc ttttgtttcc tggctgtagg cctcgtagat 60
gtgaaagtaa cccagagctc gagatatcta gtcaaaagga cgggagagaa agtttttctg 120
gaatgtgtcc aggatatgga ccatgaaaat atgttctggt atcgacaaga cccaggtctg 180
gggctacggc tgatctattt ctcatatgat gttaaaatga aagaaaaagg agatattcct 240
gaggggtaca gtgtctccag agagaagaag gagcgcttct ccctgattct ggagtccgcc 300
agcaccaacc agacatctat gtacctctgt gccagcagtt tatccttccg gcagggcctt 360
cgcgagcagt acttcgggcc gggcaccagg ctcacggtca ca 402

<210> SEQ ID NO 117
<211> LENGTH: 537
<212> TYPE: DNA
<213> ORGANISM: Artificial Sequence
<220> FEATURE:
<223> OTHER INFORMATION: TCR833 BETA CONSTANT DOMAIN

<400> SEQUENCE: 117
gaggacctga aaaacgtgtt cccacccgag gtcgctgtgt ttgagccatc agaagcagag 60
atctcccaca cccaaaaggc cacactggtg tgcctggcca caggcttcta ccccgaccac 120
gtggagctga gctggtgggt gaatgggaag gaggtgcaca gtggggtcag cacagacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga tgagtggaca caagataggg ccaaacctgt cacccagatc 360
gtcagcgccg aggcctgggg tagagcagac tgtggcttca cctccgagtc ttaccagcaa 420
ggggtcctgt ctgccaccat cctctatgag atcttgctag ggaaggccac cttgtatgcc 480
gtgctggtca gtgccctcgt gctgatggcc atggtcaaga gaaaggattc cagaggc 537

<210> SEQ ID NO 118
<211> LENGTH: 942
<212> TYPE: DNA
<213> ORGANISM: Artificial Sequence
<220> FEATURE:
<223> OTHER INFORMATION: TCR833 BETA CHAIN

<400> SEQUENCE: 118
atgggaatca ggctcctgtg tcgtgtggcc ttttgtttcc tggctgtagg cctcgtagat 60
gtgaaagtaa cccagagctc gagatatcta gtcaaaagga cgggagagaa agtttttctg 120
gaatgtgtcc aggatatgga ccatgaaaat atgttctggt atcgacaaga cccaggtctg 180
gggctacggc tgatctattt ctcatatgat gttaaaatga aagaaaaagg agatattcct 240
gaggggtaca gtgtctccag agagaagaag gagcgcttct ccctgattct ggagtccgcc 300
agcaccaacc agacatctat gtacctctgt gccagcagtt tatccttccg gcagggcctt 360
cgcgagcagt acttcgggcc gggcaccagg ctcacggtca cagaggacct gaaaaacgtg 420
ttcccacccg aggtcgctgt gtttgagcca tcagaagcag agatctccca cacccaaaag 480
gccacactgg tgtgcctggc cacaggcttc taccccgacc acgtggagct gagctggtgg 540
gtgaatggga aggaggtgca cagtggggtc agcacagacc cgcagcccct caaggagcag 600
cccgccctca atgactccag atactgcctg agcagccgcc tgagggtctc ggccaccttc 660
tggcagaacc cccgcaacca cttccgctgt caagtccagt tctacgggct ctcggagaat 720
gatgagtgga cacaagatag ggccaaacct gtcacccaga tcgtcagcgc cgaggcctgg 780
ggtagagcag actgtggctt cacctccgag tcttaccagc aaggggtcct gtctgccacc 840
atcctctatg agatcttgct agggaaggcc accttgtatg ccgtgctggt cagtgccctc 900
gtgctgatgg ccatggtcaa gagaaaggat tccagaggct ga 942

<210> SEQ ID NO 119
<211> LENGTH: 63
<212> TYPE: DNA
<213> ORGANISM: Artificial Sequence
<220> FEATURE:
<223> OTHER INFORMATION: LINKER

<400> SEQUENCE: 119
ggcagcggag agggcagagg aagtcttcta acatgcggtg acgtggagga gaatcccggc 60
cct 63

<210> SEQ ID NO 120
<211> LENGTH: 1827
<212> TYPE: DNA
<213> ORGANISM: Artificial Sequence
<220> FEATURE:
<223> OTHER INFORMATION: TCR833 FUSION

<400> SEQUENCE: 120
atgatatcct tgagagtttt actggtgatc ctgtggcttc agttaagctg ggtttggagc 60
caacggaagg aggtggagca ggatcctgga cccttcaatg ttccagaggg agccactgtc 120

```
gctttcaact gtacttacag caacagtgct tctcagtctt tcttctggta cagacaggat    180

tgcaggaaag aacctaagtt gctgatgtcc gtatactcca gtggtaacga agatggaagg    240

tttacagcac agctcaatag agccagccag tatatttccc tgctcatcag agactccaag    300

ctcagtgatt cagccaccta cctctgtgcg gtgaaccccc cggacacagg ctttcagaaa    360

cttgtatttg gaactggcac ccgacttctg gtcagtccaa atatccagaa ccctgaccct    420

gccgtgtacc agctgagaga ctctaaatcc agtgacaagt ctgtctgcct attcaccgat    480

tttgattctc aaacaaatgt gtcacaaagt aaggattctg atgtgtatat cacagacaaa    540

actgtgttgg acatgcgcag catggacttc aagagcaaca gtgctgtggc ctggagcaac    600

aaatctgact ttgcatgtgc aaacgccttc aacaacagca ttattccaga agacaccttc    660

ttccccagcc cagaaagttc ctgtgatgtc aagctggtcg agaaaagctt tgaaacagat    720

acgaacctaa actttcaaaa cctgtcagtg attgggttcc gaatcctcct cctgaaagtg    780

gccgggttta atctgctcat gacgctgcgg ctgtggtcca gcggcagcgg agagggcaga    840

ggaagtcttc taacatgcgg tgacgtggag gagaatcccg gccctatggg aatcaggctc    900

ctgtgtcgtg tggccttttg tttcctggct gtaggcctcg tagatgtgaa agtaacccag    960

agctcgagat atctagtcaa aaggacggga gagaaagttt ttctggaatg tgtccaggat   1020

atggaccatg aaaatatgtt ctggtatcga caagacccag gtctggggct acggctgatc   1080

tatttctcat atgatgttaa aatgaaagaa aaaggagata ttcctgaggg gtacagtgtc   1140

tccagagaga agaaggagcg cttctccctg attctggagt ccgccagcac caaccagaca   1200

tctatgtacc tctgtgccag cagtttatcc ttccggcagg gccttcgcga gcagtacttc   1260

gggccgggca ccaggctcac ggtcacagag gacctgaaaa acgtgttccc acccgaggtc   1320

gctgtgtttg agccatcaga agcagagatc tcccacaccc aaaaggccac actggtgtgc   1380

ctggccacag gcttctaccc cgaccacgtg gagctgagct ggtgggtgaa tgggaaggag   1440

gtgcacagtg gggtcagcac agacccgcag cccctcaagg agcagcccgc cctcaatgac   1500

tccagatact gcctgagcag ccgcctgagg gtctcggcca ccttctggca gaaccccggc   1560

aaccacttcc gctgtcaagt ccagttctac gggctctcgg agaatgatga gtggacacaa   1620

gatagggcca aacctgtcac ccagatcgtc agcgccgagg cctggggtag agcagactgt   1680

ggcttcacct ccgagtctta ccagcaaggg gtcctgtctg ccaccatcct ctatgagatc   1740

ttgctaggga aggccacctt gtatgccgtg ctggtcagtg ccctcgtgct gatggccatg   1800

gtcaagagaa aggattccag aggctga                                       1827
```

<210> SEQ ID NO 121
<211> LENGTH: 15
<212> TYPE: DNA
<213> ORGANISM: Artificial Sequence
<220> FEATURE:
<223> OTHER INFORMATION: TRAV17 CDR1

<400> SEQUENCE: 121

```
actagtataa acaat                                                      15
```

<210> SEQ ID NO 122
<211> LENGTH: 21
<212> TYPE: DNA
<213> ORGANISM: Artificial Sequence
<220> FEATURE:
<223> OTHER INFORMATION: TRAV17 CDR2

<400> SEQUENCE: 122
atacgttcaa atgaaagaga g 21

<210> SEQ ID NO 123
<211> LENGTH: 36
<212> TYPE: DNA
<213> ORGANISM: Artificial Sequence
<220> FEATURE:
<223> OTHER INFORMATION: TRAV17 CDR3

<400> SEQUENCE: 123
tgtgctacgg accctggagg cttcaaaact atcttt 36

<210> SEQ ID NO 124
<211> LENGTH: 422
<212> TYPE: DNA
<213> ORGANISM: Artificial Sequence
<220> FEATURE:
<223> OTHER INFORMATION: TCR897 ALPHA CONSTANT DOMAIN

<400> SEQUENCE: 124
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgttgg acatgcgcag catggacttc aagagcaaca 180
gtgctgtggc ctggagcaac aaatctgact ttgcatgtgc aaacgccttc aacaacagca 240
ttattccaga agacaccttc ttccccagcc cagaaagttc ctgtgatgtc aagctggtcg 300
agaaaagctt tgaaacagat acgaacctaa actttcaaaa cctgtcagtg attgggttcc 360
gaatcctcct cctgaaagtg gccgggttta atctgctcat gacgctgcgg ctgtggtcca 420
gc 422

<210> SEQ ID NO 125
<211> LENGTH: 813
<212> TYPE: DNA
<213> ORGANISM: Artificial Sequence
<220> FEATURE:
<223> OTHER INFORMATION: TCR897 ALPHA CHAIN

<400> SEQUENCE: 125
atggaaactc tcctgggagt gtctttggtg attctatggc ttcaactggc tagggtgaac 60
agtcaacagg gagaagagga tcctcaggcc ttgagcatcc aggagggtga aaatgccacc 120
atgaactgca gttacaaaac tagtataaac aatttacagt ggtatagaca aaattcaggt 180
agaggccttg tccacctaat tttaatacgt tcaaatgaaa gagagaaaca cagtggaaga 240
ttaagagtca cgcttgacac ttccaagaaa agcagttcct tgttgatcac ggcttcccgg 300
gcagcagaca ctgcttctta cttctgtgct acggaccctg gaggcttcaa aactatcttt 360
ggagcaggaa caagactatt tgttaaagca aatatccaga accctgaccc tgccgtgtac 420
cagctgagag actctaaatc cagtgacaag tctgtctgcc tattcaccga ttttgattct 480
caaacaaatg tgtcacaaag taaggattct gatgtgtata tcacagacaa aactgtgttg 540
gacatgcgca gcatggactt caagagcaac agtgctgtgg cctggagcaa caaatctgac 600
tttgcatgtg caaacgcctt caacaacagc attattccag aagacacctt cttccccagc 660
ccagaaagtt cctgtgatgt caagctggtc gagaaaagct ttgaaacaga tacgaaccta 720
aactttcaaa acctgtcagt gattgggttc cgaatcctcc tcctgaaagt ggccgggttt 780
aatctgctca tgacgctgcg gctgtggtcc agc 813

<210> SEQ ID NO 126
<211> LENGTH: 15
<212> TYPE: DNA
<213> ORGANISM: Artificial Sequence
<220> FEATURE:
<223> OTHER INFORMATION: TRBV11-2 CDR1

<400> SEQUENCE: 126
tctggccatg ctacc 15

<210> SEQ ID NO 127
<211> LENGTH: 18
<212> TYPE: DNA
<213> ORGANISM: Artificial Sequence
<220> FEATURE:
<223> OTHER INFORMATION: TRBV11-2 CDR2

<400> SEQUENCE: 127
tttcagaata acggtgta 18

<210> SEQ ID NO 128
<211> LENGTH: 48
<212> TYPE: DNA
<213> ORGANISM: Artificial Sequence
<220> FEATURE:
<223> OTHER INFORMATION: TRBV11-2 CDR3

<400> SEQUENCE: 128
tgtgccagca gcttatatgg ggggtcgatc tcctacgagc agtacttc 48

<210> SEQ ID NO 129
<211> LENGTH: 537
<212> TYPE: DNA
<213> ORGANISM: Artificial Sequence
<220> FEATURE:
<223> OTHER INFORMATION: TCR897 BETA CONSTANT DOMAIN

<400> SEQUENCE: 129
gaggacctga aaaacgtgtt cccacccgag gtcgctgtgt ttgagccatc agaagcagag 60
atctcccaca cccaaaaggc cacactggtg tgcctggcca caggcttcta ccccgaccac 120
gtggagctga gctggtgggt gaatgggaag gaggtgcaca gtggggtcag cacagacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga tgagtggaca caagataggg ccaaacctgt cacccagatc 360
gtcagcgccg aggcctgggg tagagcagac tgtggcttca cctccgagtc ttaccagcaa 420
ggggtcctgt ctgccaccat cctctatgag atcttgctag ggaaggccac cttgtatgcc 480
gtgctggtca gtgccctcgt gctgatggcc atggtcaaga gaaaggattc cagaggc 537

<210> SEQ ID NO 130
<211> LENGTH: 945
<212> TYPE: DNA
<213> ORGANISM: Artificial Sequence
<220> FEATURE:
<223> OTHER INFORMATION: TCR897 BETA CHAIN

<400> SEQUENCE: 130
atgggcacca ggctcctctg ctgggcggcc ctctgtctcc tgggagcaga actcacagaa 60
gctggagttg cccagtctcc cagatataag attatagaga aaaggcagag tgtggctttt 120
tggtgcaatc ctatatctgg ccatgctacc ctttactggt accagcagat cctgggacag 180
ggcccaaagc ttctgattca gtttcagaat aacggtgtag tggatgattc acagttgcct 240
aaggatcgat tttctgcaga gaggctcaaa ggagtagact ccactctcaa gatccagcct 300
gcaaagcttg aggactcggc cgtgtatctc tgtgccagca gcttatatgg ggggtcgatc 360
tcctacgagc agtacttcgg gccgggcacc aggctcacgg tcacagagga cctgaaaaac 420
gtgttcccac ccgaggtcgc tgtgtttgag ccatcagaag cagagatctc ccacacccaa 480
aaggccacac tggtgtgcct ggccacaggc ttctaccccg accacgtgga gctgagctgg 540
tgggtgaatg ggaaggaggt gcacagtggg gtcagcacag acccgcagcc cctcaaggag 600
cagcccgccc tcaatgactc cagatactgc ctgagcagcc gcctgagggt ctcggccacc 660
ttctggcaga acccccgcaa ccacttccgc tgtcaagtcc agttctacgg gctctcggag 720
aatgatgagt ggacacaaga tagggccaaa cctgtcaccc agatcgtcag cgccgaggcc 780
tggggtagag cagactgtgg cttcacctcc gagtcttacc agcaaggggt cctgtctgcc 840
accatcctct atgagatctt gctagggaag gccaccttgt atgccgtgct ggtcagtgcc 900
ctcgtgctga tggccatggt caagagaaag gattccagag gctga 945

<210> SEQ ID NO 131
<211> LENGTH: 63
<212> TYPE: DNA
<213> ORGANISM: Artificial Sequence
<220> FEATURE:
<223> OTHER INFORMATION: LINKER

<400> SEQUENCE: 131
ggcagcggag agggcagagg aagtcttcta acatgcggtg acgtggagga gaatcccggc 60
cct 63

<210> SEQ ID NO 132
<211> LENGTH: 1821
<212> TYPE: DNA
<213> ORGANISM: Artificial Sequence
<220> FEATURE:
<223> OTHER INFORMATION: TCR897 FUSION

<400> SEQUENCE: 132
atggaaactc tcctgggagt gtctttggtg attctatggc ttcaactggc tagggtgaac 60
agtcaacagg gagaagagga tcctcaggcc ttgagcatcc aggagggtga aaatgccacc 120
atgaactgca gttacaaaac tagtataaac aatttacagt ggtatagaca aaattcaggt 180
agaggccttg tccacctaat tttaatacgt tcaaatgaaa gagagaaaca cagtggaaga 240
ttaagagtca cgcttgacac ttccaagaaa agcagttcct tgttgatcac ggcttcccgg 300
gcagcagaca ctgcttctta cttctgtgct acggaccctg gaggcttcaa aactatcttt 360
ggagcaggaa caagactatt tgttaaagca aatatccaga accctgaccc tgccgtgtac 420
cagctgagag actctaaatc cagtgacaag tctgtctgcc tattcaccga ttttgattct 480
caaacaaatg tgtcacaaag taaggattct gatgtgtata tcacagacaa aactgtgttg 540
gacatgcgca gcatggactt caagagcaac agtgctgtgg cctggagcaa caaatctgac 600
tttgcatgtg caaacgcctt caacaacagc attattccag aagacacctt cttccccagc 660
ccagaaagtt cctgtgatgt caagctggtc gagaaaagct ttgaaacaga tacgaaccta 720
aactttcaaa acctgtcagt gattgggttc cgaatcctcc tcctgaaagt ggccgggttt 780
aatctgctca tgacgctgcg gctgtggtcc agcggcagcg gagagggcag aggaagtctt 840

```
ctaacatgcg gtgacgtgga ggagaatccc ggccctatgg gcaccaggct cctctgctgg    900

gcggccctct gtctcctggg agcagaactc acagaagctg gagttgccca gtctcccaga    960

tataagatta tagagaaaag gcagagtgtg gctttttggt gcaatcctat atctggccat   1020

gctacccttt actggtacca gcagatcctg ggacagggcc caaagcttct gattcagttt   1080

cagaataacg gtgtagtgga tgattcacag ttgcctaagg atcgattttc tgcagagagg   1140

ctcaaaggag tagactccac tctcaagatc cagcctgcaa agcttgagga ctcggccgtg   1200

tatctctgtg ccagcagctt atatgggggg tcgatctcct acgagcagta cttcgggccg   1260

ggcaccaggc tcacggtcac agaggacctg aaaaacgtgt tcccacccga ggtcgctgtg   1320

tttgagccat cagaagcaga gatctcccac acccaaaagg ccacactggt gtgcctggcc   1380

acaggcttct accccgacca cgtggagctg agctggtggg tgaatgggaa ggaggtgcac   1440

agtggggtca gcacagaccc gcagcccctc aaggagcagc ccgccctcaa tgactccaga   1500

tactgcctga gcagccgcct gagggtctcg gccaccttct ggcagaaccc ccgcaaccac   1560

ttccgctgtc aagtccagtt ctacgggctc tcggagaatg atgagtggac acaagatagg   1620

gccaaacctg tcacccagat cgtcagcgcc gaggcctggg gtagagcaga ctgtggcttc   1680

acctccgagt cttaccagca aggggtcctg tctgccacca tcctctatga gatcttgcta   1740

gggaaggcca ccttgtatgc cgtgctggtc agtgccctcg tgctgatggc catggtcaag   1800

agaaaggatt ccagaggctg a                                             1821
```

<210> SEQ ID NO 133
<211> LENGTH: 21
<212> TYPE: DNA
<213> ORGANISM: Artificial Sequence
<220> FEATURE:
<223> OTHER INFORMATION: TRAV19 CDR1

<400> SEQUENCE: 133

```
acccgtgata ctacttatta c                                               21
```

<210> SEQ ID NO 134
<211> LENGTH: 24
<212> TYPE: DNA
<213> ORGANISM: Artificial Sequence
<220> FEATURE:
<223> OTHER INFORMATION: TRAV19 CDR2

<400> SEQUENCE: 134

```
cggaactctt ttgatgagca aaat                                            24
```

<210> SEQ ID NO 135
<211> LENGTH: 39
<212> TYPE: DNA
<213> ORGANISM: Artificial Sequence
<220> FEATURE:
<223> OTHER INFORMATION: TRAV19 CDR3

<400> SEQUENCE: 135

```
tgtgctctga gtgaggcagg aacctacaaa tacatcttt                            39
```

<210> SEQ ID NO 136
<211> LENGTH: 422
<212> TYPE: DNA
<213> ORGANISM: Artificial Sequence
<220> FEATURE:
<223> OTHER INFORMATION: TCR896 ALPHA CONSTANT DOMAIN

<400> SEQUENCE: 136
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgttgg acatgcgcag catggacttc aagagcaaca 180
gtgctgtggc ctggagcaac aaatctgact ttgcatgtgc aaacgccttc aacaacagca 240
ttattccaga agacaccttc ttccccagcc cagaaagttc ctgtgatgtc aagctggtcg 300
agaaaagctt tgaaacagat acgaacctaa actttcaaaa cctgtcagtg attgggttcc 360
gaatcctcct cctgaaagtg gccgggttta atctgctcat gacgctgcgg ctgtggtcca 420
gc 422

<210> SEQ ID NO 137
<211> LENGTH: 825
<212> TYPE: DNA
<213> ORGANISM: Artificial Sequence
<220> FEATURE:
<223> OTHER INFORMATION: TCR896 ALPHA CHAIN

<400> SEQUENCE: 137
atgctgactg ccagcctgtt gagggcagtc atagcctcca tctgtgttgt atccagcatg 60
gctcagaagg taactcaagc gcagactgaa atttctgtgg tggagaagga ggatgtgacc 120
ttggactgtg tgtatgaaac ccgtgatact acttattact tattctggta caagcaacca 180
ccaagtggag aattggtttt ccttattcgt cggaactctt ttgatgagca aaatgaaata 240
agtggtcggt attcttggaa cttccagaaa tccaccagtt ccttcaactt caccatcaca 300
gcctcacaag tcgtggactc agcagtatac ttctgtgctc tgagtgaggc aggaacctac 360
aaatacatct ttggaacagg caccaggctg aaggtattag caaatatcca gaaccctgac 420
cctgccgtgt accagctgag agactctaaa tccagtgaca agtctgtctg cctattcacc 480
gattttgatt ctcaaacaaa tgtgtcacaa agtaaggatt ctgatgtgta tatcacagac 540
aaaactgtgt tggacatgcg cagcatggac ttcaagagca acagtgctgt ggcctggagc 600
aacaaatctg actttgcatg tgcaaacgcc ttcaacaaca gcattattcc agaagacacc 660
ttcttcccca gcccagaaag ttcctgtgat gtcaagctgg tcgagaaaag ctttgaaaca 720
gatacgaacc taaactttca aaacctgtca gtgattgggt tccgaatcct cctcctgaaa 780
gtggccgggt ttaatctgct catgacgctg cggctgtggt ccagc 825

<210> SEQ ID NO 138
<211> LENGTH: 15
<212> TYPE: DNA
<213> ORGANISM: Artificial Sequence
<220> FEATURE:
<223> OTHER INFORMATION: TRBV9 CDR1

<400> SEQUENCE: 138
tctggagacc tctct 15

<210> SEQ ID NO 139
<211> LENGTH: 24
<212> TYPE: DNA
<213> ORGANISM: Artificial Sequence
<220> FEATURE:
<223> OTHER INFORMATION: TRBV9 CDR2

<400> SEQUENCE: 139
cggaactctt ttgatgagca aaat 24

<210> SEQ ID NO 140
<211> LENGTH: 39
<212> TYPE: DNA
<213> ORGANISM: Artificial Sequence
<220> FEATURE:
<223> OTHER INFORMATION: TRBV9 CDR3

<400> SEQUENCE: 140
tgtgctctga gtgaggcagg aacctacaaa tacatcttt 39

<210> SEQ ID NO 141
<211> LENGTH: 537
<212> TYPE: DNA
<213> ORGANISM: Artificial Sequence
<220> FEATURE:
<223> OTHER INFORMATION: TCR896 BETA CONSTANT DOMAIN

<400> SEQUENCE: 141
gaggacctga aaaacgtgtt cccacccgag gtcgctgtgt ttgagccatc agaagcagag 60
atctcccaca cccaaaaggc cacactggtg tgcctggcca caggcttcta ccccgaccac 120
gtggagctga gctggtgggt gaatgggaag gaggtgcaca gtggggtcag cacagacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga tgagtggaca caagataggg ccaaacctgt cacccagatc 360
gtcagcgccg aggcctgggg tagagcagac tgtggcttca cctccgagtc ttaccagcaa 420
ggggtcctgt ctgccaccat cctctatgag atcttgctag ggaaggccac cttgtatgcc 480
gtgctggtca gtgccctcgt gctgatggcc atggtcaaga gaaaggattc cagaggc 537

<210> SEQ ID NO 142
<211> LENGTH: 939
<212> TYPE: DNA
<213> ORGANISM: Artificial Sequence
<220> FEATURE:
<223> OTHER INFORMATION: TCR896 BETA CHAIN

<400> SEQUENCE: 142
atgggcttca ggctcctctg ctgtgtggcc ttttgtctcc tgggagcagg cccagtggat 60
tctggagtca cacaaacccc aaagcacctg atcacagcaa ctggacagcg agtgacgctg 120
agatgctccc ctaggtctgg agacctctct gtgtactggt accaacagag cctggaccag 180
ggcctccagt tcctcattca gtattataat ggagaagaga gagcaaaagg aaacattctt 240
gaacgattct ccgcacaaca gttccctgac ttgcactctg aactaaacct gagctctctg 300
gagctggggg actcagcttt gtatttctgt gccagcagcg tagctggggg gggacaagag 360
acccagtact tcgggccagg cacgcggctc ctggtgctcg aggacctgaa aaacgtgttc 420
ccacccgagg tcgctgtgtt tgagccatca gaagcagaga tctcccacac ccaaaaggcc 480
acactggtgt gcctggccac aggcttctac cccgaccacg tggagctgag ctggtgggtg 540
aatgggaagg aggtgcacag tggggtcagc acagacccgc agcccctcaa ggagcagccc 600
gccctcaatg actccagata ctgcctgagc agccgcctga gggtctcggc caccttctgg 660
cagaaccccc gcaaccactt ccgctgtcaa gtccagttct acgggctctc ggagaatgat 720
gagtggacac aagatagggc caaacctgtc acccagatcg tcagcgccga ggcctggggt 780
agagcagact gtggcttcac ctccgagtct taccagcaag ggtcctgtc tgccaccatc 840

```
ctctatgaga tcttgctagg gaaggccacc ttgtatgccg tgctggtcag tgccctcgtg    900

ctgatggcca tggtcaagag aaaggattcc agaggctga                           939
```

<210> SEQ ID NO 143
<211> LENGTH: 63
<212> TYPE: DNA
<213> ORGANISM: Artificial Sequence
<220> FEATURE:
<223> OTHER INFORMATION: LINKER

<400> SEQUENCE: 143

```
ggcagcggag agggcagagg aagtcttcta acatgcggtg acgtggagga gaatcccggc     60

cct                                                                   63
```

<210> SEQ ID NO 144
<211> LENGTH: 1827
<212> TYPE: DNA
<213> ORGANISM: Artificial Sequence
<220> FEATURE:
<223> OTHER INFORMATION: TCR896 FUSION

<400> SEQUENCE: 144

```
atgctgactg ccagcctgtt gagggcagtc atagcctcca tctgtgttgt atccagcatg     60

gctcagaagg taactcaagc gcagactgaa atttctgtgg tggagaagga ggatgtgacc    120

ttggactgtg tgtatgaaac ccgtgatact acttattact tattctggta caagcaacca    180

ccaagtggag aattggtttt ccttattcgt cggaactctt ttgatgagca aaatgaaata    240

agtggtcggt attcttggaa cttccagaaa tccaccagtt ccttcaactt caccatcaca    300

gcctcacaag tcgtggactc agcagtatac ttctgtgctc tgagtgaggc aggaacctac    360

aaatacatct ttggaacagg caccaggctg aaggtattag caaatatcca gaaccctgac    420

cctgccgtgt accagctgag agactctaaa tccagtgaca agtctgtctg cctattcacc    480

gattttgatt ctcaaacaaa tgtgtcacaa agtaaggatt ctgatgtgta tatcacagac    540

aaaactgtgt tggacatgcg cagcatggac ttcaagagca acagtgctgt ggcctggagc    600

aacaaatctg actttgcatg tgcaaacgcc ttcaacaaca gcattattcc agaagacacc    660

ttcttcccca gcccagaaag ttcctgtgat gtcaagctgg tcgagaaaag ctttgaaaca    720

gatacgaacc taaactttca aaacctgtca gtgattgggt tccgaatcct cctcctgaaa    780

gtggccgggt ttaatctgct catgacgctg cggctgtggt ccagcggcag cggagagggc    840

agaggaagtc ttctaacatg cggtgacgtg gaggagaatc ccggccctat gggcttcagg    900

ctcctctgct gtgtggcctt ttgtctcctg ggagcaggcc cagtggattc tggagtcaca    960

caaaccccaa agcacctgat cacagcaact ggacagcgag tgacgctgag atgctcccct   1020

aggtctggag acctctctgt gtactggtac caacagagcc tggaccaggg cctccagttc   1080

ctcattcagt attataatgg agaagagaga gcaaaaggaa acattcttga acgattctcc   1140

gcacaacagt tccctgactt gcactctgaa ctaaacctga gctctctgga gctgggggac   1200

tcagctttgt atttctgtgc cagcagcgta gctggggggg gacaagagac ccagtacttc   1260

gggccaggca cgcggctcct ggtgctcgag gacctgaaaa acgtgttccc acccgaggtc   1320

gctgtgtttg agccatcaga agcagagatc tcccacaccc aaaaggccac actggtgtgc   1380

ctggccacag gcttctaccc cgaccacgtg gagctgagct ggtgggtgaa tgggaaggag   1440

gtgcacagtg ggtcagcac agacccgcag cccctcaagg agcagcccgc cctcaatgac   1500

tccagatact gcctgagcag ccgcctgagg gtctcggcca ccttctggca gaacccccgc   1560
```

aaccacttcc gctgtcaagt ccagttctac gggctctcgg agaatgatga gtggacacaa 1620
gatagggcca aacctgtcac ccagatcgtc agcgccgagg cctggggtag agcagactgt 1680
ggcttcacct ccgagtctta ccagcaaggg gtcctgtctg ccaccatcct ctatgagatc 1740
ttgctaggga aggccacctt gtatgccgtg ctggtcagtg ccctcgtgct gatggccatg 1800
gtcaagagaa aggattccag aggctga 1827

<210> SEQ ID NO 145
<211> LENGTH: 15
<212> TYPE: DNA
<213> ORGANISM: Artificial Sequence
<220> FEATURE:
<223> OTHER INFORMATION: TRAV17 CDR1

<400> SEQUENCE: 145
actagtataa acaat 15

<210> SEQ ID NO 146
<211> LENGTH: 21
<212> TYPE: DNA
<213> ORGANISM: Artificial Sequence
<220> FEATURE:
<223> OTHER INFORMATION: TRAV17 CDR2

<400> SEQUENCE: 146
atacgttcaa atgaaagaga g 21

<210> SEQ ID NO 147
<211> LENGTH: 36
<212> TYPE: DNA
<213> ORGANISM: Artificial Sequence
<220> FEATURE:
<223> OTHER INFORMATION: TRAV17 CDR3

<400> SEQUENCE: 147
gctacttttc ctaactttgg aaatgagaaa ttaacc 36

<210> SEQ ID NO 148
<211> LENGTH: 422
<212> TYPE: DNA
<213> ORGANISM: Artificial Sequence
<220> FEATURE:
<223> OTHER INFORMATION: TCR847 ALPHA CONSTANT DOMAIN

<400> SEQUENCE: 148
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgttgg acatgcgcag catggacttc aagagcaaca 180
gtgctgtggc ctggagcaac aaatctgact ttgcatgtgc aaacgccttc aacaacagca 240
ttattccaga agacaccttc ttccccagcc cagaaagttc ctgtgatgtc aagctggtcg 300
agaaaagctt tgaaacagat acgaacctaa actttcaaaa cctgtcagtg attgggttcc 360
gaatcctcct cctgaaagtg gccgggttta atctgctcat gacgctgcgg ctgtggtcca 420
gc 422

<210> SEQ ID NO 149
<211> LENGTH: 819
<212> TYPE: DNA
<213> ORGANISM: Artificial Sequence
<220> FEATURE:

<223> OTHER INFORMATION: TCR847 ALPHA CHAIN

<400> SEQUENCE: 149
atggaaactc tcctgggagt gtctttggtg attctatggc ttcaactggc tagggtgaac 60
agtcaacagg gagaagagga tcctcaggcc ttgagcatcc aggagggtga aaatgccacc 120
atgaactgca gttacaaaac tagtataaac aatttacagt ggtatagaca aaattcaggt 180
agaggccttg tccacctaat tttaatacgt tcaaatgaaa gagagaaaca cagtggaaga 240
ttaagagtca cgcttgacac ttccaagaaa agcagttcct tgttgatcac ggcttcccgg 300
gcagcagaca ctgcttctta cttctgtgct acttttccta actttggaaa tgagaaatta 360
acctttggga ctggaacaag actcaccatc atacccaata tccagaaccc tgaccctgcc 420
gtgtaccagc tgagagactc taaatccagt gacaagtctg tctgcctatt caccgatttt 480
gattctcaaa caaatgtgtc acaaagtaag gattctgatg tgtatatcac agacaaaact 540
gtgttggaca tgcgcagcat ggacttcaag agcaacagtg ctgtggcctg gagcaacaaa 600
tctgactttg catgtgcaaa cgccttcaac aacagcatta ttccagaaga caccttcttc 660
cccagcccag aaagttcctg tgatgtcaag ctggtcgaga aaagctttga aacagatacg 720
aacctaaact ttcaaaacct gtcagtgatt gggttccgaa tcctcctcct gaaagtggcc 780
gggtttaatc tgctcatgac gctgcggctg tggtccagc 819

<210> SEQ ID NO 150
<211> LENGTH: 14
<212> TYPE: DNA
<213> ORGANISM: Artificial Sequence
<220> FEATURE:
<223> OTHER INFORMATION: TRBV10-3 CDR1

<400> SEQUENCE: 150
gagaaccacc gcta 14

<210> SEQ ID NO 151
<211> LENGTH: 18
<212> TYPE: DNA
<213> ORGANISM: Artificial Sequence
<220> FEATURE:
<223> OTHER INFORMATION: TRBV10-3 CDR2

<400> SEQUENCE: 151
tcatatggtg ttaaagat 18

<210> SEQ ID NO 152
<211> LENGTH: 36
<212> TYPE: DNA
<213> ORGANISM: Artificial Sequence
<220> FEATURE:
<223> OTHER INFORMATION: TRBV10-3 CDR3

<400> SEQUENCE: 152
gccatcagtg agtcggagcg gtactacgag cagtac 36

<210> SEQ ID NO 153
<211> LENGTH: 537
<212> TYPE: DNA
<213> ORGANISM: Artificial Sequence
<220> FEATURE:
<223> OTHER INFORMATION: TCR847 BETA CONSTANT DOMAIN

<400> SEQUENCE: 153
gaggacctga aaaacgtgtt cccacccgag gtcgctgtgt ttgagccatc agaagcagag 60
atctcccaca cccaaaaggc cacactggtg tgcctggcca caggcttcta ccccgaccac 120
gtggagctga gctggtgggt gaatgggaag gaggtgcaca gtggggtcag cacagacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga tgagtggaca caagataggg ccaaacctgt cacccagatc 360
gtcagcgccg aggcctgggg tagagcagac tgtggcttca cctccgagtc ttaccagcaa 420
ggggtcctgt ctgccaccat cctctatgag atcttgctag ggaaggccac cttgtatgcc 480
gtgctggtca gtgccctcgt gctgatggcc atggtcaaga gaaaggattc cagaggc 537

<210> SEQ ID NO 154
<211> LENGTH: 936
<212> TYPE: DNA
<213> ORGANISM: Artificial Sequence
<220> FEATURE:
<223> OTHER INFORMATION: TCR847 BETA CHAIN

<400> SEQUENCE: 154
atgggcacaa ggttgttctt ctatgtggcc ctttgtctcc tgtggacagg acacatggat 60
gctggaatca cccagagccc aagacacaag gtcacagaga caggaacacc agtgactctg 120
agatgtcacc agactgagaa ccaccgctat atgtactggt atcgacaaga cccggggcat 180
gggctgaggc tgatccatta ctcatatggt gttaaagata ctgacaaagg agaagtctca 240
gatggctata gtgtctccag atcaaagaca gaggatttcc tcctcactct ggagtccgct 300
accagctccc agacatctgt gtacttctgt gccatcagtg agtcggagcg gtactacgag 360
cagtacttcg ggccgggcac caggctcacg gtcacagagg acctgaaaaa cgtgttccca 420
cccgaggtcg ctgtgtttga gccatcagaa gcagagatct cccacaccca aaaggccaca 480
ctggtgtgcc tggccacagg cttctacccc gaccacgtgg agctgagctg gtgggtgaat 540
gggaaggagg tgcacagtgg ggtcagcaca gacccgcagc ccctcaagga gcagcccgcc 600
ctcaatgact ccagatactg cctgagcagc cgcctgaggg tctcggccac cttctggcag 660
aacccccgca accacttccg ctgtcaagtc cagttctacg ggctctcgga gaatgatgag 720
tggacacaag atagggccaa acctgtcacc cagatcgtca gcgccgaggc ctggggtaga 780
gcagactgtg gcttcacctc cgagtcttac cagcaagggg tcctgtctgc caccatcctc 840
tatgagatct tgctagggaa ggccaccttg tatgccgtgc tggtcagtgc cctcgtgctg 900
atggccatgg tcaagagaaa ggattccaga ggctga 936

<210> SEQ ID NO 155
<211> LENGTH: 63
<212> TYPE: DNA
<213> ORGANISM: Artificial Sequence
<220> FEATURE:
<223> OTHER INFORMATION: LINKER

<400> SEQUENCE: 155
ggcagcggag agggcagagg aagtcttcta acatgcggtg acgtggagga gaatcccggc 60
cct 63

<210> SEQ ID NO 156
<211> LENGTH: 1818
<212> TYPE: DNA
<213> ORGANISM: Artificial Sequence
<220> FEATURE:

<223> OTHER INFORMATION: TCR847 FUSION

<400> SEQUENCE: 156
atggaaactc tcctgggagt gtctttggtg attctatggc ttcaactggc tagggtgaac 60
agtcaacagg gagaagagga tcctcaggcc ttgagcatcc aggagggtga aaatgccacc 120
atgaactgca gttacaaaac tagtataaac aatttacagt ggtatagaca aaattcaggt 180
agaggccttg tccacctaat tttaatacgt tcaaatgaaa gagagaaaca cagtggaaga 240
ttaagagtca cgcttgacac ttccaagaaa agcagttcct tgttgatcac ggcttcccgg 300
gcagcagaca ctgcttctta cttctgtgct acttttccta actttggaaa tgagaaatta 360
acctttggga ctggaacaag actcaccatc atacccaata tccagaaccc tgaccctgcc 420
gtgtaccagc tgagagactc taaatccagt gacaagtctg tctgcctatt caccgatttt 480
gattctcaaa caaatgtgtc acaaagtaag gattctgatg tgtatatcac agacaaaact 540
gtgttggaca tgcgcagcat ggacttcaag agcaacagtg ctgtggcctg gagcaacaaa 600
tctgactttg catgtgcaaa cgccttcaac aacagcatta ttccagaaga caccttcttc 660
cccagcccag aaagttcctg tgatgtcaag ctggtcgaga aaagctttga aacagatacg 720
aacctaaact ttcaaaacct gtcagtgatt gggttccgaa tcctcctcct gaaagtggcc 780
gggtttaatc tgctcatgac gctgcggctg tggtccagcg gcagcggaga gggcagagga 840
agtcttctaa catgcggtga cgtggaggag aatcccggcc ctatgggcac aaggttgttc 900
ttctatgtgg ccctttgtct cctgtggaca ggacacatgg atgctggaat cacccagagc 960
ccaagacaca aggtcacaga gacaggaaca ccagtgactc tgagatgtca ccagactgag 1020
aaccaccgct atatgtactg gtatcgacaa gacccggggc atgggctgag gctgatccat 1080
tactcatatg gtgttaaaga tactgacaaa ggagaagtct cagatggcta tagtgtctcc 1140
agatcaaaga cagaggattt cctcctcact ctggagtccg ctaccagctc ccagacatct 1200
gtgtacttct gtgccatcag tgagtcggag cggtactacg agcagtactt cgggccgggc 1260
accaggctca cggtcacaga ggacctgaaa aacgtgttcc cacccgaggt cgctgtgttt 1320
gagccatcag aagcagagat ctcccacacc caaaaggcca cactggtgtg cctggccaca 1380
ggcttctacc ccgaccacgt ggagctgagc tggtgggtga atgggaagga ggtgcacagt 1440
ggggtcagca cagacccgca gcccctcaag gagcagcccg ccctcaatga ctccagatac 1500
tgcctgagca gccgcctgag ggtctcggcc accttctggc agaacccccg caaccacttc 1560
cgctgtcaag tccagttcta cggctctcg gagaatgatg agtggacaca agatagggcc 1620
aaacctgtca cccagatcgt cagcgccgag gcctggggta gagcagactg tggcttcacc 1680
tccgagtctt accagcaagg ggtcctgtct gccaccatcc tctatgagat cttgctaggg 1740
aaggccacct tgtatgccgt gctggtcagt gccctcgtgc tgatggccat ggtcaagaga 1800
aaggattcca gaggctga 1818

<210> SEQ ID NO 157
<211> LENGTH: 21
<212> TYPE: DNA
<213> ORGANISM: Artificial Sequence
<220> FEATURE:
<223> OTHER INFORMATION: TRAV4 CDR1

<400> SEQUENCE: 157
aacattgcta caaatgatta t 21

<210> SEQ ID NO 158
<211> LENGTH: 15
<212> TYPE: DNA
<213> ORGANISM: Artificial Sequence
<220> FEATURE:
<223> OTHER INFORMATION: TRAV4 CDR2

<400> SEQUENCE: 158
ggatacaaga caaaa 15

<210> SEQ ID NO 159
<211> LENGTH: 42
<212> TYPE: DNA
<213> ORGANISM: Artificial Sequence
<220> FEATURE:
<223> OTHER INFORMATION: TRAV4 CDR3

<400> SEQUENCE: 159
ctcgtgggtg acttcaactc aaattccggg tatgcactca ac 42

<210> SEQ ID NO 160
<211> LENGTH: 422
<212> TYPE: DNA
<213> ORGANISM: Artificial Sequence
<220> FEATURE:
<223> OTHER INFORMATION: TCR864 ALPHA CONSTANT DOMAIN

<400> SEQUENCE: 160
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgttgg acatgcgcag catggacttc aagagcaaca 180
gtgctgtggc ctggagcaac aaatctgact ttgcatgtgc aaacgccttc aacaacagca 240
ttattccaga agacaccttc ttccccagcc cagaaagttc ctgtgatgtc aagctggtcg 300
agaaaagctt tgaaacagat acgaacctaa actttcaaaa cctgtcagtg attgggttcc 360
gaatcctcct cctgaaagtg gccgggttta atctgctcat gacgctgcgg ctgtggtcca 420
gc 422

<210> SEQ ID NO 161
<211> LENGTH: 813
<212> TYPE: DNA
<213> ORGANISM: Artificial Sequence
<220> FEATURE:
<223> OTHER INFORMATION: TCR864 ALPHA CHAIN

<400> SEQUENCE: 161
atgaggcaag tggcgagagt gatcgtgttc ctgaccctga gtactttgag ccttgctaag 60
accacccagc ccatctccat ggactcatat gaaggacaag aagtgaacat aacctgtagc 120
cacaacaaca ttgctacaaa tgattatatc acgtggtacc aacagtttcc cagccaagga 180
ccacgattta ttattcaagg atacaagaca aaagttacaa acgaagtggc ctccctgttt 240
atccctgccg acagaaagtc cagcactctg agcctgcccc gggtttccct gagcgacact 300
gctgtgtact actgcctcgt gggtgacttc aactcaaatt ccgggtatgc actcaacttc 360
ggcaaaggca cctcgctgtt ggtcacaccc catatccaga accctgaccc tgccgtgtac 420
cagctgagag actctaaatc cagtgacaag tctgtctgcc tattcaccga ttttgattct 480
caaacaaatg tgtcacaaag taaggattct gatgtgtata tcacagacaa aactgtgttg 540
gacatgcgca gcatggactt caagagcaac agtgctgtgg cctggagcaa caaatctgac 600
tttgcatgtg caaacgcctt caacaacagc attattccag aagacacctt cttccccagc 660
ccagaaagtt cctgtgatgt caagctggtc gagaaaagct ttgaaacaga tacgaaccta 720
aactttcaaa acctgtcagt gattgggttc cgaatcctcc tcctgaaagt ggccgggttt 780
aatctgctca tgacgctgcg gctgtggtcc agc 813

<210> SEQ ID NO 162
<211> LENGTH: 15
<212> TYPE: DNA
<213> ORGANISM: Artificial Sequence
<220> FEATURE:
<223> OTHER INFORMATION: TRBV7-2 CDR1

<400> SEQUENCE: 162
tcaggtcata ctgcc 15

<210> SEQ ID NO 163
<211> LENGTH: 18
<212> TYPE: DNA
<213> ORGANISM: Artificial Sequence
<220> FEATURE:
<223> OTHER INFORMATION: TRBV7-2 CDR2

<400> SEQUENCE: 163
ttccaaggca acagtgca 18

<210> SEQ ID NO 164
<211> LENGTH: 24
<212> TYPE: DNA
<213> ORGANISM: Artificial Sequence
<220> FEATURE:
<223> OTHER INFORMATION: TRBV7-2 CDR3

<400> SEQUENCE: 164
gccagcaagg tctatggcta cacc 24

<210> SEQ ID NO 165
<211> LENGTH: 531
<212> TYPE: DNA
<213> ORGANISM: Artificial Sequence
<220> FEATURE:
<223> OTHER INFORMATION: TCR864 BETA CONSTANT DOMAIN

<400> SEQUENCE: 165
gaggacctga acaaggtgtt cccacccgag gtcgctgtgt ttgagccatc agaagcagag 60
atctcccaca cccaaaaggc cacactggtg tgcctggcca caggcttctt ccccgaccac 120
gtggagctga gctggtgggt gaatgggaag gaggtgcaca gtggggtcag cacggacccg 180
cagcccctca aggagcagcc cgccctcaat gactccagat actgcctgag cagccgcctg 240
agggtctcgg ccaccttctg gcagaacccc cgcaaccact tccgctgtca agtccagttc 300
tacgggctct cggagaatga tgagtggaca caagataggg ccaaacccgt cacccagatc 360
gtcagcgccg aggcctgggg tagagcagac tgtggcttta cctcggtgtc ctaccagcaa 420
ggggtcctgt ctgccaccat cctctatgag atcctgctag ggaaggccac cctgtatgct 480
gtgctggtca gcgcccttgt gttgatggcc atggtcaaga gaaaggattt c 531

<210> SEQ ID NO 166
<211> LENGTH: 921
<212> TYPE: DNA
<213> ORGANISM: Artificial Sequence
<220> FEATURE:
<223> OTHER INFORMATION: TCR864 BETA CHAIN

<400> SEQUENCE: 166
atgggcacca ggctcctctt ctgggtggcc ttctgtctcc tgggggcata tcacacagga 60
gctggagtct cccagtcccc cagtaacaag gtcacagaga agggaaagga tgtagagctc 120
aggtgtgatc caatttcagg tcatactgcc ctttactggt accgacagag gctggggcag 180
ggcctggagt ttttaattta cttccaaggc aacagtgcac cagacaaatc agggctgccc 240
agtgatcgct tctctgcaga gaggactggg gaatccgtct ccactctgac gatccagcgc 300
acacagcagg aggactcggc cgtgtatctc tgtgccagca aggtctatgg ctacaccttc 360
ggttcgggga ccaggttaac cgttgtagag gacctgaaca aggtgttccc acccgaggtc 420
gctgtgtttg agccatcaga agcagagatc tcccacaccc aaaaggccac actggtgtgc 480
ctggccacag gcttcttccc cgaccacgtg gagctgagct ggtgggtgaa tgggaaggag 540
gtgcacagtg gggtcagcac ggacccgcag cccctcaagg agcagcccgc cctcaatgac 600
tccagatact gcctgagcag ccgcctgagg gtctcggcca ccttctggca gaacccccgc 660
aaccacttcc gctgtcaagt ccagttctac gggctctcgg agaatgatga gtggacacaa 720
gatagggcca aacccgtcac ccagatcgtc agcgccgagg cctggggtag agcagactgt 780
ggctttacct cggtgtccta ccagcaaggg gtcctgtctg ccaccatcct ctatgagatc 840
ctgctaggga aggccaccct gtatgctgtg ctggtcagcg cccttgtgtt gatggccatg 900
gtcaagagaa aggatttctg a 921

<210> SEQ ID NO 167
<211> LENGTH: 63
<212> TYPE: DNA
<213> ORGANISM: Artificial Sequence
<220> FEATURE:
<223> OTHER INFORMATION: LINKER

<400> SEQUENCE: 167
ggcagcggag agggcagagg aagtcttcta acatgcggtg acgtggagga gaatcccggc 60
cct 63

<210> SEQ ID NO 168
<211> LENGTH: 1797
<212> TYPE: DNA
<213> ORGANISM: Artificial Sequence
<220> FEATURE:
<223> OTHER INFORMATION: TCR864 FUSION

<400> SEQUENCE: 168
atgaggcaag tggcgagagt gatcgtgttc ctgaccctga gtactttgag ccttgctaag 60
accacccagc ccatctccat ggactcatat gaaggacaag aagtgaacat aacctgtagc 120
cacaacaaca ttgctacaaa tgattatatc acgtggtacc aacagtttcc cagccaagga 180
ccacgattta ttattcaagg atacaagaca aaagttacaa acgaagtggc ctccctgttt 240
atccctgccg acagaaagtc cagcactctg agcctgcccc gggtttccct gagcgacact 300
gctgtgtact actgcctcgt gggtgacttc aactcaaatt ccgggtatgc actcaacttc 360
ggcaaaggca cctcgctgtt ggtcacaccc catatccaga accctgaccc tgccgtgtac 420
cagctgagag actctaaatc cagtgacaag tctgtctgcc tattcaccga ttttgattct 480
caaacaaatg tgtcacaaag taaggattct gatgtgtata tcacagacaa aactgtgttg 540
gacatgcgca gcatggactt caagagcaac agtgctgtgg cctggagcaa caaatctgac 600

```
tttgcatgtg caaacgcctt caacaacagc attattccag aagacacctt cttccccagc    660

ccagaaagtt cctgtgatgt caagctggtc gagaaaagct ttgaaacaga tacgaaccta    720

aactttcaaa acctgtcagt gattgggttc cgaatcctcc tcctgaaagt ggccgggttt    780

aatctgctca tgacgctgcg gctgtggtcc agcggcagcg gagagggcag aggaagtctt    840

ctaacatgcg gtgacgtgga ggagaatccc ggccctatgg gcaccaggct cctcttctgg    900

gtggccttct gtctcctggg ggcatatcac acaggagctg gagtctccca gtcccccagt    960

aacaaggtca cagagaaggg aaaggatgta gagctcaggt gtgatccaat ttcaggtcat   1020

actgcccttt actggtaccg acagaggctg ggcagggcc tggagttttt aatttacttc   1080

caaggcaaca gtgcaccaga caaatcaggg ctgcccagtg atcgcttctc tgcagagagg   1140

actggggaat ccgtctccac tctgacgatc cagcgcacac agcaggagga ctcggccgtg   1200

tatctctgtg ccagcaaggt ctatggctac accttcggtt cggggaccag gttaaccgtt   1260

gtagaggacc tgaacaaggt gttcccaccc gaggtcgctg tgtttgagcc atcagaagca   1320

gagatctccc acacccaaaa ggccacactg gtgtgcctgg ccacaggctt cttccccgac   1380

cacgtggagc tgagctggtg ggtgaatggg aaggaggtgc acagtggggt cagcacggac   1440

ccgcagcccc tcaaggagca gcccgccctc aatgactcca gatactgcct gagcagccgc   1500

ctgagggtct cggccacctt ctggcagaac ccccgcaacc acttccgctg tcaagtccag   1560

ttctacgggc tctcggagaa tgatgagtgg acacaagata gggccaaacc cgtcacccag   1620

atcgtcagcg ccgaggcctg gggtagagca gactgtggct ttacctcggt gtcctaccag   1680

caaggggtcc tgtctgccac catcctctat gagatcctgc tagggaaggc caccctgtat   1740

gctgtgctgg tcagcgccct tgtgttgatg gccatggtca agagaaagga tttctga      1797
```

<210> SEQ ID NO 169
<211> LENGTH: 92
<212> TYPE: PRT
<213> ORGANISM: Artificial Sequence
<220> FEATURE:
<223> OTHER INFORMATION: TRAV17 VARIABLE DOMAIN

<400> SEQUENCE: 169

```
Ser Gln Gln Gly Glu Glu Asp Pro Gln Ala Leu Ser Ile Gln Glu Gly
1               5                   10                  15

Glu Asn Ala Thr Met Asn Cys Ser Tyr Lys Thr Ser Ile Asn Asn Leu
            20                  25                  30

Gln Trp Tyr Arg Gln Asn Ser Gly Arg Gly Leu Val His Leu Ile Leu
        35                  40                  45

Ile Arg Ser Asn Glu Arg Glu Lys His Ser Gly Arg Leu Arg Val Thr
    50                  55                  60

Leu Asp Thr Ser Lys Lys Ser Ser Ser Leu Leu Ile Thr Ala Ser Arg
65                  70                  75                  80

Ala Ala Asp Thr Ala Ser Tyr Phe Cys Ala Thr Asp
                85                  90
```

<210> SEQ ID NO 170
<211> LENGTH: 96
<212> TYPE: PRT
<213> ORGANISM: Artificial Sequence
<220> FEATURE:
<223> OTHER INFORMATION: TRBV11-2 VARIABLE DOMAIN

<400> SEQUENCE: 170

```
Glu Ala Gly Val Ala Gln Ser Pro Arg Tyr Lys Ile Ile Glu Lys Arg
```

```
1               5                   10                  15

Gln Ser Val Ala Phe Trp Cys Asn Pro Ile Ser Gly His Ala Thr Leu
            20                  25                  30

Tyr Trp Tyr Gln Gln Ile Leu Gly Gln Gly Pro Lys Leu Leu Ile Gln
        35                  40                  45

Phe Gln Asn Asn Gly Val Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Lys Leu Glu Asp Ser Ala Val Tyr Leu Cys Ala Ser Ser Leu
                85                  90                  95


<210> SEQ ID NO 171
<211> LENGTH: 96
<212> TYPE: PRT
<213> ORGANISM: Artificial Sequence
<220> FEATURE:
<223> OTHER INFORMATION: TRAV19 VARIABLE DOMAIN

<400> SEQUENCE: 171

Ala Gln Lys Val Thr Gln Ala Gln Thr Glu Ile Ser Val Val Glu Lys
1               5                   10                  15

Glu Asp Val Thr Leu Asp Cys Val Tyr Glu Thr Arg Asp Thr Thr Tyr
            20                  25                  30

Tyr Leu Phe Trp Tyr Lys Gln Pro Pro Ser Gly Glu Leu Val Phe Leu
        35                  40                  45

Ile Arg Arg Asn Ser Phe Asp Glu Gln Asn Glu Ile Ser Gly Arg Tyr
    50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95


<210> SEQ ID NO 172
<211> LENGTH: 95
<212> TYPE: PRT
<213> ORGANISM: Artificial Sequence
<220> FEATURE:
<223> OTHER INFORMATION: TRBV9 VARIABLE DOMAIN

<400> SEQUENCE: 172

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Val
                85                  90                  95


<210> SEQ ID NO 173
<211> LENGTH: 92
<212> TYPE: PRT
<213> ORGANISM: Artificial Sequence
<220> FEATURE:
```

<223> OTHER INFORMATION: TRAV17 VARIABLE

<400> SEQUENCE: 173

Ser Gln Gln Gly Glu Glu Asp Pro Gln Ala Leu Ser Ile Gln Glu Gly
1 5 10 15

Glu Asn Ala Thr Met Asn Cys Ser Tyr Lys Thr Ser Ile Asn Asn Leu
20 25 30

Gln Trp Tyr Arg Gln Asn Ser Gly Arg Gly Leu Val His Leu Ile Leu
35 40 45

Ile Arg Ser Asn Glu Arg Glu Lys His Ser Gly Arg Leu Arg Val Thr
50 55 60

Leu Asp Thr Ser Lys Lys Ser Ser Ser Leu Leu Ile Thr Ala Ser Arg
65 70 75 80

Ala Ala Asp Thr Ala Ser Tyr Phe Cys Ala Thr Phe
85 90

<210> SEQ ID NO 174
<211> LENGTH: 95
<212> TYPE: PRT
<213> ORGANISM: Artificial Sequence
<220> FEATURE:
<223> OTHER INFORMATION: TRBV10-3 VARIABLE

<400> SEQUENCE: 174

Asp Ala Gly Ile Thr Gln Ser Pro Arg His Lys Val Thr Glu Thr Gly
1 5 10 15

Thr Pro Val Thr Leu Arg Cys His Gln Thr Glu Asn His Arg Tyr Met
20 25 30

Tyr Trp Tyr Arg Gln Asp Pro Gly His Gly Leu Arg Leu Ile His Tyr
35 40 45

Ser Tyr Gly Val Lys Asp Thr Asp Lys Gly Glu Val Ser Asp Gly Tyr
50 55 60

Ser Val Ser Arg Ser Lys Thr Glu Asp Phe Leu Leu Thr Leu Glu Ser
65 70 75 80

Ala Thr Ser Ser Gln Thr Ser Val Tyr Phe Cys Ala Ile Ser Glu
85 90 95

<210> SEQ ID NO 175
<211> LENGTH: 92
<212> TYPE: PRT
<213> ORGANISM: Artificial Sequence
<220> FEATURE:
<223> OTHER INFORMATION: TRAV4 VARIABLE

<400> SEQUENCE: 175

Leu Ala Lys Thr Thr Gln Pro Ile Ser Met Asp Ser Tyr Glu Gly Gln
1 5 10 15

Glu Val Asn Ile Thr Cys Ser His Asn Asn Ile Ala Thr Asn Asp Tyr
20 25 30

Ile Thr Trp Tyr Gln Gln Phe Pro Ser Gln Gly Pro Arg Phe Ile Ile
35 40 45

Gln Gly Tyr Lys Thr Lys Val Thr Asn Glu Val Ala Ser Leu Phe Ile
50 55 60

Pro Ala Asp Arg Lys Ser Ser Thr Leu Ser Leu Pro Arg Val Ser Leu
65 70 75 80

Ser Asp Thr Ala Val Tyr Tyr Cys Leu Val Gly Asp
85 90

<210> SEQ ID NO 176
<211> LENGTH: 95
<212> TYPE: PRT
<213> ORGANISM: Artificial Sequence
<220> FEATURE:
<223> OTHER INFORMATION: TRBV7-2 VARIABLE

<400> SEQUENCE: 176

```
Gly Ala Gly Val Ser Gln Ser Pro Ser Asn Lys Val Thr Glu Lys Gly
1               5                   10                  15

Lys Asp Val Glu Leu Arg Cys Asp Pro Ile Ser Gly His Thr Ala Leu
            20                  25                  30

Tyr Trp Tyr Arg Gln Arg Leu Gly Gln Gly Leu Glu Phe Leu Ile Tyr
        35                  40                  45

Phe Gln Gly Asn Ser Ala Pro Asp Lys Ser Gly Leu Pro Ser Asp Arg
    50                  55                  60

Phe Ser Ala Glu Arg Thr Gly Glu Ser Val Ser Thr Leu Thr Ile Gln
65                  70                  75                  80

Arg Thr Gln Gln Glu Asp Ser Ala Val Tyr Leu Cys Ala Ser Lys
                85                  90                  95
```

<210> SEQ ID NO 177
<211> LENGTH: 24
<212> TYPE: PRT
<213> ORGANISM: Artificial Sequence
<220> FEATURE:
<223> OTHER INFORMATION: RAS

<400> SEQUENCE: 177

```
Met Thr Glu Tyr Lys Leu Val Val Val Gly Ala Gly Gly Val Gly Lys
1               5                   10                  15

Ser Ala Leu Thr Ile Gln Leu Ile
            20
```

<210> SEQ ID NO 178
<211> LENGTH: 23
<212> TYPE: PRT
<213> ORGANISM: Artificial Sequence
<220> FEATURE:
<223> OTHER INFORMATION: RAS G12 Mutated Fragment

<400> SEQUENCE: 178

```
Met Thr Glu Tyr Lys Leu Val Val Val Gly Ala Gly Val Gly Lys Ser
1               5                   10                  15

Ala Leu Thr Ile Gln Leu Ile
            20
```

<210> SEQ ID NO 179
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (1)..(1)
<223> OTHER INFORMATION: Xaa can be any naturally occurring amino acid

<400> SEQUENCE: 179

```
Xaa Gly Val Gly Lys Ser Ala Leu Thr Ile
1               5                   10
```

<210> SEQ ID NO 180
<211> LENGTH: 10

<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (2)..(2)
<223> OTHER INFORMATION: Xaa can be any naturally occurring amino acid

<400> SEQUENCE: 180

Ala Xaa Gly Val Gly Lys Ser Ala Leu Thr
1 5 10

<210> SEQ ID NO 181
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (3)..(3)
<223> OTHER INFORMATION: Xaa can be any naturally occurring amino acid

<400> SEQUENCE: 181

Gly Ala Xaa Gly Val Gly Lys Ser Ala Leu
1 5 10

<210> SEQ ID NO 182
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (4)..(4)
<223> OTHER INFORMATION: Xaa can be any naturally occurring amino acid

<400> SEQUENCE: 182

Val Gly Ala Xaa Gly Val Gly Lys Ser Ala
1 5 10

<210> SEQ ID NO 183
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (5)..(5)
<223> OTHER INFORMATION: Xaa can be any naturally occurring amino acid

<400> SEQUENCE: 183

Val Val Gly Ala Xaa Gly Val Gly Lys Ser
1 5 10

<210> SEQ ID NO 184
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (6)..(6)
<223> OTHER INFORMATION: Xaa can be any naturally occurring amino acid

<400> SEQUENCE: 184

Val Val Val Gly Ala Xaa Gly Val Gly Lys
1 5 10

<210> SEQ ID NO 185
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (7)..(7)
<223> OTHER INFORMATION: Xaa can be any naturally occurring amino acid

<400> SEQUENCE: 185

Leu Val Val Val Gly Ala Xaa Gly Val Gly
1 5 10

<210> SEQ ID NO 186
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (8)..(8)
<223> OTHER INFORMATION: Xaa can be any naturally occurring amino acid

<400> SEQUENCE: 186

Lys Leu Val Val Val Gly Ala Xaa Gly Val
1 5 10

<210> SEQ ID NO 187
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (9)..(9)
<223> OTHER INFORMATION: Xaa can be any naturally occurring amino acid

<400> SEQUENCE: 187

Tyr Lys Leu Val Val Val Gly Ala Xaa Gly
1 5 10

<210> SEQ ID NO 188
<211> LENGTH: 10
<212> TYPE: PRT
<213> ORGANISM: Artificial Sequence
<220> FEATURE:
<223> OTHER INFORMATION: RAS G12 Mutated Fragment
<220> FEATURE:
<221> NAME/KEY: misc_feature
<222> LOCATION: (10)..(10)
<223> OTHER INFORMATION: Xaa can be any naturally occurring amino acid

<400> SEQUENCE: 188

Glu Tyr Lys Leu Val Val Val Gly Ala Xaa
1 5 10

<210> SEQ ID NO 189
<211> LENGTH: 10
<212> TYPE: PRT
<213> ORGANISM: Artificial Sequence
<220> FEATURE:
<223> OTHER INFORMATION: KLV_G

<400> SEQUENCE: 189

Lys Leu Val Val Val Gly Ala Gly Gly Val
1 5 10

<210> SEQ ID NO 190
<211> LENGTH: 9
<212> TYPE: PRT
<213> ORGANISM: Artificial Sequence
<220> FEATURE:
<223> OTHER INFORMATION: VV_G

<400> SEQUENCE: 190

Val Val Gly Ala Gly Gly Val Gly Lys
1 5

<210> SEQ ID NO 191
<211> LENGTH: 10
<212> TYPE: PRT
<213> ORGANISM: Artificial Sequence
<220> FEATURE:
<223> OTHER INFORMATION: VVV_G

<400> SEQUENCE: 191

Val Val Val Gly Ala Gly Gly Val Gly Lys
1 5 10

<210> SEQ ID NO 192
<211> LENGTH: 10
<212> TYPE: PRT
<213> ORGANISM: Artificial Sequence
<220> FEATURE:
<223> OTHER INFORMATION: GA_G

<400> SEQUENCE: 192

Gly Ala Gly Gly Val Gly Lys Ser Ala Leu
1 5 10

<210> SEQ ID NO 193
<211> LENGTH: 25
<212> TYPE: PRT
<213> ORGANISM: Artificial Sequence
<220> FEATURE:
<223> OTHER INFORMATION: WT

<400> SEQUENCE: 193

Met Thr Glu Tyr Lys Leu Val Val Val Gly Ala Gly Gly Val Gly Lys
1 5 10 15

Ser Ala Leu Thr Ile Gln Leu Ile Gln
20 25

<210> SEQ ID NO 194
<211> LENGTH: 25
<212> TYPE: PRT
<213> ORGANISM: Artificial Sequence
<220> FEATURE:
<223> OTHER INFORMATION: G12A

<400> SEQUENCE: 194

Met Thr Glu Tyr Lys Leu Val Val Val Gly Ala Ala Gly Val Gly Lys
1 5 10 15

Ser Ala Leu Thr Ile Gln Leu Ile Gln
20 25

<210> SEQ ID NO 195
<211> LENGTH: 25

<212> TYPE: PRT
<213> ORGANISM: Artificial Sequence
<220> FEATURE:
<223> OTHER INFORMATION: G12C

<400> SEQUENCE: 195

Met Thr Glu Tyr Lys Leu Val Val Val Gly Ala Cys Gly Val Gly Lys
1 5 10 15

Ser Ala Leu Thr Ile Gln Leu Ile Gln
20 25

<210> SEQ ID NO 196
<211> LENGTH: 25
<212> TYPE: PRT
<213> ORGANISM: Artificial Sequence
<220> FEATURE:
<223> OTHER INFORMATION: G12D

<400> SEQUENCE: 196

Met Thr Glu Tyr Lys Leu Val Val Val Gly Ala Asp Gly Val Gly Lys
1 5 10 15

Ser Ala Leu Thr Ile Gln Leu Ile Gln
20 25

<210> SEQ ID NO 197
<211> LENGTH: 25
<212> TYPE: PRT
<213> ORGANISM: Artificial Sequence
<220> FEATURE:
<223> OTHER INFORMATION: G12R

<400> SEQUENCE: 197

Met Thr Glu Tyr Lys Leu Val Val Val Gly Ala Arg Gly Val Gly Lys
1 5 10 15

Ser Ala Leu Thr Ile Gln Leu Ile Gln
20 25

<210> SEQ ID NO 198
<211> LENGTH: 25
<212> TYPE: PRT
<213> ORGANISM: Artificial Sequence
<220> FEATURE:
<223> OTHER INFORMATION: G12S

<400> SEQUENCE: 198

Met Thr Glu Tyr Lys Leu Val Val Val Gly Ala Ser Gly Val Gly Lys
1 5 10 15

Ser Ala Leu Thr Ile Gln Leu Ile Gln
20 25

<210> SEQ ID NO 199
<211> LENGTH: 25
<212> TYPE: PRT
<213> ORGANISM: Artificial Sequence
<220> FEATURE:
<223> OTHER INFORMATION: G12V

<400> SEQUENCE: 199

Met Thr Glu Tyr Lys Leu Val Val Val Gly Ala Val Gly Val Gly Lys
1 5 10 15

Ser Ala Leu Thr Ile Gln Leu Ile Gln
20 25

<210> SEQ ID NO 200

-continued

<211> LENGTH: 20
<212> TYPE: PRT
<213> ORGANISM: Artificial Sequence
<220> FEATURE:
<223> OTHER INFORMATION: CMV pp65- NLV (A*02:01)

<400> SEQUENCE: 200

Gly Ile Leu Ala Arg Asn Leu Val Pro Met Val Ala Thr Val Gln Gly
1 5 10 15

Gln Asn Leu Lys
20

<210> SEQ ID NO 201
<211> LENGTH: 20
<212> TYPE: PRT
<213> ORGANISM: Artificial Sequence
<220> FEATURE:
<223> OTHER INFORMATION: Influenza A NP - ILR (A*03:01)

<400> SEQUENCE: 201

Ala Arg Ser Ala Leu Ile Leu Arg Gly Ser Val Ala His Lys Ser Cys
1 5 10 15

Leu Pro Ala Cys
20

<210> SEQ ID NO 202
<211> LENGTH: 20
<212> TYPE: PRT
<213> ORGANISM: Artificial Sequence
<220> FEATURE:
<223> OTHER INFORMATION: EBV EBNA4 - IVT (A*11:01)

<400> SEQUENCE: 202

Lys Lys Cys Arg Ala Ile Val Thr Asp Phe Ser Val Ile Lys Ala Ile
1 5 10 15

Glu Glu Glu His
20

<210> SEQ ID NO 203
<211> LENGTH: 20
<212> TYPE: PRT
<213> ORGANISM: Artificial Sequence
<220> FEATURE:
<223> OTHER INFORMATION: CMV pp65 - TPR (B*07:02)

<400> SEQUENCE: 203

Thr Thr Glu Arg Lys Thr Pro Arg Val Thr Gly Gly Gly Ala Met Ala
1 5 10 15

Gly Ala Ser Thr
20

COMPOSITIONS AND METHODS FOR TARGETING MUTANT RAS

CROSS-REFERENCE TO RELATED APPLICATIONS

This application is the U.S. national phase application filed under 35 U.S.C. § 371 claiming benefit to International Patent Application No. PCT/US2020/014988, filed on Jan. 24, 2020, which is entitled to priority to U.S. Provisional Application Ser. No. 62/796,733, filed on Jan. 25, 2019, each of which is incorporated by reference herein in its entirety.

BACKGROUND OF THE INVENTION

Somatic mutations have been identified as common drivers of oncogenesis. An activating point mutation in the Ras gene was the first somatic point mutation identified in human cancer. RAS mutations are the most common somatic mutations found in human cancer and they contribute to the pathogenesis of a variety of highly prevalent malignancies including lung, colorectal and pancreatic ductal adenocarcinomas. Mutant RAS is an attractive target for the treatment of cancer as it is considered a driver mutation that is uniquely expressed by cancer cells and is important for tumor growth and survival. These mutations usually involve the codon 12 position of the RAS protein, and the amino acid changes are highly conserved, most frequently resulting from G12C, G12D, G12R and G12V amino acid substitutions. Pathologic RAS mutations are gain-of-function mutations that cause constitutive activation of intracellular GTPase signaling which promotes cell growth. RAS mutations may be found at high frequencies in certain cancer types. For example, G12D and G12V mutations are present in 60% to 70% of pancreatic cancers and 20% to 30% of colorectal cancers. Unfortunately, there are no effective pharmacological inhibitors of the RAS oncoproteins.

Thus, there is a need in the art for compositions and methods for treatment of mutant RAS-associated cancer. The present invention addresses and meets these and other needs.

SUMMARY OF THE INVENTION

In one aspect, the present invention provides an immunogenic composition comprising a mutant RAS peptide comprising a mutation at a position relative to G12 of wildtype RAS. In one embodiment, the peptide comprises a G12C, G12D, G12R, or G12V mutation. In one embodiment, the mutant RAS peptide comprises 9 or 10 amino acid residues.

In one embodiment, the mutant RAS peptide comprises an amino acid sequence that is at least 80% homologous to an amino acid sequence selected from SEQ ID NOs:1-16. In one embodiment, the mutant RAS peptide comprises an amino acid sequence selected from SEQ ID NOs:1-16.

In one embodiment, the present invention provides an isolated nucleic acid molecule comprising a nucleic acid sequence encoding a mutant RAS peptide comprising a mutation at a position relative to G12 of wildtype RAS.

In one embodiment, the present invention provides a cell modified to comprise or express a mutant RAS peptide comprising a mutation at a position relative to G12 of wildtype RAS. In one embodiment, the cell is an immune cell. In one embodiment, the immune cell is selected from the group consisting of an antigen presenting cell, B cell, dendritic cell, macrophage, Langerhans cell, T cell, NK cell, NK T cell.

In one aspect, the present invention provides a method of inducing an immune response in a subject comprising administering to the subject the immunological composition comprising a mutant RAS peptide comprising a mutation at a position relative to G12 of wildtype RAS or a nucleic acid molecule encoding a mutant RAS peptide comprising a mutation at a position relative to G12 of wildtype RAS.

In one embodiment, the method comprises identifying the HLA type of a subject and administering the subject a composition comprising or encoding a mutant RAS peptide comprising a mutation at a position relative to G12 of wildtype RAS, wherein the mutant RAS peptide binds to the identified HLA molecule of the subject. In one embodiment, the subject has or is at risk for having a RAS-associated cancer. In one embodiment, the cancer is selected from the group consisting of pancreatic cancer, pancreatic ductal adenocarcinoma (PDA), colon cancer, colorectal adenocarcinoma, myeloma, multiple myeloma, lung adenocarcinoma, melanoma, uterine cancer, thyroid cancer, acute myelogenous leukemia (AML), urothelial cancer, gastric adenocarcinoma and cervical adenocarcinoma, head and neck squamous cell carcinoma (SCC), Diffuse large B-cell lymphoma (DLBCL), esophageal adenocarcinoma, Chronic lymphocytic leukemia (CLL), lung SCC, small cell lung cancer (SCLC), renal papillary cancer, Hepatocellular carcinoma (HCC), breast cancer, cervical SCC, ovarian adenocarcinoma, adrenal cancer, prostate cancer, neuroblastoma, glioblastoma multiforme (GBM), medulloblastoma, Renal cell carcinoma (RCC), esophageal SCC, osteosarcoma, sarcoma, and small intestine neuroendocrine tumor (NET).

In one aspect, the present invention provides a method of inducing an immune response in a subject comprising contacting a cell with a composition comprising a mutant RAS peptide comprising a mutation at a position relative to G12 of wildtype RAS, thereby stimulating the cell; and administering the stimulated cell to the subject. In one embodiment, the method comprises contacting a naïve T cell of the subject with an antigen presenting cell presenting the mutant RAS peptide, thereby stimulating the T cell. In one embodiment, the cell is autologous to the subject. In one embodiment, the T cell and antigen presenting cell are autologous to the subject.

In one aspect, the present invention provides a composition comprising a T-cell receptor (TCR) that specifically binds to a mutant RAS (mRAS) peptide in the context of an HLA molecule selected from the group consisting of: HLA-A*02:01, HLA-A*03:01, HLA-A*11:01, and HLA-B*07:02. In one embodiment, the RAS peptide comprises a mutation at a position corresponding to G12 relative to wildtype RAS. In one embodiment, the mutation of the mRAS peptide corresponds to a mutation selected from the group consisting of G12C, G12D, G12R, and G12V; relative to wildtype RAS.

In one embodiment, the TCR comprises at least one CDR selected from the group consisting of: TRAV39 CDR1, TRAV39 CDR2, TRAV39 CDR3, TRBV20-1 CDR1, TRBV20-1 CDR2, and TRBV20-1 CDR3. In one embodiment, the TCR comprises TRAV39 CDR1, TRAV39 CDR2, TRAV39 CDR3, TRBV20-1 CDR1, TRBV20-1 CDR2, and TRBV20-1 CDR3.

In one embodiment, the TCR comprises at least one CDR selected from the group consisting of: TRAV12-1 CDR1, TRAV12-1 CDR2, TRAV12-1 CDR3, TRBV28 CDR1, TRBV28 CDR2, and TRBV28 CDR3. In one embodiment, the TCR comprises TRAV12-1 CDR1, TRAV12-1 CDR2, TRAV12-1 CDR3, TRBV28 CDR1, TRBV28 CDR2, and TRBV28 CDR3.

In one embodiment, the TCR comprises at least one CDR selected from the group consisting of: TRAV17 CDR1, TRAV17 CDR2, TRAV17 CDR3, TRBV10-3 CDR1, TRBV10-3 CDR2, and TRBV10-3 CDR3. In one embodiment, the TCR comprises TRAV17 CDR1, TRAV17 CDR2, TRAV17 CDR3, TRBV10-3 CDR1, TRBV10-3 CDR2, and TRBV10-3 CDR3.

In one embodiment, the TCR comprises at least one CDR selected from the group consisting of: TRAV17 CDR1, TRAV17 CDR2, TRAV17 CDR3, TRBV11-2 CDR1, TRBV11-2 CDR2, and TRBV11-2 CDR3. In one embodiment, the TCR comprises TRAV17 CDR1, TRAV17 CDR2, TRAV17 CDR3, TRBV11-2 CDR1, TRBV11-2 CDR2, and TRBV11-2 CDR3.

In one embodiment, the TCR comprises at least one CDR selected from the group consisting of: TRAV19 CDR1, TRAV19 CDR2, TRAV19 CDR3, TRBV9 CDR1, TRBV9 CDR2, and TRBV9 CDR3. In one embodiment, the TCR comprises TRAV19 CDR1, TRAV19 CDR2, TRAV19 CDR3, TRBV9 CDR1, TRBV9 CDR2, and TRBV9 CDR3.

In one embodiment, the TCR comprises at least one CDR selected from the group consisting of: TRAV4 CDR1, TRAV4 CDR2, TRAV4 CDR3, TRBV7-2 CDR1, TRBV7-2 CDR2, and TRBV7-2 CDR3. In one embodiment, the TCR comprises TRAV4 CDR1, TRAV4 CDR2, TRAV4 CDR3, TRBV7-2 CDR1, TRBV7-2 CDR2, and TRBV7-2 CDR3.

In one embodiment, the composition comprises a fusion polypeptide comprising a TCR α chain and a TCR β chain. In one embodiment, the fusion polypeptide comprises a linker domain. In one embodiment, the linker domain is a cleavable linker domain.

In one aspect, the present invention provides a composition comprising an isolated nucleic acid molecule encoding a TCR that specifically binds to a mutant RAS (mRAS) peptide in the context of an HLA molecule selected from the group consisting of: HLA-A*02:01, HLA-A*03:01, HLA-A*11:01, and HLA-B*07:02.

In one aspect, the present invention provides a cell modified to express a T-cell receptor (TCR) that specifically binds to a mutant RAS (mRAS) peptide in the context of an HLA molecule selected from the group consisting of: HLA-A*02:01, HLA-A*03:01, HLA-A*11:01, and HLA-B*07:02. In one embodiment, the mRAS peptide comprises a mutation at a position corresponding to G12 relative to wildtype RAS. In one embodiment, the mutation of the mRAS peptide corresponds to a mutation selected from the group consisting of G12C, G12D, G12R, and G12V; relative to wildtype RAS.

In one embodiment, the cell is modified to express a fusion polypeptide comprising a TCR α chain and a TCR β chain. In one embodiment, the cell is genetically modified by introduction of an isolated nucleic acid molecule encoding a polypeptide comprising at least one of: a TCR alpha chain and a TCR beta chain. In one embodiment, the cell is an immune cell. In one embodiment, the immune cell is selected from the group consisting of a T cell, NK cell, and NK T cell. In one embodiment, the cell is autologous to a subject having a cancer associated with RAS. In one embodiment, the cell is autologous to a subject having a HLA type selected from the group consisting of: HLA-A*02:01, HLA-A*03:01, HLA-A*11:01, and HLA-B*07:02.

In one aspect, the present invention provides a method of treating a subject having a cancer associated with mRAS comprising administering to the subject a cell modified to express a T-cell receptor (TCR) that specifically binds to a mutant RAS (mRAS) peptide in the context of an HLA molecule selected from the group consisting of: HLA-A*02:01, HLA-A*03:01, HLA-A*11:01, and HLA-B*07:02. In one embodiment, the subject has a cancer selected from the group consisting of pancreatic cancer, pancreatic ductal adenocarcinoma (PDA), colon cancer, colorectal adenocarcinoma, myeloma, multiple myeloma, lung adenocarcinoma, melanoma, uterine cancer, thyroid cancer, acute myelogenous leukemia (AML), urothelial cancer, gastric adenocarcinoma and cervical adenocarcinoma, head and neck squamous cell carcinoma (SCC), Diffuse large B-cell lymphoma (DLBCL), esophageal adenocarcinoma, Chronic lymphocytic leukemia (CLL), lung SCC, small cell lung cancer (SCLC), renal papillary cancer, Hepatocellular carcinoma (HCC), breast cancer, cervical SCC, ovarian adenocarcinoma, adrenal cancer, prostate cancer, neuroblastoma, glioblastoma multiforme (GBM), medulloblastoma, Renal cell carcinoma (RCC), esophageal SCC, osteosarcoma, sarcoma, and small intestine neuroendocrine tumor (NET).

In one embodiment, the method comprises identifying the HLA type of the subject. In one embodiment, the method comprises isolating one or more cells of the subject and modifying the one or more cells to express the TCR. In one embodiment, the method comprises modifying the one or more cells to express the TCR by contacting the one or more cells with an isolated nucleic acid molecule that encodes one or more of: a TCR alpha chain and a TCR beta chain.

BRIEF DESCRIPTION OF THE DRAWINGS

The foregoing summary, as well as the following detailed description of exemplary embodiments of the invention, will be better understood when read in conjunction with the appended drawings. It should be understood, however, that the invention is not limited to the precise arrangements and instrumentalities of the embodiments shown in the drawings. In the drawings:

FIG. 4A and FIG. 4B depicts the results of exemplary experiments demonstrating the predicted affinity of G12 mRAS peptides to various HLA molecules. FIG. 4A depicts a heatmap representing computational prediction of mRAS epitopes with <500 nM affinity using antigen.garnish. Also represented are HLA frequencies in the USA population and KRAS mutation frequencies occurring in pancreatic adenocarcinoma (PDA), colorectal carcinoma (CRC) and lung adenocarcinoma (LAC). FIG. 4B depicts a table summarizing the predicted binding of mRAS epitopes to various HLA molecules.

FIG. 5 depicts the results of exemplary experiments using a fluorescence polarization assay to determine peptide-MHC binding. The affinity of various mRAS peptides to specific HLA molecules is shown.

(FIG. 6A) Competitive peptide binding fluorescence polarization assay. Strong binding affinity is indicated by a log[IC50]<3.7 (dashed line). (FIG. 6B) Peptide stability by scintillation proximity assay. Stability of published T cell epitopes is indicated by grey area (range) and dashed line (mean).

FIG. 7A through FIG. 7E depict the results of experiments using generated monoallelic RAS tandem minigene (TMG) cell lines. (FIG. 7A) Schematic of lentiviral vector constructs. (FIG. 7B) FACS plots of HLA/RAS TMG modified K56 cell lines indicated by mCherry and GFP positivity. Verification of (FIG. 7C) HLA class I and (FIG. 7D) HLA-specific expression of RAS TMG cell lines by FACS. FIG. 7E depicts a table of wildtype and mRAS long peptide sequences as well as viral control peptides encoded by the RAS TMG construct.

(FIG. 8A) A*03:01-restricted KRAS G12D epitope VVV_D. (FIG. 8B) A*03:01-restricted KRAS G12V epitope VV_V. (FIG. 8C) A*03:01-restricted RAS G12V epitope VVV_V. (FIG. 8D) A*03:01-restricted RAS G12R epitope VV_R. (FIG. 8E) A*11:01-restricted RAS G12D epitope VV_D. (FIG. 8F) A*11:01-restricted RAS G12D epitope VVV_D. (FIG. 8G) A*11:01-restricted RAS G12V epitope VVV_V. (FIG. 8H) A*11:01-restricted RAS G12V epitope VV_V. (FIG. 8I) A*11:01-restricted RAS G12R epitope VV_R. (FIG. 8J) B*07:02-restricted RAS G12R epitope GA_R.

(FIG. 13D-FIG. 13F) Representative peptide-MHC multimer staining results of donors highlighted by red symbols.

FIG. 20 depicts a table summarizing additional TCR constructs, their KRAS mutation specificity, HLA restriction, identity of alpha and beta chains, and associated CDR3 amino acid sequences.

(FIG. 25A) Validation of TCR expression by peptide-MHC multimer staining of lentiviral-transduced Jurkat Reporter cells. (FIG. 25B) Assessment of TCR avidity by Jurkat Reporter cells. (FIG. 25C) Assessment of TCR specificity and cross-reactivity to alternative mutant KRAS epitopes by Jurkat Reporter assay. TCR831 exhibits specificity for RAS G12V (VVV_V) but not wildtype. Cross reactivity was observed to RAS G12C (VVV_C). (FIG. 25D) TCR activation of Jurkat Reporter cells following coculture with A*11:01 positive RAS G12V tumor cell lines. (FIG. 25E) Expression of TCR831 on primary CD8+ T cells. (FIG. 25F) 4-hr 51Cr assay results indicating specific lysis of K562-A*11:01 cells pulsed with G12V peptide (blue) and expressing RAS TMG construct (red)—but not wildtype (black). (FIG. 25G) 4-hr 51Cr assay results indicating specific lysis of A*11:01 positive RAS G12V tumor cell lines at effector to target ratio 10:1. Cell line coloring corresponds to that in FIG. 25C.

(FIG. 26A) Validation of TCR expression by peptide-MHC multimer staining of lentiviral-transduced Jurkat Reporter cells. (FIG. 26B) Assessment of TCR avidity by Jurkat Reporter cells. (FIG. 26C) Assessment of TCR specificity and cross-reactivity to alternative mutant RAS epitopes by Jurkat Reporter assay. TCR831 exhibits specificity for RAS G12V (VVV_V) but not wildtype. Cross reactivity was observed to RAS G12C (VVV_C). (FIG. 26D) TCR activation of Jurkat Reporter cells following coculture with A*11:01 positive RAS G12V tumor cell lines. (FIG. 26E) Expression of TCR833 on primary CD8+ T cells. (FIG. 26F) 4-hr 51Cr assay results indicating specific lysis of K562-A*11:01 cells pulsed with G12V peptide (blue) and expressing RAS TMG construct (red)—but not wildtype (black). (FIG. 26G) 4-hr 51Cr assay results indicating specific lysis of A*11:01 positive RAS G12V tumor cell lines.

(FIG. 27A) Validation of TCR expression by peptide-MHC multimer staining of lentiviral-transduced Jurkat Reporter cells. (FIG. 27B) Assessment of TCR avidity by Jurkat Reporter cells. (FIG. 27C) Assessment of TCR specificity and cross-reactivity to alternative mutant RAS epitopes by Jurkat Reporter assay. TCR897 exhibits specificity for RAS G12V (VV_V) but not wildtype. Cross reactivity was observed to RAS G12C (VV_C) and G12D (VV_D) epitopes.

(FIG. 28A) Validation of TCR expression by peptide-MHC multimer staining of lentiviral-transduced Jurkat Reporter cells. (FIG. 28B) Assessment of TCR avidity by Jurkat Reporter cells. (FIG. 28C) Assessment of TCR specificity and cross-reactivity to alternative mutant RAS epitopes by Jurkat Reporter assay. TCR896 exhibits specificity for RAS G12V (VVV_V) but not wildtype or alternatively mutated KRAS epitopes. (FIG. 28D) TCR activation of Jurkat Reporter cells following coculture with A*03:01 positive RAS G12V tumor cell lines. (FIG. 28E) Expression of TCR896 on primary CD8+ T cells. (FIG. 28F) 4-hr 51Cr assay results indicating specific lysis of K562-A*03:01 cells pulsed with G12V peptide (blue) or expressing RAS TMG construct (red)—but not wildtype (black). (FIG. 28G) 4-hr 51Cr assay results indicating specific lysis of A*03:01 positive RAS G12V tumor cell lines.

(FIG. 29A) Validation of TCR expression by peptide-MHC multimer staining of lentiviral-transduced Jurkat Reporter cells. (FIG. 29B) Assessment of TCR specificity and cross-reactivity to alternative mutant RAS epitopes by Jurkat Reporter assay. TCR847 exhibits specificity for RAS G12R (GA_R) but not wildtype or alternatively mutated RAS epitopes.

(FIG. 30A) Validation of TCR expression by peptide-MHC multimer staining of lentiviral-transduced Jurkat Reporter cells. (FIG. 30B) Assessment of TCR avidity by Jurkat Reporter cells. (FIG. 30C) Assessment of TCR specificity and cross-reactivity to alternative mutant RAS epitopes by Jurkat Reporter assay. TCR864 exhibits specificity for RAS G12R (GA_R) but not wildtype or alternatively mutated RAS epitopes. (FIG. 30D) Expression of TCR864 on primary CD8+ T cells. (FIG. 30E) 4-hr 51Cr assay results indicating specific lysis of K562-B*07:02 cells pulsed with G12R peptide (blue) or expressing RAS TMG construct (red)—but not wildtype (black).

FIG. 31 depicts a schematic of a clinical trial using dendric cell (DC) vaccination against mRAS short peptides.

DETAILED DESCRIPTION OF THE INVENTION

Figure 1:
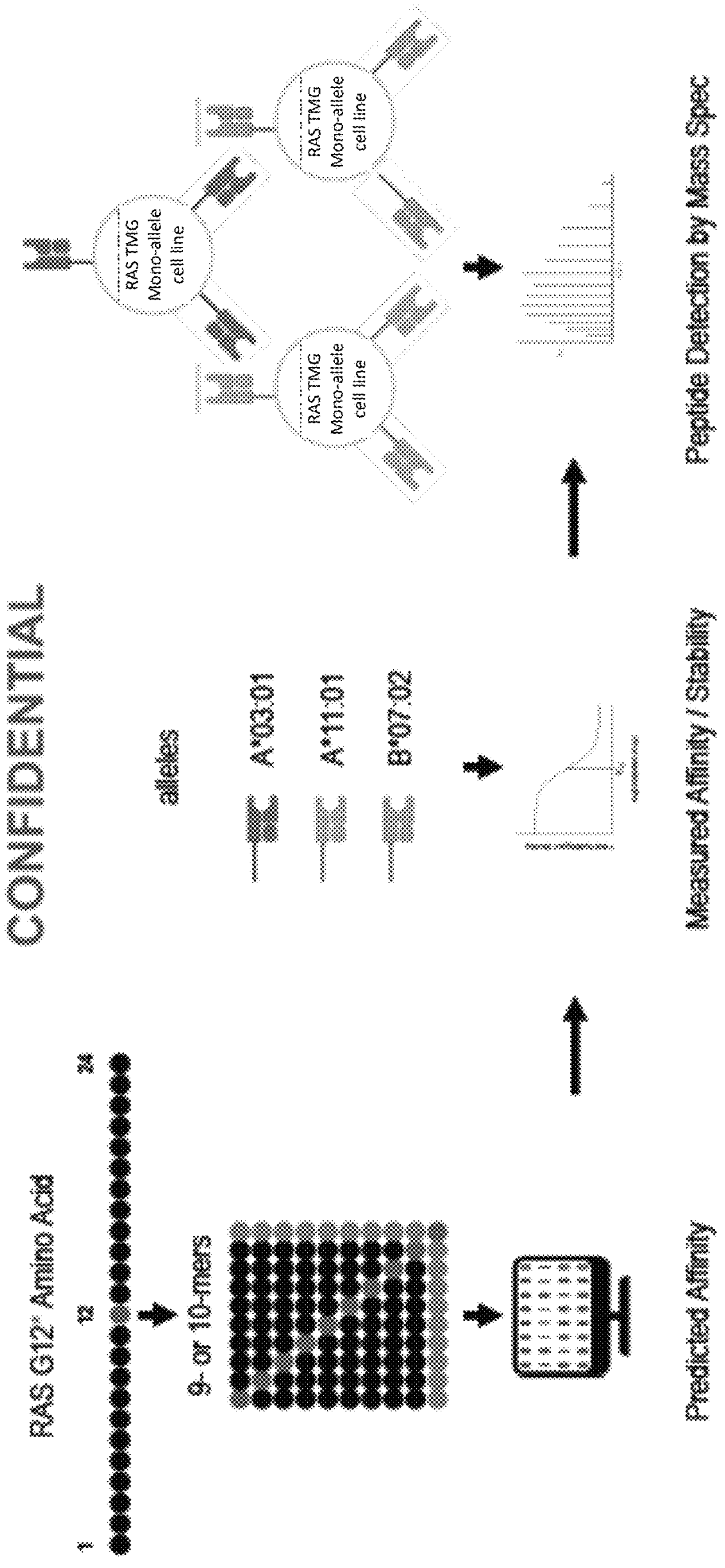
FIG. 1 depicts a schematic illustrating the discovery strategy of mutant RAS (mRAS) epitopes.

This invention relates to compositions and methods for treating cancer associated with mutant RAS (mRAS). Somatic mutations within RAS provide a form of a non-self antigen, making RAS-mutated tumors susceptible to immune-based therapeutic approaches, including, but not limited to, adoptive T cell therapy. T cells have unique T-cell receptors (TCRs) that are capable of recognizing subtle mutations within intracellular proteins that may be expressed and presented on HLA molecules by tumor cells.

The present invention is applicable to any member of the RAS family of oncogenic proteins, including but not limited to, KRAS, NRAS, and HRAS. The RAS hotspot mutations described herein (e.g., mutations at position G12) are common among KRAS-, NRAS-, and HRAS-associated cancers. Further the amino acid sequences of the RAS peptides described herein are conserved among all RAS family members. Thus, the mutant RAS peptides and TCRs described herein are applicable in inducing an immune response against mutant RAS family members to treat cancers associated with a mutant RAS family member. As used herein, "RAS" is meant to include any member of the RAS family of proteins.

The present invention is based, in part, upon the identification of antigenic HLA-restricted mutant RAS peptides. The RAS peptides described herein can be used as immunogenic compositions to induce an immune response against mRAS. In certain embodiments, the present invention relates to an immunogenic composition, such as a vaccine, that comprises an antigenic mRAS peptide described herein, or a nucleic acid molecule encoding an antigenic mRAS peptide described herein.

The present invention is based, in part, upon the identification of T cell receptor (TCR) sequences that specifically recognize HLA-restricted mutant RAS antigens. The TCR sequences described herein recognize common mutant RAS antigens in the context of highly prevalent HLA types. In certain aspects, the present invention relates to a composition comprising an isolated TCR, or to a nucleic acid molecule that encodes an isolated TCR, where the isolated TCR specifically binds to RAS, mRAS, or a fragment thereof. In one embodiment, the composition comprises a cell, for example an autologous or allogeneic T cell, genetically modified to express a TCR that specifically binds to RAS, mRAS, or fragment thereof.

In certain aspects, the present invention relates to a method for treating or preventing mRAS-associated cancer using the antigenic mRAS peptides or TCRs described herein. In one embodiment, the method comprises administering to a subject an immunogenic composition comprising an mRAS peptide or nucleic acid molecule encoding an mRAS peptide described herein. In one embodiment, the method comprises administering to a subject an immunogenic composition comprising an antigen presenting cell (APC), such as a dendritic cell, that has been loaded with one or more mRAS peptides or one or more nucleic acid molecules encoding one or more mRAS peptides described herein. In certain embodiments, the invention relates to methods using TCR therapy, for example adoptive TCR therapy. In one embodiment, the method comprises administering to a subject having a mRAS-associated cancer at least one T cell that is genetically modified to express a TCR that specifically binds to RAS, mRAS, or a fragment thereof.

Exemplary mRAS-associated cancer that is treatable by way of the compositions and methods of the present invention include, but is not limited to, pancreatic ductal adenocarcinoma (PDA), colon cancer, colorectal adenocarcinoma, myeloma, multiple myeloma, lung adenocarcinoma, melanoma, uterine cancer, thyroid cancer, acute myelogenous leukemia (AML), urothelial cancer, gastric adenocarcinoma and cervical adenocarcinoma, head and neck squamous cell carcinoma (SCC), Diffuse large B-cell lymphoma (DLBCL), esophageal adenocarcinoma, Chronic lymphocytic leukemia (CLL), lung SCC, small cell lung cancer (SCLC), renal papillary cancer, Hepatocellular carcinoma (HCC), breast cancer, cervical SCC, ovarian adenocarcinoma, adrenal cancer, prostate cancer, neuroblastoma, glioblastoma multiforme (GBM), medulloblastoma, Renal cell carcinoma (RCC), esophageal SCC, osteosarcoma, sarcoma, and small intestine neuroendocrine tumor (NET).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "inhibit" and "inhibition," as used herein, means to reduce, suppress, diminish or block an activity or function by at least about 10% relative to a control value. In some embodiments, the activity is suppressed or blocked by at least about 50% compared to a control value. In some embodiments, the activity is suppressed or blocked by at least about 75%. In some embodiments, the activity is suppressed or blocked by at least about 95%.

The terms "effective amount" and "pharmaceutically effective amount" refer to a sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The terms "patient," "subject," "individual," and the like are used interchangeably herein, and refer to any animal, in some embodiments a mammal, and in some embodiments a human, having a complement system, including a human in need of therapy for, or susceptible to, a condition or its sequelae. The individual may include, for example, dogs, cats, pigs, cows, sheep, goats, horses, rats, monkeys, and mice and humans.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

A disease or disorder is "alleviated" if the severity of a sign or symptom of the disease or disorder, the frequency with which such a sign or symptom is experienced by a patient, or both, is reduced.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

An "effective amount" or "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Operably linked" or "operatively linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "therapeutic treatment" is a treatment administered to a subject who exhibits signs of disease or disorder, for the purpose of diminishing or eliminating those signs.

As used herein, "treating a disease or disorder" means reducing the frequency and/or severity of a sign and/or symptom of the disease or disorder is experienced by a patient.

The phrase "biological sample", "sample" or "specimen" as used herein, is intended to include any sample comprising a cell, a tissue, or a bodily fluid in which expression of a nucleic acid or polypeptide can be detected. The biological sample may contain any biological material suitable for detecting the desired biomarkers, and may comprise cellular and/or non-cellular material obtained from the individual. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

"CDRs" are defined as the complementarity determining region amino acid sequences of a TCR or TCR chain.

As used herein, an "immunoassay" refers to any binding assay that uses an antibody capable of binding specifically to a target molecule to detect and quantify the target molecule.

By the term "specifically binds," as used herein with respect to a polypeptide (e.g., a TCR or TCR chain), is meant a polypeptide which recognizes and binds to a specific target molecule, but does not substantially recognize or bind other molecules in a sample. In some instances, the terms "specific binding" or "specifically binding," is used to mean that the recognition and binding is dependent upon the presence of a particular structure (e.g., an antigenic determinant or epitope) on the target molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In some embodiments, the first region comprises a first portion and the second region comprises a second portion, whereby, when the first and second portions are arranged in an antiparallel fashion, at least about 50%, and or at least about 75%, or at least about 90%, or at least about 95% of the nucleotide residues of the first portion are capable of base pairing with nucleotide residues in the second portion. In some embodiments, all nucleotide residues of the first portion are capable of base pairing with nucleotide residues in the second portion.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "hybridoma," as used herein refers to a cell resulting from the fusion of a B-lymphocyte and a fusion partner such as a myeloma cell. A hybridoma can be cloned and maintained indefinitely in cell culture and is able to produce monoclonal antibodies. A hybridoma can also be considered to be a hybrid cell.

"Isolated" means altered or removed from the natural state. For example, a nucleic acid or a peptide naturally present in its normal context in a living subject is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, "conjugated" refers to covalent attachment of one molecule to a second molecule.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis. In various embodiments, the variant sequence is at least 99%, at least 98%, at least 97%, at least 96%, at least 95%, at least 94%, at least 93%, at least 92%, at least 91%, at least 90%, at least 89%, at least 88%, at least 87%, at least 86%, at least 85% identical to the reference sequence.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

A "scanning window," as used herein, refers to a segment of a number of contiguous positions in which a sequence may be evaluated independently of any flanking sequence. A scanning window generally is shifted incrementally along the length of a sequence to be evaluated with each new segment being independently evaluated. An incremental shift may be of 1 or more than one position.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for treating mRAS-associated cancer. In various embodiments, the compositions and methods described herein can be used to kill cancer cells, decrease tumor size, inhibit tumor growth, inhibit tumor metastasis, slow tumor progression or severity, and the like.

In one aspect, the present invention relates to an immunogenic composition comprising an antigenic mRAS peptide, wherein the mRAS peptide stimulates or induces an anti-mRAS immune response. In certain embodiments, the mRAS peptide comprises a fragment of mRAS. In certain embodiments, the mRAS peptide comprises an amino acid sequence of about 5-15 amino acids. In certain embodiments, the mRAS peptide comprises an amino acid sequence having a mutation at position G12, relative to wildtype RAS. For example, in one embodiment, the mRAS peptide comprises an amino acid sequence of about 5-15 amino acids and comprising a G12C, G12D, G12R, or G12V mutation, relative to wildtype RAS.

In one aspect, the present invention provides an isolated nucleic acid molecule that encodes an mRAS peptide described herein. In one aspect, the present invention provides a cell, such as antigen presenting cell, that comprises an mRAS peptide or nucleic acid molecule encoding an mRAS peptide described herein.

In one aspect, the present invention relates to a composition comprising a polypeptide comprising one or more TCR chains (e.g., TCR alpha chain, TCR beta chain, TCR delta chain, and TCR gamma chain) that, either alone or together, specifically bind to RAS, mRAS, or fragment thereof. In one embodiment, the composition comprises a TCR comprising a TCR alpha chain and a TCR beta chain, where the TCR specifically binds to RAS, mRAS, or fragment thereof. Hereinafter, references to "TCR" refer to a heterodimer T cell receptor, individual T cell receptor chains (e.g., TCR alpha chain, TCR beta chain, TCR delta chain, and TCR gamma chain), and to functional portions and variants thereof.

In one embodiment, the TCR specifically binds to mRAS comprising a mutation at position G12, relative to wildtype RAS. For example, in certain embodiments, the TCR specifically binds to mRAS comprising a G12C, G12D, G12R, or G12V mutation, relative to wildtype RAS. In certain embodiments, the TCR specifically binds to a fragment of mRAS, wherein the fragment comprises a mutation at the position corresponding to G12. In certain embodiments, the TCR specifically binds to the mRAS fragment in the context of a specific HLA type. In one embodiment, the composition comprises a fusion polypeptide comprising a TCR alpha chain and a TCR beta chain, where the TCR alpha chain and TCR beta chain together form a heterodimer TCR. In one embodiment, the fusion polypeptide comprises a cleavable linker between the TCR alpha chain and TCR beta chain.

In one aspect, the present invention provides an isolated nucleic acid molecule that encodes a TCR described herein. In one aspect, the present invention provides a cell, such as a T-cell, that is been modified to express a TCR described herein.

In one embodiment, the present invention provides a method for treating or preventing an mRAS-associated cancer in a subject having, suspected of having, or at risk for having, an mRAS-associated cancer. Exemplary mRAS-associated cancer that is treatable or preventable by way of the compositions and methods of the present invention include, but is not limited to, pancreatic cancer, pancreatic ductal adenocarcinoma (PDA), colon cancer, colorectal adenocarcinoma, myeloma, multiple myeloma, lung adenocarcinoma, melanoma, uterine cancer, thyroid cancer, acute myelogenous leukemia (AML), urothelial cancer, gastric adenocarcinoma and cervical adenocarcinoma, head and neck squamous cell carcinoma (SCC), Diffuse large B-cell lymphoma (DLBCL), esophageal adenocarcinoma, Chronic lymphocytic leukemia (CLL), lung SCC, small cell lung cancer (SCLC), renal papillary cancer, Hepatocellular carcinoma (HCC), breast cancer, cervical SCC, ovarian adenocarcinoma, adrenal cancer, prostate cancer, neuroblastoma, glioblastoma multiforme (GBM), medulloblastoma, Renal cell carcinoma (RCC), esophageal SCC, osteosarcoma, sarcoma, and small intestine neuroendocrine tumor (NET).

In one embodiment, the method comprises administering to the subject an immunogenic composition comprising an mRAS peptide, a nucleic acid molecule encoding an mRAS peptide, or at least one cell comprising an mRAS peptide or nucleic acid molecule encoding an mRAS peptide. In one embodiment the method comprises administering an antigen presenting cell, such as a dendritic cell, that is loaded with one or more mRAS peptides or one or more nucleic acid molecules encoding one or more mRAS peptides. In some embodiments, the antigen presenting cell is an autologous cell or derived from an autologous cell. For example, in one embodiment, the method comprises isolating an autologous cell from a subject; culturing the autologous cell ex vivo; loading the isolated autologous cell with one or more mRAS peptides or one or more nucleic acid molecules encoding one or more mRAS peptides, thereby generating an antigen presenting cell presenting a mRAS peptide described herein; and administering the antigen presenting cell to the subject. In certain embodiments, the specific type of mRAS peptide used in the present method is dependent upon the specific HLA type of the subject or cells.

In one embodiment, the method comprises administering to the subject a composition comprising a TCR, a nucleic acid molecule encoding a TCR, or at least one cell expressing a TCR, where the TCR specifically binds to RAS, mRAS, or fragment thereof. In one embodiment, the method comprises adoptive TCR therapy, where autologous T cells are genetically modified to express a TCR described herein and are administered to the subject to induce an immune response against cancer cells presenting mRAS, or a fragment thereof. For example, in one embodiment, the method comprises isolating an autologous cell from a subject; culturing the autologous cell ex vivo; genetically modifying the isolated autologous cell to express a TCR described herein; and administering the genetically modified cell to the subject. In certain embodiments, the specific type of TCR used in the present method is dependent upon the specific HLA type of the subject or cells.

mRAS Peptides and Vaccines

In some embodiments, the invention provides a composition comprising an antigenic mRAS peptide. In one embodiment, the mRAS peptide stimulates or induces an anti-mRAS immune responses in a subject.

In one embodiment, the mRAS peptide comprises a mutation at position G12, relative to wildtype RAS. In one embodiment, the mRAS peptide comprises a G12C, G12D, G12R, or G12V mutation, relative to wildtype RAS. In certain embodiments, the mRAS peptide is a short fragment of full-length mRAS.

In one embodiment, the mRAS peptide has a length of about 8 to about 24 amino acid residues, or about 9 to about 11 amino acid residues. In an embodiment of the invention, the mRAS peptide comprises a mutation corresponding to G12 relative to wildtype mRAS, and where the mRAS peptide has a length of about 8 amino acid residues, about 9 amino acid residues, about 10 amino acid residues, about 11 amino acid residues, about 12 amino acid residues, about 13 amino acid residues, about 14 amino acid residues, about 15 amino acid residues, about 16 amino acid residues, about 17 amino acid residues, about 18 amino acid residues, about 19 amino acid residues, about 20 amino acid residues, about 21 amino acid residues, about 22 amino acid residues, about 23 amino acid residues, or about 24 amino acid residues.

Exemplary antigenic mRAS peptides of the present invention are provided in Table 1.

| ID | HLA Allele | mRAS mutation | mRAS peptide |
|---|---|---|---|
| KLV_C | HLA-A*02:01 | G12C | KLVVVGACGV (SEQ ID NO: 1) |
| KLV_D | HLA-A*02:01 | G12D | KLVVVGADGV (SEQ ID NO: 2) |
| KLV_R | HLA-A*02:01 | G12R | KLVVVGARGV (SEQ ID NO: 3) |
| KLV_V | HLA-A*02:01 | G12V | KLVVVGAVGV (SEQ ID NO: 4) |
| VV_C | HLA-A*03:01<br>HLA-A*11:01 | G12C | VVGACGVGK (SEQ ID NO: 5) |
| VVV_C | HLA-A*03:01<br>HLA-A*11:01 | G12C | VVVGACGVGK (SEQ ID NO: 6) |
| VV_D | HLA-A*03:01<br>HLA-A*11:01 | G12D | VVGADGVGK (SEQ ID NO: 7) |
| VVV_D | HLA-A*03:01<br>HLA-A*11:01 | G12D | VVVGADGVGK (SEQ ID NO: 8) |
| VV_R | HLA-A*03:01<br>HLA-A*11:01 | G12R | VVGARGVGK (SEQ ID NO: 9) |
| VVV_R | HLA-A*03:01<br>HLA-A*11:01 | G12R | VVVGARGVGK (SEQ ID NO: 10) |
| VV_V | HLA-A*03:01<br>HLA-A*11:01 | G12V | VVGAVGVGK (SEQ ID NO: 11) |
| VVV_V | HLA-A*03:01<br>HLA-A*11:01 | G12V | VVVGAVGVGK (SEQ ID NO: 12) |
| GA_C | HLA-B*07:02 | G12C | GACGVGKSAL (SEQ ID NO: 13) |
| GA_D | HLA-B*07:02 | G12D | GADGVGKSAL (SEQ ID NO: 14) |
| GA_R | HLA-B*07:02 | G12R | GARGVGKSAL (SEQ ID NO: 15) |
| GA_V | HLA-B*07:02 | G12V | GAVGVGKSAL (SEQ ID NO: 16) |

In one embodiment, the present invention provides an immunogenic composition for inducing an immune response against mRAS in a subject. For example, in one embodiment, the immunogenic composition is a vaccine. For a composition to be useful as a vaccine, the composition must induce an immune response to mRAS in a cell, tissue or mammal (e.g., a human). In certain instances, the vaccine induces a protective immune response in the mammal. As used herein, an "immunogenic composition" may comprise an antigen (e.g., a mRAS peptide), a nucleic acid encoding an antigen, a cell expressing or presenting an antigen or cellular component, or a combination thereof. In particular embodiments, the composition comprises or encodes all or part of any peptide antigen described herein, or an immunogenically functional equivalent thereof. In other embodiments, the composition is in a mixture that comprises an additional immunostimulatory agent or nucleic acids encoding such an agent. Immunostimulatory agents include but are not limited to an additional antigen, an immunomodulator, an antigen presenting cell, lipid nanoparticle, or an adjuvant. In other embodiments, one or more of the additional agent(s) is covalently bonded to the antigen or an immunostimulatory agent, in any combination.

In the context of the present invention, the term "vaccine" refers to a composition that induces an immune response upon inoculation into animals. In some embodiments, the induced immune response provides protective immunity. A vaccine of the present invention may vary in its composition of nucleic acid and/or cellular components. In a non-limiting example, a vaccine comprising or encoding a mRAS peptide antigen might also be formulated with an adjuvant. Of course, it will be understood that various compositions described herein may further comprise additional components. For example, one or more vaccine components may be comprised in a lipid, liposome, or lipid nanoparticle. In another non-limiting example, a vaccine may comprise one or more adjuvants. Exemplary adjuvants include, but are not limited to, alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86. Other genes which may be useful adjuvants include those encoding: MCP-I, MIP-Ia, MIP-Ip, IL-8, RANTES, L-selectin, P-selectin, E-selectin, CD34, GlyCAM-1, MadCAM-1, LFA-I, VLA-I, Mac-1, pl50.95, PECAM, ICAM-I, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-I, DR3, TRAMP, Apo-3, AIR, LARD, NGRF, DR4, DR5, KILLER, TRAIL-R2, TRICK2, DR6, Caspase ICE, Fos, c-jun, Sp-I, Ap-I, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, TAP2, anti-CTLA4-sc, anti-LAG3-Ig, anti-TIM3-Ig, and functional fragments thereof.

A vaccine of the present invention, and its various components, may be prepared and/or administered by any method disclosed herein or as would be known to one of ordinary skill in the art, in light of the present disclosure.

The induction of the immunity by mRAS peptide antigen can be detected by observing in vivo or in vitro the response of all or any part of the immune system in the host against the mRAS.

The present invention includes a cell that has been exposed or otherwise "pulsed" with an antigen (e.g., a mRAS peptide antigen). For example, an antigen presenting cell (APC), such as a dendritic cell (DC), may become Ag-loaded in vitro, e.g., by culture ex vivo in the presence of an antigen, or in vivo by exposure to an antigen.

A person skilled in the art would also readily understand that an APC can be "pulsed" in a manner that exposes the APC to an antigen for a time sufficient to promote presentation of that antigen on the surface of the APC. For example, an APC can be exposed to an antigen in the form of small peptide fragments, known as antigenic peptides, which are "pulsed" directly onto the outside of the APCs; or APCs can be incubated with antigenic peptides which are then ingested by the APCs. APCs then present the antigenic peptides on the APC surface. Antigen in peptide form may be exposed to the cell by standard "pulsing" techniques described herein and as known in the art.

The antigen-loaded APC, otherwise known as a "pulsed APC" of the invention, is produced by exposure of the APC to an antigen either in vitro or in vivo. In the case where the APC is pulsed in vitro, the APC can be plated on a culture dish and exposed to an antigen in a sufficient amount and for a sufficient period of time to allow the antigen to bind to the APC. The amount and time necessary to achieve binding of the antigen to the APC may be determined by using methods known in the art or otherwise disclosed herein. Other methods known to those of skill in the art, for example immunoassays or binding assays, may be used to detect the presence of antigen on the APC following exposure to the antigen.

In a further embodiment of the invention, the APC may be transfected with a vector which allows for the expression of a specific peptide by the APC. The peptide which is expressed by the APC may then be processed and presented on the cell surface on an MHC receptor. The transfected APC may then be used as an immunogenic composition to produce an immune response to the protein encoded by the vector.

As discussed elsewhere herein, vectors may be prepared to include a specific polynucleotide which encodes and expresses a peptide to which an immunogenic response is desired. In one embodiment, retroviral vectors are used to infect the cells. In one embodiment, adenoviral vectors are used to infect the cells.

In another embodiment, a vector may be targeted to an APC by modifying the viral vector to encode a protein or portions thereof that is recognized by a receptor on the APC, whereby occupation of the APC receptor by the vector will initiate endocytosis of the vector, allowing for processing and presentation of the antigen encoded by the nucleic acid of the viral vector.

As contemplated herein, various methods can be used for transfecting a polynucleotide into a host cell. The methods include, but are not limited to, calcium phosphate precipitation, lipofection, particle bombardment, microinjection, electroporation, colloidal dispersion systems (i.e. macromolecule complexes, nanocapsules, microspheres, beads, and lipid-based systems including oil-in-water emulsions, micelles, mixed micelles, and liposomes). These methods are understood in the art and are described in published literature so as to enable one skilled in the art to perform these methods.

In another embodiment, a polynucleotide encoding an antigen can be cloned into an expression vector and the vector can be introduced into an APC to otherwise generate a loaded APC. Various types of vectors and methods of introducing nucleic acids into a cell are discussed in the available published literature. For example, the expression vector can be transferred into a host cell by physical, chemical or biological means. See, for example, Sambrook et al. (2001, Molecular Cloning: A Laboratory Manual, Cold Spring Harbor Laboratory, New York), and in Ausubel et al.

(1997, Current Protocols in Molecular Biology, John Wiley & Sons, New York). It is readily understood that the introduction of the expression vector comprising a polynucleotide encoding an antigen yields a pulsed cell.

The present invention includes various methods for pulsing APCs including, but not limited to, loading APCs with the peptide antigen, or with cDNA or mRNA encoding the peptide antigen. However, the invention should not be construed to be limited to the specific form of the antigen used for pulsing the APC. Rather, the invention encompasses other methods known in the art for generating an antigen loaded APC. In one embodiment, the APC is transfected with mRNA encoding a defined antigen. mRNA corresponding to a gene product whose sequence is known can be rapidly generated in vitro using appropriate primers and reverse transcriptase-polymerase chain reaction (RT-PCR) coupled with transcription reactions. Transfection of an APC with an mRNA provides an advantage over other antigen-loading techniques for generating a pulsed APC. For example, the ability to amplify RNA from a microscopic amount of tissue, i.e. tumor tissue, extends the use of the APC for vaccination to a large number of patients.

There are many methods that can be used for engineering DCs and other APCs, such as mRNA-based delivering, DNA-plasmid-based delivering, all of which are encompassed in the invention. That is, any delivery system can be used to engineer immune cells to express the mRAS peptides described herein.

It is understood that an antigenic composition of the present invention may be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding the peptide antigen of the present invention in an in vitro translation system or in a living cell. In addition, an antigenic composition can comprise a cellular component isolated from a biological sample. The antigenic composition isolated and extensively dialyzed to remove one or more undesired small molecular weight molecules and/or lyophilized for more ready formulation into a desired vehicle. It is further understood that additional amino acids, mutations, chemical modification and such like, if any, that are made in a vaccine component will not substantially interfere with the antibody recognition of the epitopic sequence. A peptide sequence may be synthesized by methods known to those of ordinary skill in the art, such as, for example, peptide synthesis using automated peptide synthesis machines, such as those available from Applied Biosystems, Inc., Foster City, CA (Foster City, CA).

Longer peptides or polypeptides also may be prepared, e.g., by recombinant means. In certain embodiments, a nucleic acid encoding an antigenic composition and/or a component described herein may be used, for example, to produce an antigenic composition in vitro or in vivo for the various compositions and methods of the present invention. For example, in certain embodiments, a nucleic acid encoding an antigen is comprised in, for example, a vector in a recombinant cell. The nucleic acid may be expressed to produce a peptide or polypeptide comprising an antigenic sequence. The peptide or polypeptide may be secreted from the cell, or comprised as part of or within the cell.

In certain embodiments, an immune response may be promoted by transfecting or inoculating a mammal with a nucleic acid encoding an antigen. One or more cells comprised within a target mammal then expresses the sequences encoded by the nucleic acid after administration of the nucleic acid to the mammal. A vaccine may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector.

In another embodiment, the nucleic acid comprises a coding region that encodes all or part of the sequences encoding an appropriate antigen, or an immunologically functional equivalent thereof. Of course, the nucleic acid may comprise and/or encode additional sequences, including but not limited to those comprising one or more immunomodulators or adjuvants.

In certain embodiments, the immunologic composition comprises an immune cell stimulated by an APC that is loaded or pulsed with one or more mRAS peptide antigens described herein. For example, in one embodiment, the immunologic composition comprising a stimulated T cell that is cultured with and activated by an APC that is loaded or pulsed with one or more mRAS peptide antigens described herein. In one embodiment, the stimulated cell is derived from a naïve cell (e.g., a naïve T cell) which is then cultured with and activated by an APC that is loaded or pulsed with one or more mRAS peptide antigens described herein. In certain embodiments, the naïve cell is autologous or allogenic to the eventual recipient of the stimulated cell. In one embodiment, the naïve cell and APC are both from the same subject. In one embodiment, the naïve cell and APC are from different subjects, within the same species.

Methods for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen. These antigen-stimulated cells then proliferate. This process is referred to herein as "activation" of T cells. Therefore, CTL induction by an epitope of a polypeptide or peptide or combinations thereof can be evaluated by presenting an epitope of a polypeptide or peptide or combinations thereof to a T cell by APC, and detecting the induction of CTL. Furthermore, APCs have the effect of activating B cells, CD4+ T cells, CD8+ T cells, macrophages, eosinophils and NK cells.

A method for evaluating the inducing action of CTL using dendritic cells (DCs) as APC is well known in the art. DC is a representative APC having a robust CTL inducing action among APCs. In the methods of the invention, the epitope of a polypeptide or peptide or combinations thereof is initially expressed by the DC and then this DC is contacted with T cells. Detection of T cells having cytotoxic effects against the cells of interest after the contact with DC shows that the epitope of a polypeptide or peptide or combinations thereof has an activity of inducing the cytotoxic T cells. Furthermore, the induced immune response can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The antigens confirmed to possess CTL-inducing activity by these methods are antigens having DC activation effect and subsequent CTL-inducing activity. Furthermore, CTLs that have acquired cytotoxicity due to presentation of the antigen by APC can be also used as vaccines against antigen-associated disorders.

The induction of immunity by expression of the mRAS peptide antigen can be further confirmed by observing the induction of antibody production against mRAS. For example, when antibodies against an antigen are induced in a laboratory animal immunized with the composition encoding the antigen, and when antigen-associated pathology is suppressed by those antibodies, the composition is determined to induce immunity.

The induction of immunity by expression of the mRAS peptide antigen can be further confirmed by observing the induction of CD4+ T cells. CD4+ T cells can also lyse target cells, but mainly supply help in the induction of other types of immune responses, including CTL and antibody generation. The type of CD4+ T cell help can be characterized, as Th1, Th2, Th9, Th17, T regulatory, or T follicular helper ($T_{fh}$) cells. Each subtype of CD4+ T cell supplies help to certain types of immune responses. In one embodiment, the composition selectively induces T follicular helper cells, which drive potent antibody responses.

mRAS-Specific TCRs

In some embodiments, the invention provides a composition comprising a polypeptide that specifically binds to RAS, mRAS, or fragment thereof. In one embodiment, the polypeptide comprises a TCR that specifically binds to RAS, mRAS, or fragment thereof, in the context of a specific HLA type.

In one embodiment the TCR specifically binds to mRAS comprising a mutation at position G12, relative to wildtype RAS. For example, in certain embodiments, the TCR specifically binds to mRAS comprising a G12C, G12D, G12R, or G12V mutation, relative to wildtype RAS. In certain embodiments, the TCR specifically binds to a fragment of mRAS, wherein the fragment comprises a mutation at the position corresponding to G12.

In one embodiment of the invention, the TCR has antigenic specificity for a mRAS peptide with a mutation at G12, as described above, the mRAS peptide having any length. For example, the TCR may have antigenic specificity for a mRAS peptide with a mutation corresponding to G12, the mRAS peptide having a length of about 8 to about 24 amino acid residues, or about 9 to about 11 amino acid residues. In an embodiment of the invention, the TCR may have antigenic specificity for a mRAS peptide with a mutation corresponding to G12, the mRAS peptide having a length of about 8 amino acid residues, about 9 amino acid residues, about 10 amino acid residues, about 11 amino acid residues, about 12 amino acid residues, about 13 amino acid residues, about 14 amino acid residues, about 15 amino acid residues, about 16 amino acid residues, about 17 amino acid residues, about 18 amino acid residues, about 19 amino acid residues, about 20 amino acid residues, about 21 amino acid residues, about 22 amino acid residues, about 23 amino acid residues, or about 24 amino acid residues. Exemplary mRAS peptides with a mutation corresponding to G12, to which the TCR specifically binds, can be found in Table 1.

In certain embodiments, the TCR specifically binds to the mRAS peptide in the context of a specific HLA molecule. HLA molecules corresponding to mRAS peptides can be found in Table 1.

HLA-A*02:01 G12C

In one embodiment, the TCR specifically binds to a mRAS peptide having a G12C mutation at a position corresponding to RAS G12. In one embodiment, the TCR specifically binds to a mRAS peptide having a G12C mutation at a position corresponding to RAS G12 in the context of an HLA-A*02:01 molecule. For example, in one embodiment, the TCR specifically binds to an mRAS peptide comprising KLVVVGA<u>C</u>GV (SEQ ID NO:1). For example, in one embodiment, the TCR specifically binds to an mRAS peptide comprising KLVVVGA<u>C</u>GV (SEQ ID NO:1) in the context of an HLA-A*02:01 molecule.

HLA-A*02:01 G12D

In one embodiment, the TCR specifically binds to a mRAS peptide having a G12D mutation at a position corresponding to RAS G12. In one embodiment, the TCR specifically binds to a mRAS peptide having a G12D mutation at a position corresponding to RAS G12 in the context of an HLA-A*02:01 molecule. For example, in one embodiment, the TCR specifically binds to an mRAS peptide comprising KLVVVGA<u>D</u>GV (SEQ ID NO:2). For example, in one embodiment, the TCR specifically binds to an mRAS peptide comprising KLVVVGA<u>D</u>GV (SEQ ID NO:2) in the context of an HLA-A*02:01 molecule.

HLA-A*02:01 G12R

In one embodiment, the TCR specifically binds to a mRAS peptide having a G12R mutation at a position corresponding to RAS G12. In one embodiment, the TCR specifically binds to a mRAS peptide having a G12R mutation at a position corresponding to RAS G12 in the context of an HLA-A*02:01 molecule. For example, in one embodiment, the TCR specifically binds to an mRAS peptide comprising KLVVVGA<u>R</u>GV (SEQ ID NO:3). For example, in one embodiment, the TCR specifically binds to an mRAS peptide comprising KLVVVGA<u>R</u>GV (SEQ ID NO:3) in the context of an HLA-A*02:01 molecule.

HLA-A*02:01 G12V

In one embodiment, the TCR specifically binds to a mRAS peptide having a G12V mutation at a position corresponding to RAS G12. In one embodiment, the TCR specifically binds to a mRAS peptide having a G12V mutation at a position corresponding to RAS G12 in the context of an HLA-A*02:01 molecule. For example, in one embodiment, the TCR specifically binds to an mRAS peptide comprising KLVVVGA<u>V</u>GV (SEQ ID NO:4). For example, in one embodiment, the TCR specifically binds to an mRAS peptide comprising KLVVVGA<u>V</u>GV (SEQ ID NO:4) in the context of an HLA-A*02:01 molecule.

HLA-A*11:01 G12C

In one embodiment, the TCR specifically binds to a mRAS peptide having a G12C mutation at a position corresponding to RAS G12. In one embodiment, the TCR specifically binds to a mRAS peptide having a G12C mutation at a position corresponding to RAS G12 in the context of an HLA-A*11:01 molecule. For example, in one embodiment, the TCR specifically binds to an mRAS peptide comprising VVGA<u>C</u>GVGK (SEQ ID NO:5) or VVVGA<u>C</u>GVGK (SEQ ID NO:6). For example, in one embodiment, the TCR specifically binds to an mRAS peptide comprising VVGA<u>C</u>GVGK (SEQ ID NO:5) or VVVGA<u>C</u>GVGK (SEQ ID NO:6) in the context of an HLA-A*11:01 molecule.

HLA-A*11:01 G12D

In one embodiment, the TCR specifically binds to a mRAS peptide having a G12D mutation at a position corresponding to RAS G12. In one embodiment, the TCR specifically binds to a mRAS peptide having a G12D mutation at a position corresponding to RAS G12 in the context of an HLA-A*11:01 molecule. For example, in one embodiment, the TCR specifically binds to an mRAS peptide comprising VVGADGVGK (SEQ ID NO:7) or VVVGADGVGK (SEQ ID NO:8). For example, in one embodiment, the TCR specifically binds to an mRAS peptide comprising VVVGADGVGK (SEQ ID NO:7) or VVGADGVGK (SEQ ID NO:8) in the context of an HLA-A*11:01 molecule.

HLA-A*11:01 G12R

In one embodiment, the TCR specifically binds to a mRAS peptide having a G12R mutation at a position corresponding to RAS G12. In one embodiment, the TCR specifically binds to a mRAS peptide having a G12R mutation at a position corresponding to RAS G12 in the context of an HLA-A*11:01 molecule. For example, in one embodiment, the TCR specifically binds to an mRAS peptide comprising VVGARGVGK (SEQ ID NO:9) or VVVGARGVGK (SEQ ID NO:10). For example, in one embodiment, the TCR specifically binds to an mRAS peptide comprising VVGARGVGK (SEQ ID NO:9) or VVVGARGVGK (SEQ ID NO:10) in the context of an HLA-A*11:01 molecule.

HLA-A*11:01 G12V

In one embodiment, the TCR specifically binds to a mRAS peptide having a G12V mutation at a position corresponding to RAS G12. In one embodiment, the TCR specifically binds to a mRAS peptide having a G12V mutation at a position corresponding to RAS G12 in the context of an HLA-A*11:01 molecule. For example, in one embodiment, the TCR specifically binds to an mRAS peptide comprising VVGAVGVGK (SEQ ID NO:11) or VVVGAVGVGK (SEQ ID NO:12). For example, in one embodiment, the TCR specifically binds to an mRAS peptide comprising VVVGAVGVGK (SEQ ID NO:11) or VVGAVGVGK (SEQ ID NO:12) in the context of an HLA-A*11:01 molecule.

HLA-A*03:01 G12C

In one embodiment, the TCR specifically binds to a mRAS peptide having a G12C mutation at a position corresponding to RAS G12. In one embodiment, the TCR specifically binds to a mRAS peptide having a G12C mutation at a position corresponding to RAS G12 in the context of an HLA-A*03:01 molecule. For example, in one embodiment, the TCR specifically binds to an mRAS peptide comprising VVGACGVGK (SEQ ID NO:5) or VVVGACGVGK (SEQ ID NO:6). For example, in one embodiment, the TCR specifically binds to an mRAS peptide comprising VVGACGVGK (SEQ ID NO:5) or VVVGACGVGK (SEQ ID NO:6) in the context of an HLA-A*03:01 molecule.

HLA-A*03:01 G12D

In one embodiment, the TCR specifically binds to a mRAS peptide having a G12D mutation at a position corresponding to RAS G12. In one embodiment, the TCR specifically binds to a mRAS peptide having a G12D mutation at a position corresponding to RAS G12 in the context of an HLA-A*03:01 molecule. For example, in one embodiment, the TCR specifically binds to an mRAS peptide comprising VVGADGVGK (SEQ ID NO:7) or VVVGADGVGK (SEQ ID NO:8). For example, in one embodiment, the TCR specifically binds to an mRAS peptide comprising VVGADGVGK (SEQ ID NO:7) or VVVGADGVGK (SEQ ID NO:8) in the context of an HLA-A*03:01 molecule.

HLA-A*03:01 G12R

In one embodiment, the TCR specifically binds to a mRAS peptide having a G12R mutation at a position corresponding to RAS G12. In one embodiment, the TCR specifically binds to a mRAS peptide having a G12R mutation at a position corresponding to RAS G12 in the context of an HLA-A*03:01 molecule. For example, in one embodiment, the TCR specifically binds to an mRAS peptide comprising VVGARGVGK (SEQ ID NO:9) or VVVGARGVGK (SEQ ID NO:10). For example, in one embodiment, the TCR specifically binds to an mRAS peptide comprising VVGARGVGK (SEQ ID NO:9) or VVVGARGVGK (SEQ ID NO:10) or in the context of an HLA-A*03:01 molecule.

HLA-A*03:01 G12V

In one embodiment, the TCR specifically binds to a mRAS peptide having a G12V mutation at a position corresponding to RAS G12. In one embodiment, the TCR specifically binds to a mRAS peptide having a G12V mutation at a position corresponding to RAS G12 in the context of an HLA-A*03:01 molecule. For example, in one embodiment, the TCR specifically binds to an mRAS peptide comprising VVGAVGVGK (SEQ ID NO:11) or VVVGAVGVGK (SEQ ID NO:12). For example, in one embodiment, the TCR specifically binds to an mRAS peptide comprising VVGAVGVGK (SEQ ID NO:11) or VVVGAVGVGK (SEQ ID NO:12) or in the context of an HLA-A*03:01 molecule.

HLA-B*07:02 G12C

In one embodiment, the TCR specifically binds to a mRAS peptide having a G12C mutation at a position corresponding to RAS G12. In one embodiment, the TCR specifically binds to a mRAS peptide having a G12C mutation at a position corresponding to RAS G12 in the context of an HLA-B*07:02 molecule. For example, in one embodiment, the TCR specifically binds to an mRAS peptide comprising GACGVGKSAL (SEQ ID NO:13). For example, in one embodiment, the TCR specifically binds to an mRAS peptide comprising GACGVGKSAL (SEQ ID NO:13) in the context of an HLA-B*07:02 molecule.

HLA-B*07:02 G12D

In one embodiment, the TCR specifically binds to a mRAS peptide having a G12D mutation at a position corresponding to RAS G12. In one embodiment, the TCR specifically binds to a mRAS peptide having a G12D mutation at a position corresponding to RAS G12 in the context of an HLA-B*07:02 molecule. For example, in one embodiment, the TCR specifically binds to an mRAS peptide comprising GADGVGKSAL (SEQ ID NO:14). For example, in one embodiment, the TCR specifically binds to an mRAS peptide comprising GADGVGKSAL (SEQ ID NO:14) in the context of an HLA-B*07:02 molecule.

HLA-B*07:02 G12R

In one embodiment, the TCR specifically binds to a mRAS peptide having a G12R mutation at a position corresponding to RAS G12. In one embodiment, the TCR specifically binds to a mRAS peptide having a G12R mutation at a position corresponding to RAS G12 in the context of an HLA-B*07:02 molecule. For example, in one embodiment, the TCR specifically binds to an mRAS peptide comprising GARGVGKSAL (SEQ ID NO:15). For example, in one embodiment, the TCR specifically binds to an mRAS peptide comprising GARGVGKSAL (SEQ ID NO:15) in the context of an HLA-B*07:02 molecule.

HLA-B*07:02 G12V

In one embodiment, the TCR specifically binds to a mRAS peptide having a G12V mutation at a position corresponding to RAS G12. In one embodiment, the TCR specifically binds to a mRAS peptide having a G12V mutation at a position corresponding to RAS G12 in the context of an HLA-B*07:02 molecule. For example, in one embodiment, the TCR specifically binds to an mRAS peptide comprising GAVGVGKSAL (SEQ ID NO:16). For example, in one embodiment, the TCR specifically binds to an mRAS peptide comprising GAVGVGKSAL (SEQ ID NO:16) in the context of an HLA-B*07:02 molecule.

TCR831

In one embodiment, the TCR that specifically binds to a mRAS peptide having a G12 mutation at a position corresponding to RAS G12 comprises one or more of: a CDR1, a CDR2, and a CDR3 of a TCR alpha chain.

In one embodiment, the TCR that specifically binds to a mRAS peptide having a G12 mutation at a position corresponding to RAS G12 comprises T cell receptor alpha variable 39 (TRAV39-01*01; also referred to herein as "TRAV39") CDR1. In one embodiment, the TCR that specifically binds to a mRAS peptide having a G12 mutation at a position corresponding to RAS G12 comprises TRAV39 CDR1, wherein TRAV39 CDR1 comprises the amino acid sequence of: STTSDRL (SEQ ID NO:17).

In one embodiment, the TCR that specifically binds to a mRAS peptide having a G12 mutation at a position corresponding to RAS G12 comprises TRAV39 CDR2. In one embodiment, the TCR that specifically binds to a mRAS peptide having a G12 mutation at a position corresponding to RAS G12 comprises TRAV39 CDR2, wherein TRAV39 CDR2 comprises the amino acid sequence of: VLLSNGAVK (SEQ ID NO:18).

In one embodiment, the TCR that specifically binds to a mRAS peptide having a G12 mutation at a position corresponding to RAS G12 comprises TRAV39 CDR3. In one embodiment, the TCR that specifically binds to a mRAS peptide having a G12 mutation at a position corresponding to RAS G12 comprises TRAV39 CDR3, wherein TRAV39 CDR3 comprises the amino acid sequence of: CAVDKDGGYQKVTF (SEQ ID NO:19).

In one embodiment, the TCR that specifically binds to a mRAS peptide having a G12 mutation at a position corresponding to RAS G12 comprises TRAV39 CDR1, TRAV39 CDR2, and TRAV39 CDR3.

In one embodiment, the TCR that specifically binds to a mRAS peptide having a G12 mutation at a position corresponding to RAS G12 comprises a variable domain of TRAV39. In one embodiment, the TCR that specifically binds to a mRAS peptide having a G12 mutation at a position corresponding to RAS G12 comprises a variable domain of TRAV39, wherein the variable domain of TRAV39 comprises the amino acid sequence of:

(SEQ ID NO: 20)

ELKVEQNPLFLSMQEGKNYTIYCNYSTTSDRLYWYRQDPGKSLESLFVL

LSNGAVKQEGRLMASLDTKARLSTLHITAAVHDLSATYFCAVDKDGGYQ

KVTFGTGTKLQVIP.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 21)

IQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKL

VEKSFETDTNLNFQNLSVIGFRILLLKVAGFNLLMTLRLWSS.

In one embodiment, the TCR comprises a TCR alpha chain comprising the amino acid sequence of:

(SEQ ID NO: 22)

MKKLLAMILWLQLDRLSGELKVEQNPLFLSMQEGKNYTIYCNYSTTSDR

LYWYRQDPGKSLESLFVLLSNGAVKQEGRLMASLDTKARLSTLHITAAV

HDLSATYFCAVDKDGGYQKVTFGTGTKLQVIPNIQNPDPAVYQLRDSKS

SDKSVCLFTDFDSQTNVSQSKDSDVYITDKTVLDMRSMDFKSNSAVAWS

NKSDFACANAFNNSIIPEDTFFPSPESSCDVKLVEKSFETDTNLNFQNL

SVIGFRILLLKVAGFNLLMTLRLWSS.

In one embodiment, the TCR that specifically binds to a mRAS peptide having a G12 mutation at a position corresponding to RAS G12 comprises one or more of: a CDR1, a CDR2, and a CDR3 of a TCR beta chain.

In one embodiment, the TCR that specifically binds to a mRAS peptide having a G12 mutation at a position corresponding to RAS G12 comprises T cell receptor beta variable 20-1 (TRBV20-1*01; also referred to herein as "TRBV20") CDR1. In one embodiment, the TCR that specifically binds to a mRAS peptide having a G12 mutation at a position corresponding to RAS G12 comprises TRBV20-1 CDR1, wherein TRBV20-1 CDR1 comprises the amino acid sequence of: LDFQATTM (SEQ ID NO:23).

In one embodiment, the TCR that specifically binds to a mRAS peptide having a G12 mutation at a position corresponding to RAS G12 comprises TRBV20-1 CDR2. In one embodiment, the TCR that specifically binds to a mRAS peptide having a G12 mutation at a position corresponding to RAS G12 comprises TRBV20-1 CDR2, wherein TRBV20-1 CDR2 comprises the amino acid sequence of: TSNEGSKAT (SEQ ID NO:24).

In one embodiment, the TCR that specifically binds to a mRAS peptide having a G12 mutation at a position corresponding to RAS G12 comprises TRBV20-1 CDR3. In one embodiment, the TCR that specifically binds to a mRAS peptide having a G12 mutation at a position corresponding to RAS G12 comprises TRBV20-1 CDR3, wherein TRBV20-1 CDR3 comprises the amino acid sequence of: CSASPRAGQLSSYNSPLHF (SEQ ID NO:25).

In one embodiment, the TCR that specifically binds to a mRAS peptide having a G12 mutation at a position corresponding to RAS G12 comprises TRBV20-1 CDR1, TRBV20-1 CDR2, and TRBV20-1 CDR3.

In one embodiment, the TCR that specifically binds to a mRAS peptide having a G12 mutation at a position corresponding to RAS G12 comprises a variable domain of TRBV20-1. In one embodiment, the TCR that specifically binds to a mRAS peptide having a G12 mutation at a position corresponding to RAS G12 comprises a variable domain of TRBV20-1, wherein the variable domain of TRBV20-1 comprises the amino acid sequence of:

(SEQ ID NO: 26)
GAVVSQHPSWVICKSGTSVKIECRSLDFQATTMFWYRQFPKQSLMLMAT

SNEGSKATYEQGVEKDKFLINHASLTLSTLTVTSAHPEDSSFYICSASP

RAGQLSSYNSPLHFGNGTRLTV.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 27)
EDLNKVFPPEVAVFEPSEAEISHTQKATLVCLATGFFPDHVELSWWVNG

KEVHSGVSTDPQPLKEQPALNDSRYCLSSRLRVSATFWQNPRNHFRCQV

QFYGLSENDEWTQDRAKPVTQIVSAEAWGRADCGFTSVSYQQGVLSATI

LYEILLGKATLYAVLVSALVLMAMVKRKDF.

In one embodiment, the TCR comprises a TCR beta chain comprising the amino acid sequence of:

(SEQ ID NO: 28)
MLLLLLLLGPGISLLLPGSLAGSGLGAVVSQHPSWVICKSGTSVKIECR

SLDFQATTMFWYRQFPKQSLMLMATSNEGSKATYEQGVEKDKFLINHAS

LTLSTLTVTSAHPEDSSFYICSASPRAGQLSSYNSPLHFGNGTRLTVTE

DLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQ

FYGLSENDEWTQDRAKPVTQIVSAEAWGRADCGFTSVSYQQGVLSATIL

YEILLGKATLYAVLVSALVLMAMVKRKDF

In one embodiment, the TCR comprises (a) a TCR alpha chain comprising one or more of: TRAV39 CDR1, TRAV39 CDR2, and TRAV39 CDR3 and (b) a TCR beta chain comprising one or more of TRBV20-1 CDR1, TRBV20-1 CDR2, and TRBV20-1 CDR3. In one embodiment, the TCR comprises (a) a TCR alpha chain comprising one or more of: TRAV39 CDR1, TRAV39 CDR2, and TRAV39 CDR3 and (b) a TCR beta chain comprising one or more of TRBV20-1 CDR1, TRBV20-1 CDR2, and TRBV20-1 CDR3, and binds to an mRAS peptide comprising a G12V or a G12C mutation at a position relative to RAS G12. In one embodiment, the TCR comprises (a) a TCR alpha chain comprising one or more of: TRAV39 CDR1, TRAV39 CDR2, and TRAV39 CDR3 and (b) a TCR beta chain comprising one or more of TRBV20-1 CDR1, TRBV20-1 CDR2, and TRBV20-1 CDR3, and binds to an mRAS peptide comprising VVVGAVGVGK (SEQ ID NO:12) in the context of an HLA-A*11:01 molecule. In one embodiment, the TCR comprises (a) a TCR alpha chain comprising one or more of: TRAV39 CDR1, TRAV39 CDR2, and TRAV39 CDR3 and (b) a TCR beta chain comprising one or more of TRBV20-1 CDR1, TRBV20-1 CDR2, and TRBV20-1 CDR3, and binds to an mRAS peptide comprising VVVGACGVGK (SEQ ID NO: 6) in the context of an HLA-A*11:01 molecule.

In one embodiment, the TCR comprises (a) a TCR alpha chain comprising TRAV39 CDR1, TRAV39 CDR2, and TRAV39 CDR3 and (b) a TCR beta chain comprising TRBV20-1 CDR1, TRBV20-1 CDR2, and TRBV20-1 CDR3. In one embodiment, the TCR comprises (a) a TCR alpha chain comprising TRAV39 CDR1, TRAV39 CDR2, and TRAV39 CDR3 and (b) a TCR beta chain comprising TRBV20-1 CDR1, TRBV20-1 CDR2, and TRBV20-1 CDR3, and binds to an mRAS peptide comprising a G12V or a G12C mutation at a position relative to RAS G12. In one embodiment, the TCR comprises (a) a TCR alpha chain comprising TRAV39 CDR1, TRAV39 CDR2, and TRAV39 CDR3 and (b) a TCR beta chain comprising TRBV20-1 CDR1, TRBV20-1 CDR2, and TRBV20-1 CDR3, and binds to an mRAS peptide comprising VVVGAVGVGK (SEQ ID NO:12) in the context of an HLA-A*11:01 molecule. In one embodiment, the TCR comprises (a) a TCR alpha chain comprising TRAV39 CDR1, TRAV39 CDR2, and TRAV39 CDR3 and (b) a TCR beta chain comprising TRBV20-1 CDR1, TRBV20-1 CDR2, and TRBV20-1 CDR3, and binds to an mRAS peptide comprising VVVGACGVGK (SEQ ID NO:6) in the context of an HLA-A*11:01 molecule.

In one embodiment, the TCR that specifically binds to a mRAS peptide having a G12 mutation at a position corresponding to RAS G12 comprises at least one of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof. In one embodiment, the TCR comprises at least one of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof, and binds to an mRAS peptide comprising a G12V or a G12C mutation at a position relative to RAS G12. In one embodiment, the TCR comprises at least one of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof, and binds to an mRAS peptide comprising VVVGAVGVGK (SEQ ID NO:12) in the context of an HLA-A*11:01 molecule. In one embodiment, the TCR comprises at least one of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof, and binds to an mRAS peptide comprising VVVGACGVGK (SEQ ID NO:6) in the context of an HLA-A*11:01 molecule.

In one embodiment, the TCR that specifically binds to a mRAS peptide having a G12 mutation at a position corresponding to RAS G12 comprises all of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof. In one embodiment, the TCR comprises all of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof, and binds to an mRAS peptide comprising a G12V or a G12C mutation at a position relative to RAS G12. In one embodiment, the TCR comprises all of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof, and binds to an mRAS peptide comprising VVVGAVGVGK (SEQ ID NO:12) in the context of an HLA-A*11:01 molecule. In one embodiment, the TCR comprises all of the CDRs selected from the group consisting of: TRAV39-CDR1: SEQ ID NO:17; TRAV39-CDR2: SEQ ID NO:18; TRAV39-CDR3: SEQ ID NO:19; TRBV20-1-CDR1: SEQ ID NO:23; TRBV20-1-CDR2: SEQ ID NO:24; and TRBV20-1-CDR3: SEQ ID NO:25, or a variant or variants thereof, and binds to an mRAS peptide comprising VVVGACGVGK (SEQ ID NO:6) in the context of an HLA-A*11:01 molecule.

In one embodiment, the composition comprises a fusion protein comprising a TCR alpha chain and a TCR beta chain, described above. In one embodiment, the fusion protein comprises a linker domain separating the TCR alpha chain with the TCR beta chain. In one embodiment, the linker domain is a cleavable linker domain. For example, in one embodiment, the linker domain comprises a GSG-T2A domain. In one embodiment, the GSG-T2A comprises the amino acid sequence of: GSGEGRGSLLTCGDVEENPGP (SEQ ID NO:29).

In one embodiment, the composition comprises a fusion protein comprising the amino acid sequence of:

```
                                                   (SEQ ID NO: 30)
MKKLLAMILWLQLDRLSGELKVEQNPLFLSMQEGKNYTIYCNYSTTSDR

LYWYRQDPGKSLESLFVLLSNGAVKQEGRLMASLDTKARLSTLHITAAV

HDLSATYFCAVDKDGGYQKVTFGTGTKLQVIPNIQNPDPAVYQLRDSKS

SDKSVCLFTDFDSQTNVSQSKDSDVYITDKTVLDMRSMDFKSNSAVAWS

NKSDFACANAFNNSIIPEDTFFPSPESSCDVKLVEKSFETDTNLNFQNL

SVIGFRILLLKVAGFNLLMTLRLWSSGSGEGRGSLLTCGDVEENPGPML

LLLLLLGPGISLLLPGSLAGSGLGAVVSQHPSWVICKSGTSVKIECRSL

DFQATTMFWYRQFPKQSLMLMATSNEGSKATYEQGVEKDKFLINHASLT

LSTLTVTSAHPEDSSFYICSASPRAGQLSSYNSPLHFGNGTRLTVTEDL

NKVFPPEVAVFEPSEAEISHTQKATLVCLATGFFPDHVELSWWVNGKEV

HSGVSTDPQPLKEQPALNDSRYCLSSRLRVSATFWQNPRNHFRCQVQFY

GLSENDEWTQDRAKPVTQIVSAEAWGRADCGFTSVSYQQGVLSATILYE

ILLGKATLYAVLVSALVLMAMVKRKDF.
```

TCR833

In one embodiment, the TCR that specifically binds to a mRAS peptide having a G12 mutation at a position corresponding to RAS G12 comprises one or more of: a CDR1, a CDR2, and a CDR3 of a TCR alpha chain.

In one embodiment, the TCR that specifically binds to a mRAS peptide having a G12 mutation at a position corresponding to RAS G12 comprises T cell receptor alpha variable 12-1 (TRAV12-1*01, also referred to herein as "TRAV12-1") CDR1. In one embodiment, the TCR that specifically binds to a mRAS peptide having a G12 mutation at a position corresponding to RAS G12 comprises TRAV12-1 CDR1, wherein TRAV12-1 CDR1 comprises the amino acid sequence of: SNSASQSF (SEQ ID NO:31).

In one embodiment, the TCR that specifically binds to a mRAS peptide having a G12 mutation at a position corresponding to RAS G12 comprises TRAV12-1 CDR2. In one embodiment, the TCR that specifically binds to a mRAS peptide having a G12 mutation at a position corresponding to RAS G12 comprises TRAV12-1 CDR2, wherein TRAV12-1 CDR2 comprises the amino acid sequence of: SVYSSGNE (SEQ ID NO:32).

In one embodiment, the TCR that specifically binds to a mRAS peptide having a G12 mutation at a position corresponding to RAS G12 comprises TRAV12-1 CDR3. In one embodiment, the TCR that specifically binds to a mRAS peptide having a G12 mutation at a position corresponding to RAS G12 comprises TRAV12-1 CDR3, wherein TRAV12-1 CDR3 comprises the amino acid sequence of: CAVNPPDTGFQKLVF (SEQ ID NO:33).

In one embodiment, the TCR that specifically binds to a mRAS peptide having a G12 mutation at a position corresponding to RAS G12 comprises TRAV12-1 CDR1, TRAV12-1 CDR2, and TRAV12-1 CDR3.

In one embodiment, the TCR that specifically binds to a mRAS peptide having a G12 mutation at a position corresponding to RAS G12 comprises a variable domain of TRAV12-1. In one embodiment, the TCR that specifically binds to a mRAS peptide having a G12 mutation at a position corresponding to RAS G12 comprises a variable domain of TRAV12-1, wherein the variable domain of TRAV12-1 comprises the amino acid sequence of:

```
                                                   (SEQ ID NO: 34)
RKEVEQDPGPFNVPEGATVAFNCTYSNSASQSFFWYRQDCRKEPKLLMS

VYSSGNEDGRFTAQLNRASQYISLLIRDSKLSDSATYLCAVNPPDTGFQ

KLVFGTGTRLLVSP.
```

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

```
                                                   (SEQ ID NO: 35)
IQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKL

VEKSFETDTNLNFQNLSVIGFRILLLKVAGFNLLMTLRLWSS.
```

In one embodiment, the TCR comprises a TCR alpha chain comprising the amino acid sequence of:

```
                                                   (SEQ ID NO: 36)
MISLRVLLVILWLQLSWVWSQRKEVEQDPGPFNVPEGATVAFNCTYSNS

ASQSFFWYRQDCRKEPKLLMSVYSSGNEDGRFTAQLNRASQYISLLIRD

SKLSDSATYLCAVNPPDTGFQKLVFGTGTRLLVSPNIQNPDPAVYQLRD

SKSSDKSVCLFTDFDSQTNVSQSKDSDVYITDKTVLDMRSMDFKSNSAV

AWSNKSDFACANAFNNSIIPEDTFFPSPESSCDVKLVEKSFETDTNLNF

QNLSVIGFRILLLKVAGFNLLMTLRLWSS.
```

In one embodiment, the TCR that specifically binds to a mRAS peptide having a G12 mutation at a position corresponding to RAS G12 comprises one or more of: a CDR1, a CDR2, and a CDR3 of a TCR beta chain.

In one embodiment, the TCR that specifically binds to a mRAS peptide having a G12 mutation at a position corresponding to RAS G12 comprises T cell receptor beta variable 28 (TRBV28*01; also referred to herein as "TRBV28") CDR1. In one embodiment, the TCR that specifically binds to a mRAS peptide having a G12 mutation at a position corresponding to RAS G12 comprises TRBV28 CDR1, wherein TRBV28 CDR1 comprises the amino acid sequence of: DMDHENM (SEQ ID NO:37).

In one embodiment, the TCR that specifically binds to a mRAS peptide having a G12 mutation at a position corresponding to RAS G12 comprises TRBV28 CDR2. In one embodiment, the TCR that specifically binds to a mRAS peptide having a G12 mutation at a position corresponding to RAS G12 comprises TRBV28 CDR2, wherein TRBV28 CDR2 comprises the amino acid sequence of: FSYDVKME (SEQ ID NO:38).

In one embodiment, the TCR that specifically binds to a mRAS peptide having a G12 mutation at a position corresponding to RAS G12 comprises TRBV28 CDR3. In one embodiment, the TCR that specifically binds to a mRAS peptide having a G12 mutation at a position corresponding to RAS G12 comprises TRBV28 CDR3, wherein TRBV28 CDR3 comprises the amino acid sequence of: CASSLSFRQGLREQYF (SEQ ID NO:39).

In one embodiment, the TCR that specifically binds to a mRAS peptide having a G12 mutation at a position corresponding to RAS G12 comprises TRBV28 CDR1, TRBV28 CDR2, and TRBV28 CDR3.

In one embodiment, the TCR that specifically binds to a mRAS peptide having a G12 mutation at a position corresponding to RAS G12 comprises a variable domain of TRBV28. In one embodiment, the TCR that specifically binds to a mRAS peptide having a G12 mutation at a position corresponding to RAS G12 comprises a variable domain of TRBV28, wherein the variable domain of TRBV28 comprises the amino acid sequence of:

(SEQ ID NO: 40)
MGIRLLCRVAFCFLAVGLVDVKVTQSSRYLVKRTGEKVFLECVQDMDHE

NMFWYRQDPGLGLRLIYFSYDVKMKEKGDIPEGYSVSREKKERFSLILE

SASTNQTSMYLCASSLSFRQGLREQYFGPGTRLTVT.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 41)
EDLKNVFPPEVAVFEPSEAEISHTQKATLVCLATGFYPDHVELSWWVNG

KEVHSGVSTDPQPLKEQPALNDSRYCLSSRLRVSATFWQNPRNHFRCQV

QFYGLSENDEWTQDRAKPVTQIVSAEAWGRADCGFTSESYQQGVLSATI

LYEILLGKATLYAVLVSALVLMAMVKRKDSRG.

In one embodiment, the TCR comprises a TCR beta chain comprising the amino acid sequence of:

(SEQ ID NO: 42)
MGIRLLCRVAFCFLAVGLVDVKVTQSSRYLVKRTGEKVFLECVQDMDHE

NMFWYRQDPGLGLRLIYFSYDVKMKEKGDIPEGYSVSREKKERFSLILE

SASTNQTSMYLCASSLSFRQGLREQYFGPGTRLTVTEDLKNVFPPEVAV

FEPSEAEISHTQKATLVCLATGFYPDHVELSWWVNGKEVHSGVSTDPQP

LKEQPALNDSRYCLSSRLRVSATFWQNPRNHFRCQVQFYGLSENDEWTQ

DRAKPVTQIVSAEAWGRADCGFTSESYQQGVLSATILYEILLGKATLYA

VLVSALVLMAMVKRKDSRG

In one embodiment, the TCR comprises (a) a TCR alpha chain comprising one or more of: TRAV12-1 CDR1, TRAV12-1 CDR2, and TRAV12-1 CDR3 and (b) a TCR beta chain comprising one or more of TRBV28 CDR1, TRBV28 CDR2, and TRBV28 CDR3. In one embodiment, the TCR comprises (a) a TCR alpha chain comprising one or more of: TRAV12-1 CDR1, TRAV12-1 CDR2, and TRAV12-1 CDR3 and (b) a TCR beta chain comprising one or more of TRBV28 CDR1, TRBV28 CDR2, and TRBV28 CDR3, and binds to an mRAS peptide comprising a G12V or a G12C mutation at a position relative to RAS G12. In one embodiment, the TCR comprises (a) a TCR alpha chain comprising one or more of: TRAV12-1 CDR1, TRAV12-1 CDR2, and TRAV12-1 CDR3 and (b) a TCR beta chain comprising one or more of TRBV28 CDR1, TRBV28 CDR2, and TRBV28 CDR3, and binds to an mRAS peptide comprising VVVGAVGVGK (SEQ ID NO:12) in the context of an HLA-A*11:01 molecule. In one embodiment, the TCR comprises (a) a TCR alpha chain comprising one or more of: TRAV12-1 CDR1, TRAV12-1 CDR2, and TRAV12-1 CDR3 and (b) a TCR beta chain comprising one or more of TRBV28 CDR1, TRBV28 CDR2, and TRBV28 CDR3, and binds to an mRAS peptide comprising VVVGACGVGK (SEQ ID NO:6) in the context of an HLA-A*11:01 molecule.

In one embodiment, the TCR comprises (a) a TCR alpha chain comprising TRAV12-1 CDR1, TRAV12-1 CDR2, and TRAV12-1 CDR3 and (b) a TCR beta chain comprising TRBV28 CDR1, TRBV28 CDR2, and TRBV28 CDR3. In one embodiment, the TCR comprises (a) a TCR alpha chain comprising TRAV12-1 CDR1, TRAV12-1 CDR2, and TRAV12-1 CDR3 and (b) a TCR beta chain comprising TRBV28 CDR1, TRBV28 CDR2, and TRBV28 CDR3, and binds to an mRAS peptide comprising a G12V or a G12C mutation at a position relative to RAS G12. In one embodiment, the TCR comprises (a) a TCR alpha chain comprising TRAV12-1 CDR1, TRAV12-1 CDR2, and TRAV12-1 CDR3 and (b) a TCR beta chain comprising TRBV28 CDR1, TRBV28 CDR2, and TRBV28 CDR3, and binds to an mRAS peptide comprising VVVGAVGVGK (SEQ ID NO:12) in the context of an HLA-A*11:01 molecule. In one embodiment, the TCR comprises (a) a TCR alpha chain comprising TRAV12-1 CDR1, TRAV12-1 CDR2, and TRAV12-1 CDR3 and (b) a TCR beta chain comprising TRBV28 CDR1, TRBV28 CDR2, and TRBV28 CDR3, and binds to an mRAS peptide comprising VVVGACGVGK (SEQ ID NO:6) in the context of an HLA-A*11:01 molecule.

In one embodiment, the TCR that specifically binds to a mRAS peptide having a G12 mutation at a position corresponding to RAS G12 comprises at least one of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof. In one embodiment, the TCR comprises at least one of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof, and binds to an mRAS peptide comprising a G12V or a G12C mutation at a position relative to RAS G12. In one embodiment, the TCR comprises at least one of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof, and binds to an mRAS peptide comprising VVVGAVGVGK (SEQ ID NO:12) in the context of an HLA-A*11:01 molecule. In one embodiment, the TCR comprises at least one of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof, and binds to an mRAS peptide comprising VVVGACGVGK (SEQ ID NO:6) in the context of an HLA-A*11:01 molecule.

In one embodiment, the TCR that specifically binds to a mRAS peptide having a G12 mutation at a position corresponding to RAS G12 comprises all of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof. In one embodiment, the TCR comprises all of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof, and binds to an mRAS peptide comprising a G12V or a G12C mutation at a position relative to RAS G12. In one embodiment, the TCR comprises all of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof, and binds to an mRAS peptide comprising VVVGAVGVGK (SEQ ID NO:12) in the context of an HLA-A*11:01 molecule. In one embodiment, the TCR comprises all of the CDRs selected from the group consisting of: TRAV12-1-CDR1: SEQ ID NO:31; TRAV12-1-CDR2: SEQ ID NO:32; TRAV12-1-CDR3: SEQ ID NO:33; TRBV28-CDR1: SEQ ID NO:37; TRBV28-CDR2: SEQ ID NO:38; and TRBV28-CDR3: SEQ ID NO:39, or a variant or variants thereof, and binds to an mRAS peptide comprising VVVGACGVGK (SEQ ID NO:6) in the context of an HLA-A*11:01 molecule.

In one embodiment, the composition comprises a fusion protein comprising a TCR alpha chain and a TCR beta chain, described above. In one embodiment, the fusion protein comprises a linker domain separating the TCR alpha chain with the TCR beta chain. In one embodiment, the linker domain is a cleavable linker domain. For example, in one embodiment, the linker domain comprises a GSG-T2A domain. In one embodiment, the GSG-T2A comprises the amino acid sequence of: GSGEGRGSLLTCGDVEENPGP (SEQ ID NO:43).

In one embodiment, the composition comprises a fusion protein comprising the amino acid sequence of:

```
                                           (SEQ ID NO: 44)
MISLRVLLVILWLQLSWVWSQRKEVEQDPGPFNVPEGATVAFNCTYSNS
ASQSFFWYRQDCRKEPKLLMSVYSSGNEDGRFTAQLNRASQYISLLIRD
SKLSDSATYLCAVNPPDTGFQKLVFGTGTRLLVSPNIQNPDPAVYQLRD
SKSSDKSVCLFTDFDSQTNVSQSKDSDVYITDKTVLDMRSMDFKSNSAV
AWSNKSDFACANAFNNSIIPEDTFFPSPESSCDVKLVEKSFETDTNLNF
QNLSVIGFRILLLKVAGFNLLMTLRLWSSGSGEGRGSLLTCGDVEENPG
PMGIRLLCRVAFCFLAVGLVDVKVTQSSRYLVKRTGEKVFLECVQDMDH
ENMFWYRQDPGLGLRLIYFSYDVKMKEKGDIPEGYSVSREKKERFSLIL
ESASTNQTSMYLCASSLSFRQGLREQYFGPGTRLTVTEDLKNVFPPEVA
VFEPSEAEISHTQKATLVCLATGFYPDHVELSWWVNGKEVHSGVSTDPQ
PLKEQPALNDSRYCLSSRLRVSATFWQNPRNHFRCQVQFYGLSENDEWT
QDRAKPVTQIVSAEAWGRADCGFTSESYQQGVLSATILYEILLGKATLY
AVLVSALVLMAMVKRKDSRG.
```

TCR897

In one embodiment, the TCR that specifically binds to a mRAS peptide having a G12 mutation at a position corresponding to RAS G12 comprises one or more of: a CDR1, a CDR2, and a CDR3 of a TCR alpha chain.

In one embodiment, the TCR that specifically binds to a mRAS peptide having a G12 mutation at a position corresponding to RAS G12 comprises T cell receptor alpha variable 17 (TRAV17) CDR1. In one embodiment, the TCR that specifically binds to a mRAS peptide having a G12 mutation at a position corresponding to RAS G12 comprises TRAV17 CDR1, wherein TRAV17 CDR1 comprises the amino acid sequence of: KTSINNL (SEQ ID NO:45).

In one embodiment, the TCR that specifically binds to a mRAS peptide having a G12 mutation at a position corresponding to RAS G12 comprises TRAV17 CDR2. In one embodiment, the TCR that specifically binds to a mRAS peptide having a G12 mutation at a position corresponding to RAS G12 comprises TRAV17 CDR2, wherein TRAV17 CDR2 comprises the amino acid sequence of: LIRSNEREK (SEQ ID NO:46).

In one embodiment, the TCR that specifically binds to a mRAS peptide having a G12 mutation at a position corresponding to RAS G12 comprises TRAV17 CDR3. In one embodiment, the TCR that specifically binds to a mRAS peptide having a G12 mutation at a position corresponding to RAS G12 comprises TRAV17 CDR3, wherein TRAV17 CDR3 comprises the amino acid sequence of: CATDPGGFKTIF (SEQ ID NO:47).

In one embodiment, the TCR that specifically binds to a mRAS peptide having a G12 mutation at a position corresponding to RAS G12 comprises TRAV17 CDR1, TRAV17 CDR2, and TRAV17 CDR3.

In one embodiment, the TCR that specifically binds to a mRAS peptide having a G12 mutation at a position corresponding to RAS G12 comprises a variable domain of TRAV17. In one embodiment, the TCR that specifically binds to a mRAS peptide having a G12 mutation at a position corresponding to RAS G12 comprises a variable domain of TRAV17, wherein the variable domain of TRAV17 comprises the amino acid sequence of:

(SEQ ID NO: 169)
SQQGEEDPQALSIQEGENATMNCSYKTSINNLQWYRQNSGRGLVHLILI
RSNEREKHSGRLRVTLDTSKKSSSLLITASRAADTASYFCATD.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 48)
IQNPDPAVYQLRDSKSSDKSVCLFTDFDSQTNVSQSKDSDVYITDKTVL
DMRSMDFKSNSAVAWSNKSDFACANAFNNSIIPEDTFFPSPESSCDVKL
VEKSFETDTNLNFQNLSVIGFRILLLKVAGFNLLMTLRLWSS.

In one embodiment, the TCR comprises a TCR alpha chain comprising the amino acid sequence of:

(SEQ ID NO: 49)
METLLGVSLVILWLQLARVNSQQGEEDPQALSIQEGENATMNCSYKTSI
NNLQWYRQNSGRGLVHLILIRSNEREKHSGRLRVTLDTSKKSSSLLITA
SRAADTASYFCATDPGGFKTIFGAGTRLFVKANIQNPDPAVYQLRDSKS
SDKSVCLFTDFDSQTNVSQSKDSDVYITDKTVLDMRSMDFKSNSAVAWS
NKSDFACANAFNNSIIPEDTFFPSPESSCDVKLVEKSFETDTNLNFQNL
SVIGFRILLLKVAGFNLLMTLRLWSS.

In one embodiment, the TCR that specifically binds to a mRAS peptide having a G12 mutation at a position corresponding to RAS G12 comprises one or more of: a CDR1, a CDR2, and a CDR3 of a TCR beta chain.

In one embodiment, the TCR that specifically binds to a mRAS peptide having a G12 mutation at a position corresponding to RAS G12 comprises T cell receptor beta variable 11-2 (TRBV11-2) CDR1. In one embodiment, the TCR that specifically binds to a mRAS peptide having a G12 mutation at a position corresponding to RAS G12 comprises TRBV11-2 CDR1, wherein TRBV11-2 CDR1 comprises the amino acid sequence of: ISGHATL (SEQ ID NO:50).

In one embodiment, the TCR that specifically binds to a mRAS peptide having a G12 mutation at a position corresponding to RAS G12 comprises TRBV11-2 CDR2. In one embodiment, the TCR that specifically binds to a mRAS peptide having a G12 mutation at a position corresponding to RAS G12 comprises TRBV11-2 CDR2, wherein TRBV11-2 CDR2 comprises the amino acid sequence of: QFQNNGVV (SEQ ID NO:51).

In one embodiment, the TCR that specifically binds to a mRAS peptide having a G12 mutation at a position corresponding to RAS G12 comprises TRBV11-2 CDR3. In one embodiment, the TCR that specifically binds to a mRAS peptide having a G12 mutation at a position corresponding to RAS G12 comprises TRBV11-2 CDR3, wherein TRBV11-2 CDR3 comprises the amino acid sequence of: CASSLYGGSISYEQYF (SEQ ID NO:52).

In one embodiment, the TCR that specifically binds to a mRAS peptide having a G12 mutation at a position corresponding to RAS G12 comprises TRBV11-2 CDR1, TRBV11-2 CDR2, and TRBV11-2 CDR3.

In one embodiment, the TCR that specifically binds to a mRAS peptide having a G12 mutation at a position corresponding to RAS G12 comprises a variable domain of TRBV11-2. In one embodiment, the TCR that specifically binds to a mRAS peptide having a G12 mutation at a position corresponding to RAS G12 comprises a variable domain of TRBV11-2, wherein the variable domain of TRBV11-2 comprises the amino acid sequence of:

(SEQ ID NO: 170)
EAGVAQSPRYKIIEKRQSVAFWCNPISGHATLYWYQQILGQGPKLLIQF
QNNGVVDDSQLPKDRFSAERLKGVDSTLKIQPAKLEDSAVYLCASSL.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 53)
EDLKNVFPPEVAVFEPSEAEISHTQKATLVCLATGFYPDHVELSWWVNG
KEVHSGVSTDPQPLKEQPALNDSRYCLSSRLRVSATFWQNPRNHFRCQV
QFYGLSENDEWTQDRAKPVTQIVSAEAWGRADCGFTSESYQQGVLSATI
LYEILLGKATLYAVLVSALVLMAMVKRKDSRG.

In one embodiment, the TCR comprises a TCR beta chain comprising the amino acid sequence of:

(SEQ ID NO: 54)
MGTRLLCWAALCLLGAELTEAGVAQSPRYKIIEKRQSVAFWCNPISGHA
TLYWYQQILGQGPKLLIQFQNNGVVDDSQLPKDRFSAERLKGVDSTLKI
QPAKLEDSAVYLCASSLYGGSISYEQYFGPGTRLTVTEDLKNVFPPEVA
VFEPSEAEISHTQKATLVCLATGFYPDHVELSWWVNGKEVHSGVSTDPQ
PLKEQPALNDSRYCLSSRLRVSATFWQNPRNHFRCQVQFYGLSENDEWT
QDRAKPVTQIVSAEAWGRADCGFTSESYQQGVLSATILYEILLGKATLY
AVLVSALVLMAMVKRKDSRG

In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV11-2 CDR1, TRBV11-2 CDR2, and TRBV11-2 CDR3. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV11-2 CDR1, TRBV11-2 CDR2, and TRBV11-2 CDR3, and binds to an mRAS peptide comprising a G12V, G12C or G12D mutation at a position relative to RAS G12. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV11-2 CDR1, TRBV11-2 CDR2, and TRBV11-2 CDR3, and binds to an mRAS peptide comprising VVGAVGVGK (SEQ ID NO:11) in the context of an HLA-A*11:01 molecule. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV11-2 CDR1, TRBV11-2 CDR2, and TRBV11-2 CDR3, and binds to an mRAS peptide comprising VVGACGVGK (SEQ ID NO:5) in the context of an HLA-A*11:01 molecule. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV11-2 CDR1, TRBV11-2 CDR2, and TRBV11-2 CDR3, and binds to an mRAS peptide comprising VVGADGVGK (SEQ ID NO:7) in the context of an HLA-A*11:01 molecule. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV11-2 CDR1, TRBV11-2 CDR2, and TRBV11-2 CDR3, and binds to an mRAS peptide comprising VVGARGVGK (SEQ ID NO:9) in the context of an HLA-A*11:01 molecule.

In one embodiment, the TCR comprises (a) a TCR alpha chain comprising TRAV17 CDR1, TRAV17 CDR2, and TRAV17 CDR3 and (b) a TCR beta chain comprising TRBV11-2 CDR1, TRBV11-2 CDR2, and TRBV11-2 CDR3. In one embodiment, the TCR comprises (a) a TCR alpha chain comprising TRAV17 CDR1, TRAV17 CDR2, and TRAV17 CDR3 and (b) a TCR beta chain comprising TRBV11-2 CDR1, TRBV11-2 CDR2, and TRBV11-2 CDR3, and binds to an mRAS peptide comprising a G12V, G12C or G12D mutation at a position relative to RAS G12. In one embodiment, the TCR comprises (a) a TCR alpha chain comprising TRAV17 CDR1, TRAV17 CDR2, and TRAV17 CDR3 and (b) a TCR beta chain comprising TRBV11-2 CDR1, TRBV11-2 CDR2, and TRBV11-2 CDR3, and binds to an mRAS peptide comprising VVGAVGVGK (SEQ ID NO:11) in the context of an HLA-A*11:01 molecule. In one embodiment, the TCR comprises (a) a TCR alpha chain comprising TRAV17 CDR1, TRAV17 CDR2, and TRAV17 CDR3 and (b) a TCR beta chain comprising TRBV11-2 CDR1, TRBV11-2 CDR2, and TRBV11-2 CDR3, and binds to an mRAS peptide comprising VVGACGVGK (SEQ ID NO:5) in the context of an HLA-A*11:01 molecule. In one embodiment, the TCR comprises (a) a TCR alpha chain comprising TRAV17 CDR1, TRAV17 CDR2, and TRAV17 CDR3 and (b) a TCR beta chain comprising TRBV11-2 CDR1, TRBV11-2 CDR2, and TRBV11-2 CDR3, and binds to an mRAS peptide comprising VVGADGVGK (SEQ ID NO:7) in the context of an HLA-A*11:01 molecule. In one embodiment, the TCR comprises (a) a TCR alpha chain comprising TRAV17 CDR1, TRAV17 CDR2, and TRAV17 CDR3 and (b) a TCR beta chain comprising TRBV11-2 CDR1, TRBV11-2 CDR2, and TRBV11-2 CDR3, and binds to an mRAS peptide comprising VVGARGVGK (SEQ ID NO:9) in the context of an HLA-A*11:01 molecule.

In one embodiment, the TCR that specifically binds to a mRAS peptide having a G12 mutation at a position corresponding to RAS G12 comprises at least one of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof. In one embodiment, the TCR comprises at least one of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising a G12V, G12C, or G12D mutation at a position relative to RAS G12. In one embodiment, the TCR comprises at least one of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGAVGVGK (SEQ ID NO:11) in the context of an HLA-A*11:01 molecule. In one embodiment, the TCR comprises at least one of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGACGVGK (SEQ ID NO:5) in the context of an HLA-A*11:01 molecule. In one embodiment, the TCR comprises at least one of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGADGVGK (SEQ ID NO:7) in the context of an HLA-A*11:01 molecule. In one embodiment, the TCR comprises at least one of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGARGVGK (SEQ ID NO:9) in the context of an HLA-A*11:01 molecule.

In one embodiment, the TCR that specifically binds to a mRAS peptide having a G12 mutation at a position corresponding to RAS G12 comprises all of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof. In one embodiment, the TCR comprises all of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising a G12V, G12C or G12D mutation at a position relative to RAS G12. In one embodiment, the TCR comprises all of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGAVGVGK (SEQ ID NO:11) in the context of an HLA-A*11:01 molecule. In one embodiment, the TCR comprises all of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50;

TRBV11-2-CDR2: SEQ ID NO:51; and TRBV11-2-CDR3: SEQ ID NO:52, or a variant or variants thereof, and binds to an mRAS peptide comprising VVGACGVGK (SEQ ID NO:5) in the context of an HLA-A*11:01 molecule. In one embodiment, the TCR comprises all of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGADGVGK (SEQ ID NO:7) in the context of an HLA-A*11:01 molecule. In one embodiment, the TCR comprises all of the CDRs selected from the group consisting of: TRAV17-CDR1: SEQ ID NO:45; TRAV17-CDR2: SEQ ID NO:46; TRAV17-CDR3: SEQ ID NO:47; TRBV11-2-CDR1: SEQ ID NO:50; TRBV11-2-CDR2: SEQ ID NO:51; and TRBV11-2-CDR3: SEQ ID NO:52, or a variant or variants thereof, and binds to an mRAS peptide comprising VVGARGVGK (SEQ ID NO:9) in the context of an HLA-A*11:01 molecule.

In one embodiment, the composition comprises a fusion protein comprising a TCR alpha chain and a TCR beta chain, described above. In one embodiment, the fusion protein comprises a linker domain separating the TCR alpha chain with the TCR beta chain. In one embodiment, the linker domain is a cleavable linker domain. For example, in one embodiment, the linker domain comprises a GSG-T2A domain. In one embodiment, the GSG-T2A comprises the amino acid sequence of: GSGEGRGSLLTCGDVEENPGP (SEQ ID NO:55).

In one embodiment, the composition comprises a fusion protein comprising the amino acid sequence of:

(SEQ ID NO: 56)
METLLGVSLVILWLQLARVNSQQGEEDPQALSIQEGENATMNCSYKTSI
NNLQWYRQNSGRGLVHLILIRSNEREKHSGRLRVTLDTSKKSSSLLITA
SRAADTASYFCATDPGGFKTIFGAGTRLFVKANIQNPDPAVYQLRDSKS
SDKSVCLFTDFDSQTNVSQSKDSDVYITDKTVLDMRSMDFKSNSAVAWS
NKSDFACANAFNNSIIPEDTFFPSPESSCDVKLVEKSFETDTNLNFQNL
SVIGFRILLLKVAGFNLLMTLRLWSSGSGEGRGSLLTCGDVEENPGPMG
TRLLCWAALCLLGAELTEAGVAQSPRYKIIEKRQSVAFWCNPISGHATL
YWYQQILGQGPKLLIQFQNNGVVDDSQLPKDRFSAERLKGVDSTLKIQP
AKLEDSAVYLCASSLYGGSISYEQYFGPGTRLTVTEDLKNVFPPEVAVF
EPSEAEISHTQKATLVCLATGFYPDHVELSWWVNGKEVHSGVSTDPQPL
KEQPALNDSRYCLSSRLRVSATFWQNPRNHFRCQVQFYGLSENDEWTQD
RAKPVTQIVSAEAWGRADCGFTSESYQQGVLSATILYEILLGKATLYAV
LVSALVLMAMVKRKDSRG.

TCR896

In one embodiment, the TCR that specifically binds to a mRAS peptide having a G12V mutation at a position corresponding to RAS G12 comprises one or more of: a CDR1, a CDR2, and a CDR3 of a TCR alpha chain.

In one embodiment, the TCR that specifically binds to a mRAS peptide having a G12 mutation at a position corresponding to RAS G12 comprises T cell receptor alpha variable 19 (TRAV19) CDR1. In one embodiment, the TCR that specifically binds to a mRAS peptide having a G12 mutation at a position corresponding to RAS G12 comprises TRAV19 CDR1, wherein TRAV19 CDR1 comprises the amino acid sequence of: ETRDTTYYL (SEQ ID NO:57).

In one embodiment, the TCR that specifically binds to a mRAS peptide having a G12 mutation at a position corresponding to RAS G12 comprises TRAV19 CDR2. In one embodiment, the TCR that specifically binds to a mRAS peptide having a G12 mutation at a position corresponding to RAS G12 comprises TRAV19 CDR2, wherein TRAV19 CDR2 comprises the amino acid sequence of: RRNSFDEQNE (SEQ ID NO:58).

In one embodiment, the TCR that specifically binds to a mRAS peptide having a G12 mutation at a position corresponding to RAS G12 comprises TRAV19 CDR3. In one embodiment, the TCR that specifically binds to a mRAS peptide having a G12 mutation at a position corresponding to RAS G12 comprises TRAV19 CDR3, wherein TRAV19 CDR3 comprises the amino acid sequence of: CALSEAGTYKYIF (SEQ ID NO:59).

In one embodiment, the TCR that specifically binds to a mRAS peptide having a G12 mutation at a position corresponding to RAS G12 comprises TRAV19 CDR1, TRAV19 CDR2, and TRAV19 CDR3.

In one embodiment, the TCR that specifically binds to a mRAS peptide having a G12 mutation at a position corresponding to RAS G12 comprises a variable domain of TRAV19. In one embodiment, the TCR that specifically binds to a mRAS peptide having a G12 mutation at a position corresponding to RAS G12 comprises a variable domain of TRAV19, wherein the variable domain of TRAV19 comprises the amino acid sequence of:

(SEQ ID NO: 171)
AQKVTQAQTEISVVEKEDVTLDCVYETRDTTYYLFWYKQPPSGELVFLI
RRNSFDEQNEISGRYSWNFQKSTSSFNFTITASQVVDSAVYFCALSE.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 60)
IQNPDPAVYQLRDSKSSDKSVCLFTDFDSQTNVSQSKDSDVYITDKTVL
DMRSMDFKSNSAVAWSNKSDFACANAFNNSIIPEDTFFPSPESSCDVKL
VEKSFETDTNLNFQNLSVIGFRILLLKVAGFNLLMTLRLWSS.

In one embodiment, the TCR comprises a TCR alpha chain comprising the amino acid sequence of:

(SEQ ID NO: 61)
MLTASLLRAVIASICVVSSMAQKVTQAQTEISVVEKEDVTLDCVYETRD
TTYYLFWYKQPPSGELVFLIRRNSFDEQNEISGRYSWNFQKSTSSFNFT
ITASQVVDSAVYFCALSEAGTYKYIFGTGTRLKVLANIQNPDPAVYQLR
DSKSSDKSVCLFTDFDSQTNVSQSKDSDVYITDKTVLDMRSMDFKSNSA
VAWSNKSDFACANAFNNSIIPEDTFFPSPESSCDVKLVEKSFETDTNLN
FQNLSVIGFRILLLKVAGFNLLMTLRLWSS.

In one embodiment, the TCR that specifically binds to a mRAS peptide having a G12 mutation at a position corresponding to RAS G12 comprises one or more of: a CDR1, a CDR2, and a CDR3 of a TCR beta chain.

In one embodiment, the TCR that specifically binds to a mRAS peptide having a G12 mutation at a position corresponding to RAS G12 comprises T cell receptor beta variable 9 (TRBV9) CDR1. In one embodiment, the TCR that specifically binds to a mRAS peptide having a G12 mutation at a position corresponding to RAS G12 comprises TRBV9 CDR1, wherein TRBV9 CDR1 comprises the amino acid sequence of: RSGDLSV (SEQ ID NO:62).

In one embodiment, the TCR that specifically binds to a mRAS peptide having a G12 mutation at a position corresponding to RAS G12 comprises TRBV9 CDR2. In one embodiment, the TCR that specifically binds to a mRAS peptide having a G12 mutation at a position corresponding to RAS G12 comprises TRBV9 CDR2, wherein TRBV9 CDR2 comprises the amino acid sequence of: QYYNGEER (SEQ ID NO:63).

In one embodiment, the TCR that specifically binds to a mRAS peptide having a G12 mutation at a position corresponding to RAS G12 comprises TRBV9 CDR3. In one embodiment, the TCR that specifically binds to a mRAS peptide having a G12 mutation at a position corresponding to RAS G12 comprises TRBV9 CDR3, wherein TRBV9 CDR3 comprises the amino acid sequence of: CASSVAGGGQETQYF (SEQ ID NO:64).

In one embodiment, the TCR that specifically binds to a mRAS peptide having a G12 mutation at a position corresponding to RAS G12 comprises TRBV9 CDR1, TRBV9 CDR2, and TRBV9 CDR3.

In one embodiment, the TCR that specifically binds to a mRAS peptide having a G12 mutation at a position corresponding to RAS G12 comprises a variable domain of TRBV9. In one embodiment, the TCR that specifically binds to a mRAS peptide having a G12 mutation at a position corresponding to RAS G12 comprises a variable domain of TRBV9, wherein the variable domain of TRBV9 comprises the amino acid sequence of:

```
                                     (SEQ ID NO: 172)
DSGVTQTPKHLITATGQRVTLRCSPRSGDLSVYWYQQSLDQGLQFLIQY

YNGEERAKGNILERFSAQQFPDLHSELNLSSLELGDSALYFCASSV.
```

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

```
                                      (SEQ ID NO: 65)
EDLKNVFPPEVAVFEPSEAEISHTQKATLVCLATGFYPDHVELSWWVNG

KEVHSGVSTDPQPLKEQPALNDSRYCLSSRLRVSATFWQNPRNHFRCQV

QFYGLSENDEWTQDRAKPVTQIVSAEAWGRADCGFTSESYQQGVLSATI

LYEILLGKATLYAVLVSALVLMAMVKRKDSRG.
```

In one embodiment, the TCR comprises a TCR beta chain comprising the amino acid sequence of:

```
                                      (SEQ ID NO: 66)
MGFRLLCCVAFCLLGAGPVDSGVTQTPKHLITATGQRVTLRCSPRSGDL

SVYWYQQSLDQGLQFLIQYYNGEERAKGNILERFSAQQFPDLHSELNLS

SLELGDSALYFCASSVAGGGQETQYFGPGTRLLVLEDLKNVFPPEVAVF

EPSEAEISHTQKATLVCLATGFYPDHVELSWWVNGKEVHSGVSTDPQPL

KEQPALNDSRYCLSSRLRVSATFWQNPRNHFRCQVQFYGLSENDEWTQD

RAKPVTQIVSAEAWGRADCGFTSESYQQGVLSATILYEILLGKATLYAV

LVSALVLMAMVKRKDSRG
```

In one embodiment, the TCR comprises (a) a TCR alpha chain comprising one or more of: TRAV19 CDR1, TRAV19 CDR2, and TRAV19 CDR3 and (b) a TCR beta chain comprising one or more of TRBV9 CDR1, TRBV9 CDR2, and TRBV9 CDR3. In one embodiment, the TCR comprises (a) a TCR alpha chain comprising one or more of: TRAV19 CDR1, TRAV19 CDR2, and TRAV19 CDR3 and (b) a TCR beta chain comprising one or more of TRBV9 CDR1, TRBV9 CDR2, and TRBV9 CDR3, and binds to an mRAS peptide comprising a G12V mutation at a position relative to RAS G12. In one embodiment, the TCR comprises (a) a TCR alpha chain comprising one or more of: TRAV19 CDR1, TRAV19 CDR2, and TRAV19 CDR3 and (b) a TCR beta chain comprising one or more of TRBV9 CDR1, TRBV9 CDR2, and TRBV9 CDR3, and binds to an mRAS peptide comprising VVGAVGVGK (SEQ ID NO:11) OR VVVGAVGVGK (SEQ ID NO:12) in the context of an HLA-A*03:01 molecule.

In one embodiment, the TCR comprises (a) a TCR alpha chain comprising TRAV19 CDR1, TRAV19 CDR2, and TRAV19 CDR3 and (b) a TCR beta chain comprising TRBV9 CDR1, TRBV9 CDR2, and TRBV9 CDR3. In one embodiment, the TCR comprises (a) a TCR alpha chain comprising TRAV19 CDR1, TRAV19 CDR2, and TRAV19 CDR3 and (b) a TCR beta chain comprising TRBV9 CDR1, TRBV9 CDR2, and TRBV9 CDR3, and binds to an mRAS peptide comprising a G12V mutation at a position relative to RAS G12. In one embodiment, the TCR comprises (a) a TCR alpha chain comprising TRAV19 CDR1, TRAV19 CDR2, and TRAV19 CDR3 and (b) a TCR beta chain comprising TRBV9 CDR1, TRBV9 CDR2, and TRBV9 CDR3, and binds to an mRAS peptide comprising VVGAVGVGK (SEQ ID NO:11) or VVVGAVGVGK (SEQ ID NO:12) in the context of an HLA-A*03:01 molecule.

In one embodiment, the TCR that specifically binds to a mRAS peptide having a G12 mutation at a position corresponding to RAS G12 comprises at least one of the CDRs selected from the group consisting of: TRAV19-CDR1: SEQ ID NO:57; TRAV19-CDR2: SEQ ID NO:58; TRAV19-CDR3: SEQ ID NO:59; TRBV9-CDR1: SEQ ID NO:62; TRBV9-CDR2: SEQ ID NO:63; and TRBV9-CDR3: SEQ ID NO:64, or a variant or variants thereof. In one embodiment, the TCR comprises at least one of the CDRs selected from the group consisting of: TRAV19-CDR1: SEQ ID NO:57; TRAV19-CDR2: SEQ ID NO:58; TRAV19-CDR3: SEQ ID NO:59; TRBV9-CDR1: SEQ ID NO:62; TRBV9-CDR2: SEQ ID NO:63; and TRBV9-CDR3: SEQ ID NO:64, or a variant or variants thereof, and binds to an mRAS peptide comprising a G12V mutation at a position relative to RAS G12. In one embodiment, the TCR comprises at least one of the CDRs selected from the group consisting of: TRAV19-CDR1: SEQ ID NO:57; TRAV19-CDR2: SEQ ID NO:58; TRAV19-CDR3: SEQ ID NO:59; TRBV9-CDR1: SEQ ID NO:62; TRBV9-CDR2: SEQ ID NO:63; and TRBV9-CDR3: SEQ ID NO:64, or a variant or variants thereof, and binds to an mRAS peptide comprising VVGAVGVGK (SEQ ID NO:11) or VVVGAVGVGK (SEQ ID NO:12) in the context of an HLA-A*03:01 molecule.

In another embodiment, the TCR that specifically binds to a mRAS peptide having a G12 mutation at a position corresponding to RAS G12 comprises all of the CDRs of the group consisting of: TRAV19-CDR1: SEQ ID NO:57; TRAV19-CDR2: SEQ ID NO:58; TRAV19-CDR3: SEQ ID NO:59; TRBV9-CDR1: SEQ ID NO:62; TRBV9-CDR2: SEQ ID NO:63; and TRBV9-CDR3: SEQ ID NO:64, or a variant or variants thereof. In one embodiment, the TCR comprises all of the CDRs of the group consisting of: TRAV19-CDR1: SEQ ID NO:57; TRAV19-CDR2: SEQ ID NO:58; TRAV19-CDR3: SEQ ID NO:59; TRBV9-CDR1: SEQ ID NO:62; TRBV9-CDR2: SEQ ID NO:63; and TRBV9-CDR3: SEQ ID NO:64, or a variant or variants thereof, and binds to an mRAS peptide comprising a G12V mutation at a position relative to RAS G12. In one embodiment, the TCR comprises all of the CDRs of the group consisting of: TRAV19-CDR1: SEQ ID NO:57; TRAV19-CDR2: SEQ ID NO:58; TRAV19-CDR3: SEQ ID NO:59; TRBV9-CDR1: SEQ ID NO:62; TRBV9-CDR2: SEQ ID NO:63; and TRBV9-CDR3: SEQ ID NO:64, or a variant or variants thereof, and binds to an mRAS peptide comprising VVGAVGVGK (SEQ ID NO:11) or VVVGAVGVGK (SEQ ID NO:12) in the context of an HLA-A*03:01 molecule.

In one embodiment, the composition comprises a fusion protein comprising a TCR alpha chain and a TCR beta chain, described above. In one embodiment, the fusion protein comprises a linker domain separating the TCR alpha chain with the TCR beta chain. In one embodiment, the linker domain is a cleavable linker domain. For example, in one embodiment, the linker domain comprises a GSG-T2A domain. In one embodiment, the GSG-T2A comprises the amino acid sequence of: GSGEGRGSLLTCGDVEENPGP (SEQ ID NO:67).

In one embodiment, the composition comprises a fusion protein comprising the amino acid sequence of:

(SEQ ID NO: 68)

```
MLTASLLRAVIASICVVSSMAQKVTQAQTEISVVEKEDVTLDCVYETRD

TTYYLFWYKQPPSGELVFLIRRNSFDEQNEISGRYSWNFQKSTSSFNFT

ITASQVVDSAVYFCALSEAGTYKYIFGTGTRLKVLANIQNPDPAVYQLR

DSKSSDKSVCLFTDFDSQTNVSQSKDSDVYITDKTVLDMRSMDFKSNSA

VAWSNKSDFACANAFNNSIIPEDTFFPSPESSCDVKLVEKSFETDTNLN

FQNLSVIGFRILLLKVAGFNLLMTLRLWSSGSGEGRGSLLTCGDVEENP

GPMGFRLLCCVAFCLLGAGPVDSGVTQTPKHLITATGQRVTLRCSPRSG

DLSVYWYQQSLDQGLQFLIQYYNGEERAKGNILERFSAQQFPDLHSELN

LSSLELGDSALYFCASSVAGGGQETQYFGPGTRLLVLEDLKNVFPPEVA

VFEPSEAEISHTQKATLVCLATGFYPDHVELSWWVNGKEVHSGVSTDPQ

PLKEQPALNDSRYCLSSRLRVSATFWQNPRNHFRCQVQFYGLSENDEWT

QDRAKPVTQIVSAEAWGRADCGFTSESYQQGVLSATILYEILLGKATLY

AVLVSALVLMAMVKRKDSRG.
```

TCR847

In one embodiment, the TCR that specifically binds to a mRAS peptide having a G12 mutation at a position corresponding to RAS G12 comprises one or more of: a CDR1, a CDR2, and a CDR3 of a TCR alpha chain.

In one embodiment, the TCR that specifically binds to a mRAS peptide having a G12 mutation at a position corresponding to RAS G12 comprises T cell receptor alpha variable 17 (TRAV17) CDR1. In one embodiment, the TCR that specifically binds to a mRAS peptide having a G12 mutation at a position corresponding to RAS G12 comprises TRAV17 CDR1, wherein TRAV17 CDR1 comprises the amino acid sequence of: KTSINNL (SEQ ID NO:69).

In one embodiment, the TCR that specifically binds to a mRAS peptide having a G12 mutation at a position corresponding to RAS G12 comprises TRAV17 CDR2. In one embodiment, the TCR that specifically binds to a mRAS peptide having a G12 mutation at a position corresponding to RAS G12 comprises TRAV17 CDR2, wherein TRAV17 CDR2 comprises the amino acid sequence of: LIRSNEREK (SEQ ID NO:70).

In one embodiment, the TCR that specifically binds to a mRAS peptide having a G12 mutation at a position corresponding to RAS G12 comprises TRAV17 CDR3. In one embodiment, the TCR that specifically binds to a mRAS peptide having a G12 mutation at a position corresponding to RAS G12 comprises TRAV17 CDR3, wherein TRAV17 CDR3 comprises the amino acid sequence of: CATFPNFGNEKLTF (SEQ ID NO:71).

In one embodiment, the TCR that specifically binds to a mRAS peptide having a G12 mutation at a position corresponding to RAS G12 comprises TRAV17 CDR1, TRAV17 CDR2, and TRAV17 CDR3.

In one embodiment, the TCR that specifically binds to a mRAS peptide having a G12 mutation at a position corresponding to RAS G12 comprises a variable domain of TRAV17. In one embodiment, the TCR that specifically binds to a mRAS peptide having a G12 mutation at a position corresponding to RAS G12 comprises a variable domain of TRAV17, wherein the variable domain of TRAV17 comprises the amino acid sequence of:

(SEQ ID NO: 173)

```
SQQGEEDPQALSIQEGENATMNCSYKTSINNLQWYRQNSGRGLVHLILI

RSNEREKHSGRLRVTLDTSKKSSSLLITASRAADTASYFCATF.
```

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 72)

```
IQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKL

VEKSFETDTNLNFQNLSVIGFRILLLKVAGFNLLMTLRLWSS.
```

In one embodiment, the TCR comprises a TCR alpha chain comprising the amino acid sequence of:

```
                                        (SEQ ID NO: 73)
METLLGVSLVILWLQLARVNSQQGEEDPQALSIQEGENATMNCSYKTSI
NNLQWYRQNSGRGLVHLILIRSNEREKHSGRLRVTLDTSKKSSSLLITA
SRAADTASYFCATFPNFGNEKLTFGTGTRLTIIPNIQNPDPAVYQLRDS
KSSDKSVCLFTDFDSQTNVSQSKDSDVYITDKTVLDMRSMDFKSNSAVA
WSNKSDFACANAFNNSIIPEDTFFPSPESSCDVKLVEKSFETDTNLNFQ
NLSVIGFRILLLKVAGFNLLMTLRLWSS
```

In one embodiment, the TCR that specifically binds to a mRAS peptide having a G12 mutation at a position corresponding to RAS G12 comprises one or more of: a CDR1, a CDR2, and a CDR3 of a TCR beta chain.

In one embodiment, the TCR that specifically binds to a mRAS peptide having a G12 mutation at a position corresponding to RAS G12 comprises T cell receptor beta variable 10-3 (TRBV10-3) CDR1. In one embodiment, the TCR that specifically binds to a mRAS peptide having a G12 mutation at a position corresponding to RAS G12 comprises TRBV10-3 CDR1, wherein TRBV10-3 CDR1 comprises the amino acid sequence of: TENHRYM (SEQ ID NO:74).

In one embodiment, the TCR that specifically binds to a mRAS peptide having a G12 mutation at a position corresponding to RAS G12 comprises TRBV10-3 CDR2. In one embodiment, the TCR that specifically binds to a mRAS peptide having a G12 mutation at a position corresponding to RAS G12 comprises TRBV10-3 CDR2, wherein TRBV10-3 CDR2 comprises the amino acid sequence of: YSYGVKDT (SEQ ID NO:75).

In one embodiment, the TCR that specifically binds to a mRAS peptide having a G12 mutation at a position corresponding to RAS G12 comprises TRBV10-3 CDR3. In one embodiment, the TCR that specifically binds to a mRAS peptide having a G12 mutation at a position corresponding to RAS G12 comprises TRBV10-3 CDR3, wherein TRBV10-3 CDR3 comprises the amino acid sequence of: CAISESERYYEQYF (SEQ ID NO:76).

In one embodiment, the TCR that specifically binds to a mRAS peptide having a G12 mutation at a position corresponding to RAS G12 comprises TRBV10-3 CDR1, TRBV10-3 CDR2, and TRBV10-3 CDR3.

In one embodiment, the TCR that specifically binds to a mRAS peptide having a G12 mutation at a position corresponding to RAS G12 comprises a variable domain of TRBV10-3. In one embodiment, the TCR that specifically binds to a mRAS peptide having a G12 mutation at a position corresponding to RAS G12 comprises a variable domain of TRBV10-3, wherein the variable domain of TRBV10-3 comprises the amino acid sequence of:

```
                                       (SEQ ID NO: 174)
DAGITQSPRHKVTETGTPVTLRCHQTENHRYMYWYRQDPGHGLRLIHYS
YGVKDTDKGEVSDGYSVSRSKTEDFLLTLESATSSQTSVYFCAISE.
```

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

```
                                        (SEQ ID NO: 77)
EDLKNVFPPEVAVFEPSEAEISHTQKATLVCLATGFYPDHVELSWWVNG
KEVHSGVSTDPQPLKEQPALNDSRYCLSSRLRVSATFWQNPRNHFRCQV
QFYGLSENDEWTQDRAKPVTQIVSAEAWGRADCGFTSESYQQGVLSATI
LYEILLGKATLYAVLVSALVLMAMVKRKDSRG.
```

In one embodiment, the TCR comprises a TCR beta chain comprising the amino acid sequence of:

```
                                        (SEQ ID NO: 78)
MGTRLFFYVALCLLWTGHMDAGITQSPRHKVTETGTPVTLRCHQTENHR
YMYWYRQDPGHGLRLIHYSYGVKDTDKGEVSDGYSVSRSKTEDFLLTLE
SATSSQTSVYFCAISESERYYEQYFGPGTRLTVTEDLKNVFPPEVAVFE
PSEAEISHTQKATLVCLATGFYPDHVELSWWVNGKEVHSGVSTDPQPLK
EQPALNDSRYCLSSRLRVSATFWQNPRNHFRCQVQFYGLSENDEWTQDR
AKPVTQIVSAEAWGRADCGFTSESYQQGVLSATILYEILLGKATLYAVL
VSALVLMAMVKRKDSRG
```

In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV10-3 CDR1, TRBV10-3 CDR2, and TRBV10-3 CDR3. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV10-3 CDR1, TRBV10-3 CDR2, and TRBV10-3 CDR3, and binds to an mRAS peptide comprising a G12R mutation at a position relative to RAS G12. In one embodiment, the TCR comprises (a) a TCR alpha chain comprising one or more of: TRAV17 CDR1, TRAV17 CDR2, and TRAV17 CDR3 and (b) a TCR beta chain comprising one or more of TRBV10-3 CDR1, TRBV10-3 CDR2, and TRBV10-3 CDR3, and binds to an mRAS peptide comprising GARGVGKSAL (SEQ ID NO:15) in the context of an HLA-B*07:02 molecule.

In one embodiment, the TCR comprises (a) a TCR alpha chain comprising TRAV17 CDR1, TRAV17 CDR2, and TRAV17 CDR3 and (b) a TCR beta chain comprising TRBV10-3 CDR1, TRBV10-3 CDR2, and TRBV10-3 CDR3. In one embodiment, the TCR comprises (a) a TCR alpha chain comprising TRAV17 CDR1, TRAV17 CDR2, and TRAV17 CDR3 and (b) a TCR beta chain comprising TRBV10-3 CDR1, TRBV10-3 CDR2, and TRBV10-3 CDR3, and binds to an mRAS peptide comprising a G12R mutation at a position relative to RAS G12. In one embodiment, the TCR comprises (a) a TCR alpha chain comprising TRAV17 CDR1, TRAV17 CDR2, and TRAV17 CDR3 and (b) a TCR beta chain comprising TRBV10-3 CDR1, TRBV10-3 CDR2, and TRBV10-3 CDR3, and binds to an mRAS peptide comprising GARGVGKSAL (SEQ ID NO:15) in the context of an HLA-B*07:02 molecule.

In one embodiment, the TCR that specifically binds to a mRAS peptide having a G12R mutation at a position corresponding to RAS G12 comprises at least one of the CDRs selected from the group consisting of: TRAV17-CDR1: SEQ ID NO:69; TRAV17-CDR2: SEQ ID NO:70; TRAV17-CDR3: SEQ ID NO:71; TRBV10-3-CDR1: SEQ ID NO:74; TRBV10-3-CDR2: SEQ ID NO:75; and TRBV10-3-CDR3: SEQ ID NO:76, or a variant or variants thereof. In one embodiment, the TCR comprises at least one of the CDRs selected from the group consisting of: TRAV17-CDR1: SEQ ID NO:69; TRAV17-CDR2: SEQ ID NO:70; TRAV17-CDR3: SEQ ID NO:71; TRBV10-3-CDR1: SEQ ID NO:74; TRBV10-3-CDR2: SEQ ID NO:75; and TRBV10-3-CDR3: SEQ ID NO:76, or a variant or variants thereof, and binds to an mRAS peptide comprising a G12R mutation at a position relative to RAS G12. In one embodiment, the TCR comprises at least one of the CDRs selected from the group consisting of: TRAV17-CDR1: SEQ ID NO:69; TRAV17-CDR2: SEQ ID NO:70; TRAV17-CDR3: SEQ ID NO:71; TRBV10-3-CDR1: SEQ ID NO:74; TRBV10-3-CDR2: SEQ ID NO:75; and TRBV10-3-CDR3: SEQ ID NO:76, or a variant or variants thereof, and binds to an mRAS peptide comprising GARGVGKSAL (SEQ ID NO:15) in the context of an HLA-B*07:02 molecule.

In another embodiment, the TCR that specifically binds to a mRAS peptide having a G12R mutation at a position corresponding to RAS G12 comprises all of the CDRs of the group consisting of: TRAV17-CDR1: SEQ ID NO:69; TRAV17-CDR2: SEQ ID NO:70; TRAV17-CDR3: SEQ ID NO:71; TRBV10-3-CDR1: SEQ ID NO:74; TRBV10-3-CDR2: SEQ ID NO:75; and TRBV10-3-CDR3: SEQ ID NO:76, or a variant or variants thereof. In one embodiment, the TCR comprises all of the CDRs of the group consisting of: TRAV17-CDR1: SEQ ID NO:69; TRAV17-CDR2: SEQ ID NO:70; TRAV17-CDR3: SEQ ID NO:71; TRBV10-3-CDR1: SEQ ID NO:74; TRBV10-3-CDR2: SEQ ID NO:75; and TRBV10-3-CDR3: SEQ ID NO:76, or a variant or variants thereof, and binds to an mRAS peptide comprising a G12R mutation at a position relative to RAS G12. In one embodiment, the TCR comprises all of the CDRs of the group consisting of: TRAV17-CDR1: SEQ ID NO:69; TRAV17-CDR2: SEQ ID NO:70; TRAV17-CDR3: SEQ ID NO:71; TRBV10-3-CDR1: SEQ ID NO:74; TRBV10-3-CDR2: SEQ ID NO:75; and TRBV10-3-CDR3: SEQ ID NO:76, or a variant or variants thereof, and binds to an mRAS peptide comprising GARGVGKSAL (SEQ ID NO:15) in the context of an HLA-B*07:02 molecule.

In one embodiment, the composition comprises a fusion protein comprising a TCR alpha chain and a TCR beta chain, described above. In one embodiment, the fusion protein comprises a linker domain separating the TCR alpha chain with the TCR beta chain. In one embodiment, the linker domain is a cleavable linker domain. For example, in one embodiment, the linker domain comprises a GSG-T2A domain. In one embodiment, the GSG-T2A comprises the amino acid sequence of: GSGEGRGSLLTCGDVEENPGP (SEQ ID NO:79).

In one embodiment, the composition comprises a fusion protein comprising the amino acid sequence of:

(SEQ ID NO: 80)

METLLGVSLVILWLQLARVNSQQGEEDPQALSIQEGENATMNCSYKTSI

NNLQWYRQNSGRGLVHLILIRSNEREKHSGRLRVTLDTSKKSSSLLITA

SRAADTASYFCATFPNFGNEKLTFGTGTRLTIIPNIQNPDPAVYQLRDS

KSSDKSVCLFTDFDSQTNVSQSKDSDVYITDKTVLDMRSMDFKSNSAVA

WSNKSDFACANAFNNSIIPEDTFFPSPESSCDVKLVEKSFETDTNLNFQ

NLSVIGFRILLLKVAGFNLLMTLRLWSSGSGEGRGSLLTCGDVEENPGP

MGTRLFFYVALCLLWTGHMDAGITQSPRHKVTETGTPVTLRCHQTENHR

YMYWYRQDPGHGLRLIHYSYGVKDTDKGEVSDGYSVSRSKTEDFLLTLE

SATSSQTSVYFCAISESERYYEQYFGPGTRLTVTEDLKNVFPPEVAVFE

-continued

PSEAEISHTQKATLVCLATGFYPDHVELSWWVNGKEVHSGVSTDPQPLK

EQPALNDSRYCLSSRLRVSATFWQNPRNHFRCQVQFYGLSENDEWTQDR

AKPVTQIVSAEAWGRADCGFTSESYQQGVLSATILYEILLGKATLYAVL

VSALVLMAMVKRKDSRG.

TCR864

In one embodiment, the TCR that specifically binds to a mRAS peptide having a G12 mutation at a position corresponding to RAS G12 comprises one or more of: a CDR1, a CDR2, and a CDR3 of a TCR alpha chain.

In one embodiment, the TCR that specifically binds to a mRAS peptide having a G12 mutation at a position corresponding to RAS G12 comprises T cell receptor alpha variable 4 (TRAV4) CDR1. In one embodiment, the TCR that specifically binds to a mRAS peptide having a G12 mutation at a position corresponding to RAS G12 comprises TRAV4 CDR1, wherein TRAV4 CDR1 comprises the amino acid sequence of: NNIATNDYI (SEQ ID NO:81).

In one embodiment, the TCR that specifically binds to a mRAS peptide having a G12 mutation at a position corresponding to RAS G12 comprises TRAV4 CDR2. In one embodiment, the TCR that specifically binds to a mRAS peptide having a G12 mutation at a position corresponding to RAS G12 comprises TRAV4 CDR2, wherein TRAV4 CDR2 comprises the amino acid sequence of: QGYKTKV (SEQ ID NO:82).

In one embodiment, the TCR that specifically binds to a mRAS peptide having a G12 mutation at a position corresponding to RAS G12 comprises TRAV4 CDR3. In one embodiment, the TCR that specifically binds to a mRAS peptide having a G12 mutation at a position corresponding to RAS G12 comprises TRAV4 CDR3, wherein TRAV4 CDR3 comprises the amino acid sequence of: CLVGDFNSNSGYALNF (SEQ ID NO:83).

In one embodiment, the TCR that specifically binds to a mRAS peptide having a G12 mutation at a position corresponding to RAS G12 comprises TRAV4 CDR1, TRAV4 CDR2, and TRAV4 CDR3.

In one embodiment, the TCR that specifically binds to a mRAS peptide having a G12 mutation at a position corresponding to RAS G12 comprises a variable domain of TRAV4. In one embodiment, the TCR that specifically binds to a mRAS peptide having a G12 mutation at a position corresponding to RAS G12 comprises a variable domain of TRAV4, wherein the variable domain of TRAV4 comprises the amino acid sequence of:

(SEQ ID NO: 175)

LAKTTQPISMDSYEGQEVNITCSHNNIATNDYITWYQQFPSQGPRFIIQG

YKTKVTNEVASLFIPADRKSSTLSLPRVSLSDTAVYYCLVGD.

In one embodiment, the TCR that specifically binds to a mRAS peptide having a G12 mutation at a position corresponding to RAS G12 comprises a constant domain. In one embodiment, the TCR that specifically binds to a mRAS peptide having a G12 mutation at a position corresponding to RAS G12 comprises a constant domain, wherein the constant domain comprises the amino acid sequence of:

(SEQ ID NO: 84)
IQNPDPAVYQLRDSKSSDKSVCLFTDFDSQTNVSQSKDSDVYITDKTVLD
MRSMDFKSNSAVAWSNKSDFACANAFNNSIIPEDTFFPSPESSCDVKLVE
KSFETDTNLNFQNLSVIGFRILLLKVAGFNLLMTLRLWSS.

In one embodiment, the TCR comprises a TCR alpha chain comprising the amino acid sequence of:

(SEQ ID NO: 85)
MRQVARVIVFLTLSTLSLAKTTQPISMDSYEGQEVNITCSHNNIATNDYI
TWYQQFPSQGPRFIIQGYKTKVTNEVASLFIPADRKSSTLSLPRVSLSDT
AVYYCLVGDFNSNSGYALNFGKGTSLLVTPHIQNPDPAVYQLRDSKSSDK
SVCLFTDFDSQTNVSQSKDSDVYITDKTVLDMRSMDFKSNSAVAWSNKSD
FACANAFNNSIIPEDTFFPSPESSCDVKLVEKSFETDTNLNFQNLSVIGF
RILLLKVAGFNLLMTLRLWSS

In one embodiment, the TCR that specifically binds to a mRAS peptide having a G12 mutation at a position corresponding to RAS G12 comprises one or more of: a CDR1, a CDR2, and a CDR3 of a TCR beta chain.

In one embodiment, the TCR that specifically binds to a mRAS peptide having a G12 mutation at a position corresponding to RAS G12 comprises T cell receptor beta variable 7-2 (TRBV7-2) CDR1. In one embodiment, the TCR that specifically binds to a mRAS peptide having a G12 mutation at a position corresponding to RAS G12 comprises TRBV7-2 CDR1, wherein TRBV7-2 CDR1 comprises the amino acid sequence of: ISGHTAL (SEQ ID NO:86).

In one embodiment, the TCR that specifically binds to a mRAS peptide having a G12 mutation at a position corresponding to RAS G12 comprises TRBV7-2 CDR2. In one embodiment, the TCR that specifically binds to a mRAS peptide having a G12 mutation at a position corresponding to RAS G12 comprises TRBV7-2 CDR2, wherein TRBV7-2 CDR2 comprises the amino acid sequence of: YFQGNSAP (SEQ ID NO:87).

In one embodiment, the TCR that specifically binds to a mRAS peptide having a G12 mutation at a position corresponding to RAS G12 comprises TRBV7-2 CDR3. In one embodiment, the TCR that specifically binds to a mRAS peptide having a G12 mutation at a position corresponding to RAS G12 comprises TRBV7-2 CDR3, wherein TRBV7-2 CDR3 comprises the amino acid sequence of: CASKVYGYTF (SEQ ID NO:88).

In one embodiment, the TCR that specifically binds to a mRAS peptide having a G12 mutation at a position corresponding to RAS G12 comprises TRBV7-2 CDR1, TRBV7-2 CDR2, and TRBV7-2 CDR3.

In one embodiment, the TCR that specifically binds to a mRAS peptide having a G12 mutation at a position corresponding to RAS G12 comprises a variable domain of TRBV7-2. In one embodiment, the TCR that specifically binds to a mRAS peptide having a G12 mutation at a position corresponding to RAS G12 comprises a variable domain of TRBV7-2, wherein the variable domain of TRBV7-2 comprises the amino acid sequence of:

(SEQ ID NO: 176)
GAGVSQSPSNKVTEKGKDVELRCDPISGHTALYWYRQRLGQGLEFLIYFQ
GNSAPDKSGLPSDRFSAERTGESVSTLTIQRTQQEDSAVYLCASK.

In one embodiment, the TCR that specifically binds to a mRAS peptide having a G12R mutation at a position corresponding to RAS G12 comprises a constant domain. In one embodiment, the TCR that specifically binds to a mRAS peptide having a G12R mutation at a position corresponding to RAS G12 comprises a constant domain, wherein the constant domain comprises the amino acid sequence of:

(SEQ ID NO: 89)
EDLNKVFPPEVAVFEPSEAEISHTQKATLVCLATGFFPDHVELSWWVNGK
EVHSGVSTDPQPLKEQPALNDSRYCLSSRLRVSATFWQNPRNHFRCQVQF
YGLSENDEWTQDRAKPVTQIVSAEAWGRADCGFTSVSYQQGVLSATILYE
ILLGKATLYAVLVSALVLMAMVKRKDF.

In one embodiment, the TCR comprises a TCR beta chain comprising the amino acid sequence of:

(SEQ ID NO: 90)
MGTRLLFWVAFCLLGAYHTGAGVSQSPSNKVTEKGKDVELRCDPISGHTA
LYWYRQRLGQGLEFLIYFQGNSAPDKSGLPSDRFSAERTGESVSTLTIQR
TQQEDSAVYLCASKVYGYTFGSGTRLTVVEDLNKVFPPEVAVFEPSEAEI
SHTQKATLVCLATGFFPDHVELSWWVNGKEVHSGVSTDPQPLKEQPALND
SRYCLSSRLRVSATFWQNPRNHFRCQVQFYGLSENDEWTQDRAKPVTQIV
SAEAWGRADCGFTSVSYQQGVLSATILYEILLGKATLYAVLVSALVLMAM
VKRKDF

In one embodiment, the TCR comprises (a) a TCR alpha chain comprising one or more of: TRAV4 CDR1, TRAV4 CDR2, and TRAV4 CDR3 and (b) a TCR beta chain comprising one or more of TRBV7-2 CDR1, TRBV7-2 CDR2, and TRBV7-2 CDR3. In one embodiment, the TCR comprises (a) a TCR alpha chain comprising one or more of: TRAV4 CDR1, TRAV4 CDR2, and TRAV4 CDR3 and (b) a TCR beta chain comprising one or more of TRBV7-2 CDR1, TRBV7-2 CDR2, and TRBV7-2 CDR3, and binds to an mRAS peptide comprising a G12R mutation at a position relative to RAS G12. In one embodiment, the TCR comprises (a) a TCR alpha chain comprising one or more of: TRAV4 CDR1, TRAV4 CDR2, and TRAV4 CDR3 and (b) a TCR beta chain comprising one or more of TRBV7-2 CDR1, TRBV7-2 CDR2, and TRBV7-2 CDR3, and binds to an mRAS peptide comprising GARGVGKSAL (SEQ ID NO:15) in the context of an HLA-B*07:02 molecule.

In one embodiment, the TCR comprises (a) a TCR alpha chain comprising TRAV4 CDR1, TRAV4 CDR2, and TRAV4 CDR3 and (b) a TCR beta chain comprising TRBV7-2 CDR1, TRBV7-2 CDR2, and TRBV7-2 CDR3. In one embodiment, the TCR comprises (a) a TCR alpha chain comprising TRAV4 CDR1, TRAV4 CDR2, and TRAV4 CDR3 and (b) a TCR beta chain comprising TRBV7-2 CDR1, TRBV7-2 CDR2, and TRBV7-2 CDR3, and binds to an mRAS peptide comprising a G12R mutation at a position relative to RAS G12. In one embodiment, the TCR comprises (a) a TCR alpha chain comprising TRAV4 CDR1, TRAV4 CDR2, and TRAV4 CDR3 and (b) a TCR beta chain comprising TRBV7-2 CDR1, TRBV7-2 CDR2, and TRBV7-2 CDR3, and binds to an mRAS peptide comprising GARGVGKSAL (SEQ ID NO:15) in the context of an HLA-B*07:02 molecule.

In one embodiment, the TCR that specifically binds to a mRAS peptide having a G12R mutation at a position corresponding to RAS G12 comprises at least one of the CDRs selected from the group consisting of: TRAV4-CDR1: SEQ ID NO:81; TRAV4-CDR2: SEQ ID NO:82; TRAV4-CDR3: SEQ ID NO:83; TRBV7-2-CDR1: SEQ ID NO:86; TRBV7-2-CDR2: SEQ ID NO:87; and TRBV7-2-CDR3: SEQ ID NO:88, or a variant or variants thereof. In one embodiment, the TCR comprises at least one of the CDRs selected from the group consisting of: TRAV4-CDR1: SEQ ID NO:81; TRAV4-CDR2: SEQ ID NO:82; TRAV4-CDR3: SEQ ID NO:83; TRBV7-2-CDR1: SEQ ID NO:86; TRBV7-2-CDR2: SEQ ID NO:87; and TRBV7-2-CDR3: SEQ ID NO:88, or a variant or variants thereof, and binds to an mRAS peptide comprising a G12R mutation at a position relative to RAS G12. In one embodiment, the TCR comprises at least one of the CDRs selected from the group consisting of: TRAV4-CDR1: SEQ ID NO:81; TRAV4-CDR2: SEQ ID NO:82; TRAV4-CDR3: SEQ ID NO:83; TRBV7-2-CDR1: SEQ ID NO:86; TRBV7-2-CDR2: SEQ ID NO:87; and TRBV7-2-CDR3: SEQ ID NO:88, or a variant or variants thereof, and binds to an mRAS peptide comprising GARGVGKSAL (SEQ ID NO:15) in the context of an HLA-B*07:02 molecule.

In another embodiment, the TCR that specifically binds to a mRAS peptide having a G12R mutation at a position corresponding to RAS G12 comprises all of the CDRs of the group consisting of: TRAV4-CDR1: SEQ ID NO:81; TRAV4-CDR2: SEQ ID NO:82; TRAV4-CDR3: SEQ ID NO:83; TRBV7-2-CDR1: SEQ ID NO:86; TRBV7-2-CDR2: SEQ ID NO:87; and TRBV7-2-CDR3: SEQ ID NO:88, or a variant or variants thereof. In one embodiment, the TCR comprises all of the CDRs of the group consisting of: TRAV4-CDR1: SEQ ID NO:81; TRAV4-CDR2: SEQ ID NO:82; TRAV4-CDR3: SEQ ID NO:83; TRBV7-2-CDR1: SEQ ID NO:86; TRBV7-2-CDR2: SEQ ID NO:87; and TRBV7-2-CDR3: SEQ ID NO:88, or a variant or variants thereof, and binds to an mRAS peptide comprising a G12R mutation at a position relative to RAS G12. In one embodiment, the TCR comprises all of the CDRs of the group consisting of: TRAV4-CDR1: SEQ ID NO:81; TRAV4-CDR2: SEQ ID NO:82; TRAV4-CDR3: SEQ ID NO:83; TRBV7-2-CDR1: SEQ ID NO:86; TRBV7-2-CDR2: SEQ ID NO:87; and TRBV7-2-CDR3: SEQ ID NO:88, or a variant or variants thereof, and binds to an mRAS peptide comprising GARGVGKSAL (SEQ ID NO:15) in the context of an HLA-B*07:02 molecule.

In one embodiment, the composition comprises a fusion protein comprising a TCR alpha chain and a TCR beta chain, described above. In one embodiment, the fusion protein comprises a linker domain separating the TCR alpha chain with the TCR beta chain. In one embodiment, the linker domain is a cleavable linker domain. For example, in one embodiment, the linker domain comprises a GSG-T2A domain. In one embodiment, the GSG-T2A comprises the amino acid sequence of: GSGEGRGSLLTCGDVEENPGP (SEQ ID NO:91).

In one embodiment, the composition comprises a fusion protein comprising the amino acid sequence of:

(SEQ ID NO: 92)
MRQVARVIVFLTLSTLSLAKTTQPISMDSYEGQEVNITCSHNNIATNDYI

TWYQQFPSQGPRFIIQGYKTKVTNEVASLFIPADRKSSTLSLPRVSLSDT

AVYYCLVGDFNSNSGYALNFGKGTSLLVTPHIQNPDPAVYQLRDSKSSDK

SVCLFTDFDSQTNVSQSKDSDVYITDKTVLDMRSMDFKSNSAVAWSNKSD

-continued

FACANAFNNSIIPEDTFFPSPESSCDVKLVEKSFETDTNLNFQNLSVIGF

RILLLKVAGFNLLMTLRLWSSGSGEGRGSLLTCGDVEENPGPMGTRLLFW

VAFCLLGAYHTGAGVSQSPSNKVTEKGKDVELRCDPISGHTALYWYRQRL

GQGLEFLIYFQGNSAPDKSGLPSDRFSAERTGESVSTLTIQRTQQEDSAV

YLCASKVYGYTFGSGTRLTVVEDLNKVFPPEVAVFEPSEAEISHTQKATL

VCLATGFFPDHVELSWWVNGKEVHSGVSTDPQPLKEQPALNDSRYCLSSR

LRVSATFWQNPRNHFRCQVQFYGLSENDEWTQDRAKPVTQIVSAEAWGRA

DCGFTSVSYQQGVLSATILYEILLGKATLYAVLVSALVLMAMVKRKDF.

In certain embodiments the composition comprises a fusion protein comprising a linker domain separating a TCR alpha chain and a TCR beta chain. In one embodiment, the linker domain is a cleavable linker domain. Any suitable linker domain may be used such that the function of the alpha and beta chains are retained.

In certain embodiments, the composition comprises a peptide or polypeptide (e.g., a mRAS peptide antigen or TCR) comprising an amino acid sequence that is substantially homologous to the amino acid sequence of an mRAS peptide, TCR, or portion thereof, described herein and retains the function of the original amino acid sequence. For example, in certain embodiments, the amino acid sequence has a degree of identity with respect to the original amino acid sequence of at least 60%, of at least 65%, of at least 70%, of at least 75%, of at least 80%, of at least 85%, of at least 90%, of at least 91%, of at least 92%, of at least 93%, of at least 94%, of at least 95%, of at least 96%, of at least 97%, of at least 98%, of at least 99%, or of at least 99.5%.

In some embodiments, the composition comprises a peptide having one or more, two or more, three or more, four or more, five or more, six or more, seven or more, eight or more, nine or more, or ten or more mutations, such as point mutations, with respect to an amino acid sequence of an mRAS peptide or TCR, or portion thereof, described herein.

In some embodiments, the TCR comprises an amino acid sequence having at least about 85% amino acid identity with one or more of the CDR sequences described herein. The invention encompasses a TCR having CDR sequences of that are at least about 85%, 86%, 87%, 88%, 89%, 90%, 91%, 92%, 93%, 94%, 95%, 96%, 97% 99%, or 100% identical to the CDR sequences described herein.

In one embodiment, the composition comprises a polypeptide having CDR sequences of at least about 85% identity to the CDR sequences described herein. The invention encompasses a polypeptide having CDR sequences of that are at least about 85%, 86%, 87%, 88%, 89%, 90%, 91%, 92%, 93%, 94%, 95%, 96%, 97% 99%, or 100% identical to the CDR sequences described herein.

The peptide of the present invention may be made using chemical methods. For example, peptides can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer. The peptide may alternatively be made by recombinant means or by cleavage from a longer polypeptide. The composition of a peptide may be confirmed by amino acid analysis or sequencing.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein. The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA ($tRNA_{LYS}$), could be modified with an amine specific photoaffinity label.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Nucleic Acid Molecules

In one aspect, the present invention provides a composition comprising an isolated nucleic acid molecule encoding one or more of the peptides or polypeptides described herein. For example, in certain aspects, the composition comprises DNA, RNA, mRNA, or cDNA encoding one or more of the peptides or polypeptides described herein.

In one embodiment, the composition comprises one or more isolated nucleic acid molecules encoding one or more antigenic mRAS peptides described herein. For example, in one embodiment, the composition comprises one or more isolated nucleic acid molecules encoding one more of the antigenic mRAS peptides that comprise an amino acid sequence selected from SEQ ID NOs:1-16.

In one embodiment, the nucleic acid molecule comprises a nucleic acid sequence encoding an amino acid sequence selected from SEQ ID NOs:1-92. In one embodiment, the nucleic acid molecule comprises a nucleic acid sequence encoding an amino acid sequence having substantial homology to an amino acid sequence selected from SEQ ID NOs:1-92. For example, in certain embodiments, the nucleic acid molecule comprises a nucleic acid sequence encoding an amino acid sequence that is at least 60%, 70%, 75%, 80%, 85%, 90%, 91%, 92%, 93% 94%, 95%, 96%, 97%, 98%, 99%, or 99.5% identical to an amino acid sequence selected from SEQ ID NOs:1-92. In certain embodiments, the nucleic acid molecule comprises a nucleic acid sequence encoding an amino acid sequence that has one or more, two or more, three or more, four or more, five or more, six or more, seven or more, eight or more, nine or more, or ten or more mutations, such as point mutations, relative to an amino acid sequence selected from SEQ ID NOs:1-92.

In one embodiment, the composition comprises one or more isolated nucleic acid molecules encoding one or more TCRs described herein, one or more CDRs described herein, one or more alpha chains described herein, one or more beta domains described herein, one or more variable domains described herein, one or more constant domains described herein, one or more linkers described herein, or one or more fusion proteins described herein.

Nucleic Acid Molecule Encoding TCR831

In embodiment, the isolated nucleic acid molecule encodes a TCR comprising a TCR alpha chain comprising one or more of: TRAV39 CDR1, TRAV39 CDR2, and TRAV39 CDR3. In embodiment, the isolated nucleic acid molecule encodes a TCR comprising a TCR alpha chain comprising one or more of: TRAV39 CDR1 comprising the amino acid sequence of SEQ ID NO:17, TRAV39 CDR2 comprising the amino acid sequence of SEQ ID NO:18, and TRAV39 CDR3 comprising the amino acid sequence of SEQ ID NO:19. In one embodiment, the nucleic acid sequence encoding TRAV39 CDR1 comprises ACCACTTCAGA (SEQ ID NO:93). In one embodiment, the nucleic acid sequence encoding TRAV39 CDR2 comprises TTGCTATCAAATGGAGCAGTG (SEQ ID NO:94). In one embodiment, the nucleic acid sequence encoding TRAV39 CDR3 comprises GCCGTGGACAAGGATGGGGGTTACC (SEQ ID NO:95).

In one embodiment, the isolated nucleic acid molecule encodes a TCR comprising a TCR alpha chain comprising a variable domain of TRAV39 comprising the amino acid sequence of SEQ ID NO:20. In one embodiment, the nucleic acid sequence encoding the variable domain of TRAV39 comprises:

(SEQ ID NO: 96)
ATGAAGAAGCTACTAGCAATGATTCTGTGGCTTCAACTAGACCGGTTAAG

TGGAGAGCTGAAAGTGGAACAAAACCCTCTGTTCCTGAGCATGCAGGAGG

GAAAAAACTATACCATCTACTGCAATTATTCAACCACTTCAGACAGACTG

TATTGGTACAGGCAGGATCCTGGGAAAAGTCTGGAATCTCTGTTTGTGTT

GCTATCAAATGGAGCAGTGAAGCAGGAGGGACGATTAATGGCCTCACTTG

ATACCAAAGCCCGTCTCAGCACCCTCCACATCACAGCTGCCGTGCATGAC

CTCTCTGCCACCTACTTCTGTGCCGTGGACAAGGATGGGGGTTACAGAAA

GTTACCTTTGGAACTGGAACAAAGCTCCAAGTCATCCCAA.

In one embodiment, the isolated nucleic acid molecule encodes a TCR comprising a TCR alpha chain comprising a constant domain comprising the amino acid sequence of SEQ ID NO:21. In one embodiment, the nucleic acid sequence encoding the constant domain comprises:

(SEQ ID NO: 97)
ATATCCAGAACCCTGACCCTGCCGTGTACCAGCTGAGAGACTCTAAATCCA

GTGACAAGTCTGTCTGCCTATTCACCGATTTTGATTCTCAAACAAATGTGT

CACAAAGTAAGGATTCTGATGTGTATATCACAGACAAAACTGTGTTGGACA

TGCGCAGCATGGACTTCAAGAGCAACAGTGCTGTGGCCTGGAGCAACAAAT

CTGACTTTGCATGTGCAAACGCCTTCAACAACAGCATTATTCCAGAAGACA

CCTTCTTCCCCAGCCCAGAAAGTTCCTGTGATGTCAAGCTGGTCGAGAAAA

GCTTTGAAACAGATACGAACCTAAACTTTCAAAACCTGTCAGTGATTGGGT

TCCGAATCCTCCTCCTGAAAGTGGCCGGGTTTAATCTGCTCATGACGCTGC

GGCTGTGGTCCAGC.

In one embodiment, the nucleic acid molecule encodes a TCR alpha chain comprising the amino acid sequence of SEQ ID NO:22. In one embodiment, the nucleic acid sequence encoding a TCR alpha chain comprises:

(SEQ ID NO: 98)
ATGAAGAAGCTACTAGCAATGATTCTGTGGCTTCAACTAGACCGGTTAAGT

GGAGAGCTGAAAGTGGAACAAAACCCTCTGTTCCTGAGCATGCAGGAGGGA

AAAAACTATACCATCTACTGCAATTATTCAACCACTTCAGACAGACTGTAT

TGGTACAGGCAGGATCCTGGGAAAAGTCTGGAATCTCTGTTTGTGTTGCTA

TCAAATGGAGCAGTGAAGCAGGAGGGACGATTAATGGCCTCACTTGATACC

AAAGCCCGTCTCAGCACCCTCCACATCACAGCTGCCGTGCATGACCTCTCT

GCCACCTACTTCTGTGCCGTGGACAAGGATGGGGGTTACCAGAAAGTTACC

TTTGGAACTGGAACAAAGCTCCAAGTCATCCCAAATATCCAGAACCCTGAC

CCTGCCGTGTACCAGCTGAGAGACTCTAAATCCAGTGACAAGTCTGTCTGC

CTATTCACCGATTTTGATTCTCAAACAAATGTGTCACAAAGTAAGGATTCT

GATGTGTATATCACAGACAAAACTGTGTTGGACATGCGCAGCATGGACTTC

AAGAGCAACAGTGCTGTGGCCTGGAGCAACAAATCTGACTTTGCATGTGCA

AACGCCTTCAACAACAGCATTATTCCAGAAGACACCTTCTTCCCCAGCCCA

GAAAGTTCCTGTGATGTCAAGCTGGTCGAGAAAAGCTTTGAAACAGATACG

AACCTAAACTTTCAAAACCTGTCAGTGATTGGGTTCCGAATCCTCCTCCTG

AAAGTGGCCGGGTTTAATCTGCTCATGACGCTGCGGCTGTGGTCCAGC.

In embodiment, the isolated nucleic acid molecule encodes a TCR comprising a TCR beta chain comprising one or more of: TRBV20-1 CDR1, TRBV20-1 CDR2, and TRBV20-1 CDR3. In embodiment, the isolated nucleic acid molecule encodes a TCR comprising a TCR beta chain comprising one or more of: TRBV20-1 CDR1 comprising the amino acid sequence of SEQ ID NO:23, TRBV20-1 CDR2 comprising the amino acid sequence of SEQ ID NO:24, and TRBV20-1 CDR3 comprising the amino acid sequence of SEQ ID NO:25. In one embodiment, the nucleic acid sequence encoding TRBV20-1 CDR1 comprises GACTTTCAGGCCACAACT (SEQ ID NO:99). In one embodiment, the nucleic acid sequence encoding TRBV20-1 CDR2 comprises TCCAATGAGGGCTC-CAAGGCC (SEQ ID NO:100). In one embodiment, the nucleic acid sequence encoding TRBV20-1 CDR3 comprises (SEQ ID NO: 101)
AGTGCTAGCCCACGGGCGGGACAGTTGAGCTCCTATAATTCACCCCTCCA

C.

In one embodiment, the isolated nucleic acid molecule encodes a TCR comprising a TCR beta chain comprising a variable domain of TRBV20-1 comprising the amino acid sequence of SEQ ID NO:26. In one embodiment, the nucleic acid sequence encoding the variable domain of TRBV20-1 comprises:

(SEQ ID NO: 102)
ATGCTGCTGCTTCTGCTGCTTCTGGGGCCAGGTATAAGCCTCCTTCTACCT

GGGAGCTTGGCAGGCTCCGGGCTTGGTGCTGTCGTCTCTCAACATCCGAGC

TGGGTTATCTGTAAGAGTGGAACCTCTGTGAAGATCGAGTGCCGTTCCCTG

GACTTTCAGGCCACAACTATGTTTTGGTATCGTCAGTTCCCGAAACAGAGT

-continued

CTCATGCTGATGGCAACTTCCAATGAGGGCTCCAAGGCCACATACGAGCAA

GGCGTCGAGAAGGACAAGTTTCTCATCAACCATGCAAGCCTGACCTTGTCC

ACTCTGACAGTGACCAGTGCCCATCCTGAAGACAGCAGCTTCTACATCTGC

AGTGCTAGCCCACGGGCGGGACAGTTGAGCTCCTATAATTCACCCCTCCAC

TTTGGGAATGGGACCAGGCTCACTGTGAC.

In one embodiment, the isolated nucleic acid molecule encodes a TCR comprising a TCR beta chain comprising a constant domain comprising the amino acid sequence of SEQ ID NO:27. In one embodiment, the nucleic acid sequence encoding the constant domain comprises:

(SEQ ID NO: 103)

GAGGACCTGAACAAGGTGTTCCCACCCGAGGTCGCTGTGTTTGAGCCATCA

GAAGCAGAGATCTCCCACACCCAAAAGGCCACACTGGTGTGCCTGGCCACA

GGCTTCTTCCCCGACCACGTGGAGCTGAGCTGGTGGGTGAATGGGAAGGAG

GTGCACAGTGGGGTCAGCACGGACCCGCAGCCCCTCAAGGAGCAGCCCGCC

CTCAATGACTCCAGATACTGCCTGAGCAGCCGCCTGAGGGTCTCGGCCACC

TTCTGGCAGAACCCCCGCAACCACTTCCGCTGTCAAGTCCAGTTCTACGGG

CTCTCGGAGAATGATGAGTGGACACAAGATAGGGCCAAACCCGTCACCCAG

ATCGTCAGCGCCGAGGCCTGGGGTAGAGCAGACTGTGGCTTTACCTCGGTG

TCCTACCAGCAAGGGGTCCTGTCTGCCACCATCCTCTATGAGATCCTGCTA

GGGAAGGCCACCCTGTATGCTGTGCTGGTCAGCGCCCTTGTGTTGATGGCC

ATGGTCAAGAGAAAGGATTTC.

In one embodiment, the nucleic acid molecule encodes a TCR beta chain comprising the amino acid sequence of SEQ ID NO:28. In one embodiment, the nucleic acid sequence encoding a TCR beta chain comprises:

(SEQ ID NO: 104)

ATGCTGCTGCTTCTGCTGCTTCTGGGGCCAGGTATAAGCCTCCTTCTACCT

GGGAGCTTGGCAGGCTCCGGGCTTGGTGCTGTCGTCTCTCAACATCCGAGC

TGGGTTATCTGTAAGAGTGGAACCTCTGTGAAGATCGAGTGCCGTTCCCTG

GACTTTCAGGCCACAACTATGTTTTGGTATCGTCAGTTCCCGAAACAGAGT

CTCATGCTGATGGCAACTTCCAATGAGGGCTCCAAGGCCACATACGAGCAA

GGCGTCGAGAAGGACAAGTTTCTCATCAACCATGCAAGCCTGACCTTGTCC

ACTCTGACAGTGACCAGTGCCCATCCTGAAGACAGCAGCTTCTACATCTGC

AGTGCTAGCCCACGGGCGGGACAGTTGAGCTCCTATAATTCACCCCTCCAC

TTTGGGAATGGGACCAGGCTCACTGTGACAGAGGACCTGAACAAGGTGTTC

CCACCCGAGGTCGCTGTGTTTGAGCCATCAGAAGCAGAGATCTCCCACACC

CAAAAGGCCACACTGGTGTGCCTGGCCACAGGCTTCTTCCCCGACCACGTG

GAGCTGAGCTGGTGGGTGAATGGGAAGGAGGTGCACAGTGGGGTCAGCACG

GACCCGCAGCCCCTCAAGGAGCAGCCCGCCCTCAATGACTCCAGATACTGC

CTGAGCAGCCGCCTGAGGGTCTCGGCCACCTTCTGGCAGAACCCCCGCAAC

CACTTCCGCTGTCAAGTCCAGTTCTACGGGCTCTCGGAGAATGATGAGTGG

ACACAAGATAGGGCCAAACCCGTCACCCAGATCGTCAGCGCCGAGGCCTGG

-continued

GGTAGAGCAGACTGTGGCTTTACCTCGGTGTCCTACCAGCAAGGGGTCCTG

TCTGCCACCATCCTCTATGAGATCCTGCTAGGGAAGGCCACCCTGTATGCT

GTGCTGGTCAGCGCCCTTGTGTTGATGGCCATGGTCAAGAGAAAGGATTTC

TGA.

In one embodiment, the nucleic acid molecule encodes a fusion protein comprising a TCR alpha chain and a TCR beta chain. In one embodiment, the isolated nucleic acid molecule encodes a fusion protein comprising a linker domain between the TCR alpha chain and TCR beta chain. In one embodiment, the nucleic acid molecule encodes a GSG-T2A linker domain comprising the amino acid sequence of SEQ ID NO:29. In one embodiment, the nucleic acid sequence encoding a GSG-T2A linker domain comprises:

(SEQ ID NO: 105)

GGCAGCGGAGAGGGCAGAGGAAGTCTTCTAACATGCGGTGACGTGGAGGAG

AATCCCGGCCCT.

In one embodiment, the nucleic acid molecule encodes a fusion protein comprising the amino acid sequence of SEQ ID NO: 30. In one embodiment, the nucleic acid sequence encoding the fusion protein comprises (SEQ ID NO: 106)

ATGAAGAAGCTACTAGCAATGATTCTGTGGCTTCAACTAGACCGGTTAAGT

GGAGAGCTGAAAGTGGAACAAAACCCTCTGTTCCTGAGCATGCAGGAGGGA

AAAAACTATACCATCTACTGCAATTATTCAACCACTTCAGACAGACTGTAT

TGGTACAGGCAGGATCCTGGGAAAAGTCTGGAATCTCTGTTTGTGTTGCTA

TCAAATGGAGCAGTGAAGCAGGAGGGACGATTAATGGCCTCACTTGATACC

AAAGCCCGTCTCAGCACCCTCCACATCACAGCTGCCGTGCATGACCTCTCT

GCCACCTACTTCTGTGCCGTGGACAAGGATGGGGGTTACCAGAAAGTTACC

TTTGGAACTGGAACAAAGCTCCAAGTCATCCCAAATATCCAGAACCCTGAC

CCTGCCGTGTACCAGCTGAGAGACTCTAAATCCAGTGACAAGTCTGTCTGC

CTATTCACCGATTTTGATTCTCAAACAAATGTGTCACAAAGTAAGGATTCT

GATGTGTATATCACAGACAAAACTGTGTTGGACATGCGCAGCATGGACTTC

AAGAGCAACAGTGCTGTGGCCTGGAGCAACAAATCTGACTTTGCATGTGCA

AACGCCTTCAACAACAGCATTATTCCAGAAGACACCTTCTTCCCCAGCCCA

GAAAGTTCCTGTGATGTCAAGCTGGTCGAGAAAAGCTTTGAAACAGATACG

AACCTAAACTTTCAAAACCTGTCAGTGATTGGGTTCCGAATCCTCCTCCTG

AAAGTGGCCGGGTTTAATCTGCTCATGACGCTGCGGCTGTGGTCCAGCGGC

AGCGGAGAGGGCAGAGGAAGTCTTCTAACATGCGGTGACGTGGAGGAGAAT

CCCGGCCCTATGCTGCTGCTTCTGCTGCTTCTGGGGCCAGGTATAAGCCTC

CTTCTACCTGGGAGCTTGGCAGGCTCCGGGCTTGGTGCTGTCGTCTCTCAA

CATCCGAGCTGGGTTATCTGTAAGAGTGGAACCTCTGTGAAGATCGAGTGC

CGTTCCCTGGACTTTCAGGCCACAACTATGTTTTGGTATCGTCAGTTCCCG

AAACAGAGTCTCATGCTGATGGCAACTTCCAATGAGGGCTCCAAGGCCACA

-continued

```
TACGAGCAAGGCGTCGAGAAGGACAAGTTTCTCATCAACCATGCAAGCCTG
ACCTTGTCCACTCTGACAGTGACCAGTGCCCATCCTGAAGACAGCAGCTTC
TACATCTGCAGTGCTAGCCCACGGGCGGGACAGTTGAGCTCCTATAATTCA
CCCCTCCACTTTGGGAATGGGACCAGGCTCACTGTGACAGAGGACCTGAAC
AAGGTGTTCCCACCCGAGGTCGCTGTGTTTGAGCCATCAGAAGCAGAGATC
TCCCACACCCAAAAGGCCACACTGGTGTGCCTGGCCACAGGCTTCTTCCCC
GACCACGTGGAGCTGAGCTGGTGGGTGAATGGGAAGGAGGTGCACAGTGGG
GTCAGCACGGACCCGCAGCCCCTCAAGGAGCAGCCCGCCCTCAATGACTCC
AGATACTGCCTGAGCAGCCGCCTGAGGGTCTCGGCCACCTTCTGGCAGAAC
CCCCGCAACCACTTCCGCTGTCAAGTCCAGTTCTACGGGCTCTCGGAGAAT
GATGAGTGGACACAAGATAGGGCCAAACCCGTCACCCAGATCGTCAGCGCC
GAGGCCTGGGGTAGAGCAGACTGTGGCTTTACCTCGGTGTCCTACCAGCAA
GGGGTCCTGTCTGCCACCATCCTCTATGAGATCCTGCTAGGGAAGGCCACC
CTGTATGCTGTGCTGGTCAGCGCCCTTGTGTTGATGGCCATGGTCAAGAGA
AAGGATTTCTGA.
```

Nucleic Acid Molecule Encoding TCR833

In embodiment, the isolated nucleic acid molecule encodes a TCR comprising a TCR alpha chain comprising one or more of: TRAV12-1 CDR1, TRAV12-1 CDR2, and TRAV12-1 CDR3. In embodiment, the isolated nucleic acid molecule encodes a TCR comprising a TCR alpha chain comprising one or more of: TRAV12-1 CDR1 comprising the amino acid sequence of SEQ ID NO:32, TRAV12-1 CDR2 comprising the amino acid sequence of SEQ ID NO:32, and TRAV12-1 CDR3 comprising the amino acid sequence of SEQ ID NO:33. In one embodiment, the nucleic acid sequence encoding TRAV12-1 CDR1 comprises AACAGTGCTTCTCAGTCT (SEQ ID NO:107). In one embodiment, the nucleic acid sequence encoding TRAV12-1 CDR2 comprises GTATACTCCAGTGGTAAC (SEQ ID NO:108). In one embodiment, the nucleic acid sequence encoding TRAV12-1 CDR3 comprises GCGGT-GAACCCCCCGGACACAGGCTTTCAGAAACTTGTA (SEQ ID NO:109).

In one embodiment, the isolated nucleic acid molecule encodes a TCR comprising a TCR alpha chain comprising a variable domain of TRAV12-1 comprising the amino acid sequence of SEQ ID NO:34. In one embodiment, the nucleic acid sequence encoding the variable domain of TRAV12-1 comprises:

```
                                        (SEQ ID NO: 110)
ATGATATCCTTGAGAGTTTTACTGGTGATCCTGTGGCTTCAGTTAAGCTGG
GTTTGGAGCCAACGGAAGGAGGTGGAGCAGGATCCTGGACCCTTCAATGTT
CCAGAGGGAGCCACTGTCGCTTTCAACTGTACTTACAGCAACAGTGCTTCT
CAGTCTTTCTTCTGGTACAGACAGGATTGCAGGAAAGAACCTAAGTTGCTG
ATGTCCGTATACTCCAGTGGTAACGAAGATGGAAGGTTTACAGCACAGCTC
AATAGAGCCAGCCAGTATATTTCCCTGCTCATCAGAGACTCCAAGCTCAGT
GATTCAGCCACCTACCTCTGTGCGGTGAACCCCCCGGACACAGGCTTTCAG
AAACTTGTATTTGGAACTGGCACCCGACTTCTGGTCAGTCCAA.
```

In one embodiment, the isolated nucleic acid molecule encodes a TCR comprising a TCR alpha chain comprising a constant domain comprising the amino acid sequence of SEQ ID NO:35. In one embodiment, the nucleic acid sequence encoding the constant domain comprises:

```
                                        (SEQ ID NO: 111)
ATATCCAGAACCCTGACCCTGCCGTGTACCAGCTGAGAGACTCTAAATCCA
GTGACAAGTCTGTCTGCCTATTCACCGATTTTGATTCTCAAACAAATGTGT
CACAAAGTAAGGATTCTGATGTGTATATCACAGACAAAACTGTGTTGGACA
TGCGCAGCATGGACTTCAAGAGCAACAGTGCTGTGGCCTGGAGCAACAAAT
CTGACTTTGCATGTGCAAACGCCTTCAACAACAGCATTATTCCAGAAGACA
CCTTCTTCCCCAGCCCAGAAAGTTCCTGTGATGTCAAGCTGGTCGAGAAAA
GCTTTGAAACAGATACGAACCTAAACTTTCAAAACCTGTCAGTGATTGGGT
TCCGAATCCTCCTCCTGAAAGTGGCCGGGTTTAATCTGCTCATGACGCTGC
GGCTGTGGTCCAGC.
```

In one embodiment, the nucleic acid molecule encodes a TCR alpha chain comprising the amino acid sequence of SEQ ID NO:36. In one embodiment, the nucleic acid sequence encoding a TCR alpha chain comprises:

```
                                        (SEQ ID NO: 112)
ATGATATCCTTGAGAGTTTTACTGGTGATCCTGTGGCTTCAGTTAAGCTGG
GTTTGGAGCCAACGGAAGGAGGTGGAGCAGGATCCTGGACCCTTCAATGTT
CCAGAGGGAGCCACTGTCGCTTTCAACTGTACTTACAGCAACAGTGCTTCT
CAGTCTTTCTTCTGGTACAGACAGGATTGCAGGAAAGAACCTAAGTTGCTG
ATGTCCGTATACTCCAGTGGTAACGAAGATGGAAGGTTTACAGCACAGCTC
AATAGAGCCAGCCAGTATATTTCCCTGCTCATCAGAGACTCCAAGCTCAGT
GATTCAGCCACCTACCTCTGTGCGGTGAACCCCCCGGACACAGGCTTTCAG
AAACTTGTATTTGGAACTGGCACCCGACTTCTGGTCAGTCCAAATATCCAG
AACCCTGACCCTGCCGTGTACCAGCTGAGAGACTCTAAATCCAGTGACAAG
TCTGTCTGCCTATTCACCGATTTTGATTCTCAAACAAATGTGTCACAAAGT
AAGGATTCTGATGTGTATATCACAGACAAAACTGTGTTGGACATGCGCAGC
ATGGACTTCAAGAGCAACAGTGCTGTGGCCTGGAGCAACAAATCTGACTTT
GCATGTGCAAACGCCTTCAACAACAGCATTATTCCAGAAGACACCTTCTTC
CCCAGCCCAGAAAGTTCCTGTGATGTCAAGCTGGTCGAGAAAAGCTTTGAA
ACAGATACGAACCTAAACTTTCAAAACCTGTCAGTGATTGGGTTCCGAATC
CTCCTCCTGAAAGTGGCCGGGTTTAATCTGCTCATGACGCTGCGGCTGTGG
TCCAGC.
```

In embodiment, the isolated nucleic acid molecule encodes a TCR comprising a TCR beta chain comprising one or more of: TRBV28 CDR1, TRBV28 CDR2, and TRBV28 CDR3. In embodiment, the isolated nucleic acid molecule encodes a TCR comprising a TCR beta chain comprising one or more of: TRBV28 CDR1 comprising the amino acid sequence of SEQ ID NO:37, TRBV28 CDR2 comprising the amino acid sequence of SEQ ID NO:38, and TRBV28 CDR3 comprising the amino acid sequence of SEQ ID NO:39. In one embodiment, the nucleic acid sequence encoding TRBV28 CDR1 comprises ATGGAC-CATGAAAAT (SEQ ID NO:113). In one embodiment, the nucleic acid sequence encoding TRBV28 CDR2 comprises TCATATGATGTTAAAATG (SEQ ID NO:114). In one embodiment, the nucleic acid sequence encoding TRBV28 CDR3 comprises (SEQ ID NO: 115)
GCCAGCAGTTTATCCTTCCGGCAGGGCCTTCGCGAGCAGTAC.

In one embodiment, the isolated nucleic acid molecule encodes a TCR comprising a TCR beta chain comprising a variable domain of TRBV28 comprising the amino acid sequence of SEQ ID NO:40. In one embodiment, the nucleic acid sequence encoding the variable domain of TRBV28 comprises:

(SEQ ID NO: 116)
ATGGGAATCAGGCTCCTGTGTCGTGTGGCCTTTTGTTTCCTGGCTGTAGGC

CTCGTAGATGTGAAAGTAACCCAGAGCTCGAGATATCTAGTCAAAAGGACG

GGAGAGAAAGTTTTTCTGGAATGTGTCCAGGATATGGACCATGAAAATATG

TTCTGGTATCGACAAGACCCAGGTCTGGGGCTACGGCTGATCTATTTCTCA

TATGATGTTAAAATGAAAGAAAAAGGAGATATTCCTGAGGGGTACAGTGTC

TCCAGAGAGAAGAAGGAGCGCTTCTCCCTGATTCTGGAGTCCGCCAGCACC

AACCAGACATCTATGTACCTCTGTGCCAGCAGTTTATCCTTCCGGCAGGGC

CTTCGCGAGCAGTACTTCGGGCCGGGCACCAGGCTCACGGTCACA.

In one embodiment, the isolated nucleic acid molecule encodes a TCR comprising a TCR beta chain comprising a constant domain comprising the amino acid sequence of SEQ ID NO:41. In one embodiment, the nucleic acid sequence encoding the constant domain comprises:

(SEQ ID NO: 117)
GAGGACCTGAAAAACGTGTTCCCACCCGAGGTCGCTGTGTTTGAGCCATCA

GAAGCAGAGATCTCCCACACCCAAAAGGCCACACTGGTGTGCCTGGCCACA

GGCTTCTACCCCGACCACGTGGAGCTGAGCTGGTGGGTGAATGGGAAGGAG

GTGCACAGTGGGGTCAGCACAGACCCGCAGCCCCTCAAGGAGCAGCCCGCC

CTCAATGACTCCAGATACTGCCTGAGCAGCCGCCTGAGGGTCTCGGCCACC

TTCTGGCAGAACCCCCGCAACCACTTCCGCTGTCAAGTCCAGTTCTACGGG

CTCTCGGAGAATGATGAGTGGACACAAGATAGGGCCAAACCTGTCACCCAG

ATCGTCAGCGCCGAGGCCTGGGGTAGAGCAGACTGTGGCTTCACCTCCGAG

TCTTACCAGCAAGGGGTCCTGTCTGCCACCATCCTCTATGAGATCTTGCTA

GGGAAGGCCACCTTGTATGCCGTGCTGGTCAGTGCCCTCGTGCTGATGGCC

ATGGTCAAGAGAAAGGATTCCAGAGGC.

In one embodiment, the nucleic acid molecule encodes a TCR beta chain comprising the amino acid sequence of SEQ ID NO:42. In one embodiment, the nucleic acid sequence encoding a TCR beta chain comprises:

(SEQ ID NO: 118)
ATGGGAATCAGGCTCCTGTGTCGTGTGGCCTTTTGTTTCCTGGCTGTAGGC

CTCGTAGATGTGAAAGTAACCCAGAGCTCGAGATATCTAGTCAAAAGGACG

GGAGAGAAAGTTTTTCTGGAATGTGTCCAGGATATGGACCATGAAAATATG

-continued
TTCTGGTATCGACAAGACCCAGGTCTGGGGCTACGGCTGATCTATTTCTCA

TATGATGTTAAAATGAAAGAAAAAGGAGATATTCCTGAGGGGTACAGTGTC

TCCAGAGAGAAGAAGGAGCGCTTCTCCCTGATTCTGGAGTCCGCCAGCACC

AACCAGACATCTATGTACCTCTGTGCCAGCAGTTTATCCTTCCGGCAGGGC

CTTCGCGAGCAGTACTTCGGGCCGGGCACCAGGCTCACGGTCACAGAGGAC

CTGAAAAACGTGTTCCCACCCGAGGTCGCTGTGTTTGAGCCATCAGAAGCA

GAGATCTCCCACACCCAAAAGGCCACACTGGTGTGCCTGGCCACAGGCTTC

TACCCCGACCACGTGGAGCTGAGCTGGTGGGTGAATGGGAAGGAGGTGCAC

AGTGGGGTCAGCACAGACCCGCAGCCCCTCAAGGAGCAGCCCGCCCTCAAT

GACTCCAGATACTGCCTGAGCAGCCGCCTGAGGGTCTCGGCCACCTTCTGG

CAGAACCCCCGCAACCACTTCCGCTGTCAAGTCCAGTTCTACGGGCTCTCG

GAGAATGATGAGTGGACACAAGATAGGGCCAAACCTGTCACCCAGATCGTC

AGCGCCGAGGCCTGGGGTAGAGCAGACTGTGGCTTCACCTCCGAGTCTTAC

CAGCAAGGGGTCCTGTCTGCCACCATCCTCTATGAGATCTTGCTAGGGAAG

GCCACCTTGTATGCCGTGCTGGTCAGTGCCCTCGTGCTGATGGCCATGGTC

AAGAGAAAGGATTCCAGAGGCTGA.

In one embodiment, the nucleic acid molecule encodes a fusion protein comprising a TCR alpha chain and a TCR beta chain. In one embodiment, the isolated nucleic acid molecule encodes a fusion protein comprising a linker domain between the TCR alpha chain and TCR beta chain. In one embodiment, the nucleic acid molecule encodes a GSG-T2A linker domain comprising the amino acid sequence of SEQ ID NO:43. In one embodiment, the nucleic acid sequence encoding a GSG-T2A linker domain comprises:

(SEQ ID NO: 119)
GGCAGCGGAGAGGGCAGAGGAAGTCTTCTAACATGCGGTGACGTGGAGGA

GAATCCCGGCCCT.

In one embodiment, the nucleic acid molecule encodes a fusion protein comprising the amino acid sequence of SEQ ID NO:44. In one embodiment, the nucleic acid sequence encoding the fusion protein comprises (SEQ ID NO: 120)
ATGATATCCTTGAGAGTTTTACTGGTGATCCTGTGGCTTCAGTTAAGCT

GGGTTTGGAGCCAACGGAAGGAGGTGGAGCAGGATCCTGGACCCTTCAA

TGTTCCAGAGGGAGCCACTGTCGCTTTCAACTGTACTTACAGCAACAGT

GCTTCTCAGTCTTTCTTCTGGTACAGACAGGATTGCAGGAAAGAACCTA

AGTTGCTGATGTCCGTATACTCCAGTGGTAACGAAGATGGAAGGTTTAC

AGCACAGCTCAATAGAGCCAGCCAGTATATTTCCCTGCTCATCAGAGAC

TCCAAGCTCAGTGATTCAGCCACCTACCTCTGTGCGGTGAACCCCCCGG

ACACAGGCTTTCAGAAACTTGTATTTGGAACTGGCACCCGACTTCTGGT

CAGTCCAAATATCCAGAACCCTGACCCTGCCGTGTACCAGCTGAGAGAC

TCTAAATCCAGTGACAAGTCTGTCTGCCTATTCACCGATTTTGATTCTC

AAACAAATGTGTCACAAAGTAAGGATTCTGATGTGTATATCACAGACAA

-continued

AACTGTGTTGGACATGCGCAGCATGGACTTCAAGAGCAACAGTGCTGTG

GCCTGGAGCAACAAATCTGACTTTGCATGTGCAAACGCCTTCAACAACA

GCATTATTCCAGAAGACACCTTCTTCCCCAGCCCAGAAAGTTCCTGTGA

TGTCAAGCTGGTCGAGAAAAGCTTTGAAACAGATACGAACCTAAACTTT

CAAAACCTGTCAGTGATTGGGTTCCGAATCCTCCTCCTGAAAGTGGCCG

GGTTTAATCTGCTCATGACGCTGCGGCTGTGGTCCAGCGGCAGCGGAGA

GGGCAGAGGAAGTCTTCTAACATGCGGTGACGTGGAGGAGAATCCCGGC

CCTATGGGAATCAGGCTCCTGTGTCGTGTGGCCTTTTGTTTCCTGGCTG

TAGGCCTCGTAGATGTGAAAGTAACCCAGAGCTCGAGATATCTAGTCAA

AAGGACGGGAGAGAAAGTTTTTCTGGAATGTGTCCAGGATATGGACCAT

GAAAATATGTTCTGGTATCGACAAGACCCAGGTCTGGGGCTACGGCTGA

TCTATTTCTCATATGATGTTAAAATGAAAGAAAAAGGAGATATTCCTGA

GGGGTACAGTGTCTCCAGAGAGAAGAAGGAGCGCTTCTCCCTGATTCTG

GAGTCCGCCAGCACCAACCAGACATCTATGTACCTCTGTGCCAGCAGTT

TATCCTTCCGGCAGGGCCTTCGCGAGCAGTACTTCGGGCCGGGCACCAG

GCTCACGGTCACAGAGGACCTGAAAAACGTGTTCCCACCCGAGGTCGCT

GTGTTTGAGCCATCAGAAGCAGAGATCTCCCACACCCAAAAGGCCACAC

TGGTGTGCCTGGCCACAGGCTTCTACCCCGACCACGTGGAGCTGAGCTG

GTGGGTGAATGGGAAGGAGGTGCACAGTGGGGTCAGCACAGACCCGCAG

CCCCTCAAGGAGCAGCCCGCCCTCAATGACTCCAGATACTGCCTGAGCA

GCCGCCTGAGGGTCTCGGCCACCTTCTGGCAGAACCCCCGCAACCACTT

CCGCTGTCAAGTCCAGTTCTACGGGCTCTCGGAGAATGATGAGTGGACA

CAAGATAGGGCCAAACCTGTCACCCAGATCGTCAGCGCCGAGGCCTGGG

GTAGAGCAGACTGTGGCTTCACCTCCGAGTCTTACCAGCAAGGGGTCCT

GTCTGCCACCATCCTCTATGAGATCTTGCTAGGGAAGGCCACCTTGTAT

GCCGTGCTGGTCAGTGCCCTCGTGCTGATGGCCATGGTCAAGAGAAAGG

ATTCCAGAGGCTGA.

Nucleic Acid Molecule Encoding TCR897

In embodiment, the isolated nucleic acid molecule encodes a TCR comprising a TCR alpha chain comprising one or more of: TRAV17 CDR1, TRAV17 CDR2, and TRAV17 CDR3. In embodiment, the isolated nucleic acid molecule encodes a TCR comprising a TCR alpha chain comprising one or more of: TRAV17 CDR1 comprising the amino acid sequence of SEQ ID NO:45, TRAV17 CDR2 comprising the amino acid sequence of SEQ ID NO:46, and TRAV17 CDR3 comprising the amino acid sequence of SEQ ID NO:47. In one embodiment, the nucleic acid sequence encoding TRAV17 CDR1 comprises ACTAGTATAAACAAT (SEQ ID NO:121). In one embodiment, the nucleic acid sequence encoding TRAV17 CDR2 comprises ATACGTTCAAATGAAAGAGAG (SEQ ID NO:122). In one embodiment, the nucleic acid sequence encoding TRAV17 CDR3 comprises (SEQ ID NO: 123)
TGTGCTACGGACCCTGGAGGCTTCAAAACTATCTTT.

In one embodiment, the isolated nucleic acid molecule encodes a TCR comprising a TCR alpha chain comprising a constant domain comprising the amino acid sequence of SEQ ID NO:48. In one embodiment, the nucleic acid sequence encoding the constant domain comprises:

(SEQ ID NO: 124)
ATATCCAGAACCCTGACCCTGCCGTGTACCAGCTGAGAGACTCTAAATCC

AGTGACAAGTCTGTCTGCCTATTCACCGATTTTGATTCTCAAACAAATGT

GTCACAAAGTAAGGATTCTGATGTGTATATCACAGACAAAACTGTGTTGG

ACATGCGCAGCATGGACTTCAAGAGCAACAGTGCTGTGGCCTGGAGCAAC

AAATCTGACTTTGCATGTGCAAACGCCTTCAACAACAGCATTATTCCAGA

AGACACCTTCTTCCCCAGCCCAGAAAGTTCCTGTGATGTCAAGCTGGTCG

AGAAAAGCTTTGAAACAGATACGAACCTAAACTTTCAAAACCTGTCAGTG

ATTGGGTTCCGAATCCTCCTCCTGAAAGTGGCCGGGTTTAATCTGCTCAT

GACGCTGCGGCTGTGGTCCAGC.

In one embodiment, the nucleic acid molecule encodes a TCR alpha chain comprising the amino acid sequence of SEQ ID NO:49. In one embodiment, the nucleic acid sequence encoding a TCR alpha chain comprises:

(SEQ ID NO: 125)
ATGGAAACTCTCCTGGGAGTGTCTTTGGTGATTCTATGGCTTCAACTGGC

TAGGGTGAACAGTCAACAGGGAGAAGAGGATCCTCAGGCCTTGAGCATCC

AGGAGGGTGAAAATGCCACCATGAACTGCAGTTACAAAACTAGTATAAAC

AATTTACAGTGGTATAGACAAAATTCAGGTAGAGGCCTTGTCCACCTAAT

TTTAATACGTTCAAATGAAAGAGAGAAACACAGTGGAAGATTAAGAGTCA

CGCTTGACACTTCCAAGAAAAGCAGTTCCTTGTTGATCACGGCTTCCCGG

GCAGCAGACACTGCTTCTTACTTCTGTGCTACGGACCCTGGAGGCTTCAA

AACTATCTTTGGAGCAGGAACAAGACTATTTGTTAAAGCAAATATCCAGA

ACCCTGACCCTGCCGTGTACCAGCTGAGAGACTCTAAATCCAGTGACAAG

TCTGTCTGCCTATTCACCGATTTTGATTCTCAAACAAATGTGTCACAAAG

TAAGGATTCTGATGTGTATATCACAGACAAAACTGTGTTGGACATGCGCA

GCATGGACTTCAAGAGCAACAGTGCTGTGGCCTGGAGCAACAAATCTGAC

TTTGCATGTGCAAACGCCTTCAACAACAGCATTATTCCAGAAGACACCTT

CTTCCCCAGCCCAGAAAGTTCCTGTGATGTCAAGCTGGTCGAGAAAAGCT

TTGAAACAGATACGAACCTAAACTTTCAAAACCTGTCAGTGATTGGGTTC

CGAATCCTCCTCCTGAAAGTGGCCGGGTTTAATCTGCTCATGACGCTGCG

GCTGTGGTCCAGC.

In embodiment, the isolated nucleic acid molecule encodes a TCR comprising a TCR beta chain comprising one or more of: TRBV11-2 CDR1, TRBV11-2 CDR2, and TRBV11-2 CDR3. In embodiment, the isolated nucleic acid molecule encodes a TCR comprising a TCR beta chain comprising one or more of: TRBV11-2 CDR1 comprising the amino acid sequence of SEQ ID NO:50, TRBV11-2 CDR2 comprising the amino acid sequence of SEQ ID NO:51, and TRBV11-2 CDR3 comprising the amino acid sequence of SEQ ID NO:52. In one embodiment, the nucleic acid sequence encoding TRBV11-2 CDR1 comprises TCTGGCCATGCTACC (SEQ ID NO:126). In one embodiment, the nucleic acid sequence encoding TRBV11-2 CDR2 comprises TTTCAGAATAACGGTGTA (SEQ ID NO:127). In one embodiment, the nucleic acid sequence encoding TRBV11-2 CDR3 comprises TGTGCCAGCAGCTTATATGGGGGGTCGATCTCCTACGAGCAGTACTTC (SEQ ID NO:128).

In one embodiment, the isolated nucleic acid molecule encodes a TCR comprising a TCR beta chain comprising a constant domain comprising the amino acid sequence of SEQ ID NO:53. In one embodiment, the nucleic acid sequence encoding the constant domain comprises:

```
                                       (SEQ ID NO: 129)
GAGGACCTGAAAAACGTGTTCCCACCCGAGGTCGCTGTGTTTGAGCCATC

AGAAGCAGAGATCTCCCACACCCAAAAGGCCACACTGGTGTGCCTGGCCA

CAGGCTTCTACCCCGACCACGTGGAGCTGAGCTGGTGGGTGAATGGGAAG

GAGGTGCACAGTGGGGTCAGCACAGACCCGCAGCCCCTCAAGGAGCAGCC

CGCCCTCAATGACTCCAGATACTGCCTGAGCAGCCGCCTGAGGGTCTCGG

CCACCTTCTGGCAGAACCCCCGCAACCACTTCCGCTGTCAAGTCCAGTTC

TACGGGCTCTCGGAGAATGATGAGTGGACACAAGATAGGGCCAAACCTGT

CACCCAGATCGTCAGCGCCGAGGCCTGGGGTAGAGCAGACTGTGGCTTCA

CCTCCGAGTCTTACCAGCAAGGGGTCCTGTCTGCCACCATCCTCTATGAG

ATCTTGCTAGGGAAGGCCACCTTGTATGCCGTGCTGGTCAGTGCCCTCGT

GCTGATGGCCATGGTCAAGAGAAAGGATTCCAGAGGC.
```

In one embodiment, the nucleic acid molecule encodes a TCR beta chain comprising the amino acid sequence of SEQ ID NO:54. In one embodiment, the nucleic acid sequence encoding a TCR beta chain comprises:

```
                                       (SEQ ID NO: 130)
ATGGGCACCAGGCTCCTCTGCTGGGCGGCCCTCTGTCTCCTGGGAGCAGA

ACTCACAGAAGCTGGAGTTGCCCAGTCTCCCAGATATAAGATTATAGAGA

AAAGGCAGAGTGTGGCTTTTTGGTGCAATCCTATATCTGGCCATGCTACC

CTTTACTGGTACCAGCAGATCCTGGGACAGGGCCCAAAGCTTCTGATTCA

GTTTCAGAATAACGGTGTAGTGGATGATTCACAGTTGCCTAAGGATCGAT

TTTCTGCAGAGAGGCTCAAAGGAGTAGACTCCACTCTCAAGATCCAGCCT

GCAAAGCTTGAGGACTCGGCCGTGTATCTCTGTGCCAGCAGCTTATATGG

GGGGTCGATCTCCTACGAGCAGTACTTCGGGCCGGGCACCAGGCTCACGG

TCACAGAGGACCTGAAAAACGTGTTCCCACCCGAGGTCGCTGTGTTTGAG

CCATCAGAAGCAGAGATCTCCCACACCCAAAAGGCCACACTGGTGTGCCT

GGCCACAGGCTTCTACCCCGACCACGTGGAGCTGAGCTGGTGGGTGAATG

GGAAGGAGGTGCACAGTGGGGTCAGCACAGACCCGCAGCCCCTCAAGGAG

CAGCCCGCCCTCAATGACTCCAGATACTGCCTGAGCAGCCGCCTGAGGGT

CTCGGCCACCTTCTGGCAGAACCCCCGCAACCACTTCCGCTGTCAAGTCC

AGTTCTACGGGCTCTCGGAGAATGATGAGTGGACACAAGATAGGGCCAAA

CCTGTCACCCAGATCGTCAGCGCCGAGGCCTGGGGTAGAGCAGACTGTGG

CTTCACCTCCGAGTCTTACCAGCAAGGGGTCCTGTCTGCCACCATCCTCT
```

-continued

```
ATGAGATCTTGCTAGGGAAGGCCACCTTGTATGCCGTGCTGGTCAGTGCC

CTCGTGCTGATGGCCATGGTCAAGAGAAAGGATTCCAGAGGCTGA.
```

In one embodiment, the nucleic acid molecule encodes a fusion protein comprising a TCR alpha chain and a TCR beta chain. In one embodiment, the isolated nucleic acid molecule encodes a fusion protein comprising a linker domain between the TCR alpha chain and TCR beta chain. In one embodiment, the nucleic acid molecule encodes a GSG-T2A linker domain comprising the amino acid sequence of SEQ ID NO:55. In one embodiment, the nucleic acid sequence encoding a GSG-T2A linker domain comprises:

```
                                       (SEQ ID NO: 131)
GGCAGCGGAGAGGGCAGAGGAAGTCTTCTAACATGCGGTGACGTGGAGGA

GAATCCCGGCCCT.
```

In one embodiment, the nucleic acid molecule encodes a fusion protein comprising the amino acid sequence of SEQ ID NO:56. In one embodiment, the nucleic acid sequence encoding the fusion protein comprises

```
                                       (SEQ ID NO: 132)
ATGGAAACTCTCCTGGGAGTGTCTTTGGTGATTCTATGGCTTCAACTGGC

TAGGGTGAACAGTCAACAGGGAGAAGAGGATCCTCAGGCCTTGAGCATCC

AGGAGGGTGAAAATGCCACCATGAACTGCAGTTACAAAACTAGTATAAAC

AATTTACAGTGGTATAGACAAAATTCAGGTAGAGGCCTTGTCCACCTAAT

TTTAATACGTTCAAATGAAAGAGAGAAACACAGTGGAAGATTAAGAGTCA

CGCTTGACACTTCCAAGAAAAGCAGTTCCTTGTTGATCACGGCTTCCCGG

GCAGCAGACACTGCTTCTTACTTCTGTGCTACGGACCCTGGAGGCTTCAA

AACTATCTTTGGAGCAGGAACAAGACTATTTGTTAAAGCAAATATCCAGA

ACCCTGACCCTGCCGTGTACCAGCTGAGAGACTCTAAATCCAGTGACAAG

TCTGTCTGCCTATTCACCGATTTTGATTCTCAAACAAATGTGTCACAAAG

TAAGGATTCTGATGTGTATATCACAGACAAAACTGTGTTGGACATGCGCA

GCATGGACTTCAAGAGCAACAGTGCTGTGGCCTGGAGCAACAAATCTGAC

TTTGCATGTGCAAACGCCTTCAACAACAGCATTATTCCAGAAGACACCTT

CTTCCCCAGCCCAGAAAGTTCCTGTGATGTCAAGCTGGTCGAGAAAAGCT

TTGAAACAGATACGAACCTAAACTTTCAAAACCTGTCAGTGATTGGGTTC

CGAATCCTCCTCCTGAAAGTGGCCGGGTTTAATCTGCTCATGACGCTGCG

GCTGTGGTCCAGCGGCAGCGGAGAGGGCAGAGGAAGTCTTCTAACATGCG

GTGACGTGGAGGAGAATCCCGGCCCTATGGGCACCAGGCTCCTCTGCTGG

GCGGCCCTCTGTCTCCTGGGAGCAGAACTCACAGAAGCTGGAGTTGCCCA

GTCTCCCAGATATAAGATTATAGAGAAAAGGCAGAGTGTGGCTTTTTGGT

GCAATCCTATATCTGGCCATGCTACCCTTTACTGGTACCAGCAGATCCTG

GGACAGGGCCCAAAGCTTCTGATTCAGTTTCAGAATAACGGTGTAGTGGA

TGATTCACAGTTGCCTAAGGATCGATTTTCTGCAGAGAGGCTCAAAGGAG

TAGACTCCACTCTCAAGATCCAGCCTGCAAAGCTTGAGGACTCGGCCGTG
```

-continued

```
TATCTCTGTGCCAGCAGCTTATATGGGGGGTCGATCTCCTACGAGCAGTA
CTTCGGGCCGGGCACCAGGCTCACGGTCACAGAGGACCTGAAAAACGTGT
TCCCACCCGAGGTCGCTGTGTTTGAGCCATCAGAAGCAGAGATCTCCCAC
ACCCAAAAGGCCACACTGGTGTGCCTGGCCACAGGCTTCTACCCCGACCA
CGTGGAGCTGAGCTGGTGGGTGAATGGGAAGGAGGTGCACAGTGGGGTCA
GCACAGACCCGCAGCCCCTCAAGGAGCAGCCCGCCCTCAATGACTCCAGA
TACTGCCTGAGCAGCCGCCTGAGGGTCTCGGCCACCTTCTGGCAGAACCC
CCGCAACCACTTCCGCTGTCAAGTCCAGTTCTACGGGCTCTCGGAGAATG
ATGAGTGGACACAAGATAGGGCCAAACCTGTCACCCAGATCGTCAGCGCC
GAGGCCTGGGGTAGAGCAGACTGTGGCTTCACCTCCGAGTCTTACCAGCA
AGGGGTCCTGTCTGCCACCATCCTCTATGAGATCTTGCTAGGGAAGGCCA
CCTTGTATGCCGTGCTGGTCAGTGCCCTCGTGCTGATGGCCATGGTCAAG
AGAAAGGATTCCAGAGGCTGA.
```

Nucleic Acid Molecule Encoding TCR896

In embodiment, the isolated nucleic acid molecule encodes a TCR comprising a TCR alpha chain comprising one or more of: TRAV19 CDR1, TRAV19 CDR2, and TRAV19 CDR3. In embodiment, the isolated nucleic acid molecule encodes a TCR comprising a TCR alpha chain comprising one or more of: TRAV19 CDR1 comprising the amino acid sequence of SEQ ID NO:57, TRAV19 CDR2 comprising the amino acid sequence of SEQ ID NO:58, and TRAV19 CDR3 comprising the amino acid sequence of SEQ ID NO:59. In one embodiment, the nucleic acid sequence encoding TRAV19 CDR1 comprises ACCCGTGATACTACTTATTAC (SEQ ID NO:133). In one embodiment, the nucleic acid sequence encoding TRAV19 CDR2 comprises CGGAACTCTTTTGATGAGCAAAAT (SEQ ID NO:134). In one embodiment, the nucleic acid sequence encoding TRAV19 CDR3 comprises

```
                                        (SEQ ID NO: 135)
TGTGCTCTGAGTGAGGCAGGAACCTACAAATACATCTTT.
```

In one embodiment, the isolated nucleic acid molecule encodes a TCR comprising a TCR alpha chain comprising a constant domain comprising the amino acid sequence of SEQ ID NO:60. In one embodiment, the nucleic acid sequence encoding the constant domain comprises:

```
                                        (SEQ ID NO: 136)
ATATCCAGAACCCTGACCCTGCCGTGTACCAGCTGAGAGACTCTAAATCC
AGTGACAAGTCTGTCTGCCTATTCACCGATTTTGATTCTCAAACAAATGT
GTCACAAAGTAAGGATTCTGATGTGTATATCACAGACAAAACTGTGTTGG
ACATGCGCAGCATGGACTTCAAGAGCAACAGTGCTGTGGCCTGGAGCAAC
AAATCTGACTTTGCATGTGCAAACGCCTTCAACAACAGCATTATTCCAGA
AGACACCTTCTTCCCCAGCCCAGAAAGTTCCTGTGATGTCAAGCTGGTCG
AGAAAAGCTTTGAAACAGATACGAACCTAAACTTTCAAAACCTGTCAGTG
ATTGGGTTCCGAATCCTCCTCCTGAAAGTGGCCGGGTTTAATCTGCTCAT
GACGCTGCGGCTGTGGTCCAGC.
```

In one embodiment, the nucleic acid molecule encodes a TCR alpha chain comprising the amino acid sequence of SEQ ID NO:61. In one embodiment, the nucleic acid sequence encoding a TCR alpha chain comprises:

```
                                        (SEQ ID NO: 137)
ATGCTGACTGCCAGCCTGTTGAGGGCAGTCATAGCCTCCATCTGTGTTGT
ATCCAGCATGGCTCAGAAGGTAACTCAAGCGCAGACTGAAATTTCTGTGG
TGGAGAAGGAGGATGTGACCTTGGACTGTGTGTATGAAACCCGTGATACT
ACTTATTACTTATTCTGGTACAAGCAACCACCAAGTGGAGAATTGGTTTT
CCTTATTCGTCGGAACTCTTTTGATGAGCAAAATGAAATAAGTGGTCGGT
ATTCTTGGAACTTCCAGAAATCCACCAGTTCCTTCAACTTCACCATCACA
GCCTCACAAGTCGTGGACTCAGCAGTATACTTCTGTGCTCTGAGTGAGGC
AGGAACCTACAAATACATCTTTGGAACAGGCACCAGGCTGAAGGTATTAG
CAAATATCCAGAACCCTGACCCTGCCGTGTACCAGCTGAGAGACTCTAAA
TCCAGTGACAAGTCTGTCTGCCTATTCACCGATTTTGATTCTCAAACAAA
TGTGTCACAAAGTAAGGATTCTGATGTGTATATCACAGACAAAACTGTGT
TGGACATGCGCAGCATGGACTTCAAGAGCAACAGTGCTGTGGCCTGGAGC
AACAAATCTGACTTTGCATGTGCAAACGCCTTCAACAACAGCATTATTCC
AGAAGACACCTTCTTCCCCAGCCCAGAAAGTTCCTGTGATGTCAAGCTGG
TCGAGAAAAGCTTTGAAACAGATACGAACCTAAACTTTCAAAACCTGTCA
GTGATTGGGTTCCGAATCCTCCTCCTGAAAGTGGCCGGGTTTAATCTGCT
CATGACGCTGCGGCTGTGGTCCAGC.
```

In embodiment, the isolated nucleic acid molecule encodes a TCR comprising a TCR beta chain comprising one or more of: TRBV9 CDR1, TRBV9 CDR2, and TRBV9 CDR3. In embodiment, the isolated nucleic acid molecule encodes a TCR comprising a TCR beta chain comprising one or more of: TRBV9 CDR1 comprising the amino acid sequence of SEQ ID NO:62, TRBV9 CDR2 comprising the amino acid sequence of SEQ ID NO:63, and TRBV9 CDR3 comprising the amino acid sequence of SEQ ID NO:64. In one embodiment, the nucleic acid sequence encoding TRBV9 CDR1 comprises TCTGGAGACCTCTCT (SEQ ID NO:138). In one embodiment, the nucleic acid sequence encoding TRBV9 CDR2 comprises CGGAACTCTTTTGATGAGCAAAAT (SEQ ID NO:139). In one embodiment, the nucleic acid sequence encoding TRBV9 CDR3 comprises

```
                                        (SEQ ID NO: 140)
TGTGCTCTGAGTGAGGCAGGAACCTACAAATACATCTTT.
```

In one embodiment, the isolated nucleic acid molecule encodes a TCR comprising a TCR beta chain comprising a constant domain comprising the amino acid sequence of SEQ ID NO:65. In one embodiment, the nucleic acid sequence encoding the constant domain comprises:

```
                                        (SEQ ID NO: 141)
GAGGACCTGAAAAACGTGTTCCCACCCGAGGTCGCTGTGTTTGAGCCATC
AGAAGCAGAGATCTCCCACACCCAAAAGGCCACACTGGTGTGCCTGGCCA
CAGGCTTCTACCCCGACCACGTGGAGCTGAGCTGGTGGGTGAATGGGAAG
GAGGTGCACAGTGGGGTCAGCACAGACCCGCAGCCCCTCAAGGAGCAGCC
```

-continued

CGCCCTCAATGACTCCAGATACTGCCTGAGCAGCCGCCTGAGGGTCTCGG

CCACCTTCTGGCAGAACCCCCGCAACCACTTCCGCTGTCAAGTCCAGTTC

TACGGGCTCTCGGAGAATGATGAGTGGACACAAGATAGGGCCAAACCTGT

CACCCAGATCGTCAGCGCCGAGGCCTGGGGTAGAGCAGACTGTGGCTTCA

CCTCCGAGTCTTACCAGCAAGGGGTCCTGTCTGCCACCATCCTCTATGAG

ATCTTGCTAGGGAAGGCCACCTTGTATGCCGTGCTGGTCAGTGCCCTCGT

GCTGATGGCCATGGTCAAGAGAAAGGATTCCAGAGGC.

In one embodiment, the nucleic acid molecule encodes a TCR beta chain comprising the amino acid sequence of SEQ ID NO:66. In one embodiment, the nucleic acid sequence encoding a TCR beta chain comprises:

(SEQ ID NO: 142)

ATGGGCTTCAGGCTCCTCTGCTGTGTGGCCTTTTGTCTCCTGGGAGCAGG

CCCAGTGGATTCTGGAGTCACACAAACCCCAAAGCACCTGATCACAGCAA

CTGGACAGCGAGTGACGCTGAGATGCTCCCCTAGGTCTGGAGACCTCTCT

GTGTACTGGTACCAACAGAGCCTGGACCAGGGCCTCCAGTTCCTCATTCA

GTATTATAATGGAGAAGAGAGAGCAAAAGGAAACATTCTTGAACGATTCT

CCGCACAACAGTTCCCTGACTTGCACTCTGAACTAAACCTGAGCTCTCTG

GAGCTGGGGGACTCAGCTTTGTATTTCTGTGCCAGCAGCGTAGCTGGGGG

GGGACAAGAGACCCAGTACTTCGGGCCAGGCACGCGGCTCCTGGTGCTCG

AGGACCTGAAAAACGTGTTCCCACCCGAGGTCGCTGTGTTTGAGCCATCA

GAAGCAGAGATCTCCCACACCCAAAAGGCCACACTGGTGTGCCTGGCCAC

AGGCTTCTACCCCGACCACGTGGAGCTGAGCTGGTGGGTGAATGGGAAGG

AGGTGCACAGTGGGGTCAGCACAGACCCGCAGCCCCTCAAGGAGCAGCCC

GCCCTCAATGACTCCAGATACTGCCTGAGCAGCCGCCTGAGGGTCTCGGC

CACCTTCTGGCAGAACCCCCGCAACCACTTCCGCTGTCAAGTCCAGTTCT

ACGGGCTCTCGGAGAATGATGAGTGGACACAAGATAGGGCCAAACCTGTC

ACCCAGATCGTCAGCGCCGAGGCCTGGGGTAGAGCAGACTGTGGCTTCAC

CTCCGAGTCTTACCAGCAAGGGGTCCTGTCTGCCACCATCCTCTATGAGA

TCTTGCTAGGGAAGGCCACCTTGTATGCCGTGCTGGTCAGTGCCCTCGTG

CTGATGGCCATGGTCAAGAGAAAGGATTCCAGAGGCTGA.

In one embodiment, the nucleic acid molecule encodes a fusion protein comprising a TCR alpha chain and a TCR beta chain. In one embodiment, the isolated nucleic acid molecule encodes a fusion protein comprising a linker domain between the TCR alpha chain and TCR beta chain. In one embodiment, the nucleic acid molecule encodes a GSG-T2A linker domain comprising the amino acid sequence of SEQ ID NO:67. In one embodiment, the nucleic acid sequence encoding a GSG-T2A linker domain comprises:

(SEQ ID NO: 143)

GGCAGCGGAGAGGGCAGAGGAAGTCTTCTAACATGCGGTGACGTGGAGG

AGAATCCCGGCCCT.

In one embodiment, the nucleic acid molecule encodes a fusion protein comprising the amino acid sequence of SEQ ID NO:68. In one embodiment, the nucleic acid sequence encoding the fusion protein comprises (SEQ ID NO: 144)

ATGCTGACTGCCAGCCTGTTGAGGGCAGTCATAGCCTCCATCTGTGTTG

TATCCAGCATGGCTCAGAAGGTAACTCAAGCGCAGACTGAAATTTCTGT

GGTGGAGAAGGAGGATGTGACCTTGGACTGTGTGTATGAAACCCGTGAT

ACTACTTATTACTTATTCTGGTACAAGCAACCACCAAGTGGAGAATTGG

TTTTCCTTATTCGTCGGAACTCTTTTGATGAGCAAAATGAAATAAGTGG

TCGGTATTCTTGGAACTTCCAGAAATCCACCAGTTCCTTCAACTTCACC

ATCACAGCCTCACAAGTCGTGGACTCAGCAGTATACTTCTGTGCTCTGA

GTGAGGCAGGAACCTACAAATACATCTTTGGAACAGGCACCAGGCTGAA

GGTATTAGCAAATATCCAGAACCCTGACCCTGCCGTGTACCAGCTGAGA

GACTCTAAATCCAGTGACAAGTCTGTCTGCCTATTCACCGATTTTGATT

CTCAAACAAATGTGTCACAAAGTAAGGATTCTGATGTGTATATCACAGA

CAAAACTGTGTTGGACATGCGCAGCATGGACTTCAAGAGCAACAGTGCT

GTGGCCTGGAGCAACAAATCTGACTTTGCATGTGCAAACGCCTTCAACA

ACAGCATTATTCCAGAAGACACCTTCTTCCCCAGCCCAGAAAGTTCCTG

TGATGTCAAGCTGGTCGAGAAAAGCTTTGAAACAGATACGAACCTAAAC

TTTCAAAACCTGTCAGTGATTGGGTTCCGAATCCTCCTCCTGAAAGTGG

CCGGGTTTAATCTGCTCATGACGCTGCGGCTGTGGTCCAGCGGCAGCGG

AGAGGGCAGAGGAAGTCTTCTAACATGCGGTGACGTGGAGGAGAATCCC

GGCCCTATGGGCTTCAGGCTCCTCTGCTGTGTGGCCTTTTGTCTCCTGG

GAGCAGGCCCAGTGGATTCTGGAGTCACACAAACCCCAAAGCACCTGAT

CACAGCAACTGGACAGCGAGTGACGCTGAGATGCTCCCCTAGGTCTGGA

GACCTCTCTGTGTACTGGTACCAACAGAGCCTGGACCAGGGCCTCCAGT

TCCTCATTCAGTATTATAATGGAGAAGAGAGAGCAAAAGGAAACATTCT

TGAACGATTCTCCGCACAACAGTTCCCTGACTTGCACTCTGAACTAAAC

CTGAGCTCTCTGGAGCTGGGGGACTCAGCTTTGTATTTCTGTGCCAGCA

GCGTAGCTGGGGGGGGACAAGAGACCCAGTACTTCGGGCCAGGCACGCG

GCTCCTGGTGCTCGAGGACCTGAAAAACGTGTTCCCACCCGAGGTCGCT

GTGTTTGAGCCATCAGAAGCAGAGATCTCCCACACCCAAAAGGCCACAC

TGGTGTGCCTGGCCACAGGCTTCTACCCCGACCACGTGGAGCTGAGCTG

GTGGGTGAATGGGAAGGAGGTGCACAGTGGGGTCAGCACAGACCCGCAG

CCCCTCAAGGAGCAGCCCGCCCTCAATGACTCCAGATACTGCCTGAGCA

GCCGCCTGAGGGTCTCGGCCACCTTCTGGCAGAACCCCCGCAACCACTT

CCGCTGTCAAGTCCAGTTCTACGGGCTCTCGGAGAATGATGAGTGGACA

CAAGATAGGGCCAAACCTGTCACCCAGATCGTCAGCGCCGAGGCCTGGG

GTAGAGCAGACTGTGGCTTCACCTCCGAGTCTTACCAGCAAGGGGTCCT

GTCTGCCACCATCCTCTATGAGATCTTGCTAGGGAAGGCCACCTTGTAT

GCCGTGCTGGTCAGTGCCCTCGTGCTGATGGCCATGGTCAAGAGAAAGG

ATTCCAGAGGCTGA.

Nucleic Acid Molecule Encoding TCR847

In embodiment, the isolated nucleic acid molecule encodes a TCR comprising a TCR alpha chain comprising one or more of: TRAV17 CDR1, TRAV17 CDR2, and TRAV17 CDR3. In embodiment, the isolated nucleic acid molecule encodes a TCR comprising a TCR alpha chain comprising one or more of: TRAV17 CDR1 comprising the amino acid sequence of SEQ ID NO:69, TRAV17 CDR2 comprising the amino acid sequence of SEQ ID NO:70, and TRAV17 CDR3 comprising the amino acid sequence of SEQ ID NO:71. In one embodiment, the nucleic acid sequence encoding TRAV17 CDR1 comprises ACT-AGTATAAACAAT (SEQ ID NO:145). In one embodiment, the nucleic acid sequence encoding TRAV17 CDR2 comprises ATACGTTCAAATGAAAGAGAG (SEQ ID NO:146). In one embodiment, the nucleic acid sequence encoding TRAV17 CDR3 comprises (SEQ ID NO: 147)
GCTACTTTTCCTAACTTTGGAAATGAGAAATTAACC.

In one embodiment, the isolated nucleic acid molecule encodes a TCR comprising a TCR alpha chain comprising a constant domain comprising the amino acid sequence of SEQ ID NO:72. In one embodiment, the nucleic acid sequence encoding the constant domain comprises:

(SEQ ID NO: 148)
ATATCCAGAACCCTGACCCTGCCGTGTACCAGCTGAGAGACTCTAAATC

CAGTGACAAGTCTGTCTGCCTATTCACCGATTTTGATTCTCAAACAAAT

GTGTCACAAAGTAAGGATTCTGATGTGTATATCACAGACAAAACTGTGT

TGGACATGCGCAGCATGGACTTCAAGAGCAACAGTGCTGTGGCCTGGAG

CAACAAATCTGACTTTGCATGTGCAAACGCCTTCAACAACAGCATTATT

CCAGAAGACACCTTCTTCCCCAGCCCAGAAAGTTCCTGTGATGTCAAGC

TGGTCGAGAAAAGCTTTGAAACAGATACGAACCTAAACTTTCAAAACCT

GTCAGTGATTGGGTTCCGAATCCTCCTCCTGAAAGTGGCCGGGTTTAAT

CTGCTCATGACGCTGCGGCTGTGGTCCAGC.

In one embodiment, the nucleic acid molecule encodes a TCR alpha chain comprising the amino acid sequence of SEQ ID NO:73. In one embodiment, the nucleic acid sequence encoding a TCR alpha chain comprises:

(SEQ ID NO: 149)
ATGGAAACTCTCCTGGGAGTGTCTTTGGTGATTCTATGGCTTCAACTGG

CTAGGGTGAACAGTCAACAGGGAGAAGAGGATCCTCAGGCCTTGAGCAT

CCAGGAGGGTGAAAATGCCACCATGAACTGCAGTTACAAAACTAGTATA

AACAATTTACAGTGGTATAGACAAAATTCAGGTAGAGGCCTTGTCCACC

TAATTTTAATACGTTCAAATGAAAGAGAGAAACACAGTGGAAGATTAAG

AGTCACGCTTGACACTTCCAAGAAAAGCAGTTCCTTGTTGATCACGGCT

TCCCGGGCAGCAGACACTGCTTCTTACTTCTGTGCTACTTTTCCTAACT

TTGGAAATGAGAAATTAACCTTTGGGACTGGAACAAGACTCACCATCAT

ACCCAATATCCAGAACCCTGACCCTGCCGTGTACCAGCTGAGAGACTCT

AAATCCAGTGACAAGTCTGTCTGCCTATTCACCGATTTTGATTCTCAA

-continued

CAAATGTGTCACAAAGTAAGGATTCTGATGTGTATATCACAGACAAAAC

TGTGTTGGACATGCGCAGCATGGACTTCAAGAGCAACAGTGCTGTGGCC

TGGAGCAACAAATCTGACTTTGCATGTGCAAACGCCTTCAACAACAGCA

TTATTCCAGAAGACACCTTCTTCCCCAGCCCAGAAAGTTCCTGTGATGT

CAAGCTGGTCGAGAAAAGCTTTGAAACAGATACGAACCTAAACTTTCAA

AACCTGTCAGTGATTGGGTTCCGAATCCTCCTCCTGAAAGTGGCCGGGT

TTAATCTGCTCATGACGCTGCGGCTGTGGTCCAGC.

In embodiment, the isolated nucleic acid molecule encodes a TCR comprising a TCR beta chain comprising one or more of: TRBV10-3 CDR1, TRBV10-3 CDR2, and TRBV10-3 CDR3. In embodiment, the isolated nucleic acid molecule encodes a TCR comprising a TCR beta chain comprising one or more of: TRBV10-3 CDR1 comprising the amino acid sequence of SEQ ID NO:74, TRBV10-3 CDR2 comprising the amino acid sequence of SEQ ID NO:75, and TRBV10-3 CDR3 comprising the amino acid sequence of SEQ ID NO:76. In one embodiment, the nucleic acid sequence encoding TRBV10-3 CDR1 comprises GAGAACCACCGCTA (SEQ ID NO:150). In one embodiment, the nucleic acid sequence encoding TRBV10-3 CDR2 comprises TCATATGGTGTTAAAGAT (SEQ ID NO:151). In one embodiment, the nucleic acid sequence encoding TRBV10-3 CDR3 comprises GCCATCAGTGAGTCG-GAGCGGTACTACGAGCAGTAC (SEQ ID NO:152).

In one embodiment, the isolated nucleic acid molecule encodes a TCR comprising a TCR beta chain comprising a constant domain comprising the amino acid sequence of SEQ ID NO:77. In one embodiment, the nucleic acid sequence encoding the constant domain comprises:

(SEQ ID NO: 153)
GAGGACCTGAAAAACGTGTTCCCACCCGAGGTCGCTGTGTTTGAGCCAT

CAGAAGCAGAGATCTCCCACACCCAAAAGGCCACACTGGTGTGCCTGGC

CACAGGCTTCTACCCCGACCACGTGGAGCTGAGCTGGTGGGTGAATGGG

AAGGAGGTGCACAGTGGGGTCAGCACAGACCCGCAGCCCCTCAAGGAGC

AGCCCGCCCTCAATGACTCCAGATACTGCCTGAGCAGCCGCCTGAGGGT

CTCGGCCACCTTCTGGCAGAACCCCCGCAACCACTTCCGCTGTCAAGTC

CAGTTCTACGGGCTCTCGGAGAATGATGAGTGGACACAAGATAGGGCCA

AACCTGTCACCCAGATCGTCAGCGCCGAGGCCTGGGGTAGAGCAGACTG

TGGCTTCACCTCCGAGTCTTACCAGCAAGGGGTCCTGTCTGCCACCATC

CTCTATGAGATCTTGCTAGGGAAGGCCACCTTGTATGCCGTGCTGGTCA

GTGCCCTCGTGCTGATGGCCATGGTCAAGAGAAAGGATTCCAGAGGC.

In one embodiment, the nucleic acid molecule encodes a TCR beta chain comprising the amino acid sequence of SEQ ID NO:78. In one embodiment, the nucleic acid sequence encoding a TCR beta chain comprises:

(SEQ ID NO: 154)
ATGGGCACAAGGTTGTTCTTCTATGTGGCCCTTTGTCTCCTGTGGACAG

GACACATGGATGCTGGAATCACCCAGAGCCCAAGACACAAGGTCACAGA

GACAGGAACACCAGTGACTCTGAGATGTCACCAGACTGAGAACCACCGC

-continued

```
TATATGTACTGGTATCGACAAGACCCGGGGCATGGGCTGAGGCTGATCC
ATTACTCATATGGTGTTAAAGATACTGACAAAGGAGAAGTCTCAGATGG
CTATAGTGTCTCCAGATCAAAGACAGAGGATTTCCTCCTCACTCTGGAG
TCCGCTACCAGCTCCCAGACATCTGTGTACTTCTGTGCCATCAGTGAGT
CGGAGCGGTACTACGAGCAGTACTTCGGGCCGGGCACCAGGCTCACGGT
CACAGAGGACCTGAAAAACGTGTTCCCACCCGAGGTCGCTGTGTTTGAG
CCATCAGAAGCAGAGATCTCCCACACCCAAAAGGCCACACTGGTGTGCC
TGGCCACAGGCTTCTACCCCGACCACGTGGAGCTGAGCTGGTGGGTGAA
TGGGAAGGAGGTGCACAGTGGGGTCAGCACAGACCCGCAGCCCCTCAAG
GAGCAGCCCGCCCTCAATGACTCCAGATACTGCCTGAGCAGCCGCCTGA
GGGTCTCGGCCACCTTCTGGCAGAACCCCCGCAACCACTTCCGCTGTCA
AGTCCAGTTCTACGGGCTCTCGGAGAATGATGAGTGGACACAAGATAGG
GCCAAACCTGTCACCCAGATCGTCAGCGCCGAGGCCTGGGGTAGAGCAG
ACTGTGGCTTCACCTCCGAGTCTTACCAGCAAGGGGTCCTGTCTGCCAC
CATCCTCTATGAGATCTTGCTAGGGAAGGCCACCTTGTATGCCGTGCTG
GTCAGTGCCCTCGTGCTGATGGCCATGGTCAAGAGAAAGGATTCCAGAG
GCTGA.
```

In one embodiment, the nucleic acid molecule encodes a fusion protein comprising a TCR alpha chain and a TCR beta chain. In one embodiment, the isolated nucleic acid molecule encodes a fusion protein comprising a linker domain between the TCR alpha chain and TCR beta chain. In one embodiment, the nucleic acid molecule encodes a GSG-T2A linker domain comprising the amino acid sequence of SEQ ID NO:79. In one embodiment, the nucleic acid sequence encoding a GSG-T2A linker domain comprises:

```
                                            (SEQ ID NO: 155)
GGCAGCGGAGAGGGCAGAGGAAGTCTTCTAACATGCGGTGACGTGGAGG
AGAATCCCGGCCCT.
```

In one embodiment, the nucleic acid molecule encodes a fusion protein comprising the amino acid sequence of SEQ ID NO:80. In one embodiment, the nucleic acid sequence encoding the fusion protein comprises

```
                                            (SEQ ID NO: 156)
ATGGAAACTCTCCTGGGAGTGTCTTTGGTGATTCTATGGCTTCAACTGG
CTAGGGTGAACAGTCAACAGGGAGAAGAGGATCCTCAGGCCTTGAGCAT
CCAGGAGGGTGAAAATGCCACCATGAACTGCAGTTACAAAACTAGTATA
AACAATTTACAGTGGTATAGACAAAATTCAGGTAGAGGCCTTGTCCACC
TAATTTTAATACGTTCAAATGAAAGAGAGAAACACAGTGGAAGATTAAG
AGTCACGCTTGACACTTCCAAGAAAAGCAGTTCCTTGTTGATCACGGCT
TCCCGGGCAGCAGACACTGCTTCTTACTTCTGTGCTACTTTTCCTAACT
TTGGAAATGAGAAATTAACCTTTGGGACTGGAACAAGACTCACCATCAT
ACCCAATATCCAGAACCCTGACCCTGCCGTGTACCAGCTGAGAGACTCT
AAATCCAGTGACAAGTCTGTCTGCCTATTCACCGATTTTGATTCTCAAA
```

-continued

```
CAAATGTGTCACAAAGTAAGGATTCTGATGTGTATATCACAGACAAAAC
TGTGTTGGACATGCGCAGCATGGACTTCAAGAGCAACAGTGCTGTGGCC
TGGAGCAACAAATCTGACTTTGCATGTGCAAACGCCTTCAACAACAGCA
TTATTCCAGAAGACACCTTCTTCCCCAGCCCAGAAAGTTCCTGTGATGT
CAAGCTGGTCGAGAAAAGCTTTGAAACAGATACGAACCTAAACTTTCAA
AACCTGTCAGTGATTGGGTTCCGAATCCTCCTCCTGAAAGTGGCCGGGT
TTAATCTGCTCATGACGCTGCGGCTGTGGTCCAGCGGCAGCGGAGAGGG
CAGAGGAAGTCTTCTAACATGCGGTGACGTGGAGGAGAATCCCGGCCCT
ATGGGCACAAGGTTGTTCTTCTATGTGGCCCTTTGTCTCCTGTGGACAG
GACACATGGATGCTGGAATCACCCAGAGCCCAAGACACAAGGTCACAGA
GACAGGAACACCAGTGACTCTGAGATGTCACCAGACTGAGAACCACCGC
TATATGTACTGGTATCGACAAGACCCGGGGCATGGGCTGAGGCTGATCC
ATTACTCATATGGTGTTAAAGATACTGACAAAGGAGAAGTCTCAGATGG
CTATAGTGTCTCCAGATCAAAGACAGAGGATTTCCTCCTCACTCTGGAG
TCCGCTACCAGCTCCCAGACATCTGTGTACTTCTGTGCCATCAGTGAGT
CGGAGCGGTACTACGAGCAGTACTTCGGGCCGGGCACCAGGCTCACGGT
CACAGAGGACCTGAAAAACGTGTTCCCACCCGAGGTCGCTGTGTTTGAG
CCATCAGAAGCAGAGATCTCCCACACCCAAAAGGCCACACTGGTGTGCC
TGGCCACAGGCTTCTACCCCGACCACGTGGAGCTGAGCTGGTGGGTGAA
TGGGAAGGAGGTGCACAGTGGGGTCAGCACAGACCCGCAGCCCCTCAAG
GAGCAGCCCGCCCTCAATGACTCCAGATACTGCCTGAGCAGCCGCCTGA
GGGTCTCGGCCACCTTCTGGCAGAACCCCCGCAACCACTTCCGCTGTCA
AGTCCAGTTCTACGGGCTCTCGGAGAATGATGAGTGGACACAAGATAGG
GCCAAACCTGTCACCCAGATCGTCAGCGCCGAGGCCTGGGGTAGAGCAG
ACTGTGGCTTCACCTCCGAGTCTTACCAGCAAGGGGTCCTGTCTGCCAC
CATCCTCTATGAGATCTTGCTAGGGAAGGCCACCTTGTATGCCGTGCTG
GTCAGTGCCCTCGTGCTGATGGCCATGGTCAAGAGAAAGGATTCCAGAG
GCTGA.
```

Nucleic Acid Molecule Encoding TCR864

In embodiment, the isolated nucleic acid molecule encodes a TCR comprising a TCR alpha chain comprising one or more of: TRAV4 CDR1, TRAV4 CDR2, and TRAV4 CDR3. In embodiment, the isolated nucleic acid molecule encodes a TCR comprising a TCR alpha chain comprising one or more of: TRAV4 CDR1 comprising the amino acid sequence of SEQ ID NO:81, TRAV4 CDR2 comprising the amino acid sequence of SEQ ID NO:82, and TRAV4 CDR3 comprising the amino acid sequence of SEQ ID NO:83. In one embodiment, the nucleic acid sequence encoding TRAV4 CDR1 comprises AACATTGCTACAAATGATTAT (SEQ ID NO:157). In one embodiment, the nucleic acid sequence encoding TRAV4 CDR2 comprises GGATACAAGACAAAA (SEQ ID NO:158). In one embodiment, the nucleic acid sequence encoding TRAV4 CDR3 comprises (SEQ ID NO: 159)
CTCGTGGGTGACTTCAACTCAAATTCCGGGTATGCACTCAAC.

In one embodiment, the isolated nucleic acid molecule encodes a TCR comprising a TCR alpha chain comprising a constant domain comprising the amino acid sequence of SEQ ID NO:84. In one embodiment, the nucleic acid sequence encoding the constant domain comprises:

(SEQ ID NO: 160)
ATATCCAGAACCCTGACCCTGCCGTGTACCAGCTGAGAGACTCTAAATC

CAGTGACAAGTCTGTCTGCCTATTCACCGATTTTGATTCTCAAACAAAT

GTGTCACAAAGTAAGGATTCTGATGTGTATATCACAGACAAAACTGTGT

TGGACATGCGCAGCATGGACTTCAAGAGCAACAGTGCTGTGGCCTGGAG

CAACAAATCTGACTTTGCATGTGCAAACGCCTTCAACAACAGCATTATT

CCAGAAGACACCTTCTTCCCCAGCCCAGAAAGTTCCTGTGATGTCAAGC

TGGTCGAGAAAAGCTTTGAAACAGATACGAACCTAAACTTTCAAAACCT

GTCAGTGATTGGGTTCCGAATCCTCCTCCTGAAAGTGGCCGGGTTTAAT

CTGCTCATGACGCTGCGGCTGTGGTCCAGC.

In one embodiment, the nucleic acid molecule encodes a TCR alpha chain comprising the amino acid sequence of SEQ ID NO:85. In one embodiment, the nucleic acid sequence encoding a TCR alpha chain comprises:

(SEQ ID NO: 161)
ATGAGGCAAGTGGCGAGAGTGATCGTGTTCCTGACCCTGAGTACTTTGA

GCCTTGCTAAGACCACCCAGCCCATCTCCATGGACTCATATGAAGGACA

AGAAGTGAACATAACCTGTAGCCACAACAACATTGCTACAAATGATTAT

ATCACGTGGTACCAACAGTTTCCCAGCCAAGGACCACGATTTATTATTC

AAGGATACAAGACAAAAGTTACAAACGAAGTGGCCTCCCTGTTTATCCC

TGCCGACAGAAAGTCCAGCACTCTGAGCCTGCCCCGGGTTTCCCTGAGC

GACACTGCTGTGTACTACTGCCTCGTGGGTGACTTCAACTCAAATTCCG

GGTATGCACTCAACTTCGGCAAAGGCACCTCGCTGTTGGTCACACCCCA

TATCCAGAACCCTGACCCTGCCGTGTACCAGCTGAGAGACTCTAAATCC

AGTGACAAGTCTGTCTGCCTATTCACCGATTTTGATTCTCAAACAAATG

TGTCACAAAGTAAGGATTCTGATGTGTATATCACAGACAAAACTGTGTT

GGACATGCGCAGCATGGACTTCAAGAGCAACAGTGCTGTGGCCTGGAGC

AACAAATCTGACTTTGCATGTGCAAACGCCTTCAACAACAGCATTATTC

CAGAAGACACCTTCTTCCCCAGCCCAGAAAGTTCCTGTGATGTCAAGCT

GGTCGAGAAAAGCTTTGAAACAGATACGAACCTAAACTTTCAAAACCTG

TCAGTGATTGGGTTCCGAATCCTCCTCCTGAAAGTGGCCGGGTTTAATC

TGCTCATGACGCTGCGGCTGTGGTCCAGC.

In embodiment, the isolated nucleic acid molecule encodes a TCR comprising a TCR beta chain comprising one or more of: TRBV7-2 CDR1, TRBV7-2 CDR2, and TRBV7-2 CDR3. In embodiment, the isolated nucleic acid molecule encodes a TCR comprising a TCR beta chain comprising one or more of: TRBV47-2 CDR1 comprising the amino acid sequence of SEQ ID NO:86, TRBV7-2 CDR2 comprising the amino acid sequence of SEQ ID NO:87, and TRBV7-2 CDR3 comprising the amino acid sequence of SEQ ID NO:88. In one embodiment, the nucleic acid sequence encoding TRBV7-2 CDR1 comprises TCAGGTCATACTGCC (SEQ ID NO:162). In one embodiment, the nucleic acid sequence encoding TRBV7-2 CDR2 comprises TTCCAAGGCAACAGTGCA (SEQ ID NO:163). In one embodiment, the nucleic acid sequence encoding TRBV7-2 CDR3 comprises GCCAGCAAGGTCTATGGCTACACC (SEQ ID NO:164).

In one embodiment, the isolated nucleic acid molecule encodes a TCR comprising a TCR beta chain comprising a constant domain comprising the amino acid sequence of SEQ ID NO:89. In one embodiment, the nucleic acid sequence encoding the constant domain comprises:

(SEQ ID NO: 165)
GAGGACCTGAACAAGGTGTTCCCACCCGAGGTCGCTGTGTTTGAGCCAT

CAGAAGCAGAGATCTCCCACACCCAAAAGGCCACACTGGTGTGCCTGGC

CACAGGCTTCTTCCCCGACCACGTGGAGCTGAGCTGGTGGGTGAATGGG

AAGGAGGTGCACAGTGGGGTCAGCACGGACCCGCAGCCCCTCAAGGAGC

AGCCCGCCCTCAATGACTCCAGATACTGCCTGAGCAGCCGCCTGAGGGT

CTCGGCCACCTTCTGGCAGAACCCCCGCAACCACTTCCGCTGTCAAGTC

CAGTTCTACGGGCTCTCGGAGAATGATGAGTGGACACAAGATAGGGCCA

AACCCGTCACCCAGATCGTCAGCGCCGAGGCCTGGGGTAGAGCAGACTG

TGGCTTTACCTCGGTGTCCTACCAGCAAGGGGTCCTGTCTGCCACCATC

CTCTATGAGATCCTGCTAGGGAAGGCCACCCTGTATGCTGTGCTGGTCA

GCGCCCTTGTGTTGATGGCCATGGTCAAGAGAAAGGATTTC.

In one embodiment, the nucleic acid molecule encodes a TCR beta chain comprising the amino acid sequence of SEQ ID NO:90. In one embodiment, the nucleic acid sequence encoding a TCR beta chain comprises:

(SEQ ID NO: 166)
ATGGGCACCAGGCTCCTCTTCTGGGTGGCCTTCTGTCTCCTGGGGGCAT

ATCACACAGGAGCTGGAGTCTCCCAGTCCCCCAGTAACAAGGTCACAGA

GAAGGGAAAGGATGTAGAGCTCAGGTGTGATCCAATTTCAGGTCATACT

GCCCTTTACTGGTACCGACAGAGGCTGGGGCAGGGCCTGGAGTTTTTAA

TTTACTTCCAAGGCAACAGTGCACCAGACAAATCAGGGCTGCCCAGTGA

TCGCTTCTCTGCAGAGAGGACTGGGGAATCCGTCTCCACTCTGACGATC

CAGCGCACACAGCAGGAGGACTCGGCCGTGTATCTCTGTGCCAGCAAGG

TCTATGGCTACACCTTCGGTTCGGGGACCAGGTTAACCGTTGTAGAGGA

CCTGAACAAGGTGTTCCCACCCGAGGTCGCTGTGTTTGAGCCATCAGAA

GCAGAGATCTCCCACACCCAAAAGGCCACACTGGTGTGCCTGGCCACAG

GCTTCTTCCCCGACCACGTGGAGCTGAGCTGGTGGGTGAATGGGAAGGA

GGTGCACAGTGGGGTCAGCACGGACCCGCAGCCCCTCAAGGAGCAGCCC

GCCCTCAATGACTCCAGATACTGCCTGAGCAGCCGCCTGAGGGTCTCGG

-continued

```
CCACCTTCTGGCAGAACCCCCGCAACCACTTCCGCTGTCAAGTCCAGTT
CTACGGGCTCTCGGAGAATGATGAGTGGACACAAGATAGGGCCAAACCC
GTCACCCAGATCGTCAGCGCCGAGGCCTGGGGTAGAGCAGACTGTGGCT
TTACCTCGGTGTCCTACCAGCAAGGGGTCCTGTCTGCCACCATCCTCTA
TGAGATCCTGCTAGGGAAGGCCACCCTGTATGCTGTGCTGGTCAGCGCC
CTTGTGTTGATGGCCATGGTCAAGAGAAAGGATTTCTGA.
```

In one embodiment, the nucleic acid molecule encodes a fusion protein comprising a TCR alpha chain and a TCR beta chain. In one embodiment, the isolated nucleic acid molecule encodes a fusion protein comprising a linker domain between the TCR alpha chain and TCR beta chain. In one embodiment, the nucleic acid molecule encodes a GSG-T2A linker domain comprising the amino acid sequence of SEQ ID NO:91. In one embodiment, the nucleic acid sequence encoding a GSG-T2A linker domain comprises:

```
                                         (SEQ ID NO: 167)
GGCAGCGGAGAGGGCAGAGGAAGTCTTCTAACATGCGGTGACGTGGAGG
AGAATCCCGGCCCT.
```

In one embodiment, the nucleic acid molecule encodes a fusion protein comprising the amino acid sequence of SEQ ID NO:92. In one embodiment, the nucleic acid sequence encoding the fusion protein comprises

```
                                         (SEQ ID NO: 168)
ATGAGGCAAGTGGCGAGAGTGATCGTGTTCCTGACCCTGAGTACTTTGA
GCCTTGCTAAGACCACCCAGCCCATCTCCATGGACTCATATGAAGGACA
AGAAGTGAACATAACCTGTAGCCACAACAACATTGCTACAAATGATTAT
ATCACGTGGTACCAACAGTTTCCCAGCCAAGGACCACGATTTATTATTC
AAGGATACAAGACAAAAGTTACAAACGAAGTGGCCTCCCTGTTTATCCC
TGCCGACAGAAAGTCCAGCACTCTGAGCCTGCCCCGGGTTTCCCTGAGC
GACACTGCTGTGTACTACTGCCTCGTGGGTGACTTCAACTCAAATTCCG
GGTATGCACTCAACTTCGGCAAAGGCACCTCGCTGTTGGTCACACCCCA
TATCCAGAACCCTGACCCTGCCGTGTACCAGCTGAGAGACTCTAAATCC
AGTGACAAGTCTGTCTGCCTATTCACCGATTTTGATTCTCAAACAAATG
TGTCACAAAGTAAGGATTCTGATGTGTATATCACAGACAAAACTGTGTT
GGACATGCGCAGCATGGACTTCAAGAGCAACAGTGCTGTGGCCTGGAGC
AACAAATCTGACTTTGCATGTGCAAACGCCTTCAACAACAGCATTATTC
CAGAAGACACCTTCTTCCCCAGCCCAGAAAGTTCCTGTGATGTCAAGCT
GGTCGAGAAAAGCTTTGAAACAGATACGAACCTAAACTTTCAAAACCTG
TCAGTGATTGGGTTCCGAATCCTCCTCCTGAAAGTGGCCGGGTTTAATC
TGCTCATGACGCTGCGGCTGTGGTCCAGCGGCAGCGGAGAGGGCAGAGG
AAGTCTTCTAACATGCGGTGACGTGGAGGAGAATCCCGGCCCTATGGGC
ACCAGGCTCCTCTTCTGGGTGGCCTTCTGTCTCCTGGGGGCATATCACA
CAGGAGCTGGAGTCTCCCAGTCCCCCAGTAACAAGGTCACAGAGAAGGG
AAAGGATGTAGAGCTCAGGTGTGATCCAATTTCAGGTCATACTGCCCTT
```

-continued

```
TACTGGTACCGACAGAGGCTGGGGCAGGGCCTGGAGTTTTTAATTTACT
TCCAAGGCAACAGTGCACCAGACAAATCAGGGCTGCCCAGTGATCGCTT
CTCTGCAGAGAGGACTGGGGAATCCGTCTCCACTCTGACGATCCAGCGC
ACACAGCAGGAGGACTCGGCCGTGTATCTCTGTGCCAGCAAGGTCTATG
GCTACACCTTCGGTTCGGGGACCAGGTTAACCGTTGTAGAGGACCTGAA
CAAGGTGTTCCCACCCGAGGTCGCTGTGTTTGAGCCATCAGAAGCAGAG
ATCTCCCACACCCAAAAGGCCACACTGGTGTGCCTGGCCACAGGCTTCT
TCCCCGACCACGTGGAGCTGAGCTGGTGGGTGAATGGGAAGGAGGTGCA
CAGTGGGGTCAGCACGGACCCGCAGCCCCTCAAGGAGCAGCCCGCCCTC
AATGACTCCAGATACTGCCTGAGCAGCCGCCTGAGGGTCTCGGCCACCT
TCTGGCAGAACCCCCGCAACCACTTCCGCTGTCAAGTCCAGTTCTACGG
GCTCTCGGAGAATGATGAGTGGACACAAGATAGGGCCAAACCCGTCACC
CAGATCGTCAGCGCCGAGGCCTGGGGTAGAGCAGACTGTGGCTTTACCT
CGGTGTCCTACCAGCAAGGGGTCCTGTCTGCCACCATCCTCTATGAGAT
CCTGCTAGGGAAGGCCACCCTGTATGCTGTGCTGGTCAGCGCCCTTGTG
TTGATGGCCATGGTCAAGAGAAAGGATTTCTGA.
```

In certain embodiments, the nucleic acid sequence encoding an alpha chain constant region or beta chain constant region of a TCR comprises a nucleic acid sequence that is resistant to gene editing, such as CRISPR-mediated gene editing.

Further, the invention encompasses an isolated nucleic acid encoding an amino acid sequence having substantial identity to an amino acid sequence disclosed herein. In certain embodiments, the isolated nucleic acid sequence encodes an amino acid sequence that has at least 75%, 80%, 85%, 90%, 95%, 96%, 97%, 98%, or 99% sequence identity with an amino acid sequence disclosed herein.

Further, the invention encompasses an isolated nucleic acid having substantial identity to a nucleic acid sequence disclosed herein. In certain embodiments, the isolated nucleic acid sequence has at least 75%, 80%, 85%, 90%, 95%, 96%, 97%, 98%, or 99% sequence identity with a nucleic acid sequence disclosed herein.

The isolated nucleic acid sequence encoding a polypeptide of the invention can be obtained using any of the many recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The isolated nucleic acid may comprise any type of nucleic acid, including, but not limited to DNA and RNA. For example, in one embodiment, the composition comprises an isolated DNA molecule, including for example, an isolated cDNA molecule, encoding a polypeptide of the invention, or functional fragment thereof. In one embodiment, the composition comprises an isolated RNA molecule encoding the polypeptide of the invention, or a functional fragment thereof.

The nucleic acid molecules of the present invention can be modified to improve stability in serum or in growth medium for cell cultures. Modifications can be added to enhance stability, functionality, and/or specificity and to minimize immunostimulatory properties of the nucleic acid molecule of the invention. For example, in order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect function of the molecule.

In one embodiment of the present invention the nucleic acid molecule may contain at least one modified nucleotide analogue. For example, the ends may be stabilized by incorporating modified nucleotide analogues.

Non-limiting examples of nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is C1-C6 alkyl, alkenyl or alkynyl and halo is F, Cl, Br or I.

Other examples of modifications are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In some instances, the nucleic acid molecule comprises at least one of the following chemical modifications: 2'-H, 2'-O-methyl, or 2'-OH modification of one or more nucleotides. In certain embodiments, a nucleic acid molecule of the invention can have enhanced resistance to nucleases. For increased nuclease resistance, a nucleic acid molecule, can include, for example, 2'-modified ribose units and/or phosphorothioate linkages. For example, the 2' hydroxyl group (OH) can be modified or replaced with a number of different "oxy" or "deoxy" substituents. For increased nuclease resistance the nucleic acid molecules of the invention can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications such as 2-amino-A, 2-thio (e.g., 2-thio-U), G-clamp modifications, can also increase binding affinity to a target.

In one embodiment, the nucleic acid molecule includes a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). In one embodiment, the nucleic acid molecule includes at least one 2'-O-methyl-modified nucleotide, and in some embodiments, all of the nucleotides of the nucleic acid molecule include a 2'-O-methyl modification.

The present invention also includes a vector in which the isolated nucleic acid of the present invention is inserted. The art is replete with suitable vectors that are useful in the present invention.

In brief summary, the expression of natural or synthetic nucleic acids encoding a peptide of the invention is typically achieved by operably linking a nucleic acid encoding the peptide or portions thereof to a promoter, and incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The vectors of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to one or more types of cells by choosing the appropriate combination of AAV serotype, promoter, and delivery method In certain embodiments, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of a peptide, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the isolated nucleic acid encoding a polypeptide of the invention comprises in vitro transcribed (IVT) RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, it is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Modified Cells

In certain embodiments, the composition of the invention comprises a cell modified to comprise or express a peptide of the invention. In certain embodiments, the cell is genetically modified by contacting the cell with an isolated nucleic acid encoding a polypeptide described herein, such as a mRAS peptide, TCR or a fusion protein comprising a TCR alpha chain and TCR beta chain.

In some embodiments, the nucleic acid sequence is delivered into cells using a retroviral or lentiviral vector. For example, retroviral and lentiviral vectors expressing a peptide of the invention can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the nucleic acid sequence is delivered into cells using in vitro transcribed mRNA. In vitro transcribed mRNA can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In certain embodiments, the cell may be of any suitable cell type that can express the desired peptide. In certain embodiments, the modified cell is used in a method where the cell is introduced into a recipient. In certain embodiments, the cell is autologous, allogeneic, syngeneic or xenogeneic with respect to recipient. In certain embodiments the cell is derived from a stem cell or precursor cell. In some embodiments, the stem cell or precursor cell from which the modified cell is derived is autologous, allogeneic, syngeneic or xenogeneic with respect to recipient.

In one embodiment, the cell is an immune cell. For example, in certain embodiments, the composition comprises an immune cell that comprises or expresses one or more mRAS peptides or TCRs described herein. Exemplary immune cells that may comprise or express one or more TCRs described herein include, but are not limited to, T cells (including killer T cells, helper T cells, regulatory T cells, and gamma delta T cells), natural killer (NK) cells, and NK T cells. Exemplary immune cells that may comprise or express one or more mRAS peptides described herein include, but are not limited to, an antigen presenting cell, dendritic cell, B cell, macrophage, Langerhans cell, T cell, NK cell, NK T cell. Exemplary immune cells include, but are not limited to, T cells (including killer T cells, helper T cells, regulatory T cells, and gamma delta T cells), B cells, antigen presenting cells (APCs), natural killer (NK) cells, and NK T cells.

In one embodiment, the cell is an antigen presenting cell (APC). For example, in certain embodiments, the composition comprises an APC that is modified to comprise or express a mRAS peptide described herein. Exemplary APCs include, but is not limited to, dendritic cells (DCs), macrophages, Langerhans cells, B cells, and the like.

The disclosed compositions and methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a peptide of the invention, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 2004/0101519 and 2006/0034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Methods

The present invention provides methods of treating a subject having, or suspected of having, a mRAS-associated cancer. The method may be used to treat any cancer, including a hematological malignancy, a solid tumor, a primary or a metastasizing tumor, that is associated with a mutation in RAS, such as a mutation at position G12.

Exemplary tumors and types of cancer treatable by way of the present invention includes, but is not limited to, pancreatic cancer, pancreatic ductal adenocarcinoma (PDA), colon cancer, colorectal adenocarcinoma, myeloma, multiple myeloma, lung adenocarcinoma, melanoma, uterine cancer, thyroid cancer, acute myelogenous leukemia (AML), urothelial cancer, gastric adenocarcinoma and cervical adenocarcinoma, head and neck squamous cell carcinoma (SCC), Diffuse large B-cell lymphoma (DLBCL), esophageal adenocarcinoma, Chronic lymphocytic leukemia (CLL), lung SCC, small cell lung cancer (SCLC), renal papillary cancer, Hepatocellular carcinoma (HCC), breast cancer, cervical SCC, ovarian adenocarcinoma, adrenal cancer, prostate cancer, neuroblastoma, glioblastoma multiforme (GBM), medulloblastoma, Renal cell carcinoma (RCC), esophageal SCC, osteosarcoma, sarcoma, and small intestine neuroendocrine tumor (NET).

In certain embodiments, the present invention provides a method of inducing an immune response against mRAS in a subject. For example, administration of a composition described herein can be used to induce a specific immune response, including a T-cell-mediated immune response, against mRAS and cancer cells expressing mRAS. In certain instances, induction of an immune response directed against mRAS results in inhibition of tumor growth and tumor cell death.

In one embodiment, the method comprises contacting the subject with a composition of the invention. For example, in certain embodiments, the method comprises contacting the subject with a composition comprising an antigenic mRAS peptide described herein, a nucleic acid molecule encoding an mRAS peptide described herein, or a cell modified to comprise or express an mRAS peptide described herein. In certain embodiments, the method comprises contacting the subject with a composition polypeptide comprising a TCR described herein, a nucleic acid molecule encoding a polypeptide comprising a TCR described herein, a cell modified to express a TCR described herein.

In certain embodiments, the subject is identified as having an HLA type associated with the mRAS peptide to which the TCR binds. For example, as described herein, in certain instances the TCR binds to a specific mRAS peptide in the context of a specific HLA molecule. Thus, in certain embodiments, the method comprises identifying a subject as having the specific HLA molecule and then administering to the subject a composition comprising or encoding a TCR described herein. For example, in one embodiment, the method comprises identifying a subject as having HLA-A*11:01 molecule and administering to the subject a composition comprising a TCR, a nucleic acid encoding a TCR, or a cell expressing a TCR, where the TCR specifically binds to a mRAS peptide comprising VVGACGVGK (SEQ ID NO:5), VVVGACGVGK (SEQ ID NO:6), VVGADGVGK (SEQ ID NO:7), VVVGADGVGK (SEQ ID NO:8), VVGARGVGK (SEQ ID NO:9), VVVGARGVGK (SEQ ID NO:10), VVGAVGVGK (SEQ ID NO:11), or VVVGAVGVGK (SEQ ID NO:12). In one embodiment, the method comprises identifying a subject as having the specific HLA molecule and then administering to the subject a composition comprising or encoding a specific mRAS peptide described herein. For example, in one embodiment, the method comprises identifying a subject as having HLA-A*11:01 molecule and administering to the subject a composition comprising a mRAS peptide, a nucleic acid encoding a mRAS peptide, or a cell expressing a mRAS peptide, where the mRAS peptide comprises

```
                                (SEQ ID NO: 5)
VVGACGVGK,

                                (SEQ ID NO: 6)
VVVGACGVGK,

                                (SEQ ID NO: 7)
VVGADGVGK,

                                (SEQ ID NO: 8)
VVVGADGVGK,

                                (SEQ ID NO: 9)
VVGARGVGK,

                               (SEQ ID NO: 10)
VVVGARGVGK,

                                (SEQ ID NO:11)
VVGAVGVGK,
or

                               (SEQ ID NO: 12)
VVVGAVGVGK.
```

In one embodiment, the method comprises identifying a subject as having HLA-A*03:01 molecule and administering to the subject a composition comprising a TCR, a nucleic acid encoding a TCR, or a cell expressing a TCR, where the TCR specifically binds to a mRAS peptide comprising VVGACGVGK (SEQ ID NO:5), VVVGACGVGK (SEQ ID NO:6), VVGADGVGK (SEQ ID NO:7), VVVGADGVGK (SEQ ID NO:8), VVGARGVGK (SEQ ID NO:9), VVVGARGVGK (SEQ ID NO:10), VVGAVGVGK (SEQ ID NO:11), or VVVGAVGVGK (SEQ ID NO:12). In one embodiment, the method comprises identifying a subject as having HLA-A*03:01 molecule and administering to the subject a composition comprising a mRAS peptide, a nucleic acid encoding a mRAS peptide, or a cell expressing a mRAS peptide, where the mRAS peptide comprises VVGACGVGK (SEQ ID NO:5), VVVGACGVGK (SEQ ID NO:6), VVGADGVGK (SEQ ID NO:7), VVVGADGVGK (SEQ ID NO:8), VVGARGVGK (SEQ ID NO:9), VVVGARGVGK (SEQ ID NO:10), VVGAVGVGK (SEQ ID NO:11), or VVVGAVGVGK (SEQ ID NO:12).

In one embodiment, the method comprises identifying a subject as having HLA-A*02:01 molecule and administering to the subject a composition comprising a TCR, a nucleic acid encoding a TCR, or a cell expressing a TCR, where the TCR specifically binds to a mRAS peptide comprising KLVVVGACGV (SEQ ID NO:1), KLVVVGADGV (SEQ ID NO:2), KLVVVGARGV (SEQ ID NO:3), or KLVVVGAVGV (SEQ ID NO:4). In one embodiment, the method comprises identifying a subject as having HLA-A*02:01 molecule and administering to the subject a composition comprising a mRAS peptide, a nucleic acid encoding a mRAS peptide, or a cell expressing a mRAS peptide, where the mRAS peptide comprises KLVVVGACGV (SEQ ID NO:1), KLVVVGADGV (SEQ ID NO:2), KLVVVGARGV (SEQ ID NO:3), or KLVVVGAVGV (SEQ ID NO:4).

In one embodiment, the method comprises identifying a subject as having HLA-B*07:02 molecule and administering to the subject a composition comprising a TCR, a nucleic acid encoding a TCR, or a cell expressing a TCR, where the TCR specifically binds to a mRAS peptide comprising GACGVGKSAL (SEQ ID NO:13), GADGVGKSAL (SEQ ID NO:14), GARGVGKSAL (SEQ ID NO:15), or GAVGVGKSAL (SEQ ID NO:16). In one embodiment, the method comprises identifying a subject as having HLA-B*07:02 molecule and administering to the subject a composition comprising a mRAS peptide, a nucleic acid encoding a mRAS peptide, or a cell expressing a mRAS peptide, where the mRAS peptide comprises GACGVGKSAL (SEQ ID NO:13), GADGVGKSAL (SEQ ID NO:14), GARGVGKSAL (SEQ ID NO:15), or GAVGVGKSAL (SEQ ID NO:16).

In one embodiment, the method comprises identifying the subject as having a specific RAS mutation. For example, in one embodiment, the subject is identified as having a specific mutation at G12 relative to wildtype RAS. For example, in one embodiment, the method comprises identifying a subject as having a G12C, G12D, G12R, or G12V mutation relative to wildtype RAS.

In one embodiment, the method comprises identifying the subject as having an HLA-A*02:01 allele and a G12C RAS mutation and administering to the subject a composition comprising a TCR, a nucleic acid encoding a TCR, or a cell expressing a TCR, where the TCR specifically binds to a mRAS peptide comprising KLVVVGACGV (SEQ ID NO:1). In one embodiment, the method comprises identifying a subject as having an HLA-A*02:01 allele and a G12C RAS mutation and administering to the subject a composition comprising a mRAS peptide, a nucleic acid encoding a mRAS peptide, or a cell expressing a mRAS peptide, where the mRAS peptide comprises KLVVVGACGV (SEQ ID NO:1).

In one embodiment, the method comprises identifying the subject as having an HLA-A*02:01 allele and a G12D RAS mutation and administering to the subject a composition comprising a TCR, a nucleic acid encoding a TCR, or a cell expressing a TCR, where the TCR specifically binds to a mRAS peptide comprising KLVVVGADGV (SEQ ID NO:2). In one embodiment, the method comprises identifying a subject as having an HLA-A*02:01 allele and a G12D RAS mutation and administering to the subject a composition comprising a mRAS peptide, a nucleic acid encoding a mRAS peptide, or a cell expressing a mRAS peptide, where the mRAS peptide comprises KLVVVGADGV (SEQ ID NO:2).

In one embodiment, the method comprises identifying the subject as having an HLA-A*02:01 allele and a G12R RAS mutation and administering to the subject a composition comprising a TCR, a nucleic acid encoding a TCR, or a cell expressing a TCR, where the TCR specifically binds to a mRAS peptide comprising KLVVVGARGV (SEQ ID NO:3). In one embodiment, the method comprises identifying a subject as having an HLA-A*02:01 allele and a G12R RAS mutation and administering to the subject a composition comprising a mRAS peptide, a nucleic acid encoding a mRAS peptide, or a cell expressing a mRAS peptide, where the mRAS peptide comprises KLVVVGARGV (SEQ ID NO:3).

In one embodiment, the method comprises identifying the subject as having an HLA-A*02:01 allele and a G12V RAS mutation and administering to the subject a composition comprising a TCR, a nucleic acid encoding a TCR, or a cell expressing a TCR, where the TCR specifically binds to a mRAS peptide comprising KLVVVGAVGV (SEQ ID NO:4). In one embodiment, the method comprises identifying a subject as having an HLA-A*02:01 allele and a G12V RAS mutation and administering to the subject a composition comprising a mRAS peptide, a nucleic acid encoding a mRAS peptide, or a cell expressing a mRAS peptide, where the mRAS peptide comprises KLVVVGAVGV (SEQ ID NO:4).

In one embodiment, the method comprises identifying the subject as having an HLA-A*03:01 allele and a G12C RAS mutation and administering to the subject a composition comprising a TCR, a nucleic acid encoding a TCR, or a cell expressing a TCR, where the TCR specifically binds to a mRAS peptide comprising VVGACGVGK (SEQ ID NO:5) or VVVGACGVGK (SEQ ID NO:6). In one embodiment, the method comprises identifying a subject as having an HLA-A*03:01 allele and a G12C RAS mutation and administering to the subject a composition comprising a mRAS peptide, a nucleic acid encoding a mRAS peptide, or a cell expressing a mRAS peptide, where the mRAS peptide comprises VVGACGVGK (SEQ ID NO:5) or VVVGACGVGK (SEQ ID NO:6).

In one embodiment, the method comprises identifying the subject as having an HLA-A*03:01 allele and a G12D RAS mutation and administering to the subject a composition comprising a TCR, a nucleic acid encoding a TCR, or a cell expressing a TCR, where the TCR specifically binds to a mRAS peptide comprising VVGADGVGK (SEQ ID NO:7) or VVVGADGVGK (SEQ ID NO:8). In one embodiment, the method comprises identifying a subject as having an HLA-A*03:01 allele and a G12D RAS mutation and administering to the subject a composition comprising a mRAS peptide, a nucleic acid encoding a mRAS peptide, or a cell expressing a mRAS peptide, where the mRAS peptide comprises VVGADGVGK (SEQ ID NO:7) or VVVGADGVGK (SEQ ID NO:8).

In one embodiment, the method comprises identifying the subject as having an HLA-A*03:01 allele and a G12R RAS mutation and administering to the subject a composition comprising a TCR, a nucleic acid encoding a TCR, or a cell expressing a TCR, where the TCR specifically binds to a mRAS peptide comprising VVGARGVGK (SEQ ID NO:9) or VVVGARGVGK (SEQ ID NO:10). In one embodiment, the method comprises identifying a subject as having an HLA-A*03:01 allele and a G12R RAS mutation and administering to the subject a composition comprising a mRAS peptide, a nucleic acid encoding a mRAS peptide, or a cell expressing a mRAS peptide, where the mRAS peptide comprises VVGARGVGK (SEQ ID NO:9) or VVVGACGVGK (SEQ ID NO:10).

In one embodiment, the method comprises identifying the subject as having an HLA-A*03:01 allele and a G12V RAS mutation and administering to the subject a composition comprising a TCR, a nucleic acid encoding a TCR, or a cell expressing a TCR, where the TCR specifically binds to a mRAS peptide comprising VVGAVGVGK (SEQ ID NO:11) or VVVGAVGVGK (SEQ ID NO:12). In one embodiment, the method comprises identifying a subject as having an HLA-A*03:01 allele and a G12V RAS mutation and administering to the subject a composition comprising a mRAS peptide, a nucleic acid encoding a mRAS peptide, or a cell expressing a mRAS peptide, where the mRAS peptide comprises VVGAVGVGK (SEQ ID NO:11) or VVVGACGVGK (SEQ ID NO:12).

In one embodiment, the method comprises identifying the subject as having an HLA-A*11:01 allele and a G12C RAS mutation and administering to the subject a composition comprising a TCR, a nucleic acid encoding a TCR, or a cell expressing a TCR, where the TCR specifically binds to a mRAS peptide comprising VVGACGVGK (SEQ ID NO:5) or VVVGACGVGK (SEQ ID NO:6). In one embodiment, the method comprises identifying a subject as having an HLA-A*11:01 allele and a G12C RAS mutation and administering to the subject a composition comprising a mRAS peptide, a nucleic acid encoding a mRAS peptide, or a cell expressing a mRAS peptide, where the mRAS peptide comprises VVGACGVGK (SEQ ID NO:5) or VVVGACGVGK (SEQ ID NO:6).

In one embodiment, the method comprises identifying the subject as having an HLA-A*11:01 allele and a G12D RAS mutation and administering to the subject a composition comprising a TCR, a nucleic acid encoding a TCR, or a cell expressing a TCR, where the TCR specifically binds to a mRAS peptide comprising VVGADGVGK (SEQ ID NO:7) or VVVGADGVGK (SEQ ID NO:8). In one embodiment, the method comprises identifying a subject as having an HLA-A*11:01 allele and a G12D RAS mutation and administering to the subject a composition comprising a mRAS peptide, a nucleic acid encoding a mRAS peptide, or a cell expressing a mRAS peptide, where the mRAS peptide comprises VVGADGVGK (SEQ ID NO:7) or VVVGADGVGK (SEQ ID NO:8).

In one embodiment, the method comprises identifying the subject as having an HLA-A*11:01 allele and a G12R RAS mutation and administering to the subject a composition comprising a TCR, a nucleic acid encoding a TCR, or a cell expressing a TCR, where the TCR specifically binds to a mRAS peptide comprising VVGARGVGK (SEQ ID NO:9) or VVVGARGVGK (SEQ ID NO:10). In one embodiment, the method comprises identifying a subject as having an HLA-A*11:01 allele and a G12R RAS mutation and administering to the subject a composition comprising a mRAS peptide, a nucleic acid encoding a mRAS peptide, or a cell expressing a mRAS peptide, where the mRAS peptide comprises VVGARGVGK (SEQ ID NO:9) or VVVGACGVGK (SEQ ID NO:10).

In one embodiment, the method comprises identifying the subject as having an HLA-A*11:01 allele and a G12V RAS mutation and administering to the subject a composition comprising a TCR, a nucleic acid encoding a TCR, or a cell expressing a TCR, where the TCR specifically binds to a mRAS peptide comprising VVGAVGVGK (SEQ ID NO:11) or VVVGAVGVGK (SEQ ID NO:12). In one embodiment, the method comprises identifying a subject as having an HLA-A*11:01 allele and a G12V RAS mutation and administering to the subject a composition comprising a mRAS peptide, a nucleic acid encoding a mRAS peptide, or a cell expressing a mRAS peptide, where the mRAS peptide comprises VVGAVGVGK (SEQ ID NO:11) or VVVGACGVGK (SEQ ID NO:12).

In one embodiment, the method comprises identifying the subject as having an HLA-B*07:02 allele and a G12C RAS mutation and administering to the subject a composition comprising a TCR, a nucleic acid encoding a TCR, or a cell expressing a TCR, where the TCR specifically binds to a mRAS peptide comprising GACGVGKSAL (SEQ ID NO:13). In one embodiment, the method comprises identifying a subject as having an HLA-B*07:02 allele and a G12C RAS mutation and administering to the subject a composition comprising a mRAS peptide, a nucleic acid encoding a mRAS peptide, or a cell expressing a mRAS peptide, where the mRAS peptide comprises GACGVGKSAL (SEQ ID NO:13).

In one embodiment, the method comprises identifying the subject as having an HLA-B*07:02 allele and a G12D RAS mutation and administering to the subject a composition comprising a TCR, a nucleic acid encoding a TCR, or a cell expressing a TCR, where the TCR specifically binds to a mRAS peptide comprising GADGVGKSAL (SEQ ID NO:14). In one embodiment, the method comprises identifying a subject as having an HLA-B*07:02 allele and a G12D RAS mutation and administering to the subject a composition comprising a mRAS peptide, a nucleic acid encoding a mRAS peptide, or a cell expressing a mRAS peptide, where the mRAS peptide comprises GADGVGKSAL (SEQ ID NO:14).

In one embodiment, the method comprises identifying the subject as having an HLA-B*07:02 allele and a G12R RAS mutation and administering to the subject a composition comprising a TCR, a nucleic acid encoding a TCR, or a cell expressing a TCR, where the TCR specifically binds to a mRAS peptide comprising GARGVGKSAL (SEQ ID NO:15). In one embodiment, the method comprises identifying a subject as having an HLA-B*07:02 allele and a G12R RAS mutation and administering to the subject a composition comprising a mRAS peptide, a nucleic acid encoding a mRAS peptide, or a cell expressing a mRAS peptide, where the mRAS peptide comprises GARGVGKSAL (SEQ ID NO:15).

The subject may be identified as being of a particular HLA type or by having a specific RAS mutation using any method known in the art, including, but not limited to, DNA sequence, RNA sequencing, nextgen sequencing, PCR, immunoassays, or the like.

In one embodiment, the method comprises administering at least one cell genetically modified to express a TCR, wherein the TCR specifically binds to RAS, mRAS, or fragment thereof. For example, in certain embodiments, the method comprises administering a cell genetically modified to express a TCR, wherein the TCR specifically binds to a mRAS peptide with a mutation corresponding to G12. In certain embodiments, the method comprises administering a cell genetically modified to express a TCR, wherein the TCR specifically binds to a mRAS peptide having a G12C, G12D, G12R, or G12V mutation at a position corresponding to RAS G12.

In one embodiment, the present invention includes cellular therapy where cells are modified to comprise or express an mRAS peptide or TCR of the invention, and the cell is infused to a recipient in need thereof.

In one embodiment, the present invention includes cellular therapy where the method comprises administering to a subject a composition comprising a cell, such as an antigen presenting cell, that comprises or expresses an mRAS peptide described herein. For example, in one embodiment, the method comprises administering a composition comprising an antigen presenting cell that is loaded with an mRAS peptide described herein and expresses the mRAS peptide on the surface.

In one embodiment, the present invention includes cellular therapy where the method comprises administering to a subject a composition comprising a cell that is activated or stimulated by an antigen presenting cell that that comprises or expresses an mRAS peptide described herein. For example, in one embodiment, the method comprises contacting a cell, such as a naïve T cell, to an antigen presenting cell that is loaded with an mRAS peptide described herein and expresses the mRAS peptide on the surface; thereby activating the cell. The method comprises administering a composition comprising the activated cell to a subject. For example, in one embodiment, the method of the invention comprises the following steps: (1) providing a population of naïve T cells; (2) providing a population of dendritic cells; (3) loading or pulsing the dendritic cells with one or more mRAS peptides described herein; (4) co-culturing the naïve T cells and loaded dendritic cells; and (4) isolating the stimulated T cells. In one embodiment, the method further comprises step (5) administering the stimulated T cells to a subject in need thereof, such as a subject having, suspected of having, or at risk of having a mRAS-associated cancer.

In certain embodiments, the infused cell (e.g., an antigen presenting cell presenting an mRAS peptide) is able to stimulate an immune response in vivo. For example, in certain embodiments, the infused cell is able to activate or stimulate endogenous immune cells to target and kill tumor cells in the recipient.

In certain embodiments, the infused cell is able to kill tumor cells in the recipient. Unlike antibody therapies, in certain instances, the modified cells are able to replicate in vivo resulting in long-term persistence and surveillance that can lead to sustained tumor control.

In one embodiment, the modified T cells of the invention can undergo robust in vivo T cell expansion and can persist for an extended amount of time. In another embodiment, the modified T cells of the invention evolve into specific memory T cells that can be reactivated to inhibit any additional tumor formation or growth. For example, modified T cells of the invention can undergo robust in vivo T cell expansion and persist at high levels for an extended amount of time in blood and bone marrow and form specific memory T cells.

The compositions of the present invention may be administered either alone, or as a pharmaceutical composition in combination with diluents and/or with other components such as IL-2 or other cytokines or cell populations. Briefly, pharmaceutical compositions of the present invention may comprise a composition as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject).

The administration of the subject compositions (e.g., compositions comprising a TCR, nucleic acid molecule encoding a TCR, or genetically modified cell expressing a TCR) may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the compositions of the present invention are administered to a patient by intradermal or subcutaneous injection. In another embodiment, the compositions of the present invention are administered by i.v. injection. In certain embodiments, the compositions of be injected directly into a tumor or lymph node.

In one embodiment, the invention provides a method to treat cancer comprising treating the subject prior to, concurrently with, or subsequently to the administration of the composition of the invention, with a complementary therapy for the cancer, such as surgery, chemotherapy, chemotherapeutic agent, radiation therapy, or hormonal therapy or a combination thereof.

Chemotherapeutic agents include cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

In a further embodiment, the compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In certain embodiments, the composition of the invention is administered during surgical resection or debulking of a tumor or diseased tissue. For example, in subjects undergoing surgical treatment of diseased tissue or tumor, the composition may be administered to the site in order to further treat the tumor.

Subjects to which administration of the compositions and pharmaceutical compositions of the invention is contemplated include, but are not limited to, humans and other primates, mammals including commercially relevant mammals such as non-human primates, cattle, pigs, horses, sheep, cats, and dogs.

The dosage of the above treatments to be administered to a patient will vary with the precise nature of the condition being treated and the recipient of the treatment. The scaling of dosages for human administration can be performed according to art-accepted practices. Strategies for T cell dosing and scheduling have been discussed (Ertl et al, 2011, Cancer Res, 71:3175-81; Junghans, 2010, Journal of Translational Medicine, 8:55).

Kits

The invention also includes a kit comprising a composting comprising a mRAS peptide, a nucleic acid molecule encoding a mRAS peptide, a cell comprising or expressing an mRAS peptide, polypeptide comprising a TCR, nucleic acid molecule encoding a TCR, a cell expressing a TCR, or combinations thereof, of the invention and an instructional material which describes the use of the composition. For instance, in some embodiments, the instructional material describes administering the composition, or combinations thereof, to an individual as a therapeutic treatment or a non-treatment use as described elsewhere herein. In an embodiment, this kit further comprises a (optionally sterile) pharmaceutically acceptable carrier suitable for dissolving or suspending the therapeutic composition of the invention, for instance, prior to administering the composition to an individual. Optionally, the kit comprises an applicator for administering the composition. In certain embodiments, the kit comprises a reagent used to identify the HLA type of a subject. In certain embodiments, the kit comprises a reagent used to identify a RAS mutation (e.g., a mutation at position G12) in subject.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore and are not to be construed as limiting in any way the remainder of the disclosure.

Example 1: Identification of mRAS Neoantigens

As described herein, various computational and proteomic studies were done to identify mRAS neoantigens and their interactions with HLA types. FIG. 1 is a schematic that depicts the discovery strategy for mutant RAS epitopes, wherein an in silico model is used to predict affinity of mRAS peptides to MHC, followed by experiments to measure the affinity/stability of interactions and to detect peptides by mass spectrometry.

Figure 2:
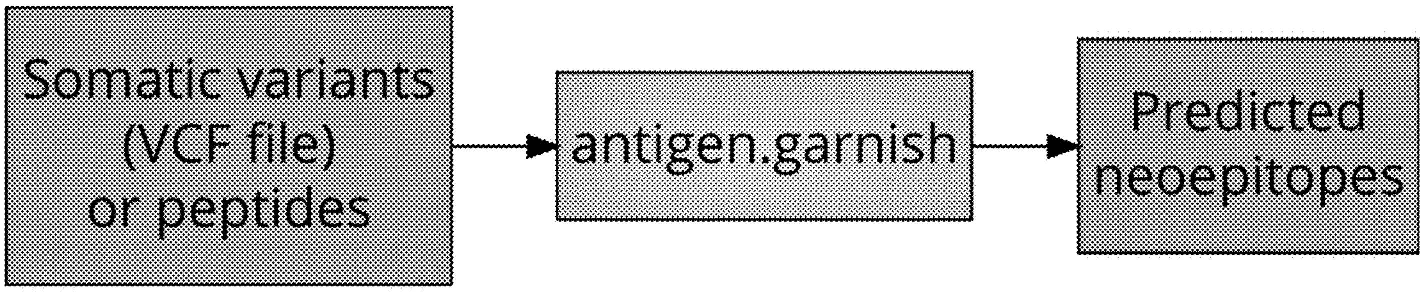
FIG. 2 depicts a schematic of an exemplary computational method used to predict neoepitopes of mRAS.

An in silico study was done to predict mRAS neoantigens, utilizing antigen.garnish software which analyzes human or murine DNA missense mutations, insertions, deletions, and fusions and computationally predicts neoepitopes uses 7 validated algorithms. The model outputs neoepitopes by MHC I/II binding affinity. For example, as shown in FIG. 2, the model was used to predict 9-10mer neoepitopes that contain a mutation at a position corresponding to G12 in RAS.

Figure 3:
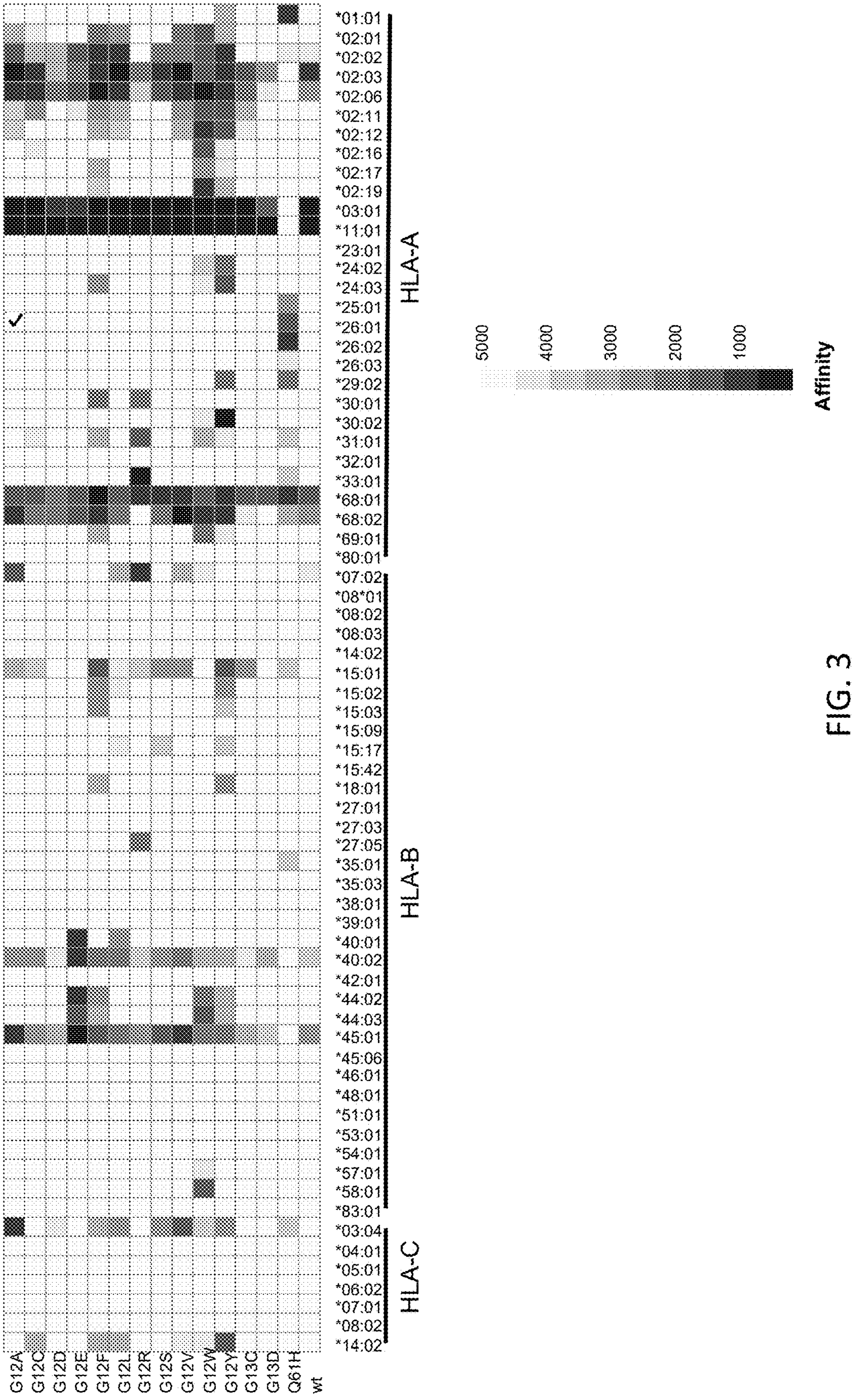
FIG. 3 depicts the results of exemplary experiments demonstrating the predicted affinity of mRAS peptides to various HLA molecules.
Figure 4A:
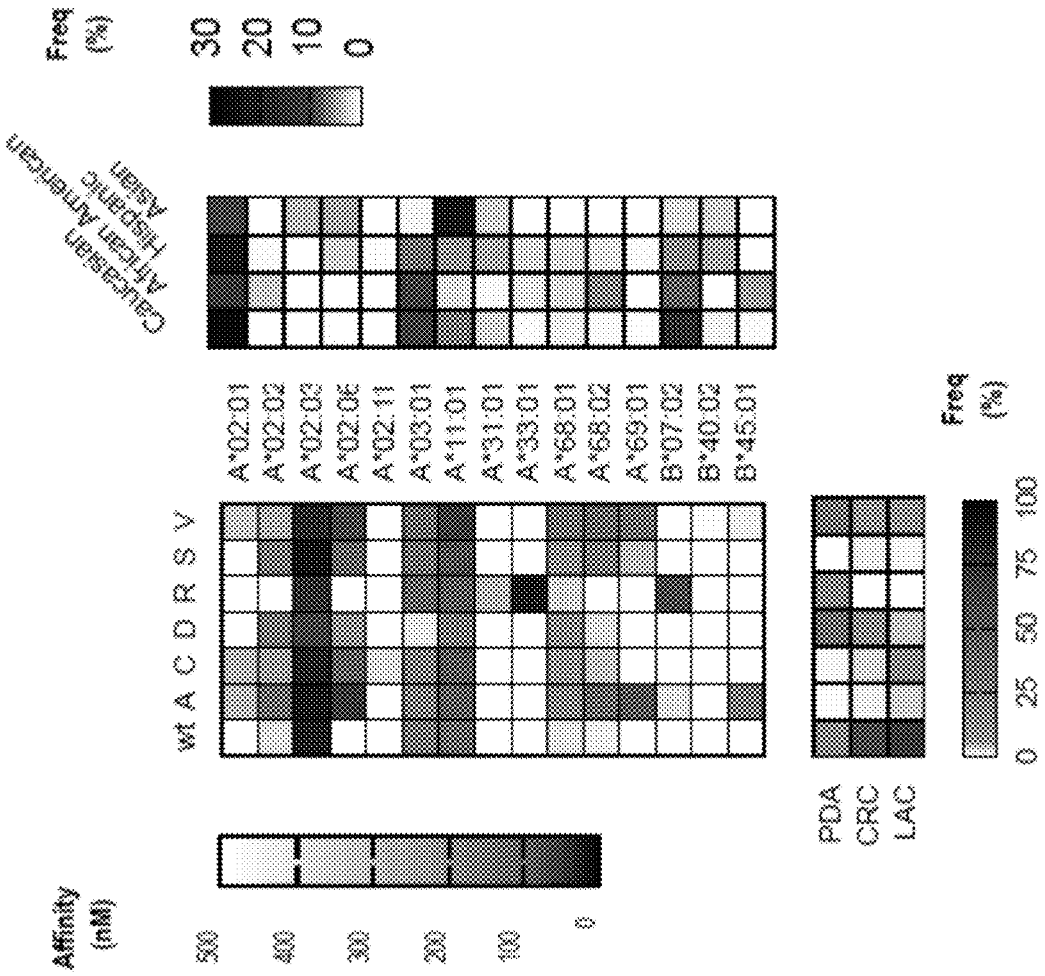

As shown in FIG. 3 and FIG. 4A and FIG. 4B, the model predicted binding of mRAS neoantigens to different HLA class I alleles. The table in FIG. 4B summarizes the mRAS short peptides predicted to bind to specific HLA types.

Figure 6A:
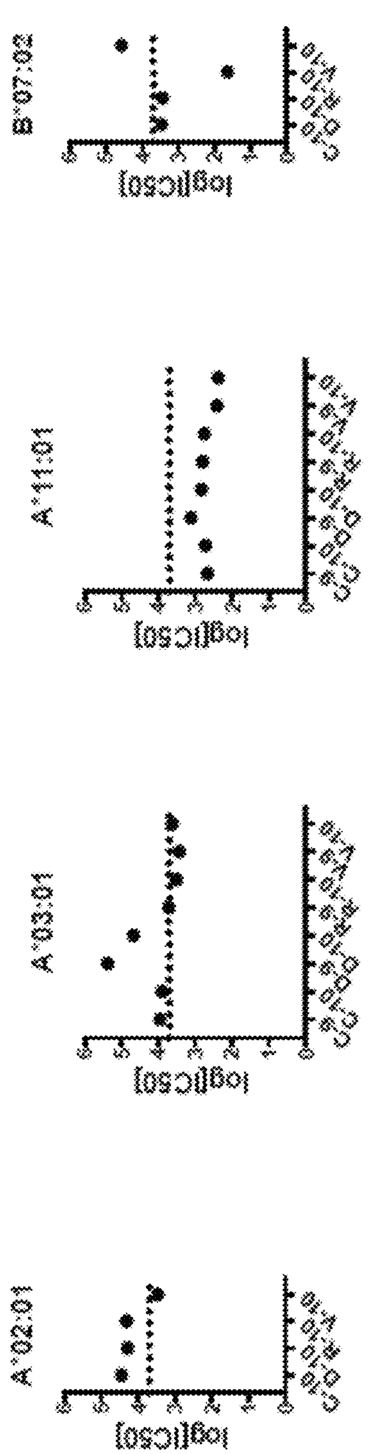
FIG. 6A and FIG. 6B depict the results of exemplary experiments providing a biochemical assessment of mRAS epitope binding.
Figure 6B:
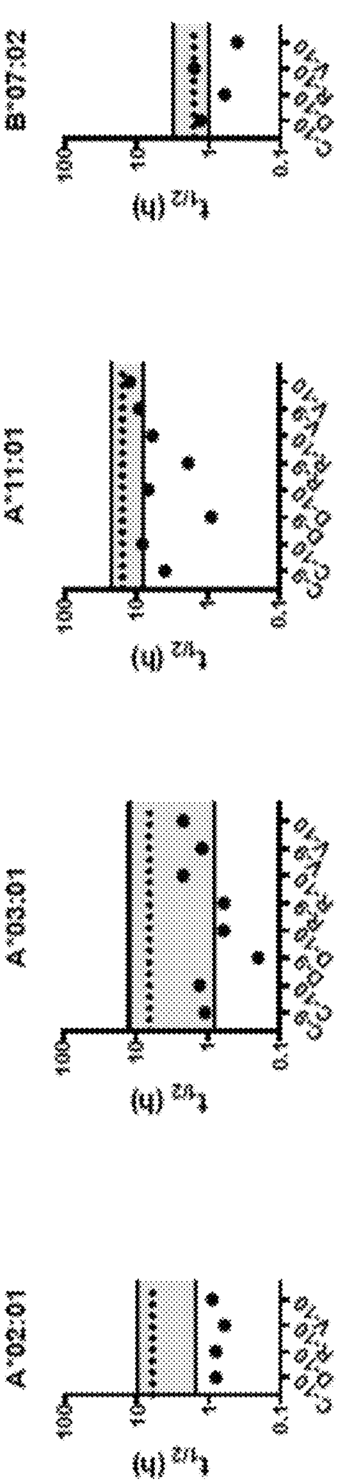

Experiments were also conducted to examine peptide-MHC binding. The fluorescence polarization assay, which uses competitive binding of peptides of interest, is shown in FIG. 5. The assay was used to measure the affinity of the various mRAS peptide sequences to HLA class I alleles of interest, summarized in the table of FIG. 5. Additional data demonstrating peptide binding in a fluorescence polarization assay is shown in FIG. 6A. Experiments were also done to investigate peptide stability by the scintillation proximity assay. The notation for the mutant RAS peptides depicted in FIG. 6A and FIG. 6B are as follows: For the A*02:01 panels, C-10=KLV_C; D-10=KLV_D; R-10=KLV_R; and V-10=KLV_V. For the A*03:01 and A*11:01 panels, C-9=VV_C; C-10=VVV_C; D-9=VV_D; D-10=VVV_D; R-9=VV_R; R-10=VVV_R; V-9=VV_V; V-10=VVV_V. For the B*07:02 panel, C-10=GA_C; D-10=GA_D; R-10=GA_R; V-10=GA V.

Figures 7A, 7B, 7C, 7D:
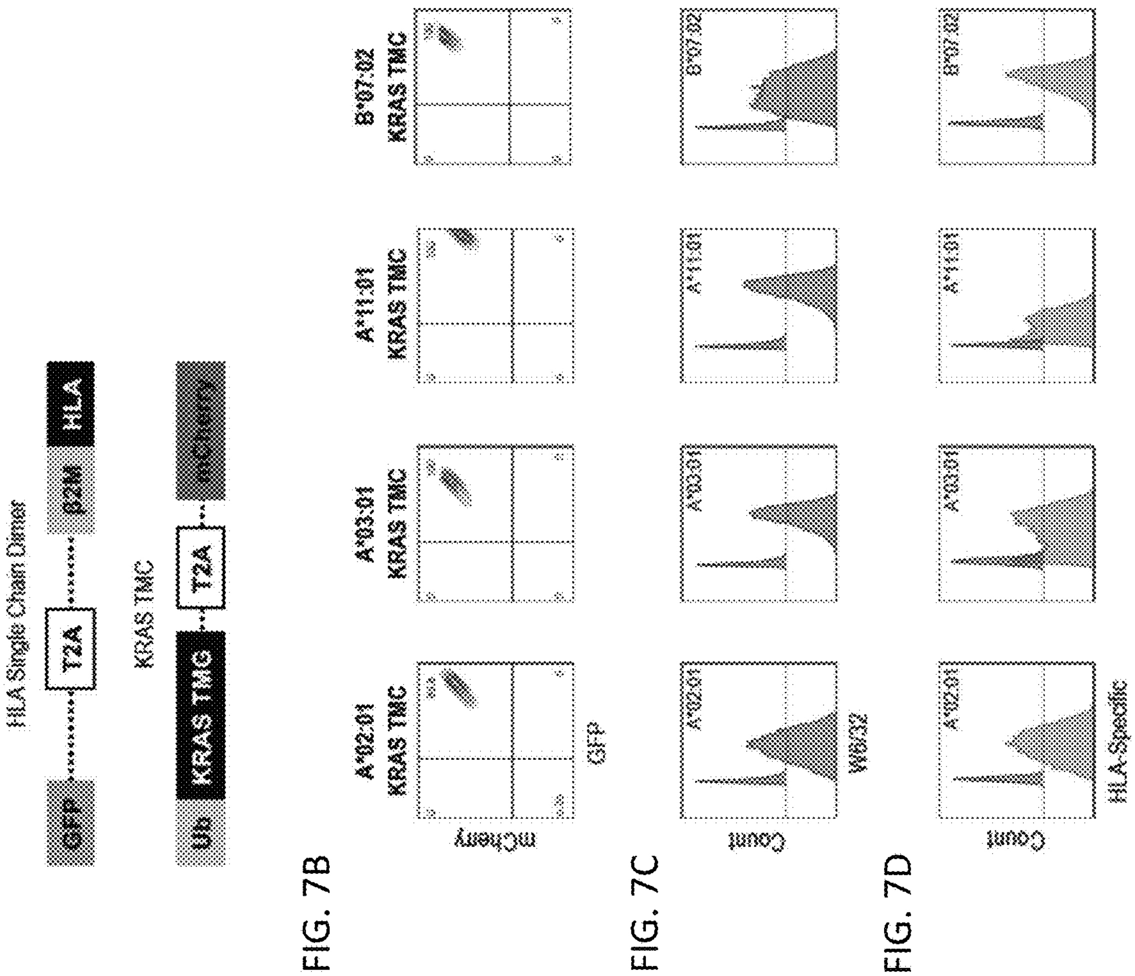
Figure 8A:
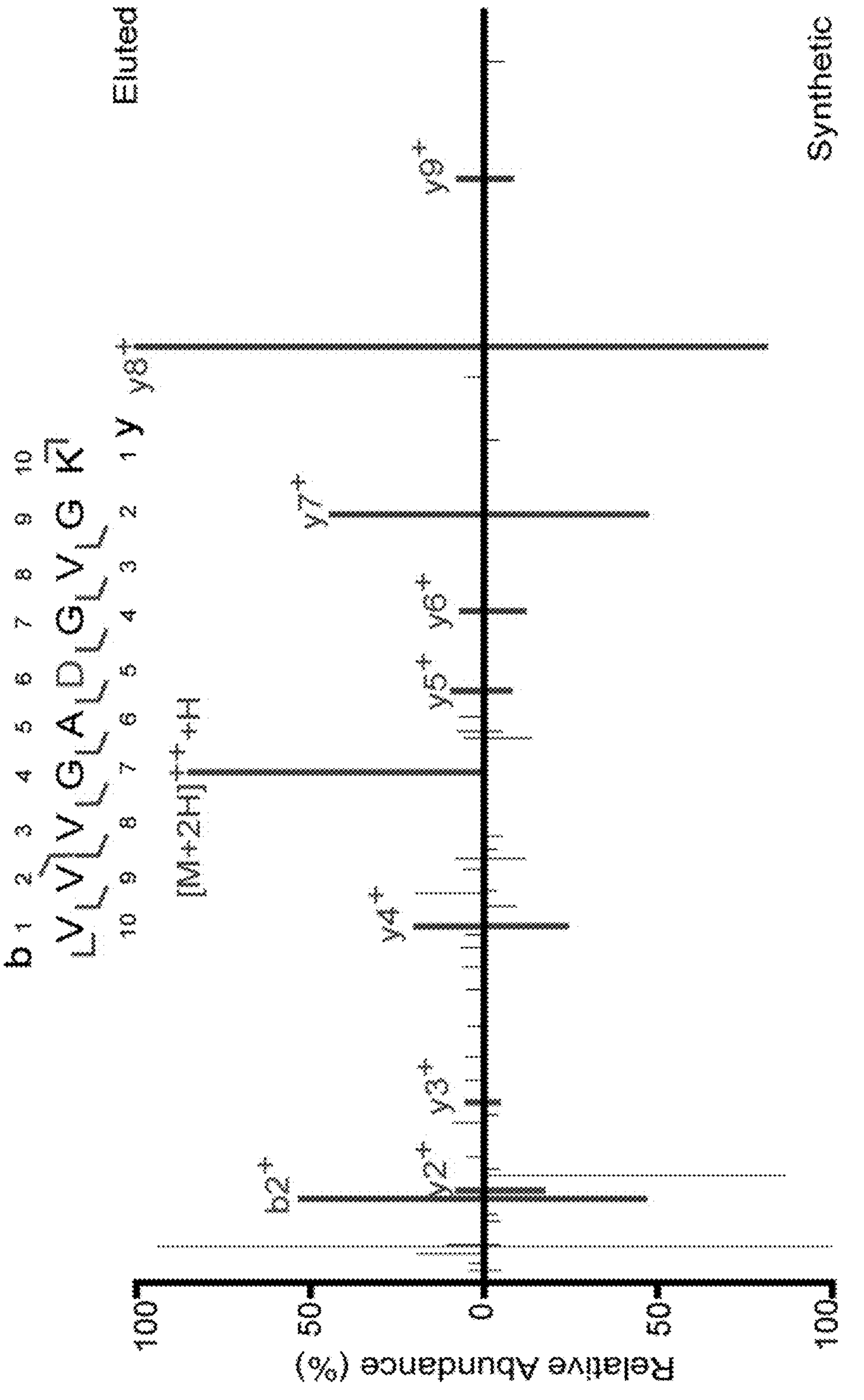
FIG. 8A through FIG. 8J depicts the results of example experiments demonstrating the detection of mRAS epitopes by HLA class I immunoprecipitation peptide elution and tandem Mass Spec (MS/MS).
Figure 8B:
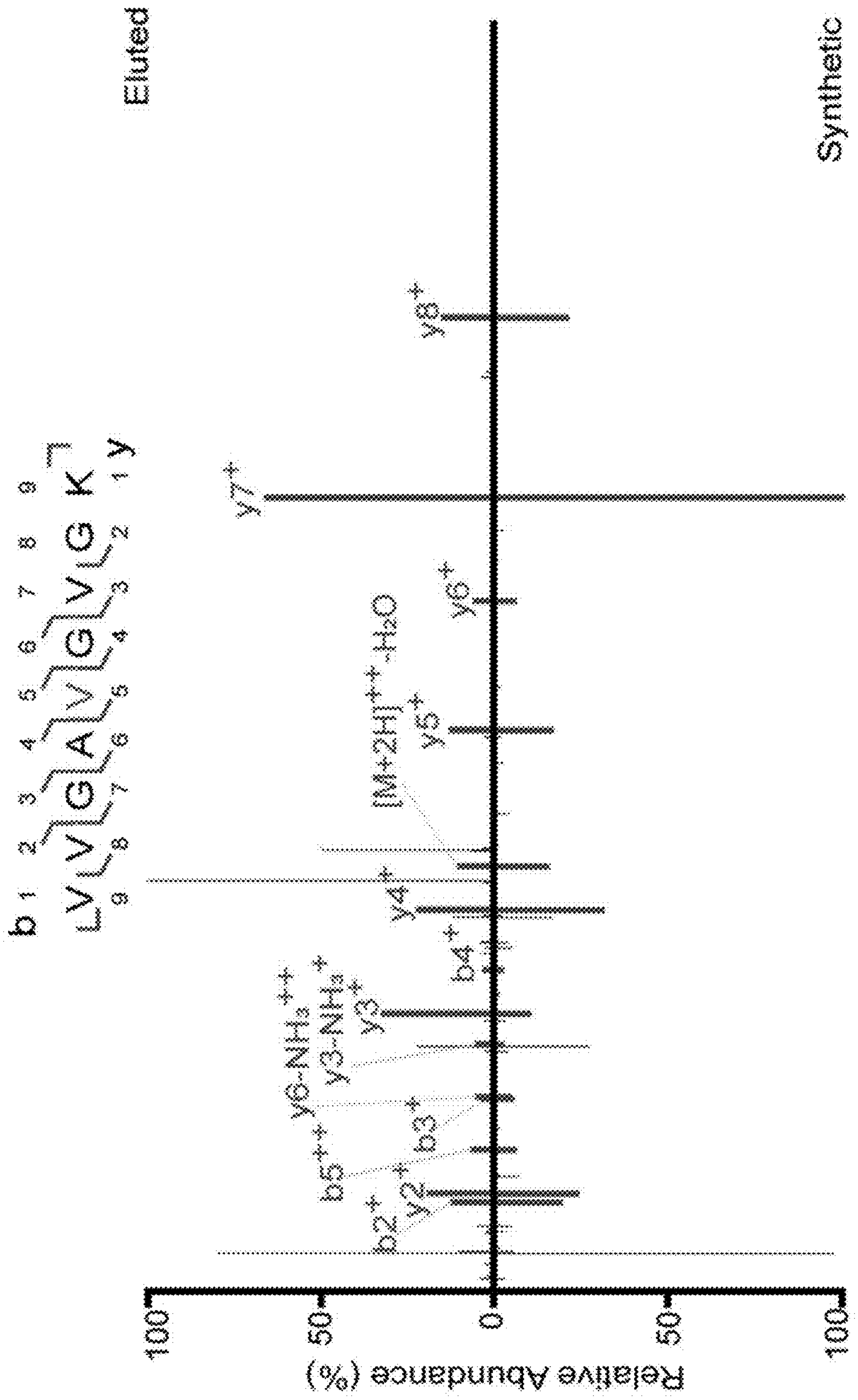
Figure 8C:
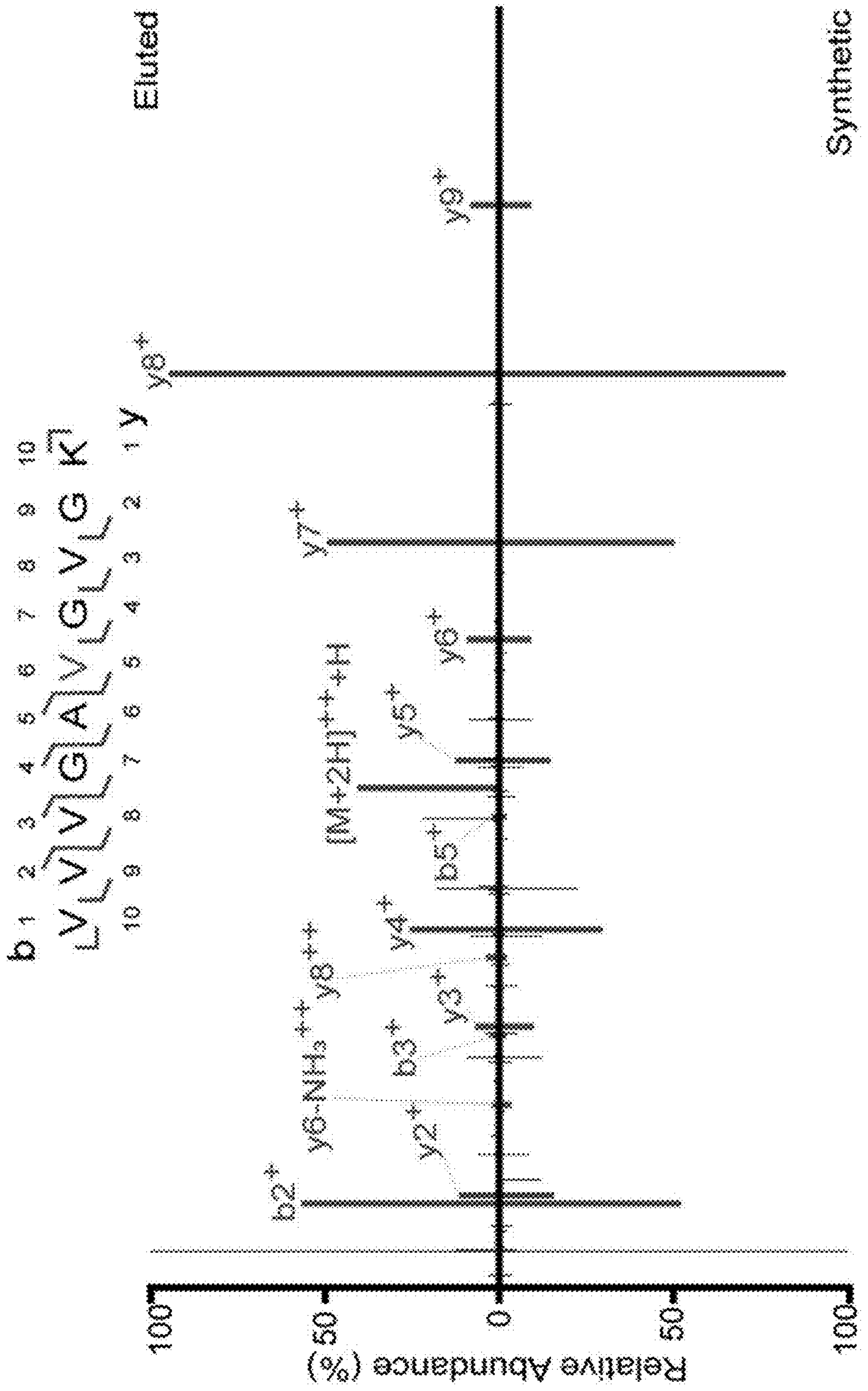
Figure 8D:
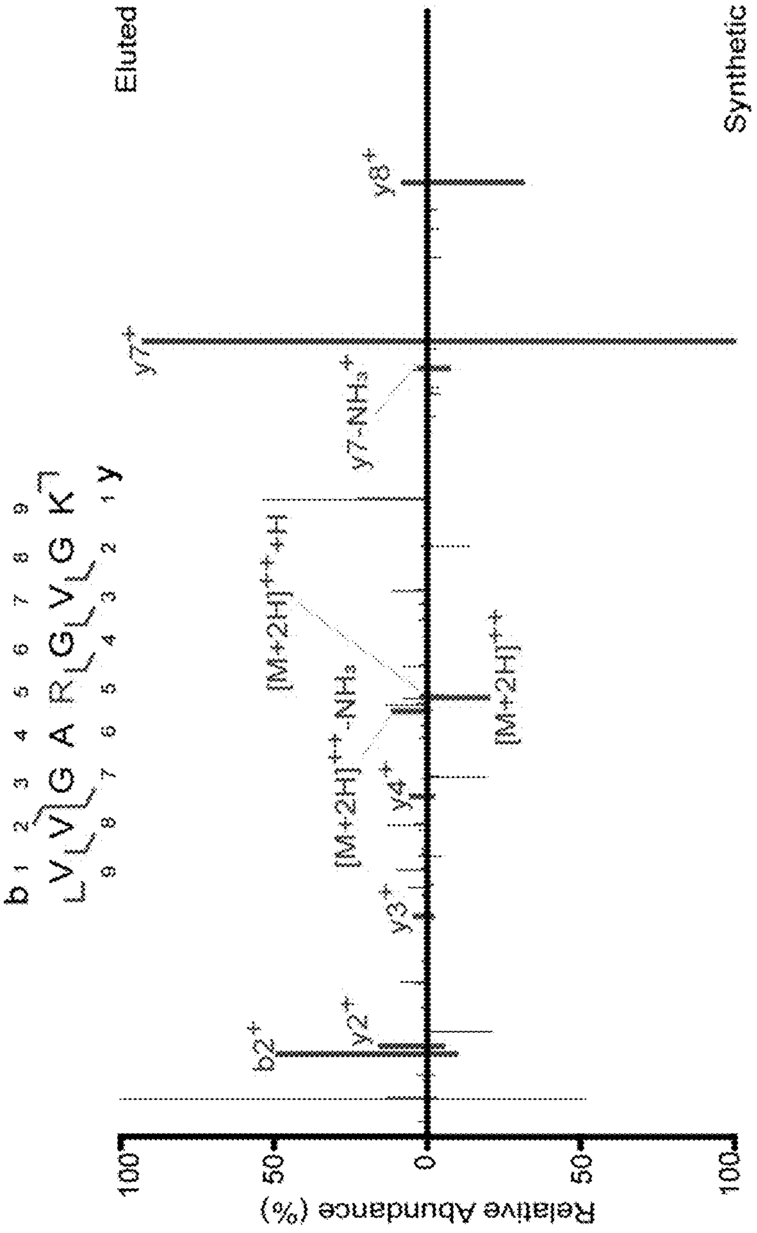
Figure 8E:
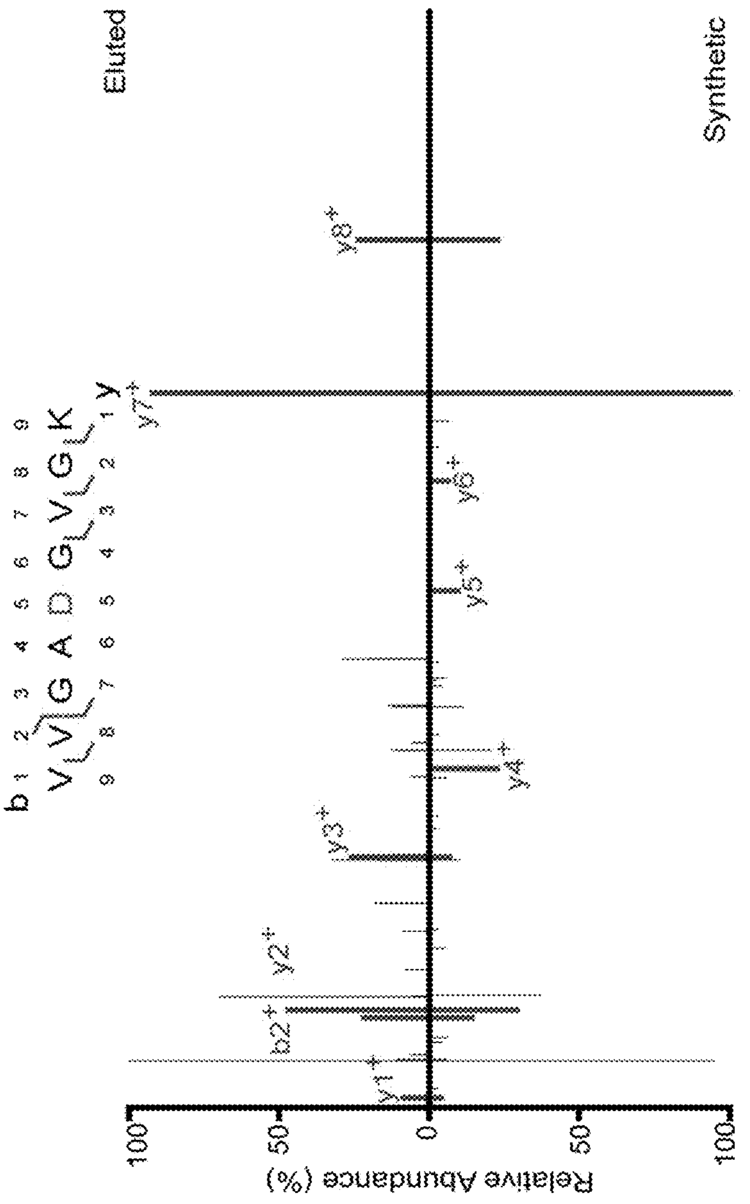
Figure 8F:
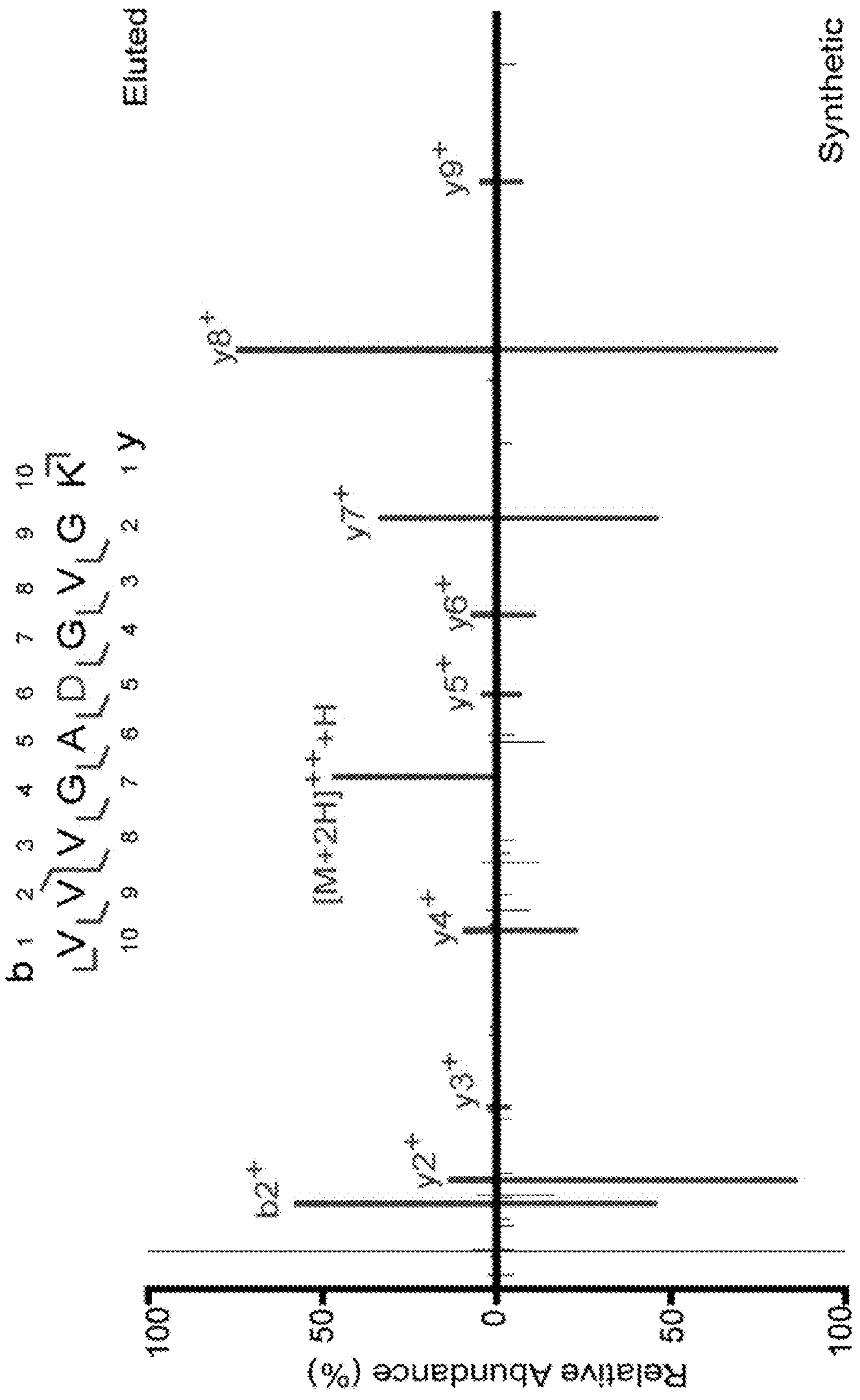
Figure 8G:
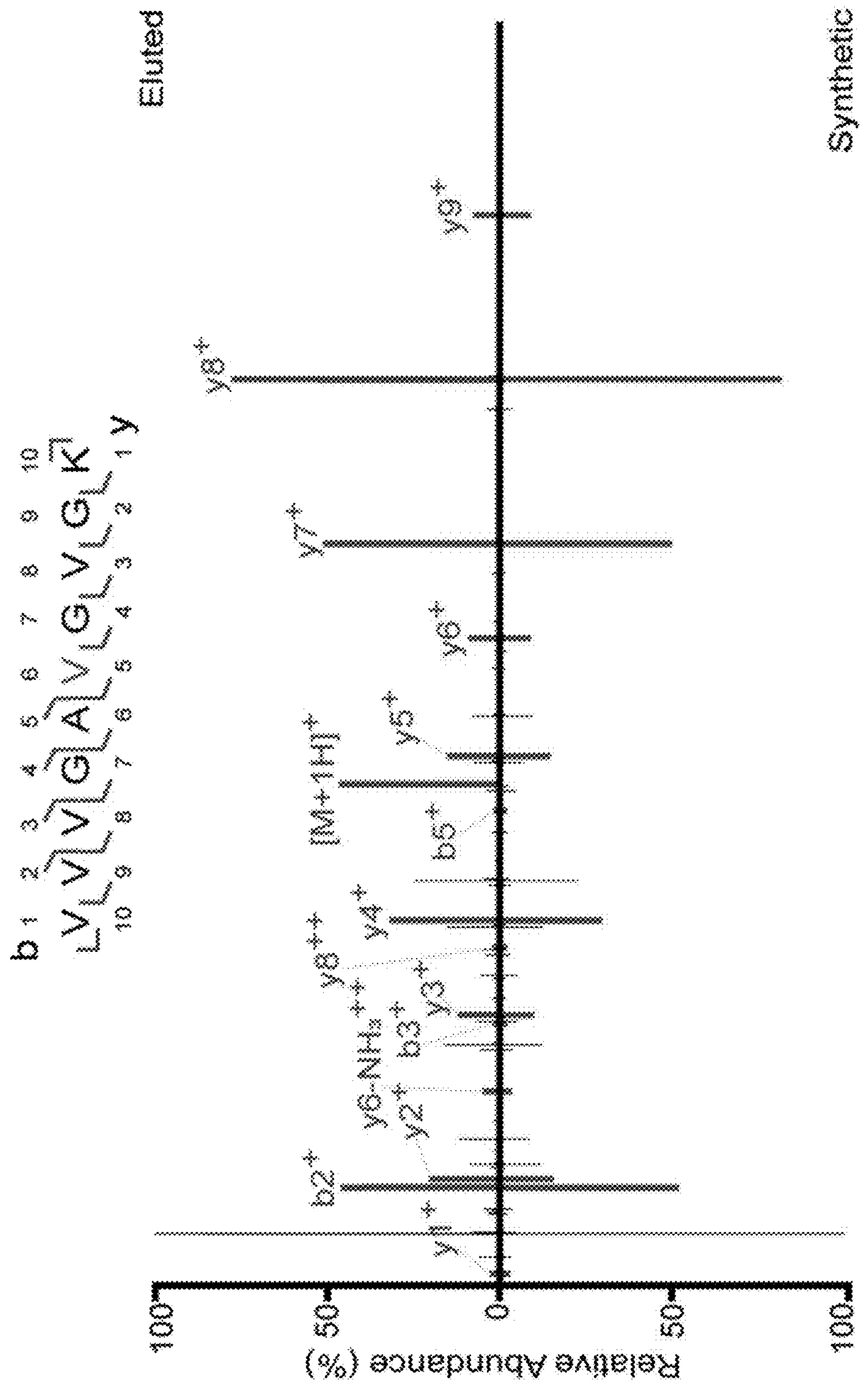
Figure 8H:
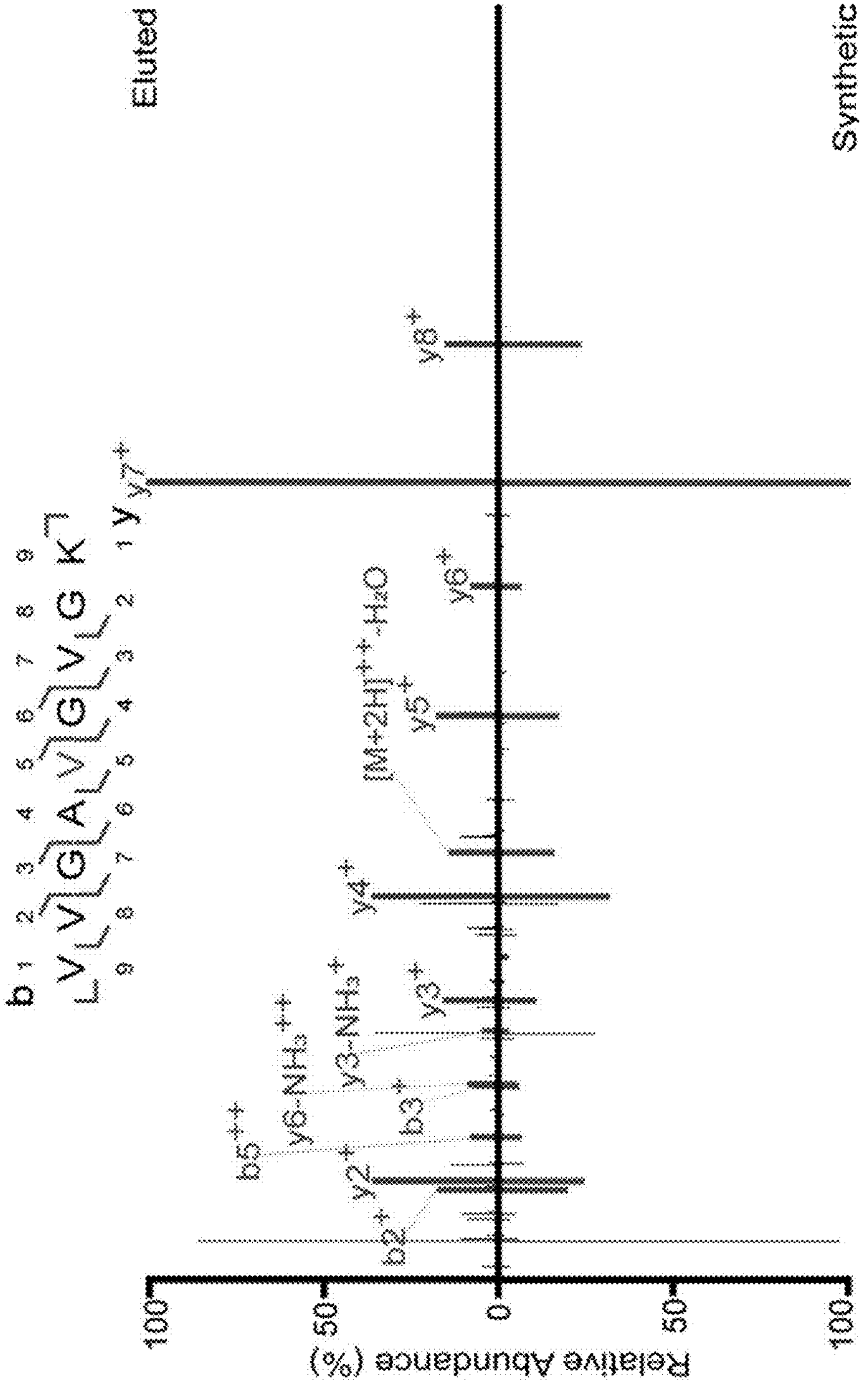
Figure 8I:
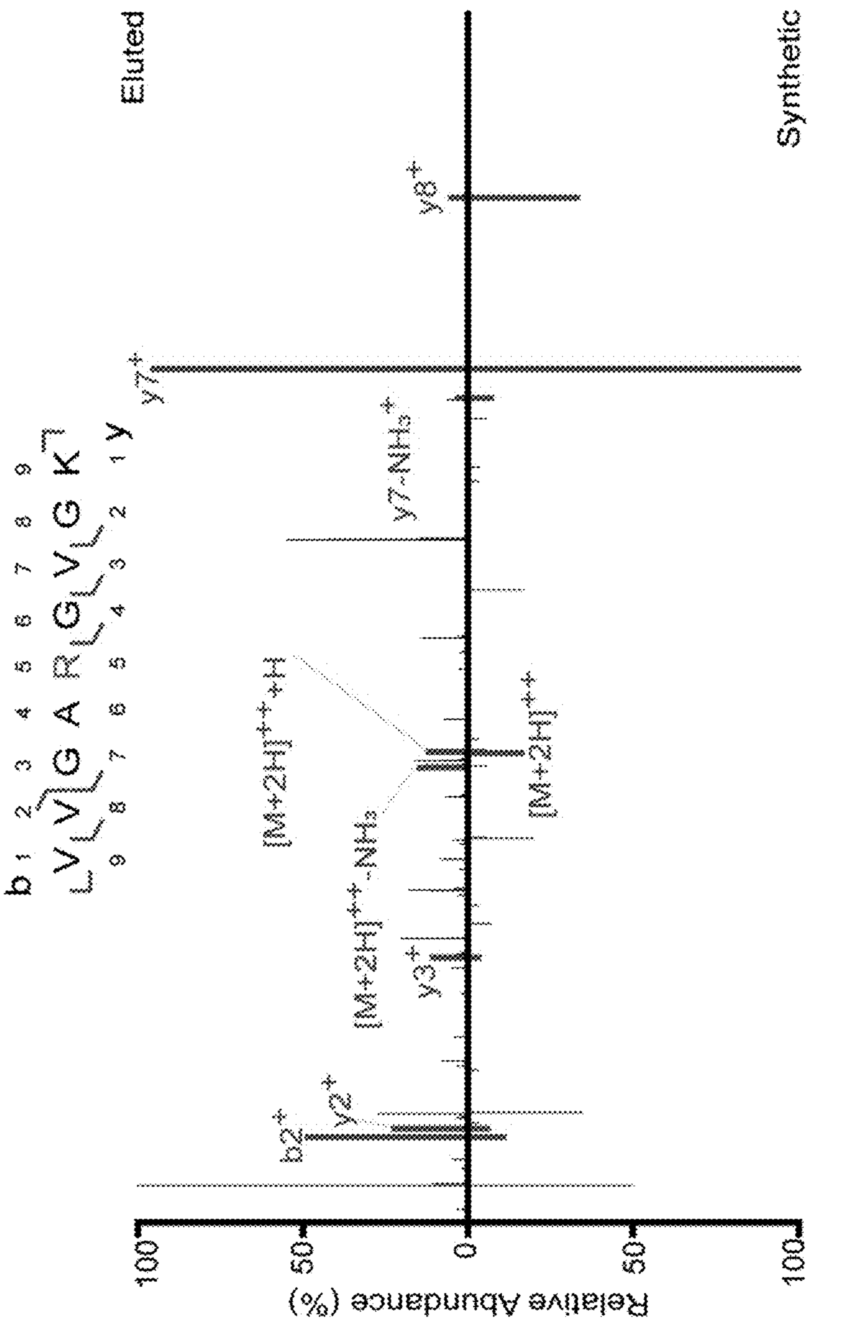
Figure 8J:
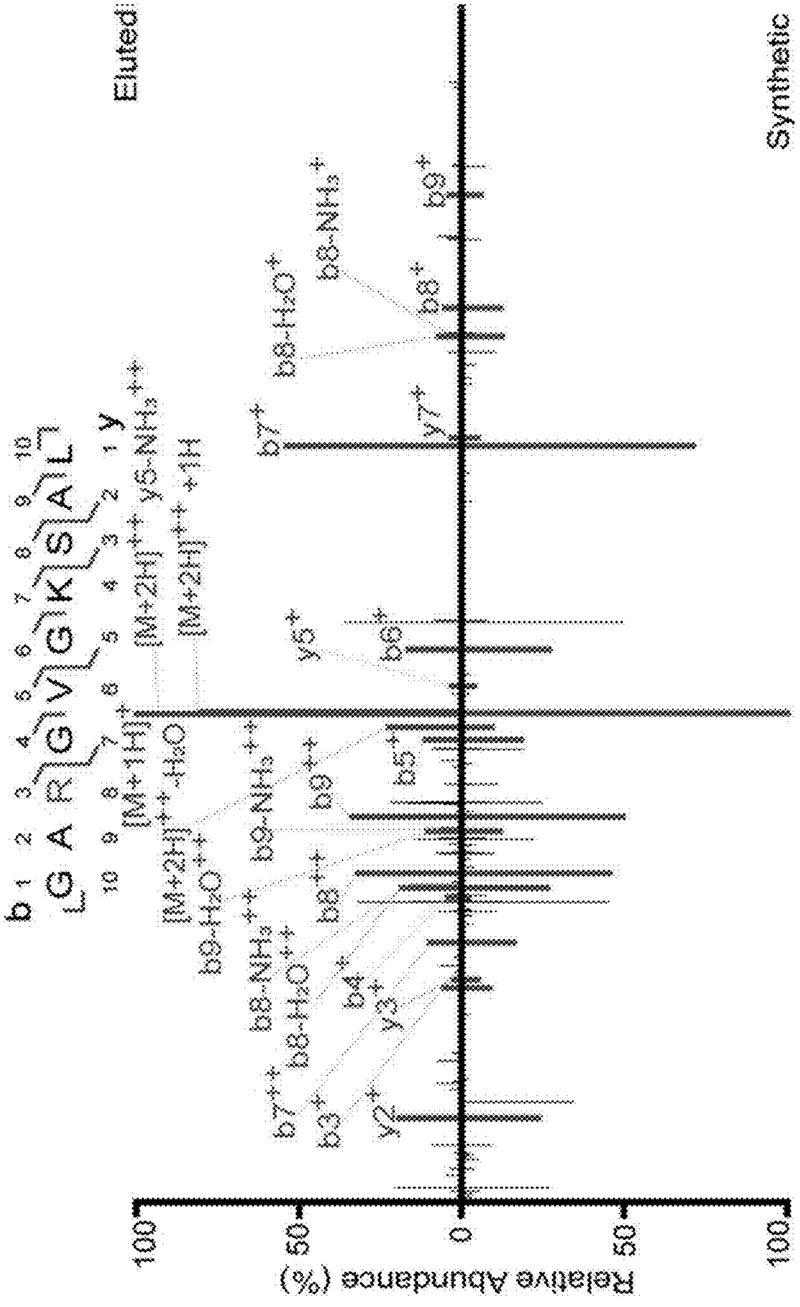

Additional antigen processing and presentation studies were done using mass spectrometry. First, monoallelic K562 cell lines were created to express specific HLA types (FIG. 7A). Further, lentiviral constructs expressing various wt RAS and mRAS peptides were generated (FIG. 7E). Monoallelic cell lines that express specific HLA types and the various RAS and mRAS peptides were then created. The expression of HLA class I and HLA-specific expression of RAS TMG cells lines were verified by FACS (FIG. 7C and FIG. 7D).

Figure 9:
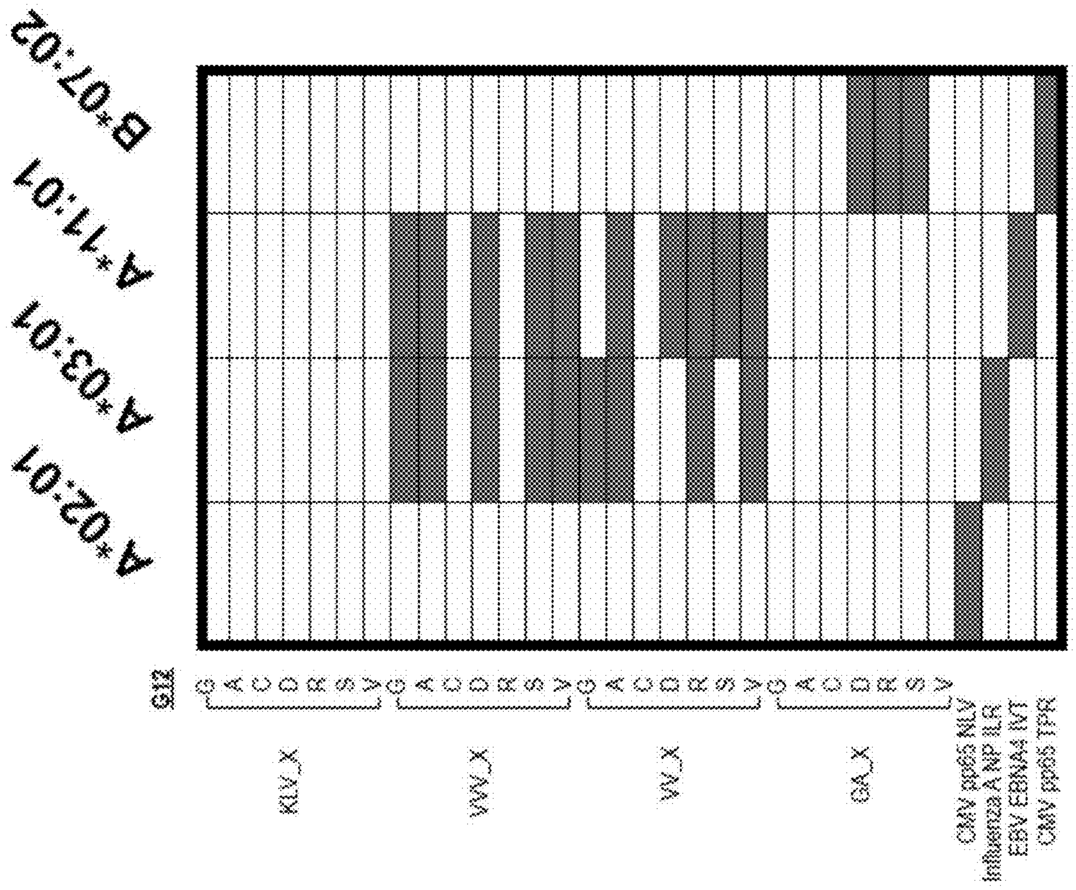
FIG. 9 is a schematic depicting a summary of mRAS epitopes detected by mass spectrometry, where shaded boxes represent binding between the epitope and HLA molecule.

The results, with respect to binding of various HLA molecules to mutant peptides are shown in FIG. 8A-FIG. 8J. A summary of mutant RAS epitopes detected by mass spectrometry is shown in FIG. 9. Interestingly, it was found that redundant epitopes exist for HLA-A*03:01 and HLA-A*11-01. Further, novel epitopes are identified for HLA-B*07:02.

Figure 10:
FIG. 10 depicts the results of exemplary experiments comparing the predicted and detected mRAS epitopes in the context of specific HLA types. Peptides highlighted in red are computationally predicted epitopes that were detected using p/MHC IP HPLC tandem mass spectrometry.

FIG. 10 presents a comparison of neoantigens identified during the in silico prediction studies (left) and the peptide-MHC binding studies (right).

In summary, the experiments presented herein identified that the highly prevalent MHC class I alleles HLA-A2 subtypes, HLA-A*03:01, HLA-A*11:01, and HLA-B*07:02 are predicted to bind to mRAS neoepitopes. Further, mRAS neoepitopes were found to have high binding affinity for the following HLA:peptide pairs: HLA-A*02:01: G12V (KLVVVGAVGV (SEQ ID NO:4)); HLA-A*03:01: G12V (VVVGAVGVGK (SEQ ID NO:12) and VVGAVGVGK (SEQ ID NO:11)) and G12R (VVVGARGVGK (SEQ ID NO:10)); HLA-A*11:01: G12C (VVVGACGVGK (SEQ ID NO:6) and VVGACGVGK (SEQ ID NO:5)), G12D (VVVGADGVGK (SEQ ID NO:8) and VVGADGVGK (SEQ ID NO:7), G12R (VVVGARGVGK (SEQ ID NO:10) and VVGARGVGK (SEQ ID NO:9)) and G12V (VVVGAVGVGK (SEQ ID NO:12) and VVGAVGVGK (SEQ ID NO:11)); HLA-B*07:02: G12R (GARGVGKSAL (SEQ ID NO:15)). Further, proteomic studies confirmed antigen processing/presentation of predicted epitopes and identified new epitopes: HLA-B*07:02: G12D (GADGVGKSAL (SEQ ID NO:14)).

Example 2: Assess mRAS Immunogenicity

Figure 11:
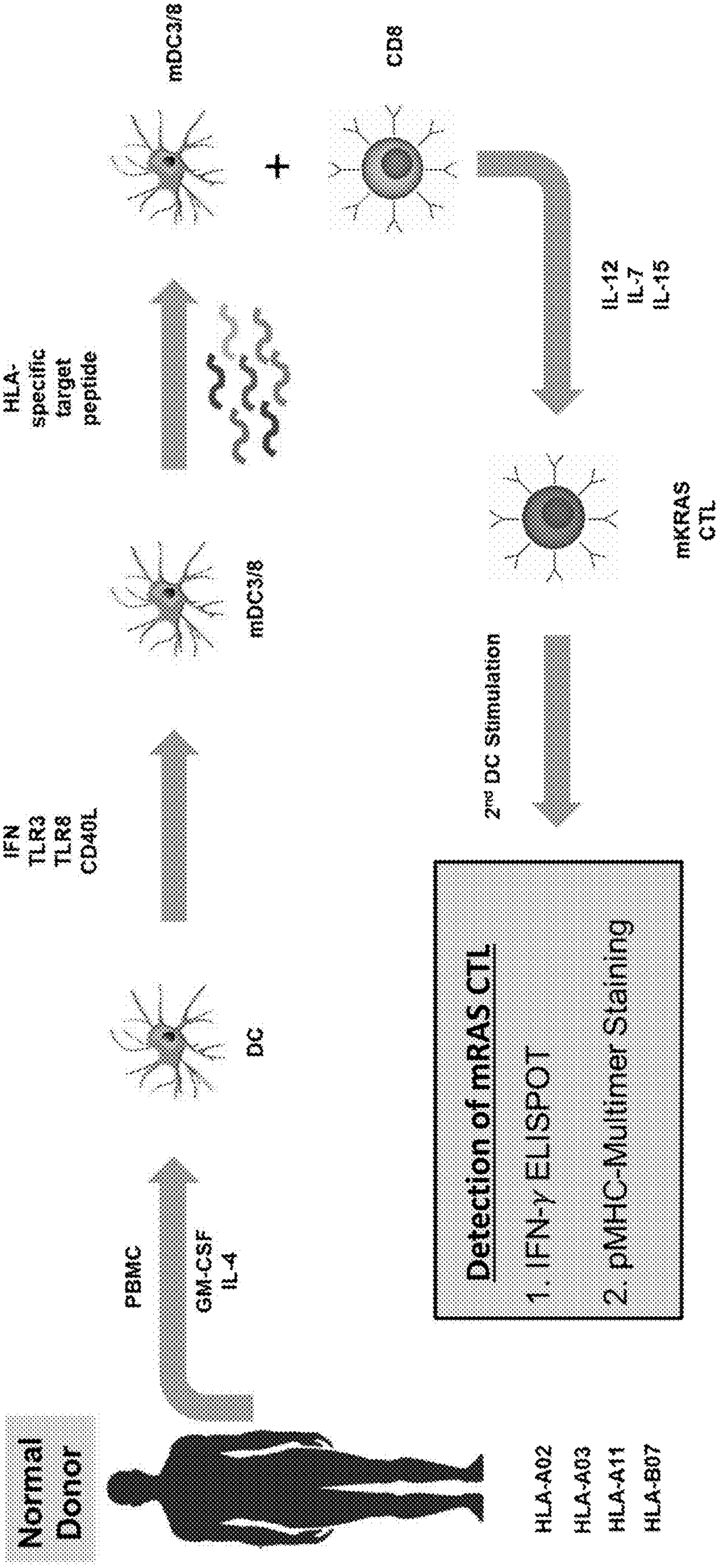
FIG. 11 depicts a schematic of experiments detailing the protocol for generating and identifying mRAS-specific CD8+ T cells.
Figure 12:
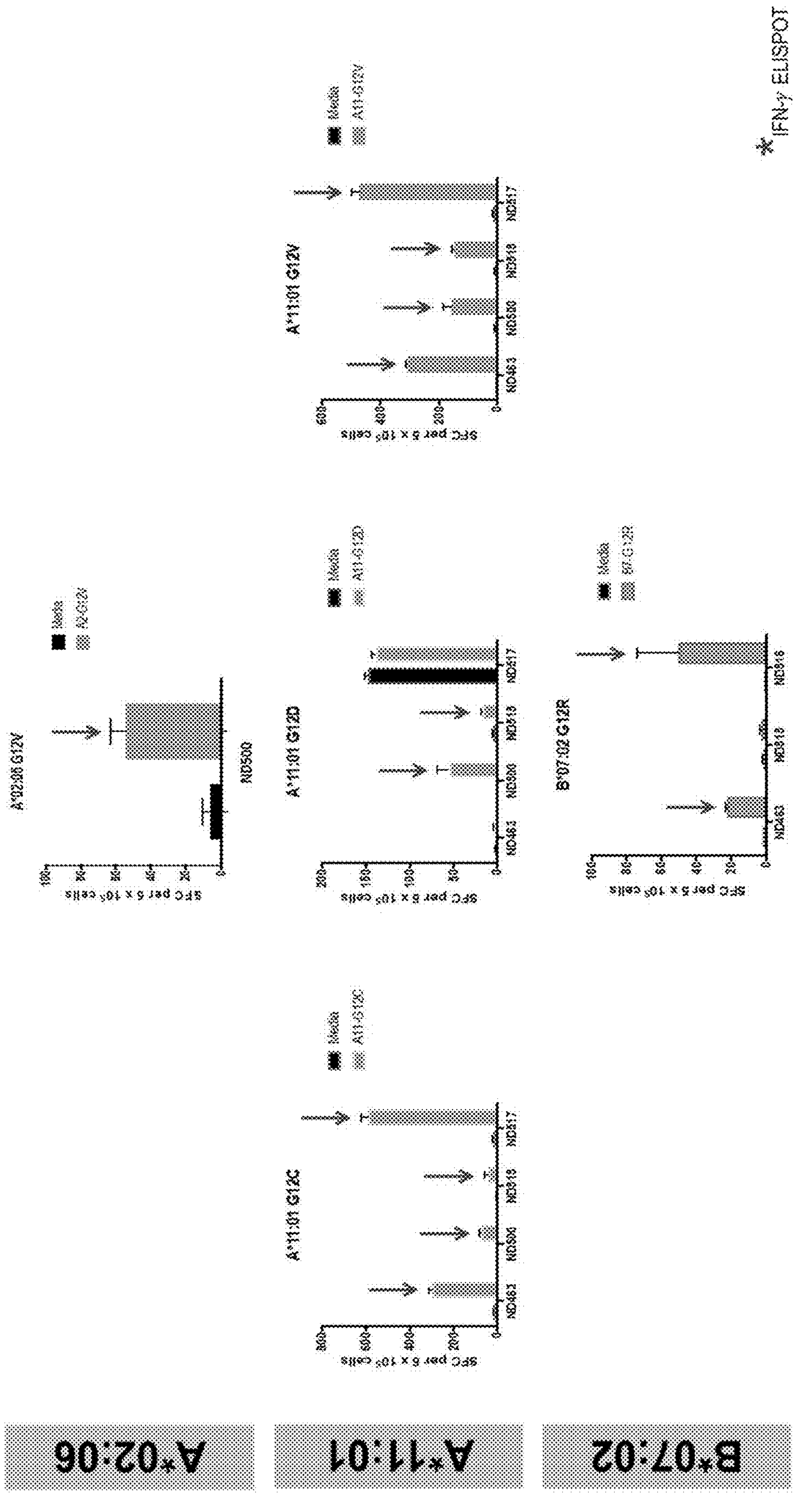
FIG. 12 depicts the results of exemplary experiments summarizing the mRAS-specific CD8+ T cell responses in healthy donors.
Figures 13A, 13B, 13C, 13D, 13E, 13F:
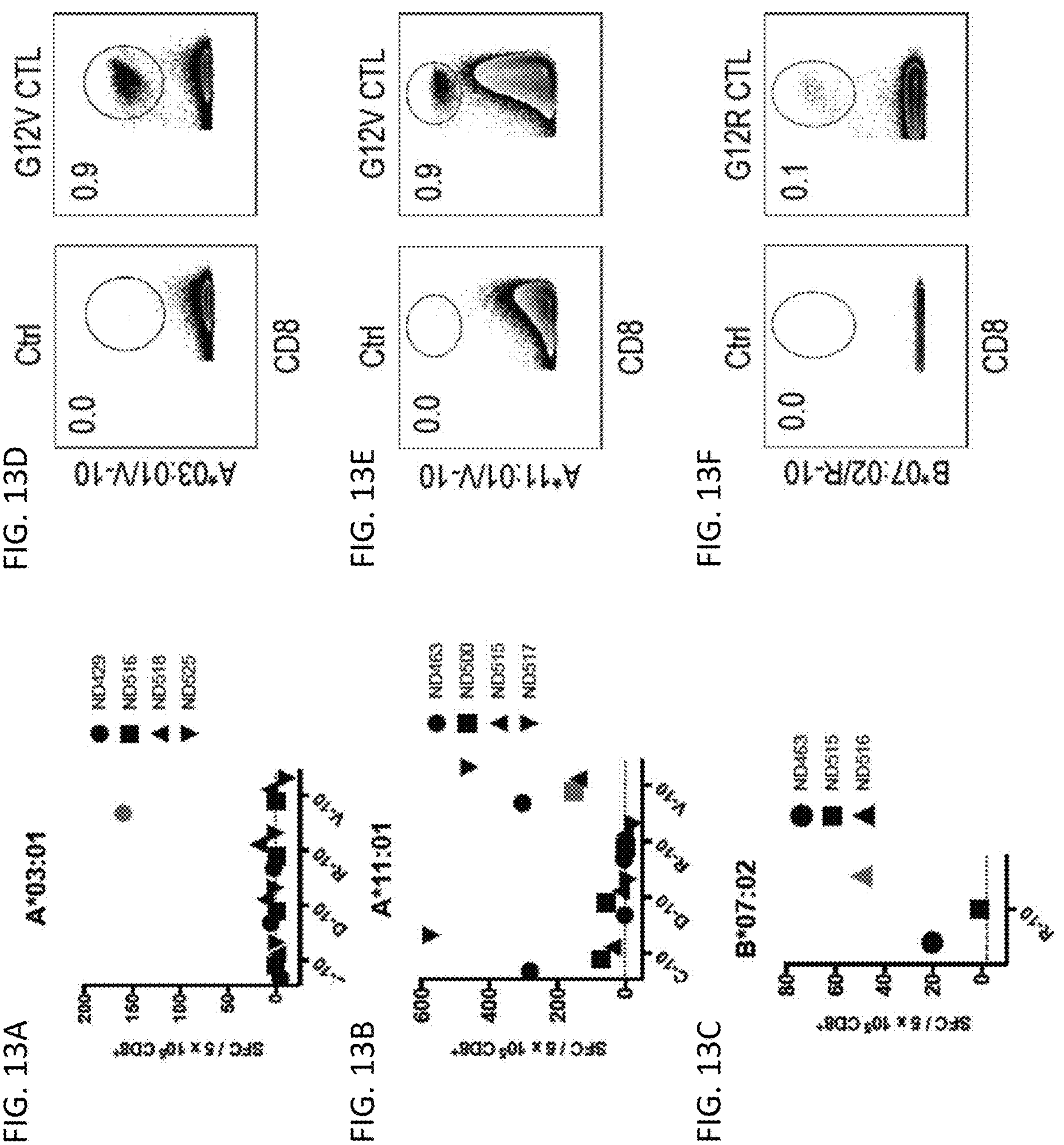
FIG. 13A through FIG. 13F depict the results of example experiments demonstrating the antigenicity of mRAS epitopes. IFN-γ ELISPOT of (FIG. 13A) A*03:01-restricted, (FIG. 13B) A*11:01-restricted and (FIG. 13C) B*07:02-restricted mRAS epitope responses.

As described herein, experiments were conducted to assess the immunogenicity of mRAS peptide-MHC recognition. PMBCs were isolated from normal donors having selected HLA types (HLA-A02, HLA-A03, HLA-A11, and HLA-B07) and stimulated as shown in FIG. 11. Experiments using IFN-γ ELISPOT assays were conducted to evaluate the CD8+ T cell responses. The summary of mRAS CTL responses is shown in FIG. 12 and FIG. 13A-FIG. 13F.

Figure 14:
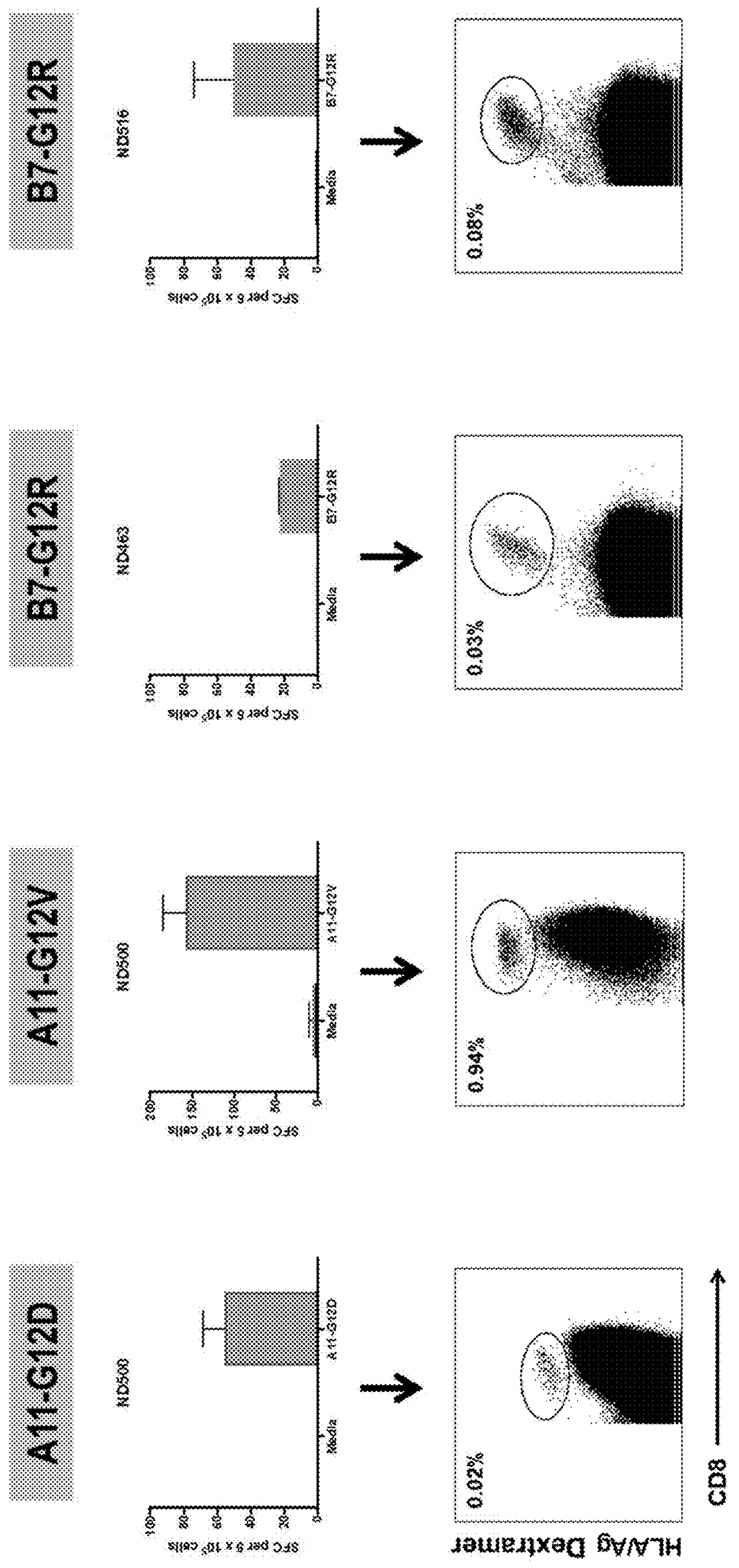
FIG. 14 depicts the results of exemplary experiments demonstrating the detection of mRAS-specific CD8+ by peptide/MHC multimer staining detects.
Figure 15:
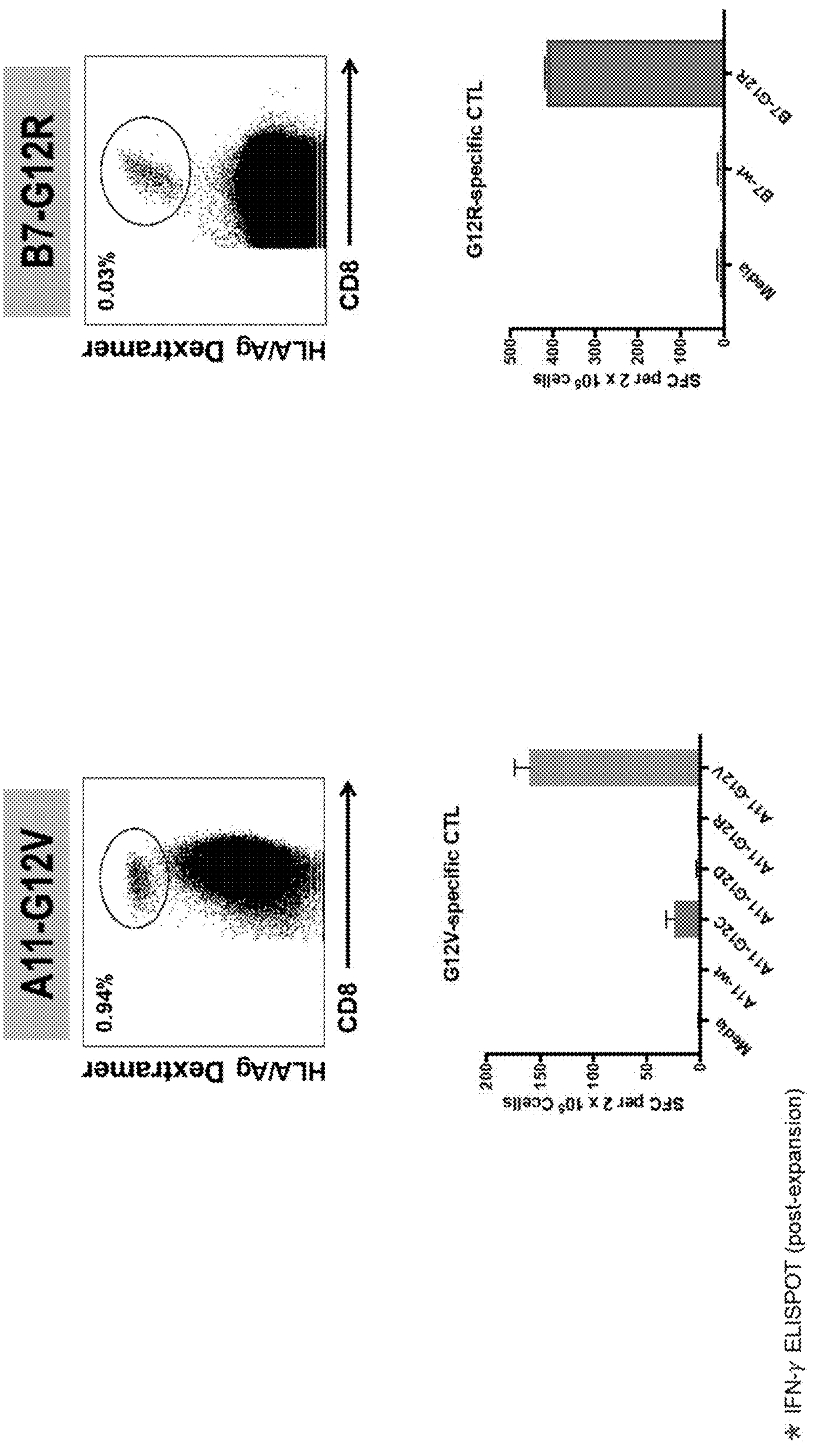
FIG. 15 depicts the results of exemplary experiments demonstrating that mRAS T cell responses are highly specific for the mRAS peptide of interest and do not exhibit any cross reactivity against wild type RAS peptide.
Figure 16:
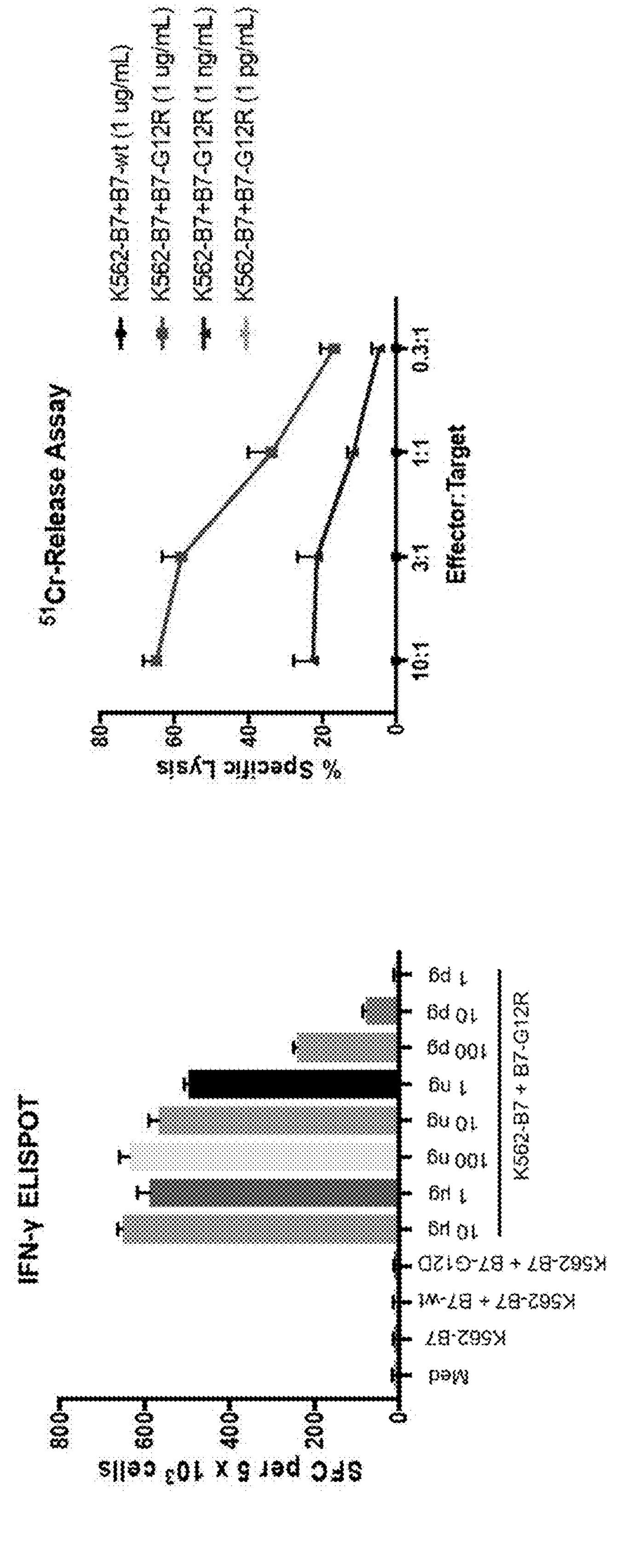
FIG. 16 depicts the results of exemplary experiments demonstrating that B7-G12R responses are of high affinity as demonstrated by IFN-gamma secretion and cytotoxicity assays. Importantly, no reactivity was detected against cell lines expressing wild type or alternatively mutated RAS peptides.

Additional experiments using pMHC-multimer staining were conducted on T cell cultures to identify mRAS-specific T cells (FIG. 14). The experiments also showed that the mRAS T cell responses are highly specific (FIG. 15). Experiments using various doses of B7-G12R was used to demonstrate the observed responses are of high affinity (FIG. 16).

Figure 17:
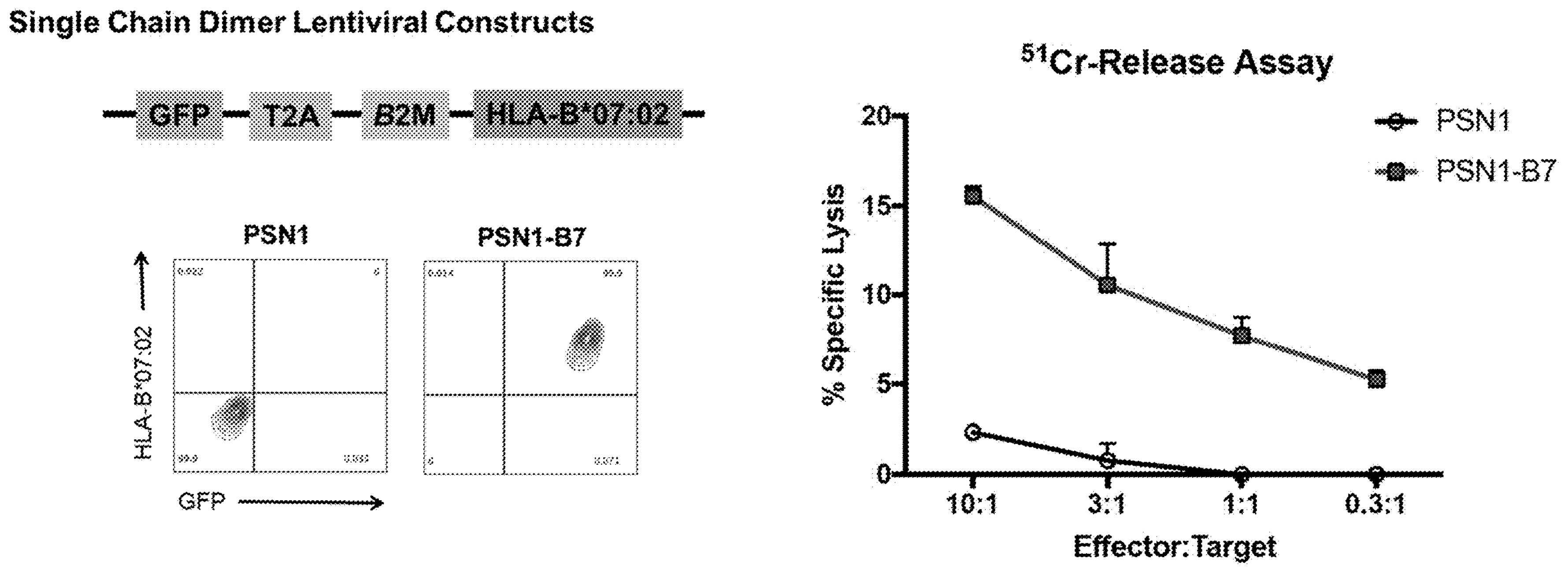
FIG. 17 depicts the results of exemplary experiments demonstrating that HLA-B*07:02-restricted RAS G12R-specific CD8+ T cells exhibit cytotoxicity against PSN, a PDA cell line with endogenous RAS G12R expression, when genetically modified to express HLA-B*07:02.

Experiments were also done to examine whether the B7-G12R CTL response can kill a G12R+ PDA cell line. As shown in FIG. 17, PSN1 cells that are modified to express HLA-B*07:02 are able to be killed via a B7-G12R CTL.

In summary, the present experiments demonstrate that mRAS neoantigen-specific T cell responses may be generated in normal donors. T cell responses were observed for HLA-A*02:06: G12V; HLA-A*11:01: G12C, G12D, G12V; and HLA-B*07:02: G12R. Further, mRAS-specific T cells may be detected and purified by pMHC multimer staining. It was also observed that mRAS T cells are highly specific for target mutation and exhibit no reactivity to wild type antigen. Finally, outsourced mRAS-specific T cells may be of sufficient affinity to target endogenously mutated tumor cell lines

Example 3: Development of mRAS-Specific TCR Therapy

As described herein, experiments were conducted to design a TCR therapy targeted against specific mRAS peptides in the context of specific HLA types.

Figure 18:
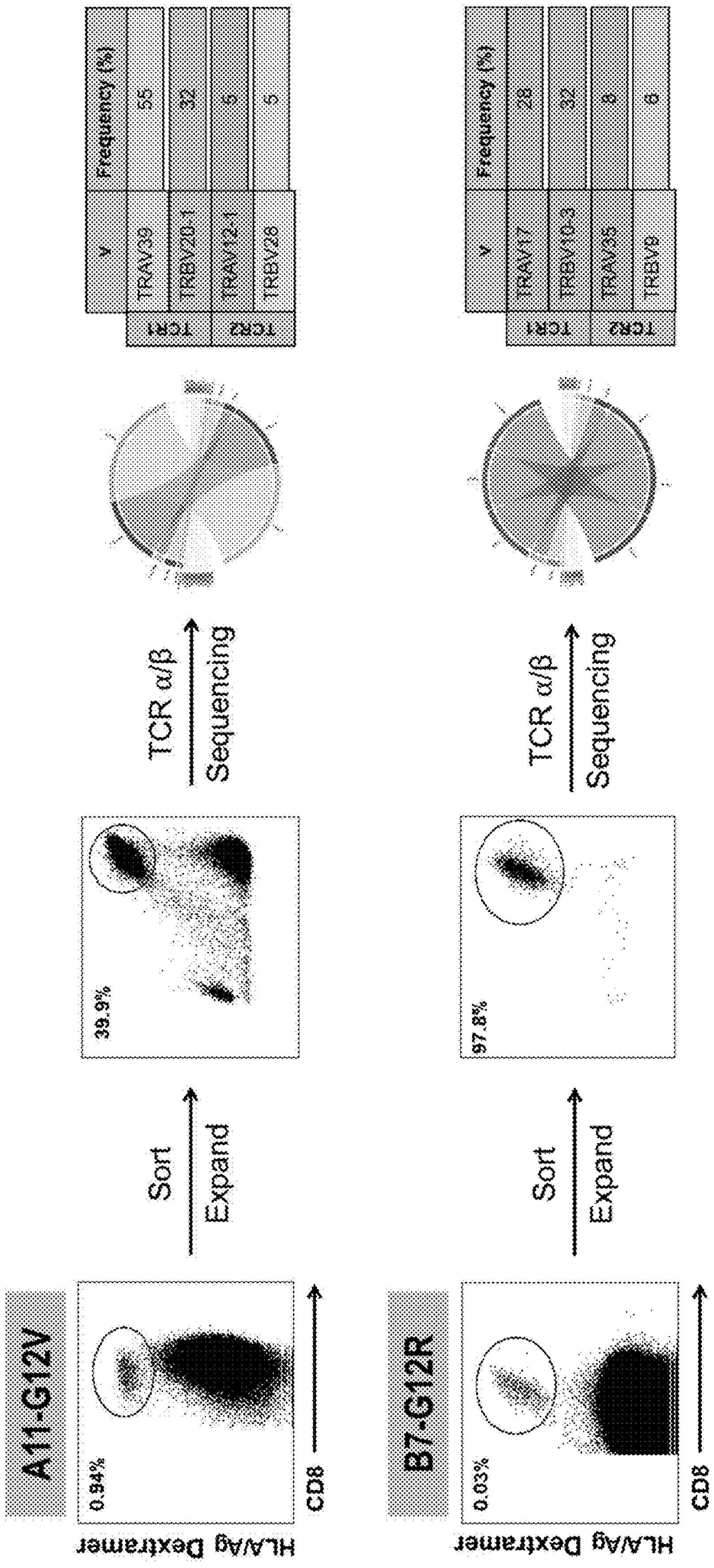
FIG. 18 depicts the results of exemplary experiments demonstrating the identification of mRAS-specific TCR sequences.

As shown in FIG. 18, T-cells observed to bind to A11-G12V and B7-G12R mRAS peptide-HLA type complexes were sorted, expanded, and subjected to TCR α/β sequencing. Two distinct CD8+ T cell clones were identified for the HLA-A*11:01 restricted G12V-specific T cells: (1) TRAV39/TRBV20-1 and TRAV12-1/TRBV28 were observed.

Figure 19:
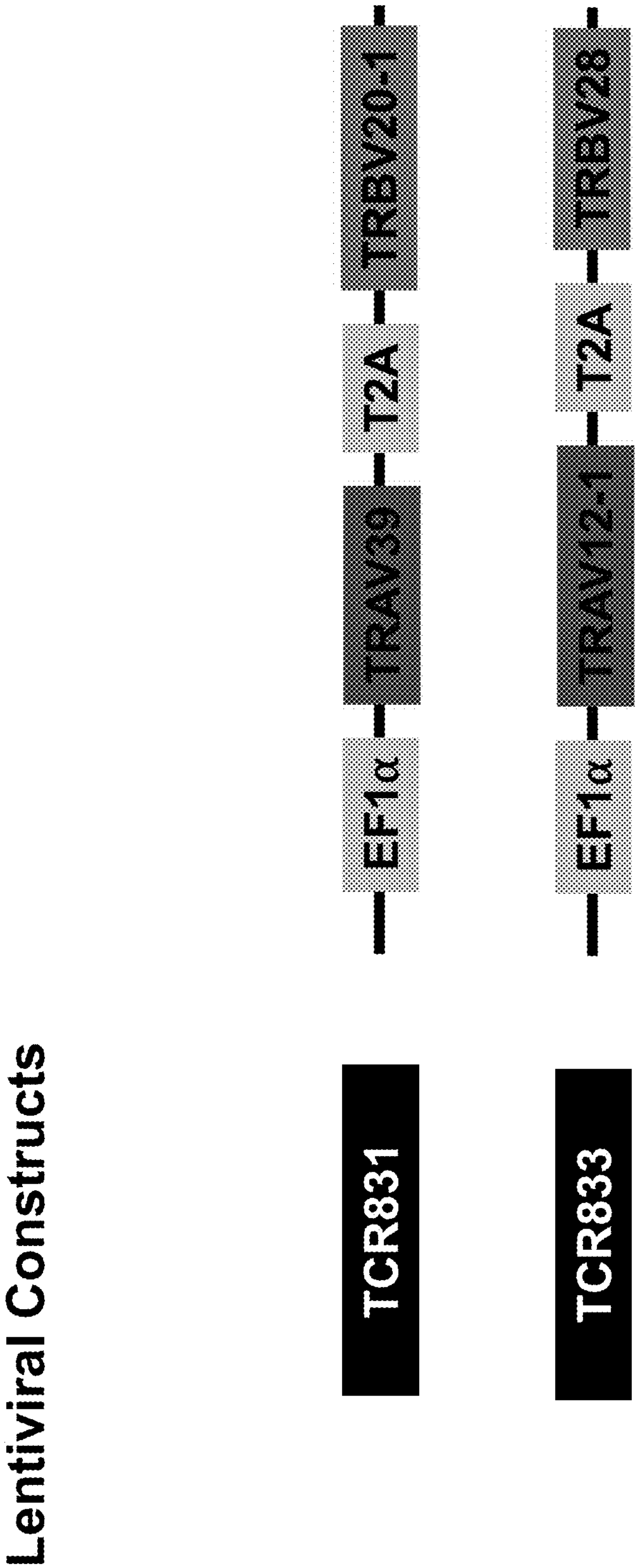
FIG. 19 depicts the design of lentiviral constructs for TCR831 and TCR833.

Based upon the sequencing, lentiviral constructs, termed TCR831 and TCR833 were designed (FIG. 19). TCR831 comprises TRAV39 and TRBV20-1, while TCR833 comprises TRAV12-1 and TRBV28. Both constructs comprise a T2A linker domain and a EF1α promoter. Similarly, additional constructs, termed TCR896, TCR897, TCR847, and TCR864 were designed, as summarized in FIG. 20. FIG. 20 also lists the RAS mutation sensitivity, HLA restriction, identity of alpha and beta chains, and associated CDR3s for all of the designed TCR constructs.

Figure 21:
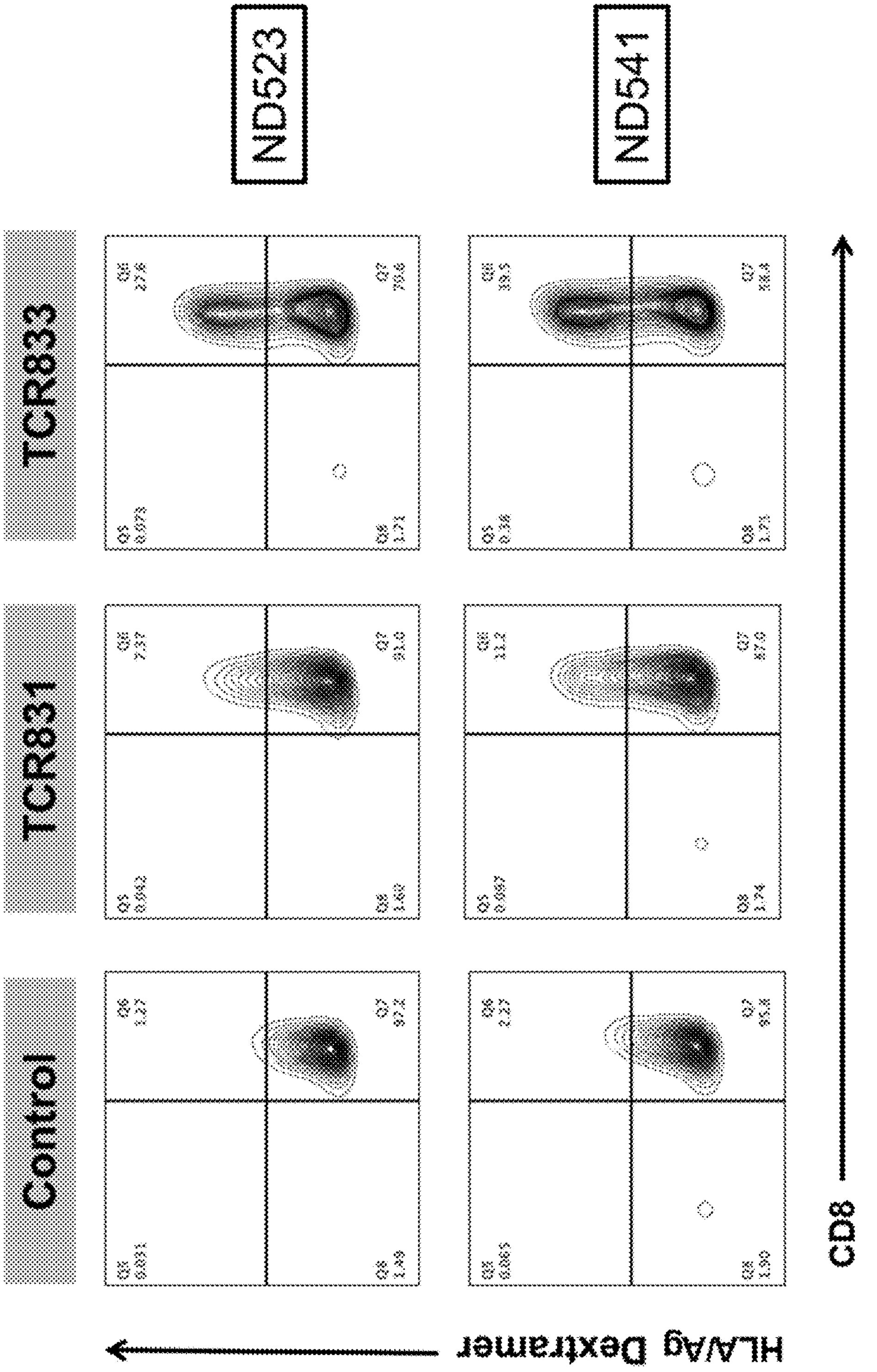
FIG. 21 depicts the results of exemplary experiments demonstrating the transgenic expression of TCR831 and TCR833 on primary CD8+ cells.
Figure 22:
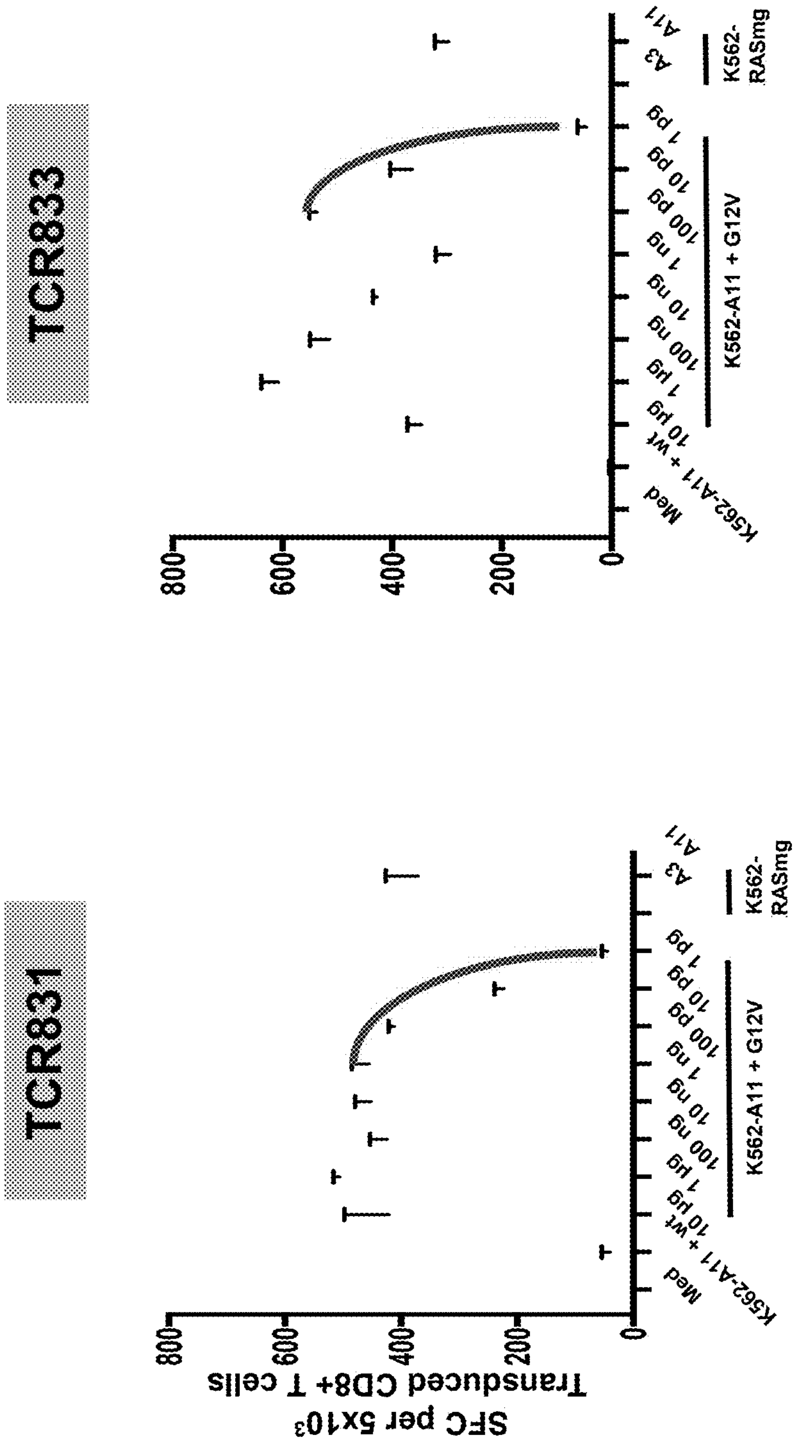
FIG. 22 depicts the results of exemplary experiments demonstrating that transgenic TCR831 and TCR833 have high affinity for HLA-A*11:01 restricted KRAS G12V and have no reactivity against wild type RAS antigen. Furthermore, TCR831 and TCR833 recognize antigen endogenously processed and presented by K562-A*11:01 cells genetically modified to express the RASmg construct.

The expression of TCR831 and TCR833 was assessed in primary CD8+ T cells (FIG. 21). The affinity of TCR831 and TCR833 was examined using an IFN-γ ELISPOT assay and using various doses of K562-A11+G12V. As shown in FIG. 22, both TCR831 and TCR833 displayed high affinity in response to mRAS G12V in the context of HLA-A*11:01.

Figure 23:
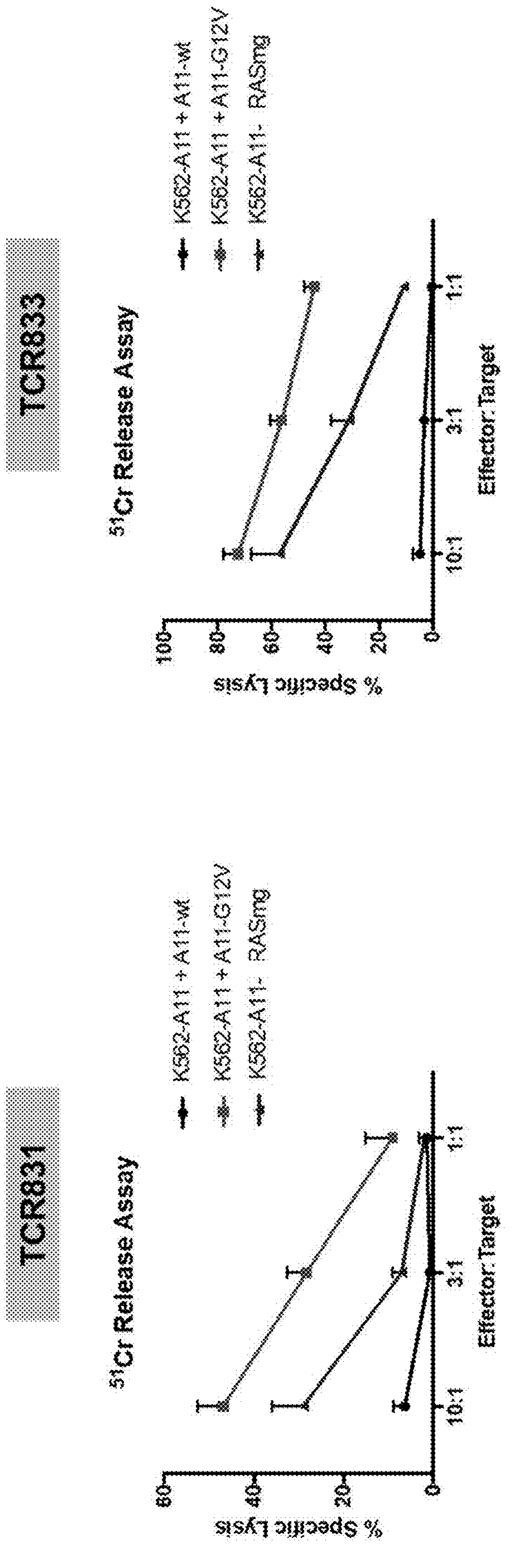
FIG. 23 depicts the results of exemplary experiments demonstrating transgenic expression of TCR831 and TCR833 confers cytotoxicity against K562-A*11:01 cells expressing RAS G12V peptide of endogenous RASmg construct but not wild type RAS G12V peptide.

Further, additional experiments using IFN-γ ELISPOT demonstrated that the transgenic TCR831 and TCR833 constructs recognize endogenous antigen (FIG. 22) where response is observed with A11 but not A3. The specificity of the transgenic TCR831 and TCR833 constructs, and their ability to recognize endogenous antigen, is also shown in FIG. 23, where a CTL response is observed in the presence of G12V but not wild-type RAS.

Figure 24:
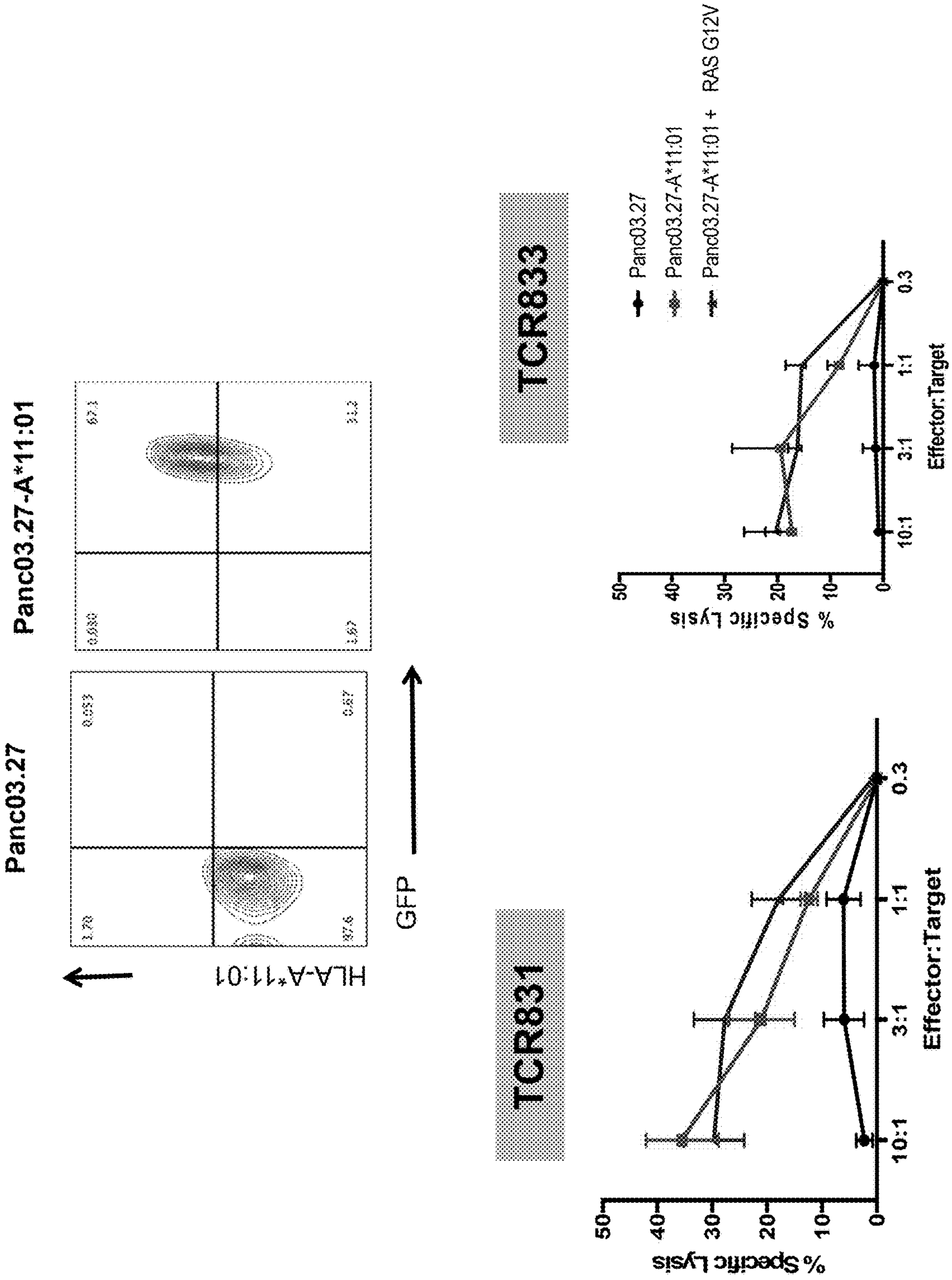
FIG. 24 depicts the results of exemplary experiments demonstrating transgenic expression of TCR831 and TCR833 confers cytotoxicity against Panc03.27, a PDA cell line with endogenous RAS G12V expression, when genetically modified to express HLA-A*11:01.

Experiments were also conducted to examine the reactivity of TCR831 and TCR833 to a G12V+ PDA cell line. The PDA cell line, Panc03.21, which harbors a KRAS G12V mutation, was modified with a lentiviral construct encoding HLA-A*11:01 molecule (FIG. 24).

Figures 25A, 25B, 25C, 25D, 25E, 25F, 25G:
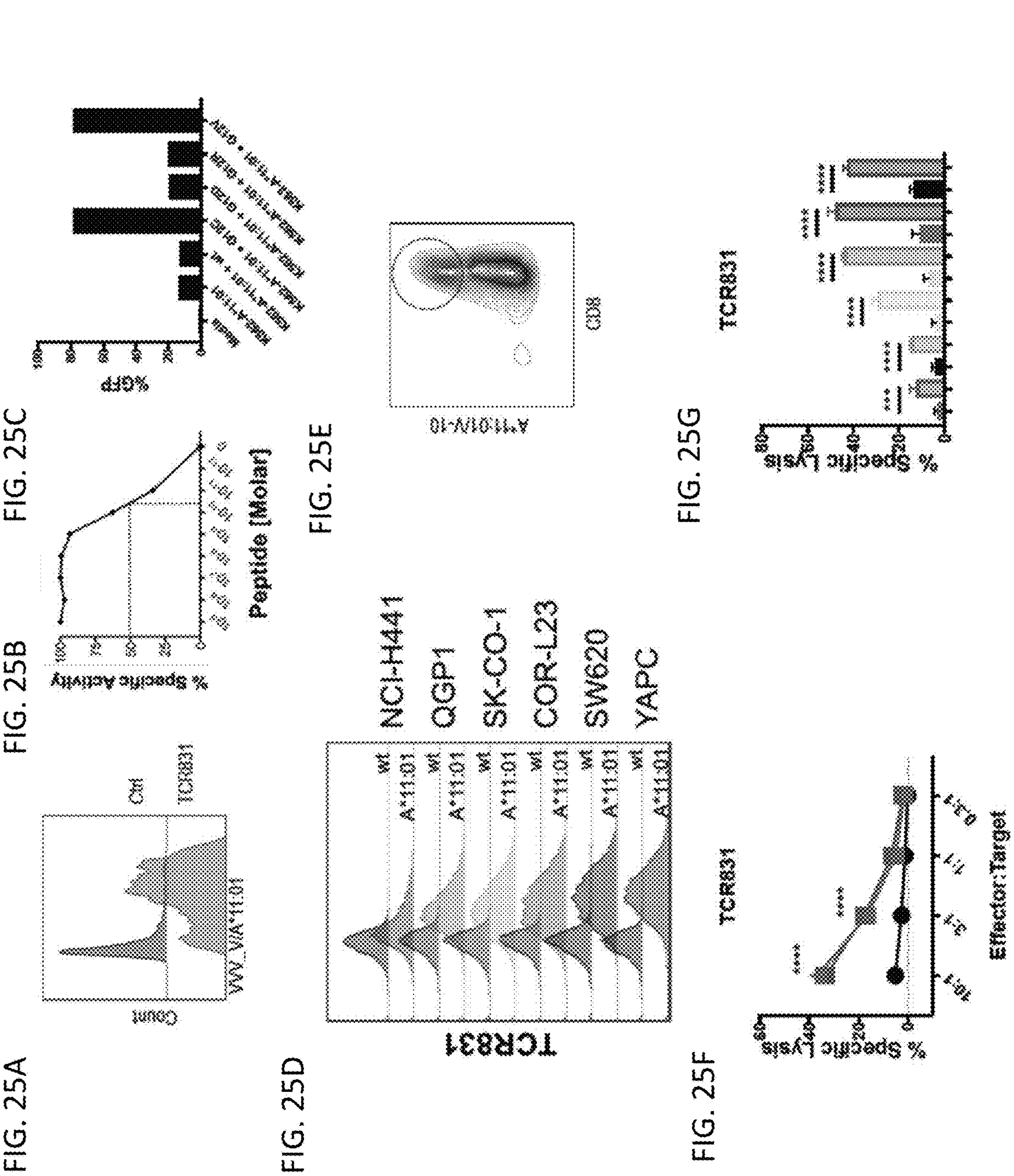
FIG. 25A through FIG. 25G depict the results of experiments characterizing TCR831 expression and function.

Further characterization of the TCR831 construct is shown in FIG. 25A-FIG. 25G. The validation of TCR831 expression by peptide-MHC multimer staining of lentiviral-transduced Jurkat Reporter cells is shown in FIG. 25A. Experiments were conducted to examine TCR831 avidity by Jurkat Reporter cells (FIG. 25B). Experiments were also conducted to assess TCR831 specificity and cross-reactivity to alternative mutant RAS epitopes by Jurkat Reporter assay. TCR831 exhibits specificity for RAS G12V (VVV_V) but not wildtype. Cross reactivity was observed to RAS G12C (VVV_C). FIG. 24D depicts TCR activation of Jurkat Reporter cells following coculture with A*11:01 positive RAS G12V tumor cell lines. FIG. 25E depicts the expression of TCR831 on primary CD8+ T cells. Experiments were also conducted using 4-hr 51Cr assay, which indicates specific lysis of K562-A*11:01 cells pulsed with G12V peptide (blue) or expressing RAS TMG construct (red)—but not wildtype (black). Further, 4-hr 51Cr assay results indicating specific lysis of A*11:01 positive RAS G12V− tumor cell lines at effector to target ratio 10:1 (FIG. 25G). Cell line coloring corresponds to that in FIG. 25D.

Figures 26A, 26B, 26C, 26D, 26E, 26F, 26G:
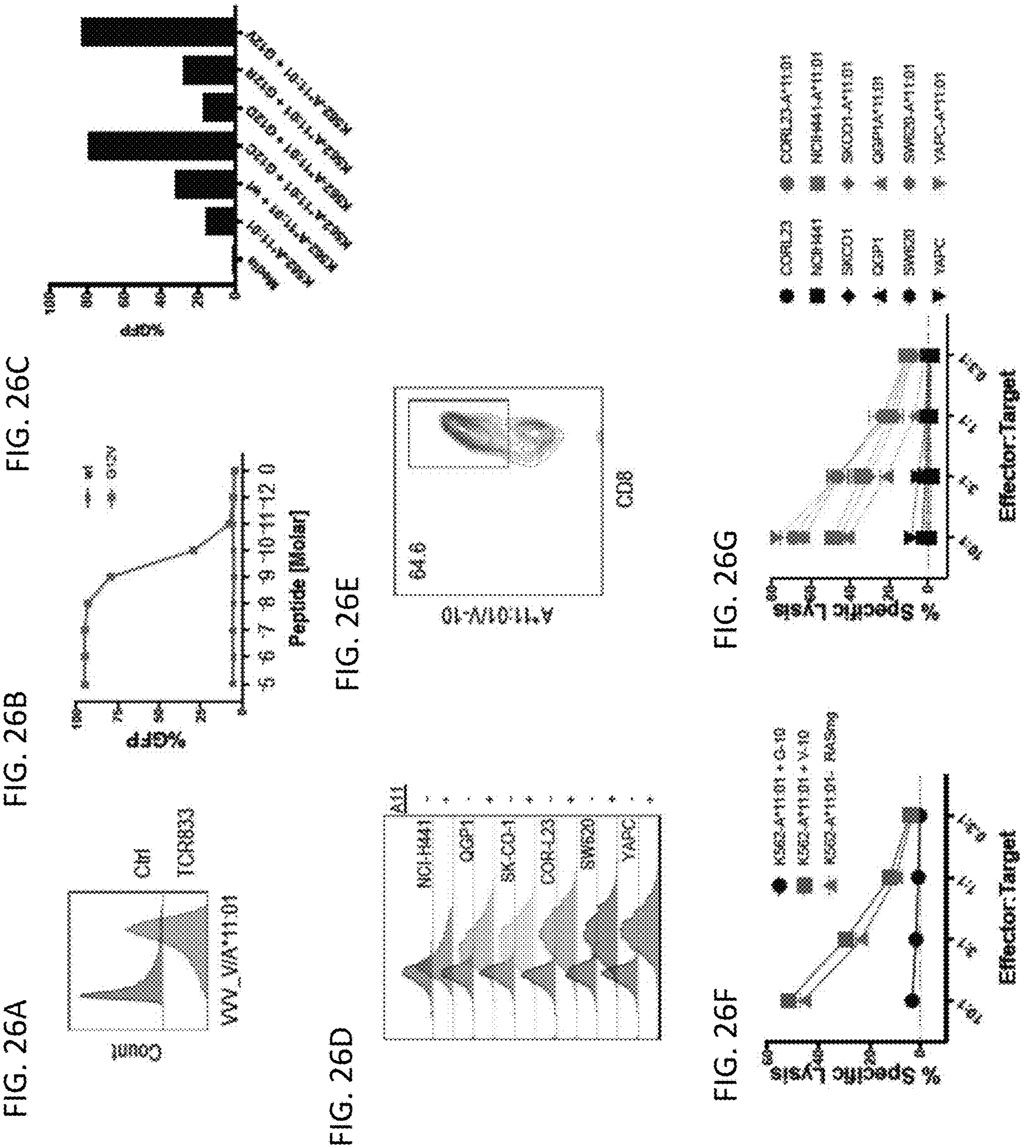
FIG. 26A through FIG. 26G depict the results of example experiments characterizing TCR833 expression and function.

Experiments were also conducted to further characterize the expression and function of TCR833. The validation of TCR833 expression by peptide-MHC multimer staining of lentiviral-transduced Jurkat Reporter cells is shown in FIG. 26A. FIG. 26B depicts the results of experiments assessing TCR833 avidity by Jurkat Reporter cells. Experiments were also conducted to assess TCR833 specificity and cross-reactivity to alternative mutant RAS epitopes by Jurkat Reporter assay. As shown in FIG. 26C, TCR833 exhibits specificity for RAS G12V (VVV_V) but not wildtype. Cross reactivity was observed to RAS G12C (VVV_C). FIG. 26D depicts TCR833 activation of Jurkat Reporter cells following coculture with A*11:01 positive RAS G12V tumor cell lines. Expression of TCR833 on primary CD8+ T cells is shown in FIG. 26E. Experiments were conducted using 4-hr 51Cr assay which indicates specific lysis of K562-A*11:01 cells pulsed with G12V peptide (blue) or expressing RAS TMG construct (red)—but not wildtype (black)(FIG. 26F). FIG. 26G depicts results from a 4-hr 51Cr assay indicating specific lysis of A*11:01 positive RAS G12V tumor cell lines.

Figure 27A:
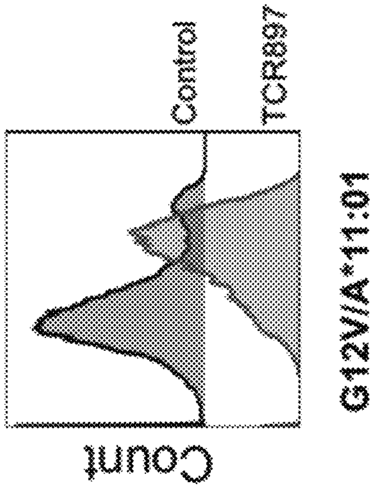
FIG. 27A through FIG. 27C depict the results of example experiments characterizing TCR897 expression and function.
Figure 27B:
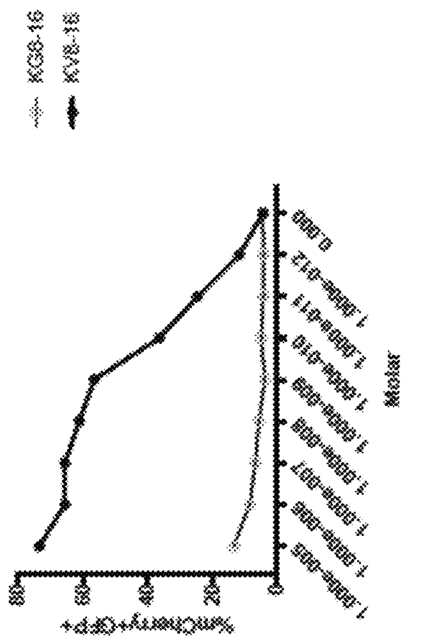
Figure 27C:
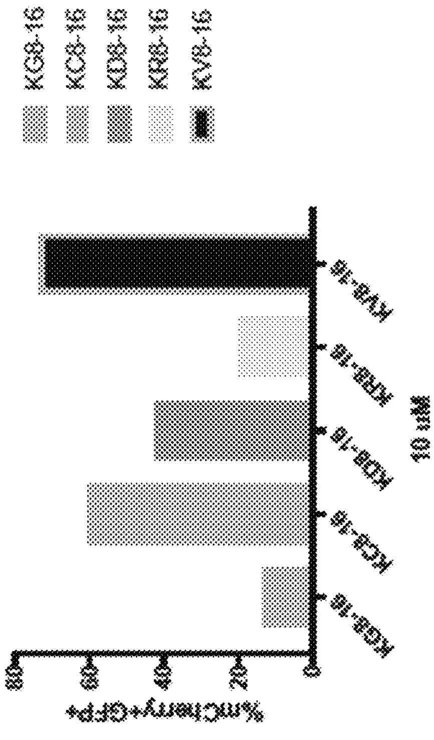

Further experiments were conducted to characterize TCR897 expression and function. TCR897 expression was validated by peptide-MHC multimer staining of lentiviral-transduced Jurkat Reporter cells, as shown in FIG. 27A. FIG. 27B depicts the results of experiments assessing TCR897 avidity by Jurkat Reporter cells. Experiments were conducted to assess TCR897 specificity and cross-reactivity to alternative mutant RAS epitopes by Jurkat Reporter assay. As shown in FIG. 27C, TCR897 exhibits specificity for RAS G12V (VV_V) but not wildtype. Cross reactivity was observed to RAS G12C (VV_C) and G12D (VV_D) epitopes.

Figures 28A, 28B, 28C, 28D, 28E, 28F, 28G:
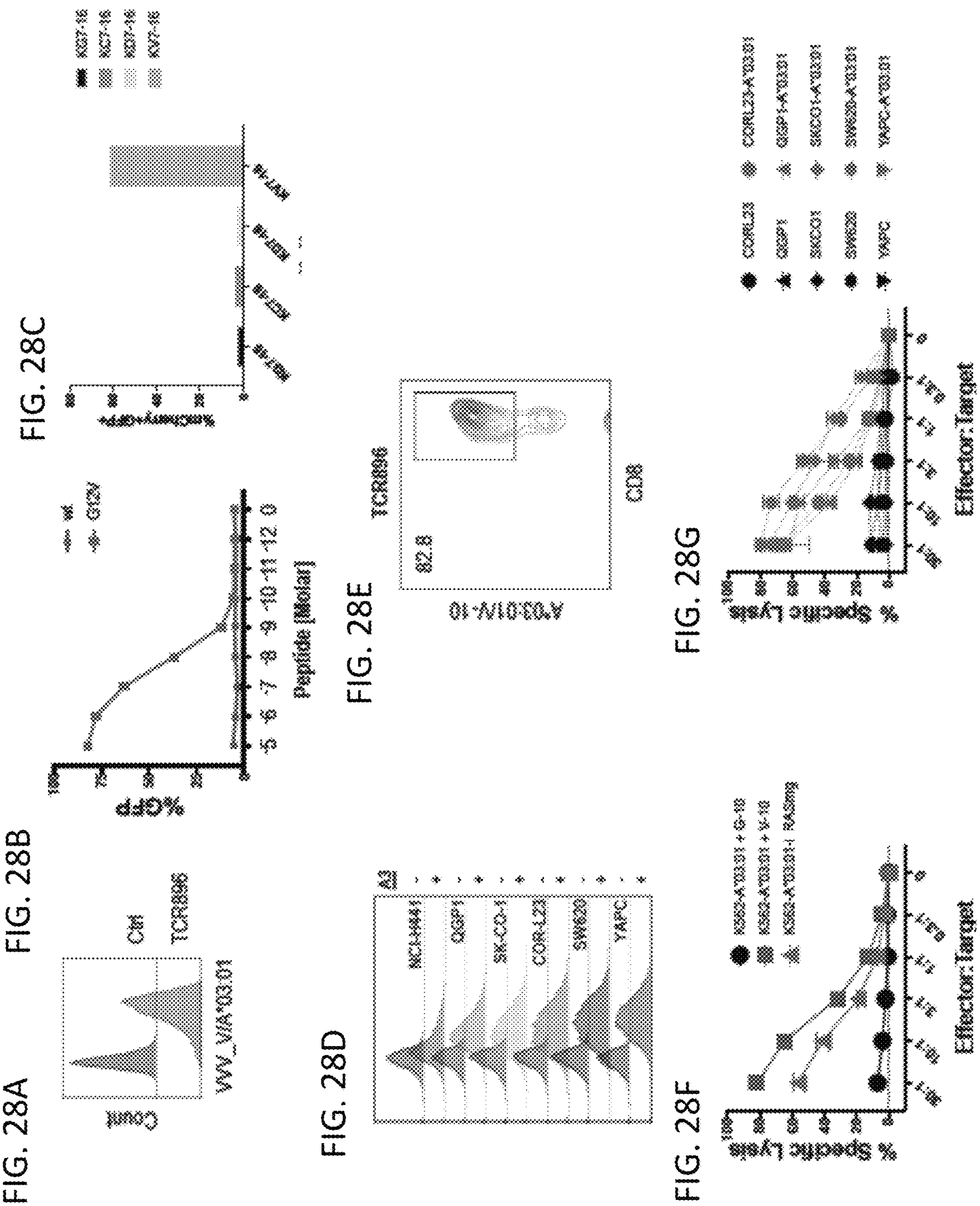
FIG. 28A through FIG. 28G depict the results of experiments characterizing TCR896 expression and function.

Further experiments were conducted to characterize TCR896 expression and function. TCR896 expression was validated by peptide-MHC multimer staining of lentiviral-transduced Jurkat Reporter cells, as shown in FIG. 28A. FIG. 28B depicts the results of experiments assessing TCR896 avidity by Jurkat Reporter cells. Experiments were conducted assessing TCR specificity and cross-reactivity to alternative mutant RAS epitopes by Jurkat Reporter assay. As shown in FIG. 28C, TCR896 exhibits specificity for RAS G12V (VVV_V) but not wildtype or alternatively mutated RAS epitopes. FIG. 28D depicts TCR activation of Jurkat Reporter cells following coculture with A*03:01 positive RAS G12V tumor cell lines. The expression of TCR896 on primary CD8+ T cells is shown in FIG. 28E. Experiments were conducted using 4-hr 51Cr assay which indicates specific lysis of K562-A*03:01 cells pulsed with G12V peptide (blue) or expressing RAS TMG construct (red)—but not wildtype (black) (FIG. 28F). FIG. 28G depicts the results of a 4-hr 51Cr assay indicating specific lysis of A*03:01 positive RAS G12V tumor cell lines.

Figure 29B:
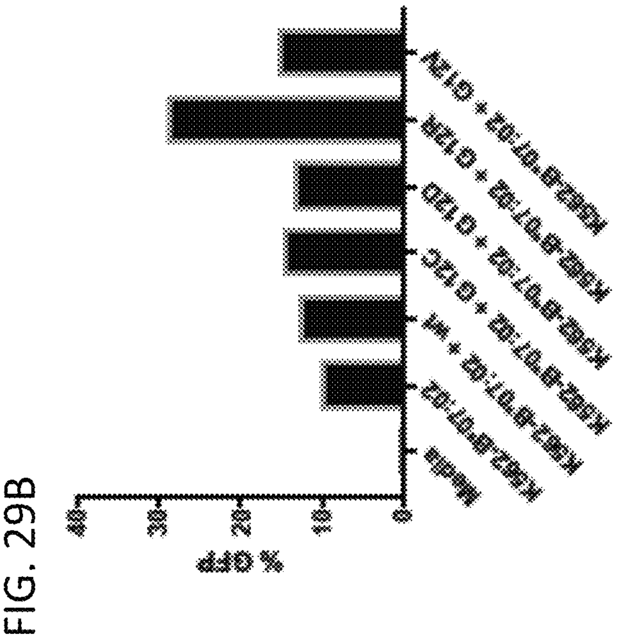
FIG. 29A and FIG. 29B depict the results of example experiments characterizing TCR847 expression and function.
Figure 29A:
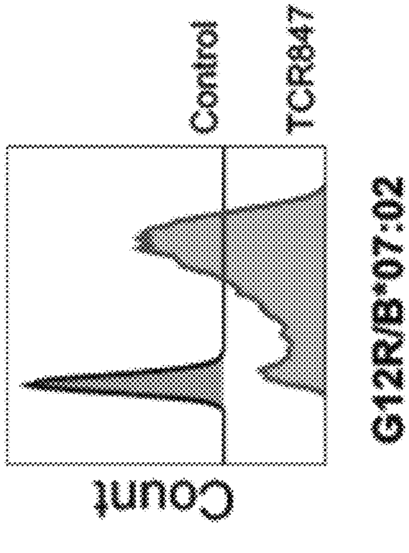

Further experiments were done to characterize TCR847 expression and function. TCR847 expression was validated by peptide-MHC multimer staining of lentiviral-transduced Jurkat Reporter cells, as shown in FIG. 29A. FIG. 29B depicts the results of experiments assessing TCR specificity and cross-reactivity to alternative mutant RAS epitopes by Jurkat Reporter assay. TCR847 exhibits specificity for RAS G12R (GA_R) but not wildtype or alternatively mutated RAS epitopes.

Figure 30A:
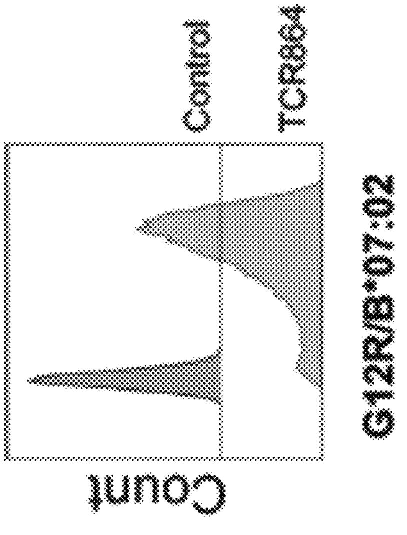
FIG. 30A through FIG. 30E depicts the results of example experiments characterizing TCR864 expression and function.
Figure 30B:
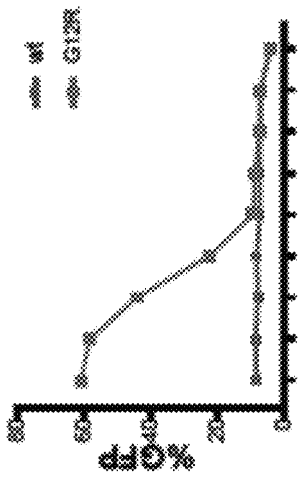
Figure 30C:
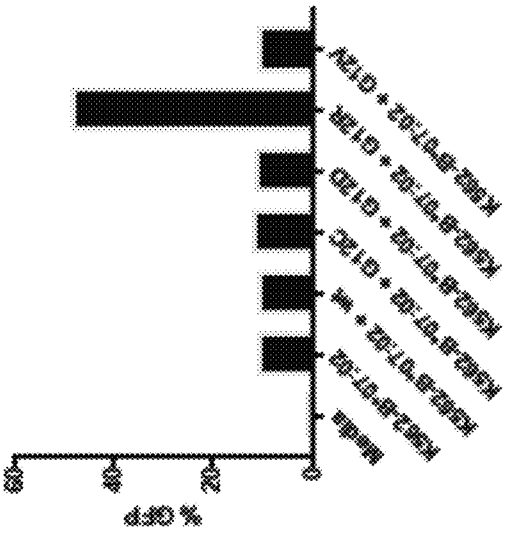
Figure 30D:
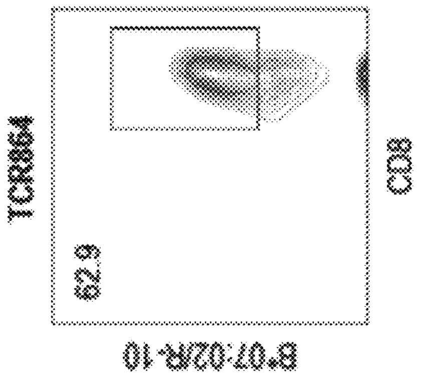
Figure 30E:
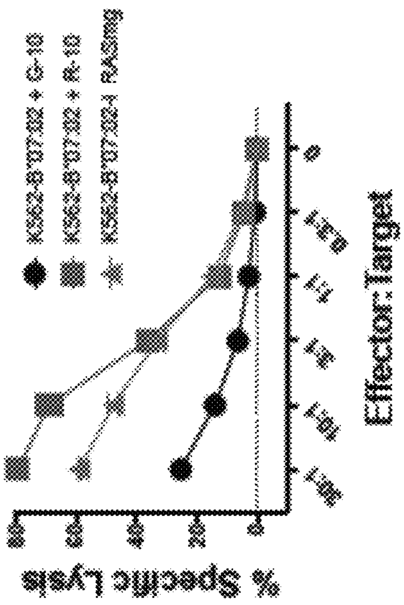

Further experiments were conducted to characterize TCR864 expression and function. TCR864 expression was validated by peptide-MHC multimer staining of lentiviral-transduced Jurkat Reporter cells, as shown in FIG. 30A. FIG. 30B depicts the results of experiments assessing TCR864 avidity by Jurkat Reporter cells. Experiments were conducted to examine TCR864 specificity and cross-reactivity to alternative mutant RAS epitopes by Jurkat Reporter assay. As shown in FIG. 30C, TCR864 exhibits specificity for RAS G12R (GA_R) but not wildtype or alternatively mutated RAS epitopes. The expression of TCR864 on primary CD8+ T cells is depicted in FIG. 30D. FIG. 30E depicts the results of experiments using 4-hr 51Cr assay which indicates specific lysis of K562-B*07:02 cells pulsed with G12R peptide (blue) or expressing RAS TMG construct (red)—but not wildtype (black).

In summary, the experiments presented herein demonstrates that mRAS-specific TCR sequences may be identified in normal donors. Further, mRAS-specific TCRs may be transgenically expressed on primary CD8+ T cells. The experiments also demonstrated that transgenic mRAS-specific TCRs exhibit high affinity and specificity.

Example 4: DC Vaccination Against mRAS Short Peptides

Figure 32:
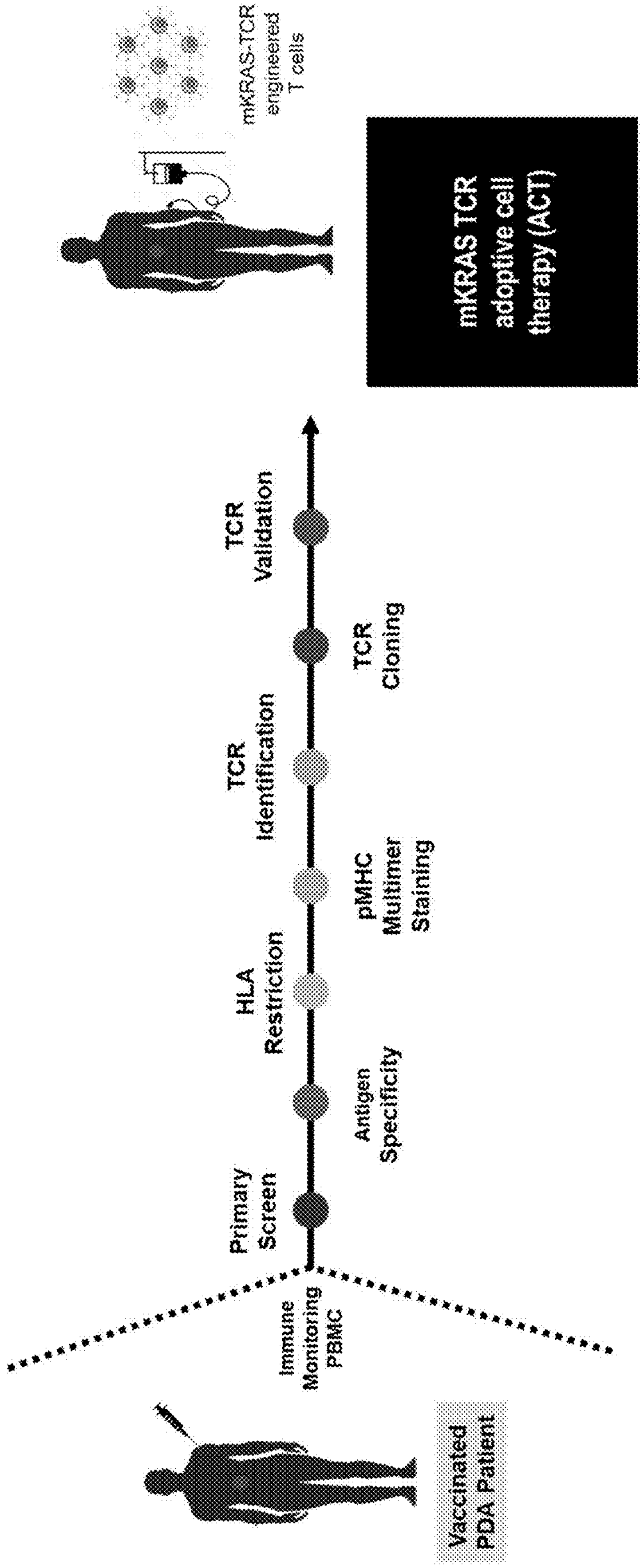
FIG. 32 depicts a schematic of experimental process used to identify mRAS TCRs in vaccinated PDA patients.

As described herein, experiments are conducted using vaccinated PDA patients. Experiments are conducted to evaluate the safety/tolerability of mDC3/8-RAS vaccine, to examine RAS-specific immunologic response to mDC3/8-RAS vaccination and to identify HLA-specific anti-RAS TCR sequences (FIG. 31). Patients are included in the study if: (1) the patient is stage I-III PDA with NED s/p surgery+/− neoadjuvant or adjuvant chemotherapy and/or radiotherapy; (2) pathologically confirmed RAS G12C, RAS G12D, RAS G12R or RAS G12V mutation; and (3) identified as HLA-A*02:01, HLA-A*03:01, HLA-A*11:01, HLA-B*07:02 and/or HLA-C*08:02. These studies can be used to further identify mRAS TCRs to develop additional adoptive cell therapies (FIG. 32).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a T-cell receptor (TCR) that specifically binds to a mutant RAS (mRAS) peptide in the context of an HLA molecule selected from the group consisting of: HLA-A*02:01, HLA-A*03:01, HLA-A*11:01, and HLA-B*07:02;

wherein a) when the HLA molecule is HLA-A*02:01, the HLA-A*02:01 comprises at least one amino acid sequence selected from the group consisting of SEQ ID NOs: 1-4;

b) when the HLA molecule is HLA-A*03:01, the HLA-A*03:01 comprises at least one amino acid sequence selected from the group consisting of SEQ ID NOs: 5-12;

c) when the HLA molecule is HLA-A*11:01, the HLA-A*11:01 comprises at least one amino acid sequence selected from the group consisting of SEQ ID NOs: 5-12; or d) when the HLA molecule is HLA-B*07:02, the HLA-B*07:02 comprises at least one amino acid sequence selected from the group consisting of SEQ ID NOs: 13-16.

2. The composition of claim 1, wherein the RAS peptide comprises a mutation at a position corresponding to G12 relative to wildtype RAS.

3. The composition of claim 2, wherein the mutation of the mRAS peptide corresponds to a mutation selected from the group consisting of G12C, G12D, G12R, and G12V; relative to wildtype RAS.

4. The composition of claim 1, wherein the TCR comprises a. at least one CDR selected from the group consisting of: TRAV39 CDR1, TRAV39 CDR2, TRAV39 CDR3, TRBV20-1 CDR1, TRBV20-1 CDR2, and TRBV20-1 CDR3;

b. at least one CDR selected from the group consisting of: TRAV12-1 CDR1, TRAV12-1 CDR2, TRAV12-1 CDR3, TRBV28 CDR1, TRBV28 CDR2, and TRBV28 CDR3;

c. at least one CDR selected from the group consisting of: TRAV17 CDR1, TRAV17 CDR2, TRAV17 CDR3, TRBV10-3 CDR1, TRBV10-3 CDR2, and TRBV10-3 CDR3;

d. at least one CDR selected from the group consisting of: TRAV17 CDR1, TRAV17 CDR2, TRAV17 CDR3, TRBV11-2 CDR1, TRBV11-2 CDR2, and TRBV11-2 CDR3;

e. at least one CDR selected from the group consisting of: TRAV19 CDR1, TRAV19 CDR2, TRAV19 CDR3, TRBV9 CDR1, TRBV9 CDR2, and TRBV9 CDR3; or f. at least one CDR selected from the group consisting of: TRAV4 CDR1, TRAV4 CDR2, TRAV4 CDR3, TRBV7-2 CDR1, TRBV7-2 CDR2, and TRBV7-2 CDR3.

5. The composition of claim 1, wherein the TCR comprises a. TRAV39 CDR1, TRAV39 CDR2, TRAV39 CDR3, TRBV20-1 CDR1, TRBV20-1 CDR2, and TRBV20-1 CDR3;

b. TRAV12-1 CDR1, TRAV12-1 CDR2, TRAV12-1 CDR3, TRBV28 CDR1, TRBV28 CDR2, and TRBV28 CDR3;

c. TRAV17 CDR1, TRAV17 CDR2, TRAV17 CDR3, TRBV10-3 CDR1, TRBV10-3 CDR2, and TRBV10-3 CDR3;

d. TRAV17 CDR1, TRAV17 CDR2, TRAV17 CDR3, TRBV11-2 CDR1, TRBV11-2 CDR2, and TRBV11-2 CDR3;

e. TRAV19 CDR1, TRAV19 CDR2, TRAV19 CDR3, TRBV9 CDR1, TRBV9 CDR2, and TRBV9 CDR3; or f. TRAV4 CDR1, TRAV4 CDR2, TRAV4 CDR3, TRBV7-2 CDR1, TRBV7-2 CDR2, and TRBV7-2 CDR3.

6. The composition of claim 1, wherein the composition comprises a fusion polypeptide comprising a TCR α chain and a TCR β chain.

7. The composition of claim 6, wherein the fusion polypeptide comprises a linker domain.

8. The composition of claim 7, wherein the linker domain is a cleavable linker domain.

* * * * *